(12) United States Patent
Hutchinson et al.

(10) Patent No.: US 9,926,318 B2
(45) Date of Patent: Mar. 27, 2018

(54) TETRACYCLIC AUTOTAXIN INHIBITORS

(71) Applicant: PharmAkea, Inc., San Diego, CA (US)

(72) Inventors: John Howard Hutchinson, San Diego, CA (US); David Lonergan, San Marcos, CA (US); Martin Rowbottom, San Diego, CA (US); Andiliy Gokching Lai, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

(21) Appl. No.: 15/036,370

(22) PCT Filed: Nov. 20, 2014

(86) PCT No.: PCT/US2014/066705
§ 371 (c)(1),
(2) Date: May 12, 2016

(87) PCT Pub. No.: WO2015/077502
PCT Pub. Date: May 28, 2015

(65) Prior Publication Data
US 2016/0264575 A1  Sep. 15, 2016

Related U.S. Application Data

(60) Provisional application No. 61/907,947, filed on Nov. 22, 2013, provisional application No. 62/038,093, filed on Aug. 15, 2014.

(51) Int. Cl.
| | |
|---|---|
| *A61K 31/437* | (2006.01) |
| *A61K 31/4985* | (2006.01) |
| *C07D 471/14* | (2006.01) |
| *C07D 471/22* | (2006.01) |
| *C07D 498/14* | (2006.01) |
| *C07D 471/12* | (2006.01) |
| *A61K 45/06* | (2006.01) |
| *A61K 31/4375* | (2006.01) |
| *A61K 31/444* | (2006.01) |
| *C07D 498/22* | (2006.01) |
| *A61K 9/10* | (2006.01) |
| *A61K 9/51* | (2006.01) |

(52) U.S. Cl.
CPC .............. *C07D 471/14* (2013.01); *A61K 9/10* (2013.01); *A61K 9/5153* (2013.01); *A61K 31/437* (2013.01); *A61K 31/4375* (2013.01); *A61K 31/444* (2013.01); *A61K 31/4985* (2013.01); *A61K 45/06* (2013.01); *C07D 471/12* (2013.01); *C07D 471/22* (2013.01); *C07D 498/14* (2013.01); *C07D 498/22* (2013.01)

(58) Field of Classification Search
CPC .............. A61K 31/437; A61K 31/4985; C07D 471/14; C07D 471/22; C07D 498/14
USPC ..................... 514/250, 287; 544/343; 546/64
See application file for complete search history.

(56) References Cited

U.S. PATENT DOCUMENTS

| | | |
|---|---|---|
| 6,143,757 A | 11/2000 | Daugan et al. |
| 6,890,933 B1 | 5/2005 | Feng et al. |
| 8,022,239 B2 | 9/2011 | Parrill-Baker et al. |
| 8,268,891 B1 | 9/2012 | Parrill-Baker et al. |
| 8,329,907 B2 | 12/2012 | Schultz et al. |
| 8,343,934 B2 | 1/2013 | Parrill-Baker et al. |
| 8,378,100 B2 | 2/2013 | Lynch et al. |
| 8,497,371 B2 | 7/2013 | Parrill-Baker et al. |
| 8,673,882 B2 | 3/2014 | Gupte et al. |
| 9,000,025 B2 | 4/2015 | Roppe et al. |
| 9,051,320 B1 | 6/2015 | Evans |
| 9,334,261 B2 | 5/2016 | Hutchinson et al. |
| 2005/0004156 A1 | 1/2005 | Feng et al. |
| 2006/0270634 A1 | 11/2006 | Miller et al. |
| 2010/0016258 A1 | 1/2010 | Lynch et al. |
| 2010/0136650 A1 | 6/2010 | Parrill-Baker et al. |
| 2010/0222341 A1 | 9/2010 | Schiemann et al. |
| 2011/0110886 A1 | 5/2011 | Braddock |
| 2011/0160148 A1 | 6/2011 | Parrill-Baker et al. |
| 2011/0230471 A1 | 9/2011 | Staehle et al. |
| 2011/0237583 A1 | 9/2011 | Schiemann et al. |
| 2012/0015959 A1 | 1/2012 | Staehle et al. |
| 2012/0015976 A1 | 1/2012 | Schultz et al. |
| 2012/0059016 A1 | 3/2012 | Schiemann et al. |
| 2012/0100592 A1 | 4/2012 | Parrill-Baker et al. |
| 2012/0115852 A1 | 5/2012 | Schultz et al. |
| 2012/0190650 A1 | 7/2012 | Gupte et al. |
| 2012/0202827 A1 | 8/2012 | Schiemann et al. |
| 2012/0316162 A1 | 12/2012 | Schiemann et al. |

(Continued)

FOREIGN PATENT DOCUMENTS

| | | |
|---|---|---|
| CN | 1095841 C | 12/2002 |
| JP | 2013129632 A | 7/2013 |

(Continued)

OTHER PUBLICATIONS

Albers et al. Boronic acid-based inhibitor of autotaxin reveals rapid turnover of LPA in the circulation. PNAS USA 107:7257-7262 (2010).

(Continued)

*Primary Examiner* — Brenda L Coleman
(74) *Attorney, Agent, or Firm* — Wilson Sonsini Goodrich & Rosati

(57) ABSTRACT

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

17 Claims, No Drawings

(56) References Cited

U.S. PATENT DOCUMENTS

| | | |
|---|---|---|
| 2013/0012505 A1 | 1/2013 | Staehle et al. |
| 2013/0029948 A1 | 1/2013 | Roppe et al. |
| 2013/0150326 A1 | 6/2013 | Roppe et al. |
| 2014/0171403 A1 | 6/2014 | Legrand et al. |
| 2014/0171404 A1 | 6/2014 | Furminger et al. |

FOREIGN PATENT DOCUMENTS

| | | |
|---|---|---|
| WO | WO-0228865 A2 | 4/2002 |
| WO | WO-2009151644 A2 | 12/2009 |
| WO | WO-2010040080 A1 | 4/2010 |
| WO | WO-2010060532 A1 | 6/2010 |
| WO | WO-2010063352 A1 | 6/2010 |
| WO | WO-2010112124 A1 | 10/2010 |
| WO | WO-2010115491 A2 | 10/2010 |
| WO | WO-2011002918 A1 | 1/2011 |
| WO | WO-2011006569 A1 | 1/2011 |
| WO | WO-2011053597 A1 | 5/2011 |
| WO | WO-2011103430 A1 | 8/2011 |
| WO | WO-2012024620 A2 | 2/2012 |
| WO | WO-2012100018 A1 | 7/2012 |
| WO | WO-2012112964 A2 | 8/2012 |
| WO | WO-2012112966 A1 | 8/2012 |
| WO | WO-2012166415 A1 | 12/2012 |
| WO | WO-2013054185 A1 | 4/2013 |
| WO | WO-2014031170 A1 | 2/2014 |
| WO | WO-2014097151 A2 | 6/2014 |
| WO | WO-2015042052 A1 | 3/2015 |
| WO | WO-2015042053 A1 | 3/2015 |
| WO | WO-2015048301 A1 | 4/2015 |
| WO | WO-2015077502 A1 | 5/2015 |
| WO | WO-2015077503 A1 | 5/2015 |

OTHER PUBLICATIONS

Albers et al. Chemical evolution of autotaxin inhibitors. Chem. Rev. 112:2593-2603 (2012).

Albers et al. Discovery and optimization of boronic acid based inhibitors of autotaxin. J. Med. Chem. 53:4958-4967 (2010).

Albers et al. Structure-based design of novel boronic acid-based inhibitors of autotaxin. J. Med. Chem. 54:4619-4626 (2011).

Antunes et al. In silico prediction of novel phosphodiesterase type-5 inhibitors derived from Sildenafil, Vardenafil and Tadalafil. Bioorganic & Medicinal Chemistry 16:7599-7606 (2008).

Baker et al. Carba analogs of cyclic phosphatidic acid are selective inhibitors of autotaxin and cancer cell invasion and metastasis. J. Biol. Chem. 281:22786-22793 (2006).

Barbayianni et al. Autotaxin inhibitors: a patent review. Expert Opin Ther Pat. 23(9)1123-1132 (2013).

Cui et al. alpha- and beta-substituted phosphonate analogs of LPA as autotaxin inhibitors. Bioorg. Med. Chem. 16:2212-2225 (2008).

Cui et al. Synthesis and biological evaluation of phosphonate derivatives as autotaxin (ATX) inhibitors. Bioorg. Med. Chem. Lett. 17:1634-1640 (2007).

Daugan et al. The Discovery of Tadalafil: A Novel and Highly Selective PDE5 Inhibitor. 2: 2,3,6,7,12,12a-hexahydropyrazino[1',2'1,6]pyrido[3,4-b]indole-1,4-dione Analogues. J Med Chem 46:4525-4532 (2003).

Durgam et al. Synthesis and pharmacological evaluation of second-generation phosphatidic acid derivatives as lysophosphatidic acid receptor ligands. Bioorg. Med. Chem. Lett. 16:633-640 (2006).

Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 48:4919-4930 (2005).

East et al. Synthesis and structure-activity relationships of tyrosine-based inhibitors of autotaxin (ATX). Bioorg. Med. Chem. Lett. 20:7132-7136 (2010).

Federico et al. Therapeutic potential of autotaxin/lysophospholipase d inhibitors. Curr Drug Targets 9(8):698-708 (2008).

Ferry et al. S32826, A Nanomolar Inhibitor of Autotaxin: Discovery, Synthesis and Applications as a Pharmacological Tool. J. Pharmacol. Exp. Ther. 327:809-819 (2008).

Gajewak et al. Synthesis, pharmacology, and cell biology of sn-2-aminooxy analogues of lysophosphatidic acid. Org. Lett. 10:1111-1114 (2008).

Gendaszewska-Darmach et al. The chemical synthesis of metabolically stabilized 2-OMe-LPA analogues and preliminary studies of their inhibitory activity toward autotaxin. Bioorg. Med. Chem. Lett. 22:2698-2700 (2012).

Gierse et al. A novel autotaxin inhibitor reduces lysophosphatidic acid levels in plasma and the site of inflammation. J. Pharmacol. Exp. 334:310-317 (2010).

Gududuru et al. Identification of Darmstoff analogs as selective agonists and antagonists of lysophosphatidic acid receptors. Bioorg. Med. Chem. Lett. 16:451-456 (2006).

Gupte et al. Benzyl and naphthalene methylphosphonic acid inhibitors of autotaxin with anti-invasive and anti-metastatic activity. ChemMedChem 6:922-935 (2011).

Gupte et al. Synthesis and pharmacological evaluation of the stereoisomers of 3-carba cyclic-phosphatidic acid. Bioorg. Med. Chem. Lett. 20:7525-7528 (2010).

Hoeglund et al. Characterization of non-lipid autotaxin inhibitors. Bioorg. Med. Chem. 18:769-776 (2010).

Hoeglund et al. Optimization of a pipemidic acid autotaxin inhibitor. J. Med. Chem. 53:1056-1066 (2010).

Jiang et al. Alpha-substituted phosphonate analogues of lysophosphatidic acid (LPA) selectively inhibit production and action of LPA. ChemMedChem 2:679-690 (2007).

Jiang et al. Aromatic phosphonates inhibit the lysophospholipase D activity of autotaxin. Bioorg. Med. Chem. Lett. 21:5098-5101 (2011).

Kano et al. LPA and its analogs-attractive tools for elucidation of LPA biology and drug development. Curr. Med. Chem. 15:2122-2131 (2008).

Klein et al. Solid-phase synthesis of new fused tetra, penta and hexacyclic β-carboline derivatives. Tetrahedron Letters 44:2211-2215 (2003).

Moulharat et al. Molecular pharmacology of adipocyte-secreted autotaxin. Chem.-Biol. Interact. 172:115-124 (2008).

North et al. Pharmacophore development and application toward the identification of novel, small-molecule autotaxin inhibitors. J. Med. Chem. 53:3095-3105 (2010).

Parrill et al. Autotaxin Inhibitors: A Perspective on Initial Medicinal Chemistry Efforts. Expert Opin Ther Pat 20(12):1619-1625 (2010).

Parrill et al. Virtual screening approaches for the identification of non-lipid autotaxin inhibitors. Bioorg. Med. Chem. 16:1784-1795 (2008).

PCT/US2014/066705 International Preliminary Report on Patentability dated Jun. 2, 2016.

PCT/US2014/066705 International Search Report and Written Opinion dated Mar. 9, 2015.

Saunders et al. Identification of small-molecule inhibitors of autotaxin that inhibit melanoma cell migration and invasion. Mol. Cancer Ther. 7:3352-3362 (2008).

Tanaka et al. Efficient synthesis of 3-O-thia-cPA and preliminary analysis of its biological activity toward autotaxin. Bioorg. Med. Chem. Lett. 21:4180-4182 (2011).

Van Meeteren et al. Anticancer activity of FTY720: phosphorylated FTY720 inhibits autotaxin, a metastasis-enhancing and angiogenic lysophospholipase D. Cancer Lett. 266:203-208 (2008).

Van Meeteren et al. Inhibition of autotaxin by lysophosphatidic acid and sphingosine 1-phosphate. J. Biol. Chem. 280:21155-21161 (2005).

Zhang et al. Dual activity lysophosphatidic acid receptor pan-antagonist/autotaxin inhibitor reduces breast cancer cell migration in vitro and causes tumor regression in vivo. Cancer Res 69:5441-5449 (2009).

TETRACYCLIC AUTOTAXIN INHIBITORS

RELATED APPLICATIONS

This application is filed pursuant to 35 U.S.C. § 371 as a United States National Phase Application of International Application No. PCT/US2014/066705 entitled "TETRACYCLIC AUTOTAXIN INHIBITORS" filed Nov. 20, 2014, which claims the benefit of U.S. Provisional Application No. 61/907,947 entitled "TETRACYCLIC AUTOTAXIN INHIBITORS" filed on Nov. 22, 2013, and U.S. Provisional Patent Application No. 62/038,093 entitled "TETRACYCLIC AUTOTAXIN INHIBITORS" filed on Aug. 15, 2014, each incorporated herein by reference in its entirety.

FIELD OF THE INVENTION

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

BACKGROUND OF THE INVENTION

Lysophosphatidic acid (LPA) is a lipid mediator that functions, for example, as a mitogen, chemoattractant, and survival factor for many cell types. LPA signaling is implicated in, for example, cancer and fibrotic diseases.

SUMMARY OF THE INVENTION

Compounds described herein are autotaxin (ATX) inhibitors. In some embodiments, the autotaxin inhibitors described herein are useful as agents for the treatment or prevention of diseases or conditions in which ATX and/or LPA participates, is involved in the etiology or pathology of the disease, or is otherwise associated with at least one symptom of the disease. Inhibition of the physiological activity of ATX and/or LPA is useful in a variety of diseases or conditions. The ATX-LPA signaling pathway has been implicated in fibrotic diseases and cancer.

Compounds described herein are used in the treatment of diseases or conditions in which autotaxin activity contributes to the symptomology or progression of the disease, disorder or condition. In one aspect, the methods, compounds, pharmaceutical compositions, and medicaments described herein comprise autotaxin inhibitors.

In one aspect, described herein is a compound of Formula (Ia), or a pharmaceutically acceptable salt, or solvate thereof:

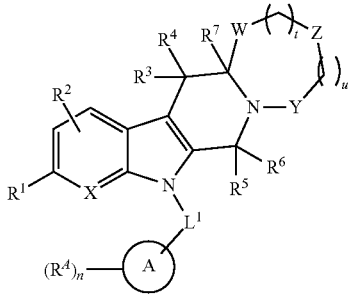

Formula (Ia)

wherein, $R^1$ is H, halogen, —CN, $C_1$-$C_4$alkyl, —$CF_3$, or $C_1$-$C_4$deuteroalkyl;

$R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

$R^3$ is H, F, $C_1$-$C_4$alkyl, or $C_1$-$C_4$fluoroalkyl;

$R^4$ is H, F, $C_1$-$C_4$alkyl, or $C_1$-$C_4$fluoroalkyl;

$R^5$ is H, F, $C_1$-$C_4$alkyl, or $C_1$-$C_4$fluoroalkyl;

$R^6$ is H, F, $C_1$-$C_4$alkyl, or $C_1$-$C_4$fluoroalkyl;

$R^7$ is H, or F;

$R^8$ is independently selected from H, —OH, —$OR^9$, $C_1$-$C_6$alkyl, $C_1$-$C_6$fluoroalkyl;

$L^1$ is absent, substituted or unsubstituted $C_1$-$C_4$alkylene or substituted or unsubstituted $C_3$-$C_7$ cycloalkylene;

A is a substituted or unsubstituted aryl, substituted or unsubstituted monocyclic heteroaryl, substituted or unsubstituted bicyclic heteroaryl, substituted or unsubstituted monocyclic heterocycloalkyl, substituted or unsubstituted bicyclic heterocycloalkyl;

each $R^4$ substituent is independently H, halogen, OH, —$OR^9$, —CN, —$NO_2$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_8$cycloalkyl, substituted or unsubstituted $C_2$-$C_{10}$heterocycloalkyl, substituted or unsubstituted aryl, —$C_1$-$C_4$alkylene-substituted or unsubstituted aryl, substituted or unsubstituted heteroaryl, —$C_1$-$C_4$alkylene-substituted or unsubstituted heteroaryl, —C(=O)$R^9$, —S(=O)$_2R^9$, —S(=O)$R^9$, —$SR^9$, —S(=O)$_2$N($R^{10}$)$_2$, —$NR^{10}$S(=O)$_2R^9$, —OC(=O)$R^9$, —$CO_2R^{10}$, —$OC_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$;

or two $R^4$ groups may be taken together with the intervening atoms connecting the two $R^4$ groups to form a substituted or unsubstituted ring containing 0-3 heteroatoms selected from —O—, —$NR^{11}$— and —S—;

n is 0, 1, 2, 3, or 4;

X is —CH=, —N=, or —CF=;

W is —C(=O)—, —C(=S)—, or —$CH_2$—;

Y is —C(=O)—, —C(=S)—, —$CH_2$— or —$CF_2$—;

Z is —$CH_2$—, —O—, >N—($C_1$-$C_6$alkyl), —Z'—, —Z'—NH— or —NH—Z'—;

Z' is >N-$L^2$-B-$L^3$-Q;

$L^2$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

B is absent, —O—, —S—, —S(=O)—, —S(=O)$_2$—, —$NR^{11}$—, —C(=O)—, —C(=O)$NR^{10}$—, or —$NR^{10}$C(=O)—;

$L^3$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

Q is —$CO_2H$, —$CO_2$($C_1$-$C_6$alkyl), —OH, —B(OH)$_2$, —C(=O)NHSO$_2R^9$, —C(=O)N($R^{10}$)$_2$, —C(=O)NH—OH, —C(=O)NH—CN, —$SO_2$NHC(=O)$R^9$, —OP(=O)(OH)$_2$, —P(=O)(OH)$_2$, tetrazolyl, carboxylic acid bioisostere, substituted or unsubstituted monocyclic heterocycle, —S(=O)$_2R^9$, —S(=O)$R^9$, —$SR^9$, —S(=O)$_2$N($R^{10}$)$_2$, —$NR^{10}$S(=O)$_2R^9$, —OC(=O)$R^9$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$;

each $R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, —$C_1$-$C_4$alkylene-substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl;

or two $R^{10}$ groups attached to the same N atom are taken together with the N atom to which they are attached to form a substituted or unsubstituted heterocycle;

$R^{11}$ is H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl, —S(=O)$_2$R$^9$, —C(=O)R$^9$, —CO$_2$R$^{10}$, or —C(=O)N(R$^{10}$)$_2$;

t is 0 or 1;
u is 0 or 1.

For any and all of the embodiments, substituents are selected from among a subset of the listed alternatives. For example, in some embodiments, t is 0 or 1. In other embodiments, t is 0. In some embodiments, u is 0 or 1. In some embodiments, u is 0.

In some embodiments, Z is —CH$_2$—, —O—, >N—($C_1$-$C_6$alkyl), or —Z'—; Z' is >N-L$^2$-B-L$^3$-Q; L$^2$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene; B is absent, —O—, —S—, —S(=O)—, —S(=O)$_2$—, —NR$^{11}$—, —C(=O)—, —C(=O)NR$^{10}$—, or —NR$^{10}$C(=O)—; L$^3$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene; Q is —CO$_2$H, —CO$_2$($C_1$-$C_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, or carboxylic acid bioisostere.

In some embodiments, Z is —Z'—.

In some embodiments, $L^2$ is $C_1$-$C_6$alkylene, or $C_3$-$C_6$cycloalkylene; B is absent; $L^3$ is absent.

In some embodiments, $L^2$ is $C_1$-$C_6$alkylene; B is absent; $L^3$ is absent or $C_3$-$C_6$cycloalkylene.

In some embodiments, $L^2$ is $C_1$-$C_6$alkylene; Q is —CO$_2$H, —CO$_2$($C_1$-$C_6$alkyl), —B(OH)$_2$, —C(=O)NHSO$_2$R$^9$, —C(=O)N(R$^{10}$)$_2$, tetrazolyl, or carboxylic acid bioisostere.

In some embodiments, $L^2$ is absent, —CH$_2$—, —CH$_2$CH$_2$—, —CH$_2$CH$_2$CH$_2$—, or —CH$_2$CH$_2$CH$_2$CH$_2$—; Q is —CO$_2$H, or —CO$_2$($C_1$-$C_6$alkyl).

In some embodiments, $R^3$ is H, F, Cl, Br, —CN, —OH, —CH$_3$, or —CF$_3$; $R^4$ is H, F, Cl, Br, —CN, —OH, —CH$_3$, or —CF$_3$; or $R^3$ and $R^4$ are taken together with the carbon atom to which they are attached to form —C(=O)— or cyclopropyl.

In some embodiments, $R^3$ is H.
In some embodiments, $R^4$ is H.
In some embodiments, $R^5$ is H, F, Cl, —CH$_3$, or —CF$_3$; $R^6$ is H, F, Cl, —CH$_3$, or —CF$_3$.

In some embodiments, $R^5$ is H.
In some embodiments, $R^6$ is H.
In some embodiments, $R^7$ is H, F, Cl, —CH$_3$, or —CF$_3$.
In some embodiments, $R^7$ is H.
In some embodiments, $L^1$ is a absent or $C_1$alkylene;

A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L^1$ is absent, —CH$_2$—, —CH$_2$CH$_2$—, —CH$_2$CH$_2$CH$_2$—, or —CH$_2$CH$_2$CH$_2$CH$_2$—.

In some embodiments, $L^1$ is —CH$_2$—.
In some embodiments, A is phenyl.
In some embodiments, A is pyridinyl, pyrimidinyl, pyrazinyl, pyridazinyl, or triazinyl.
In some embodiments, A is pyridinyl.
In some embodiments, A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.
In some embodiments, A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $R^1$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^1$ is H, F, Cl, Br, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

In some embodiments, $R^1$ is H, F or Cl.

In some embodiments, $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy.

In some embodiments, $R^2$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$.

In some embodiments, $R^2$ is H, F, or Cl.
In some embodiments, t is 0.
In some embodiments, u is 0.
In some embodiments, the compound has the following structure of Formula (II):

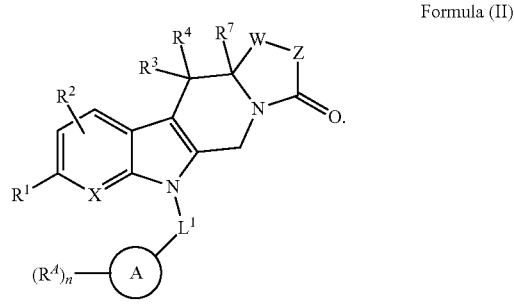

Formula (II)

In some embodiments, the compound has the following structure of Formula (III) or Formula (IV):

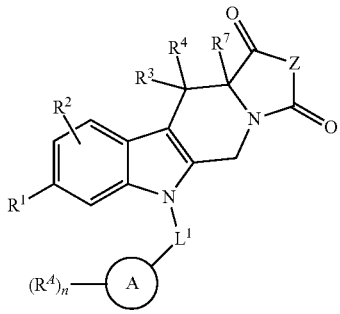

Formula (III)

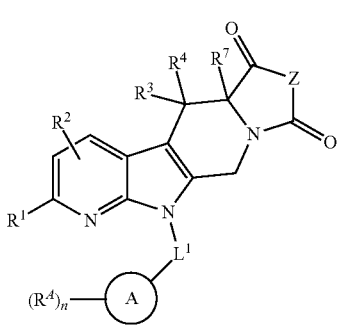

Formula (IV)

In some embodiments, the compound has the following structure of Formula (V):

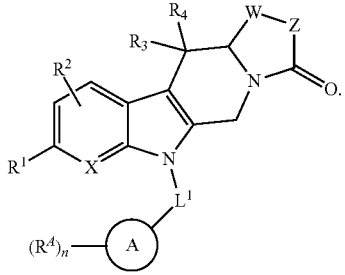

Formula (V)

Any combination of the groups described above for the various variables is contemplated herein. Throughout the specification, groups and substituents thereof are chosen by one skilled in the field to provide stable moieties and compounds.

In some embodiments, a compound of formula (Ia), or a pharmaceutically acceptable salt, or solvate thereof, is:
4-(6-(4-fluorobenzyl)-1,3-dioxo-11,11a-dihydro-1H-imidazo[1',5':1,6]pyrido[3,4-b]indol-2(3H,5H,6H)-yl)butanoic acid (compound no. 1-1);
(S)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid (compound no. 1-2);
(R)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid (compound no. 1-3);
3-(6-(4-fluorobenzyl)-1,3-dioxo-11,11a-dihydro-1H-imidazo[1',5':1,6]pyrido[3,4-b]indol-2(3H,5H,6H)-yl)propanoic acid (compound no. 1-4);
3-(6-(4-fluorobenzyl)-1,3-dioxo-11,11a-dihydro-1H-imidazo[1',5':1,6]pyrido[3,4-b]indol-2(3H,5H,6H)-yl)propanoic acid (compound no. 1-5; Enantiomer A);
3-(6-(4-fluorobenzyl)-1,3-dioxo-11,11a-dihydro-1H-imidazo[1',5':1,6]pyrido[3,4-b]indol-2(3H,5H,6H)-yl)propanoic acid (compound no. 1-6; Enantiomer B);
4-(1,3-dioxo-6-(3-phenylpropyl)-11,11a-dihydro-1H-imidazo[1',5':1,6]pyrido[3,4-b]indol-2(3H,5H,6H)-yl)butanoic acid (compound no. 1-7);
6-(4-fluorobenzyl)-5,6,11,11a-tetrahydrooxazolo[3',4':1,6]pyrido[3,4-b]indol-3(1H)-one (compound no. 1-8);
(S)-6-(4-fluorobenzyl)-5,6,11,11a-tetrahydrooxazolo[3',4':1,6]pyrido[3,4-b]indol-3(1H)-one (compound no. 1-9);
(R)-6-(4-fluorobenzyl)-5,6,11,11a-tetrahydrooxazolo[3',4':1,6]pyrido[3,4-b]indol-3(1H)-one (compound no. 1-10);
(S)-4-(6-((6-methoxypyridin-3-yl)methyl)-1,3-dioxo-11,11a-dihydro-1H-imidazo[1',5':1,6]pyrido[3,4-b]indol-2(3H,5H,6H)-yl)butanoic acid (compound no. 1-11);
(S)-3-(6-((6-methoxypyridin-3-yl)methyl)-1,3-dioxo-11,11a-dihydro-1H-imidazo[1',5':1,6]pyrido[3,4-b]indol-2(3H,5H,6H)-yl)propanoic acid (compound no. 1-12);
6-(4-fluorobenzyl)-2-methyl-5,6,11,11a-tetrahydro-1H-imidazo[1',5':1,6]pyrido[3,4-b]indol-3(2H)-one (compound no. 1-14);
6-(4-fluorobenzyl)-2-methyl-5,6,11,11a-tetrahydro-1H-imidazo[1',5':1,6]pyrido[3,4-b]indole-1,3(2H)-dione (compound no. 1-129);
6-(4-fluorobenzyl)-2-(2-hydroxyethyl)-5,6,11,11a-tetrahydro-1H-imidazo[1',5':1,6]pyrido[3,4-b]indole-1,3(2H)-dione (compound no. 1-121);
2-(6-(4-fluorobenzyl)-1,3-dioxo-5,6,11,11a-tetrahydro-1H-imidazo[1',5':1,6]pyrido[3,4-b]indol-2(3H)-yl)acetonitrile (compound no. 1-139);
2-(6-(4-fluorobenzyl)-1,3-dioxo-5,6,11,11a-tetrahydro-1H-imidazo[1',5':1,6]pyrido[3,4-b]indol-2(3H)-yl)acetic acid (compound no. 1-19);
7-(4-fluorobenzyl)-2,3,6,7,12,12a-hexahydropyrazino[1',2':1,6]pyrido[3,4-b]indole-1,4-dione (compound no. 1-16);
2-(7-(4-fluorobenzyl)-1,4-dioxo-3,4,6,7,12,12a-hexahydropyrazino[1',2':1,6]pyrido[3,4-b]indol-2(1H)-yl)acetic acid (compound no. 1-23);
3-(7-(4-fluorobenzyl)-1,4-dioxo-3,4,6,7,12,12a-hexahydropyrazino[1',2':1,6]pyrido[3,4-b]indol-2(1H)-yl)propanoic acid (compound no. 1-24);
(S)-4-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylbutanoic acid (compound no. 1-39);
(S)-4-(6-(4-fluorobenzyl)-1,3-dioxo-5,6,11,11a-tetrahydro-1H-imidazo[1',5':1,6]pyrido[3,4-b]indol-2(3H)-yl)-3,3-dimethylbutanoic acid (compound no. 1-42);
(S)-4-(8-chloro-6-(4-fluorobenzyl)-1,3-dioxo-5,6,11,11a-tetrahydro-1H-imidazo[1',5':1,6]pyrido[3,4-b]indol-2(3H)-yl)butanoic acid (compound no. 1-27);
(S)-8-chloro-6-(4-fluorobenzyl)-5,6,11,11a-tetrahydro-1H-imidazo[1',5':1,6]pyrido[3,4-b]indole-1,3(2H)-dione (compound no. 1-26);
(S)-3-(6-((6-chloropyridin-3-yl)methyl)-1,3-dioxo-5,6,11,11a-tetrahydro-1H-imidazo[1',5':1,6]pyrido[3,4-b]indol-2(3H)-yl)propanoic acid (compound no. 1-84);
(S)-1-((6-((6-methoxypyridin-3-yl)methyl)-1,3-dioxo-5,6,11,11a-tetrahydro-1H-imidazo[1',5':1,6]pyrido[3,4-b]indol-2(3H)-yl)methyl)cyclopropane-1-carboxylic acid (compound no. 1-18);
(S)-3-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylpropanoic acid (compound no. 1-30);

(S)-1-((6-(4-fluorobenzyl)-1,3-dioxo-5,6,11,11a-tetrahydro-1H-imidazo[1',5':1,6]pyrido[3,4-b]indol-2(3H)-yl)methyl)cyclopropane-1-carboxylic acid (compound no. 1-34);

3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (compound no. C114);

3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (compound no. C114 Enantiomer A);

3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (compound no. C114 Enantiomer B);

(S)-3-(6-(4-fluorobenzyl)-1-oxo-3-thioxo-5,6,11,11a-tetrahydro-1H-imidazo[1',5':1,6]pyrido[3,4-b]indol-2(3H)-yl)propanoic acid (compound no. E1);

3-(6-(4-fluorobenzyl)-11,11-dimethyl-1,3-dioxo-5,6,11,11a-tetrahydro-1H-imidazo[1',5':1,6]pyrido[3,4-b]indol-2(3H)-yl)propanoic acid (compound no. A11);

2-(6-(4-fluorobenzyl)-3-oxo-11,11a-dihydro-1H-imidazo[1',5':1,6]pyrido[3,4-b]indol-2(3H,5H,6H)-yl)acetic acid (compound no. 1-20);

3-(6-(4-fluorobenzyl)-3-oxo-11,11a-dihydro-1H-imidazo[1',5':1,6]pyrido[3,4-b]indol-2(3H,5H,6H)-yl)propanoic acid (compound no. 1-21);

(S)-3-(1,3-dioxo-6-((2-(trifluoromethyl)thiazol-5-yl)methyl)-11,11a-dihydro-1H-imidazo[1',5':1,6]pyrido[3,4-b]indol-2(3H,5H,6H)-yl)propanoic acid (compound no. 1-102);

(S)-3-(6-(4-methoxybenzyl)-1,3-dioxo-11,11a-dihydro-1H-imidazo[1',5':1,6]pyrido[3,4-b]indol-2(3H,5H,6H)-yl)propanoic acid (compound no. 1-131);

(S)-3-(6-(2,4-dichlorobenzyl)-1,3-dioxo-11,11a-dihydro-1H-imidazo[1',5':1,6]pyrido[3,4-b]indol-2(3H,5H,6H)-yl)propanoic acid (compound no. 1-132);

(S)-3-(6-(4-chloro-2-fluorobenzyl)-1,3-dioxo-11,11a-dihydro-1H-imidazo[1',5':1,6]pyrido[3,4-b]indol-2(3H,5H,6H)-yl)propanoic acid (compound no. 1-133);

(S)-3-(6-(2,4-difluorobenzyl)-1,3-dioxo-11,11a-dihydro-1H-imidazo[1',5':1,6]pyrido[3,4-b]indol-2(3H,5H,6H)-yl)propanoic acid (compound no. 1-134);

(S)-3-(6-((6-fluoropyridin-3-yl)methyl)-1,3-dioxo-11,11a-dihydro-1H-imidazo[1',5':1,6]pyrido[3,4-b]indol-2(3H,5H,6H)-yl)propanoic acid (compound no. 1-135);

(S)-6-(4-fluorobenzyl)-3-thioxo-2,3,5,6,11,11a-hexahydro-1H-imidazo[1',5':1,6]pyrido[3,4-b]indol-1-one (compound no. E2);

(S)-3(6-(4-fluorobenzyl)-3-oxo-1-thioxo-5,6,11,11a-tetrahydro-1H-imidazo[1',5':1,6]pyrido[3,4-b]indol-2(3H)-yl)propanoic acid (compound no. 1-141);

3-{8-[(p-fluorophenyl)methyl]-12,14-dioxo-6.8.11.13-tetrazatetracyclo[7.7.0.02,7.011,15]hexadeca-1(9),2(7),3,5-tetraene-13-yl}-2,2-dimethyl propionic acid (compound no. C111);

8-[p-fluorophenyl)methyl]-12-thioxo-6.8.11.13-tetrazatetracyclo[7.7.0.02,7.011,15]hexadeca-1(9),2(7),3,5-tetraen-14-one (compound no. E3);

3-{8-[(p-fluorophenyl)methyl]-16,16-dimethyl-12,14-dioxo-6.8.11.13-tetrazatetracyclo[7.7.0.02,7.011,15]hexadeca-1 (9),2(7),3,5-tetraene-13-yl}propionic acid (compound no. C11);

(S)-3-(6-(4-fluorobenzyl)-1,3-dioxo-11,11a-dihydro-1H-imidazo[1',5':1,6]pyrido[3,4-b]indol-2(3H,5H,6H)-yl)-N-(methylsulfonyl)propanamide (compound no. 1-142);

(S)-3-(6-(4-fluorobenzyl)-1,3-dioxo-11,11a-dihydro-1H-imidazo[1',5':1,6]pyrido[3,4-b]indol-2(3H,5H,6H)-yl)-N-(phenylsulfonyl)propanamide (compound no. 1-143);

3-(6-(4-fluorobenzyl)-11,11a-methyl-1,3-dioxo-11,11a-dihydro-1H-imidazo[1',5':1,6]pyrido[3,4-b]indol-2(3H,5H,6H)-yl)propanoic acid (compound no. A113);

2-((2H-tetrazol-5-yl)methyl)-6-(4-fluorobenzyl)-5,6,11,11a-tetrahydro-1H-imidazo[1',5':1,6]pyrido[3,4-b]indole-1,3(2H)-dione (compound no. 1-140); or 3-{8-[(p-fluorophenyl)methyl]-16,16-dimethyl-12,14-dioxo-6.8.11.13-tetrazatetracyclo[7.7.0.02,7.011,15]hexadeca-1 (9),2(7),3,5-tetraene-13-yl}-2,2-dimethylpropionic acid (compound no. C13).

In one aspect, described herein is a compound of Formula (VI), or a pharmaceutically acceptable salt, or solvate thereof:

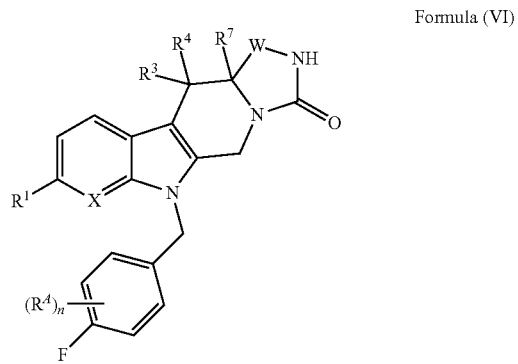

Formula (VI)

wherein,
$R^1$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl;

$R^3$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

$R^4$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

$R^7$ is H, or F;

each $R^4$ substituent is independently H, halogen, OH, —O—$C_1$-$C_4$alkyl, —CN, $C_1$-$C_6$alkyl, $C_1$-$C_6$fluoroalkyl, or $C_1$-$C_6$deuteroalkyl;

n is 0, or 1;

X is —CH=, —N=, or —CF=; and

W is —C(=O)—, —C(=S)—, or —CH$_2$—.

In some embodiments, $R^1$ is H, F, Cl, Br, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

In some embodiments, $R^1$ is H or Cl.

In some embodiments, $R^3$ is H or —CH$_3$.

In some embodiments, $R^4$ is H or —CH$_3$.

In some embodiments, n is 0.

In some embodiments, X is —CH= or —N=.

In some embodiments, W is —C(=O)—, or —CH$_2$—.

In some embodiments, a compound of formula (VI), or a pharmaceutically acceptable salt, or solvate thereof, is:

6-(4-fluorobenzyl)-5,6,11,11a-tetrahydro-1H-imidazo[1',5':1,6]pyrido[3,4-b]indol-3(2H)-one (compound no. 1-13);

6-(4-fluorobenzyl)-5,6,11,11a-tetrahydro-1H-imidazo[1',5':1,6]pyrido[3,4-b]indole-1,3(2H)-dione (compound no. 1-15);

(S)-6-(4-fluorobenzyl)-5,6,11,11a-tetrahydro-1H-imidazo[1',5':1,6]pyrido[3,4-b]indole-1,3(2H)-dione (compound no. 1-130);

8-[p-fluorophenyl)methyl]-6.8.11.13-tetrazatetracyclo[7.7.0.02, 7.011,15]hexadeca-1(9),2(7),3,5-tetraen-12,14-dione (compound no. C109);

6-(4-fluorobenzyl)-11,11-dimethyl-5,6,11,11a-tetrahydro-1H-imidazo[1',5':1,6]pyrido[3,4-b]indole-1,3(2H)-dione (compound no. A110);

6-(4-fluorobenzyl)-11,11-dimethyl-5,6,11,11a-tetrahydro-1H-imidazo[1',5':1,6]pyrido[3,4-b]indole-1,3(2H)-dione (compound no. A110 Enantiomer A); or 6-(4-fluorobenzyl)-11,11-dimethyl-5,6,11,11a-tetrahydro-1H-imidazo[1',5':1,6]pyrido[3,4-b]indole-1,3(2H)-dione (compound no. A110 Enantiomer B).

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In another aspect, described herein is a method for treating or preventing cancer, or fibrosis, or combinations thereof in a mammal comprising administering a therapeutically effective amount of a compound described herein, or a pharmaceutically acceptable salt, or solvate thereof, to the mammal in need thereof.

In one aspect, described herein is a method for treating or preventing cancer in a mammal comprising administering a therapeutically effective amount of a compound described herein, or a pharmaceutically acceptable salt, or solvate thereof, to the mammal in need thereof. In some embodiments, the cancer is a solid tumor. In some embodiments, the cancer is amenable to treatment with an autotaxin inhibitor. In some embodiments, the method further comprises administering a second therapeutic agent to the mammal in addition to the compound described herein, or a pharmaceutically acceptable salt, or solvate thereof.

In one aspect, described herein is a method for the treatment or prevention of fibrosis in a mammal comprising administering a therapeutically effective amount of a compound described herein, or a pharmaceutically acceptable salt, or solvate thereof, to the mammal in need thereof. In other embodiments, the fibrosis is amenable to treatment with an autotaxin inhibitor. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) t administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of ATX dependent diseases or conditions are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autotaxin and LPA

Autotaxin (ATX, NPP2, or ENPP2), an approximately 120 kDa glycoprotein, is a secreted nucleotide pyrophosphatase/phosphodiesterase (NPP) with lysophospholipase D activity that converts extracellular lysophosphatidylcholine (LPC) and other lysophospholipids to lysophosphatidic acid (LPA). ATX is considered to be responsible for the majority of circulating LPA production.

LPA acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses. For example, lysophospholipids, such as lysophosphatidic acid (LPA), are known to affect such biological functions as cellular proliferation, differentiation, survival, migration, adhesion, invasion, and morphogenesis. In addition, LPA is known to play a role in such processes as platelet activation, smooth muscle contraction, actin stress fiber formation, and cell migration.

ATX and LPA have been detected in various biological fluids such as serum, plasma, cerebrospinal fluid, seminal fluid, urine, and saliva, both in animals and humans, suggesting that they are potential biomarkers to predict certain diseases. For example, serum ATX concentration and activity is elevated in patients with chronic liver diseases and in pregnant women. In addition, ATX concentration has been found to be lower in postoperative cancer patients as a result of postoperative damage or poor nutritional state. In addition, ATX is known to be essential for normal development. For example, ATX-deficient mice die at embryonic day 9.5 with profound vascular defects in both the yolk sac and the embryo. Furthermore, at embryonic day 8.5 ATX-deficient embryos were found to have malformed allantois, neural tube defects, and asymmetric headfolds.

Cancer

ATX has been demonstrated to increase cell motility, neovascularization, proliferation and aggressiveness of tumors. It is upregulated in numerous tumor lineages, such as breast, renal, liver, glioblastoma, ovarian and prostate cancer.

In some embodiments, disclosed herein are methods of treating cancer with a compound disclosed herein.

ATX is a prometastatic enzyme initially isolated from the conditioned medium of human melanoma cells. In addition, ATX overexpression is frequently observed in malignant tumor tissues such as breast cancer, renal cancer, Hodgkin lymphoma, hepatocellular carcinoma, pancreatic cancer and glioblastoma. LPA also contributes to tumorigenesis by increasing motility and invasiveness of cells.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Fibrosis

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is primary fibrosis. In some embodiments, the fibrotic condition is idiopathic. In some embodiments, the fibrotic condition is associated with (e.g., is secondary to) a disease; a toxin; an insult (e.g., an environmental hazard); a medical treatment, or a combination thereof.

In some embodiments, the fibrotic condition is a fibrotic condition of the lung (pulmonary fibrosis), a fibrotic condition of the liver (renal fibrosis), a fibrotic condition of the heart or vasculature (cardiac fibrosis), a fibrotic condition of the kidney (renal fibrosis), a fibrotic condition of the skin, a fibrotic condition of the gastrointestinal tract, or a combination thereof.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrotic condition of the lung treated with the methods of the invention is associated with (e.g., secondary to) a cancer treatment.

In some embodiments, the fibrotic condition is a fibrotic condition of the liver.

In some embodiments, the fibrotic condition is a fibrotic condition of the heart.

In some embodiments, the fibrotic condition is a fibrotic condition of the kidney.

In some embodiments, the fibrotic condition is a fibrotic condition of the skin.

In some embodiments, the fibrotic condition is a fibrotic condition of the gastrointestinal tract.

Compounds

Compounds described herein, including pharmaceutically acceptable salts, prodrugs, active metabolites and pharmaceutically acceptable solvates thereof, are autotaxin inhibitors.

In one aspect, described herein is a compound of Formula (I), or a pharmaceutically acceptable salt, or solvate thereof:

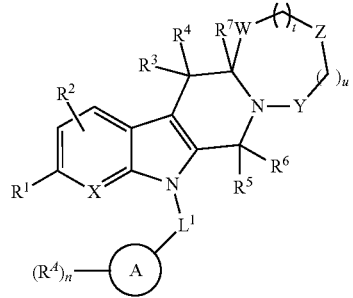

wherein, $R^1$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, C$_1$-C$_4$alkyl, C$_1$-C$_4$fluoroalkyl, C$_1$-C$_4$deuteroalkyl, C$_1$-C$_4$hydroxyalkyl, C$_1$-C$_4$heteroalkyl, or C$_3$-C$_6$cycloalkyl;

$R^2$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy;

$R^3$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

$R^4$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

or $R^3$ and $R^4$ are taken together with the carbon atom to which they are attached to form —C(=O)—, —C(=NR$^8$)—, a substituted or unsubstituted cycloalkyl ring, or a substituted or unsubstituted heterocyclic ring containing 1 or 2 heteroatoms selected from —O—, —NR$^{11}$—, and —S—;

$R^5$ is H, F, $C_1$-$C_4$alkyl, —O—$C_1$-$C_4$alkyl, or $C_1$-$C_4$fluoroalkyl;

$R^6$ is H, F, $C_1$-$C_4$alkyl, —O—$C_1$-$C_4$alkyl, or $C_1$-$C_4$fluoroalkyl;

$R^7$ is H, F, $C_1$-$C_4$alkyl, —O—$C_1$-$C_4$alkyl, or $C_1$-$C_4$fluoroalkyl;

or $R^3$ and $R^7$ are taken together with the intervening atoms connecting the $R^3$ and $R^7$ groups to form a double bond;

or $R^3$ and $R^7$ are taken together with the intervening atoms connecting the $R^3$ and $R^7$ groups to form a cyclopropyl ring;

$R^8$ is independently selected from H, —OH, —OR$^9$, $C_1$-$C_6$alkyl, $C_1$-$C_6$fluoroalkyl;

$L^1$ is absent, substituted or unsubstituted $C_1$-$C_4$alkylene or substituted or unsubstituted $C_3$-$C_7$ cycloalkylene;

A is a substituted or unsubstituted aryl, substituted or unsubstituted monocyclic heteroaryl, substituted or unsubstituted bicyclic heteroaryl, substituted or unsubstituted monocyclic heterocycloalkyl, substituted or unsubstituted bicyclic heterocycloalkyl;

each $R^A$ substituent is independently H, halogen, OH, —OR$^9$, —CN, —NO$_2$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_8$cycloalkyl, substituted or unsubstituted $C_2$-$C_{10}$heterocycloalkyl, substituted or unsubstituted aryl, —$C_1$-$C_4$alkylene-substituted or unsubstituted aryl, substituted or unsubstituted heteroaryl, —$C_1$-$C_4$alkylene-substituted or unsubstituted heteroaryl, —C(=O)R$^9$, —S(=O)$_2$R$^9$, —S(=O)R$^9$, —SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$;

or two $R^A$ groups may be taken together with the intervening atoms connecting the two $R^A$ groups to form a substituted or unsubstituted ring containing 0-3 heteroatoms selected from —O—, —NR$^{11}$— and —S—;

n is 0, 1, 2, 3, or 4;

X is —CH=, —N=, or —CF=;

W is —C(=O)—, —C(=S)—, or —CH$_2$—;

Y is —C(=O)—, —C(=S)—, —CH$_2$— or —CF$_2$—;

Z is —CH$_2$—, —O—, —NH—, >N—(C$_1$-C$_6$alkyl), —Z'—, —Z'—NH— or —NH—Z'—;

Z' is >N-L$^2$-B-L$^3$-Q;

L$^2$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

B is absent, —O—, —S—, —S(=O)—, —S(=O)$_2$—, —NR$^{11}$—, —C(=O)—, —C(=O)NR$^{10}$—, or —NR$^{10}$C(=O)—;

L$^3$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

Q is —CO$_2$H, —CO$_2$(C$_1$-C$_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, carboxylic acid bioisostere, substituted or unsubstituted monocyclic heterocycle, —S(=O)$_2$R$^9$, —S(=O)R$^9$, —SR$^9$, —S(=O)$_2$N(R$^{10}$)$_2$, —NR$^{10}$S(=O)$_2$R$^9$, —OC(=O)R$^9$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$;

each $R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, —$C_1$-$C_4$alkylene-substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl;

or two $R^{10}$ groups attached to the same N atom are taken together with the N atom to which they are attached to form a substituted or unsubstituted heterocycle;

$R^{11}$ is H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl, —S(=O)$_2$R$^9$, —C(=O)R$^9$, —CO$_2$R$^{10}$, or —C(=O)N(R$^{10}$)$_2$;

t is 0 or 1;

u is 0 or 1.

In one aspect, described herein is a compound of Formula (Ia), or a pharmaceutically acceptable salt, or solvate thereof:

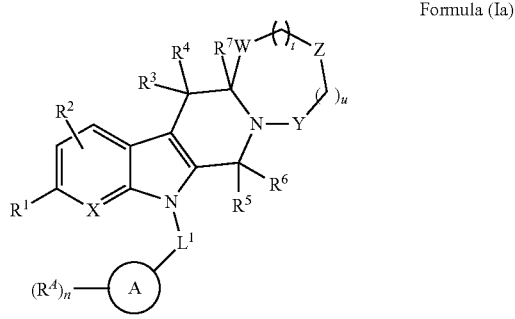

Formula (Ia)

wherein, $R^1$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, or $C_3$-$C_6$cycloalkyl;

$R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

$R^3$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

$R^4$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

or $R^3$ and $R^4$ are taken together with the carbon atom to which they are attached to form —C(=O)—, —C(=NR$^8$)—, a substituted or unsubstituted cycloalkyl ring, or a substituted or unsubstituted heterocyclic ring containing 1 or 2 heteroatoms selected from —O—, —NR$^{11}$— and —S—;

$R^5$ is H, F, $C_1$-$C_4$alkyl, —O—$C_1$-$C_4$alkyl, or $C_1$-$C_4$fluoroalkyl;

$R^6$ is H, F, $C_1$-$C_4$alkyl, —O—$C_1$-$C_4$alkyl, or $C_1$-$C_4$fluoroalkyl;

$R^7$ is H, F, $C_1$-$C_4$alkyl, —O—$C_1$-$C_4$alkyl, or $C_1$-$C_4$fluoroalkyl;

or $R^3$ and $R^7$ are taken together with the intervening atoms connecting the $R^3$ and $R^7$ groups to form a double bond;

or $R^3$ and $R^7$ are taken together with the intervening atoms connecting the $R^3$ and $R^7$ groups to form a cyclopropyl ring;

$R^8$ is independently selected from H, —OH, —OR$^9$, $C_1$-$C_6$alkyl, $C_1$-$C_6$fluoroalkyl;

$L^1$ is absent, substituted or unsubstituted $C_1$-$C_4$alkylene or substituted or unsubstituted $C_3$-$C_7$ cycloalkylene;

A is a substituted or unsubstituted aryl, substituted or unsubstituted monocyclic heteroaryl, substituted or unsubstituted bicyclic heteroaryl, substituted or unsubstituted monocyclic heterocycloalkyl, substituted or unsubstituted bicyclic heterocycloalkyl;

each $R^A$ substituent is independently H, halogen, OH, —OR$^9$, —CN, —NO$_2$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_8$cycloalkyl, substituted or unsubstituted $C_2$-$C_{10}$heterocycloalkyl, substituted or unsubstituted aryl, —$C_1$-$C_4$alkylene-substituted or unsubstituted aryl, substituted or unsubstituted heteroaryl, —$C_1$-$C_4$alkylene-substituted or unsubstituted heteroaryl, —C(=O)R$^9$, —S(=O)$_2$R$^9$, —S(=O)R$^9$, —SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$;

or two $R^A$ groups may be taken together with the intervening atoms connecting the two $R^A$ groups to form a substituted or unsubstituted ring containing 0-3 heteroatoms selected from —O—, —NR$^{11}$— and —S—;

n is 0, 1, 2, 3, or 4;

X is —CH=, —N=, or —CF=;

W is —C(=O)—, —C(=S)—, or —CH$_2$—;

Y is —C(=O)—, —C(=S)—, —CH$_2$— or —CF$_2$—;

Z is —CH$_2$—, —O—, >N—(C$_1$-$C_6$alkyl), —Z'—, —Z'—NH— or —NH—Z'—;

Z' is >N-L$^2$-B-L$^3$-Q;

$L^2$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

B is absent, —O—, —S—, —S(=O)—, —S(=O)$_2$—, —NR$^{11}$—, —C(=O)—, —C(=O)NR$^{10}$—, or —NR$^{10}$C(=O)—;

$L^3$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene;

Q is —CO$_2$H, —CO$_2$(C$_1$-$C_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, carboxylic acid bioisostere, substituted or unsubstituted monocyclic heterocycle, —S(=O)$_2$R$^9$, —S(=O)R$^9$, —SR$^9$, —S(=O)$_2$N(R$^{10}$)$_2$, —NR$^{10}$S(=O)$_2$R$^9$, —OC(=O)R$^9$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$;

each $R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, —$C_1$-$C_4$alkylene-substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl;

or two $R^{10}$ groups attached to the same N atom are taken together with the N atom to which they are attached to form a substituted or unsubstituted heterocycle;

$R^{11}$ is H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl, —S(=O)$_2$R$^9$, —C(=O)R$^9$, —CO$_2$R$^{10}$, or —C(=O)N(R$^{10}$)$_2$ t is 0 or 1;

u is 0 or 1.

In one aspect, described herein is a compound of Formula (Ib), or a pharmaceutically acceptable salt, or solvate thereof:

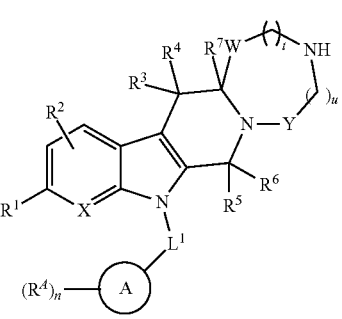

Formula (Ib)

wherein, $R^1$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, or $C_3$-$C_6$cycloalkyl;

$R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

$R^3$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

$R^4$ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

or $R^3$ and $R^4$ are taken together with the carbon atom to which they are attached to form —C(=O)—, —C(=NR$^8$)—, a substituted or unsubstituted cycloalkyl ring, or a substituted or unsubstituted heterocyclic ring containing 1 or 2 heteroatoms selected from —O—, —NR$^{11}$—, and —S—;

$R^5$ is H, F, $C_1$-$C_4$alkyl, —O—$C_1$-$C_4$alkyl, or $C_1$-$C_4$fluoroalkyl;

$R^6$ is H, F, $C_1$-$C_4$alkyl, —O—$C_1$-$C_4$alkyl, or $C_1$-$C_4$fluoroalkyl;

$R^7$ is H, F, $C_1$-$C_4$alkyl, —O—$C_1$-$C_4$alkyl, or $C_1$-$C_4$fluoroalkyl;

or $R^3$ and $R^7$ are taken together with the intervening atoms connecting the $R^3$ and $R^7$ groups to form a double bond;

or $R^3$ and $R^7$ are taken together with the intervening atoms connecting the $R^3$ and $R^7$ groups to form a cyclopropyl ring;

$R^8$ is independently selected from H, —OH, —OR$^9$, $C_1$-$C_6$alkyl, $C_1$-$C_6$fluoroalkyl;

$L^1$ is absent, substituted or unsubstituted $C_1$-$C_4$alkylene or substituted or unsubstituted $C_3$-$C_7$ cycloalkylene;

A is a substituted or unsubstituted aryl, substituted or unsubstituted monocyclic heteroaryl, substituted or unsubstituted bicyclic heteroaryl, substituted or unsubstituted monocyclic heterocycloalkyl, substituted or unsubstituted bicyclic heterocycloalkyl;

each $R^A$ substituent is independently H, halogen, OH, —OR$^9$, —CN, —NO$_2$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_8$cycloalkyl, substituted or unsubstituted $C_2$-$C_{10}$heterocycloalkyl, substituted or unsubstituted aryl, —$C_1$-$C_4$alkylene-substituted or unsubstituted aryl, substituted or unsubstituted heteroaryl, —$C_1$-$C_4$alkylene-substituted or unsubstituted heteroaryl, —C(=O)R$^9$, —S(=O)$_2$R$^9$, —S(=O)R$^9$, —SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$;

or two $R^A$ groups may be taken together with the intervening atoms connecting the two $R^A$ groups to form a substituted or unsubstituted ring containing 0-3 heteroatoms selected from —O—, —NR$^{11}$— and —S—;

n is 0, 1, 2, 3, or 4;

X is —CH=, —N=, or —CF=;

W is —C(=O)—, —C(=S)—, or —CH$_2$—;

Y is —C(=O)—, —C(=S)—, —CH$_2$— or —CF$_2$—;

each $R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, —$C_1$-$C_4$alkylene-substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl;

or two $R^{10}$ groups attached to the same N atom are taken together with the N atom to which they are attached to form a substituted or unsubstituted heterocycle;

$R^{11}$ is H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl, —S(=O)$_2$R$^9$, —C(=O)R$^9$, —CO$_2$R$^{10}$, or —C(=O)N(R$^{10}$)$_2$;

t is 0 or 1;

u is 0 or 1.

For any and all of the embodiments, substituents are selected from among a subset of the listed alternatives. For example, in some embodiments, t is 0 or 1. In other embodiments, t is 0. In some embodiments, u is 0 or 1. In some embodiments, u is 0.

In some embodiments, Z is —CH$_2$—, —O—, —NH—, >N—(C$_1$-C$_6$alkyl), or —Z'—; Z' is >N-L$^2$-B-L$^3$-Q; L$^2$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene; B is absent, —O—, —S—, —S(=O)—, —S(=O)$_2$—, —NR$^{11}$—, —C(=O)—, —C(=O)NR$^{10}$—, or —NR$^{10}$C(=O)—; L$^3$ is absent, substituted or unsubstituted $C_1$-$C_6$alkylene, substituted or unsubstituted $C_1$-$C_6$fluoroalkylene, or substituted or unsubstituted $C_3$-$C_6$cycloalkylene; Q is —CO$_2$H, —CO$_2$(C$_1$-C$_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, or carboxylic acid bioisostere.

In some embodiments, Z is —CH$_2$—, —O—, >N—(C$_1$-C$_6$alkyl), or —Z'—. In some embodiments, Z is —Z'—. In some embodiments, Z is —NH—.

In some embodiments, L$^2$ is $C_1$-$C_6$alkylene, or $C_3$-$C_6$cycloalkylene; B is absent; L$^3$ is absent.

In some embodiments, L$^2$ is $C_1$-$C_6$alkylene; B is absent; L$^3$ is absent or $C_3$-$C_6$cycloalkylene.

In some embodiments, L$^2$ is $C_1$-$C_6$alkylene; Q is —CO$_2$H, —CO$_2$(C$_1$-C$_6$alkyl), —B(OH)$_2$, —C(=O)NHSO$_2$R$^9$, —C(=O)N(R$^{10}$)$_2$, tetrazolyl, or carboxylic acid bioisostere.

In some embodiments, L$^2$ is absent, —CH$_2$—, —CH$_2$CH$_2$—, —CH$_2$CH$_2$CH$_2$—, or —CH$_2$CH$_2$CH$_2$CH$_2$—; Q is —CO$_2$H, or —CO$_2$(C$_1$-C$_6$alkyl).

In some embodiments, $R^3$ is H, F, Cl, Br, —CN, —OH, —CH$_3$, or —CF$_3$; $R^4$ is H, F, Cl, Br, —CN, —OH, —CH$_3$, or —CF$_3$; or $R^3$ and $R^4$ are taken together with the carbon atom to which they are attached to form —C(=O)— or cyclopropyl.

In some embodiments, $R^3$ is H or —CH$_3$. In some embodiments, $R^4$ is H or —CH$_3$.

In some embodiments, $R^3$ is H.

In some embodiments, $R^4$ is H.

In some embodiments, $R^5$ is H, F, Cl, —CH$_3$, or —CF$_3$.

In some embodiments, $R^6$ is H, F, Cl, —CH$_3$, or —CF$_3$.

In some embodiments, $R^5$ is H.

In some embodiments, $R^6$ is H.

In some embodiments, $R^3$ is H, and $R^4$ is H. In some embodiments, $R^5$ is H; and $R^6$ is H. In some embodiments, $R^3$ is H; $R^4$ is H, $R^5$ is H; and $R^6$ is H.

In some embodiments, $R^7$ is H, F, Cl, —CH$_3$, or —CF$_3$.

In some embodiments, $R^7$ is H.

In some embodiments, $L^1$ is absent or C$_{1-4}$alkylene.

In some embodiments, A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L^1$ is absent, —CH$_2$—, —CH$_2$CH$_2$—, —CH$_2$CH$_2$CH$_2$—, or —CH$_2$CH$_2$CH$_2$CH$_2$—.

In some embodiments, $L^1$ is —CH$_2$—.

In some embodiments, A is phenyl.

In some embodiments, A is pyridinyl, pyrimidinyl, pyrazinyl, pyridazinyl, or triazinyl.

In some embodiments, A is pyridinyl.

In some embodiments, A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $R^1$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, C$_1$-C$_4$fluoroalkoxy, or C$_1$-C$_4$hydroxyalkyl.

In some embodiments, $R^1$ is H, F, Cl, Br, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

In some embodiments, $R^1$ is H, F or Cl. In some embodiments, $R^1$ is H or Cl.

In some embodiments, $R^2$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy.

In some embodiments, $R^2$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$.

In some embodiments, $R^2$ is H, F, or Cl. In some embodiments, $R^2$ is H.

In some embodiments, t is 0.

In some embodiments, u is 0.

In some embodiments, t is 0; and u is 0.

In some embodiments, n is 0.

In some embodiments, X is —CH= or —N=. In some embodiments, X is —CH=. In some embodiments, X is —N=.

In some embodiments, W is —C(=O)— or —CH$_2$—. In some embodiments, W is —C(=O)—.

In some embodiments, W is —CH$_2$—. In some embodiments, W is —C(=S)—.

In some embodiments, Y is —C(=O)—. In some embodiments, Y is —C(=S)—. In some embodiments, Y is —CH$_2$—. In some embodiments, Y is —CF$_2$—.

In some embodiments, the compound has the following structure of Formula (II):

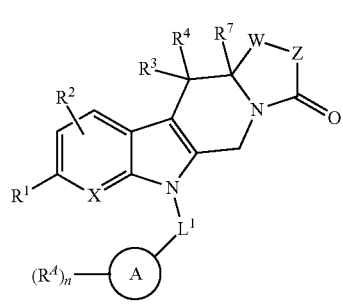

Formula (II)

or a pharmaceutically acceptable salt, or solvate thereof.

In some embodiments, the compound has the following structure of Formula (III) or Formula (IV):

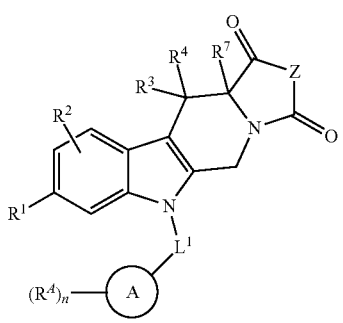

Formula (III)

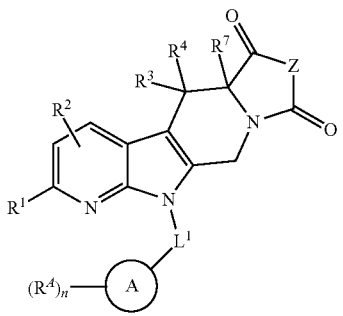

Formula (IV)

or a pharmaceutically acceptable salt, or solvate thereof.

In some embodiments, the compound has the following structure of Formula (V):

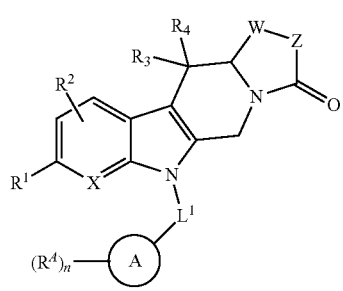

Formula (V)

or a pharmaceutically acceptable salt, or solvate thereof.

In some embodiments, compounds described herein include compounds having the following structure:

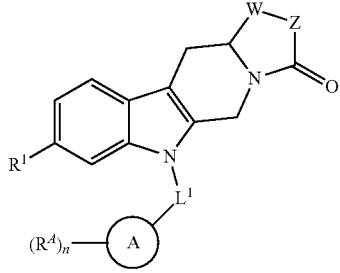

or a pharmaceutically acceptable salt, or solvate thereof.

In some embodiments, compounds described herein include compounds having the following structure:

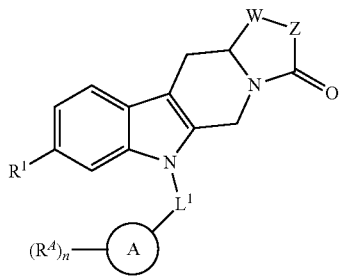

wherein,
$R^1$ is as described in Table 1;
$L^1$ is —CH$_2$—, —CH$_2$CH$_2$— or —CH$_2$CH$_2$CH$_2$—;

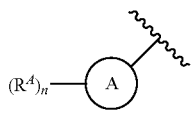

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl;
W is as described in Table 1;
Z is as described in Table 1;
or a pharmaceutically acceptable salt, or solvate thereof.

In some embodiments,

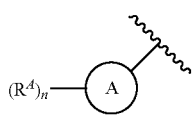

is as described in Table 1, and/or Table 2. In some embodiments, $L^1$ is as described in Table 1, and/or Table 2. In some embodiments,

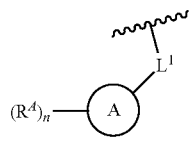

is as described in Table 1, and/or Table 2.
In some embodiments, $L^1$ is —CH$_2$—, —CH$_2$CH$_2$— or —CH$_2$CH$_2$CH$_2$—;

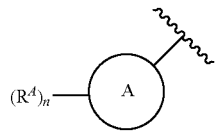

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl.

In some embodiments,

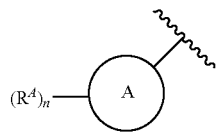

is phenyl; 4-fluorophenyl; 4-chlorophenyl; 2-methoxypyridin-5-yl; 2-ethoxypyridin-5-yl; 2-chloropyridin-5-yl.
In some embodiments, $L^1$ is —CH$_2$—, —CH$_2$CH$_2$— or —CH$_2$CH$_2$CH$_2$—;

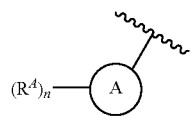

is phenyl; 4-fluorophenyl; 4-chlorophenyl; 2-methoxypyridin-5-yl; 2-ethoxypyridin-5-yl; 2-chloropyridin-5-yl.
In some embodiments, W is as described in Table 1.
In some embodiments, Z is as described in Table 1.
In some embodiments, $R^1$ is as described in Table 1.
In some embodiments, compounds described herein have the following structure:

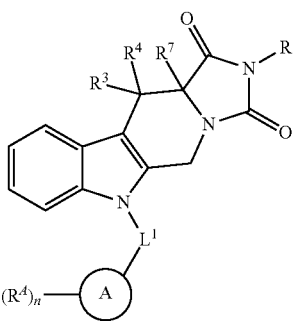

or a pharmaceutically acceptable salt, or solvate thereof.

In some embodiments, compounds described herein have the following structure:

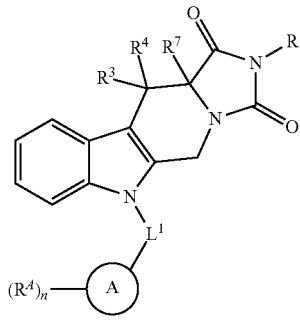

wherein,
L$^1$ is —CH$_2$—, —CH$_2$CH$_2$— or —CH$_2$CH$_2$CH$_2$—;

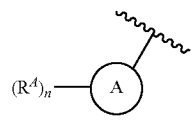

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl;

R$^3$, R$^4$, R$^7$, are as described in Table 2;

or a pharmaceutically acceptable salt, or solvate thereof.

In some embodiments, R is -L$^2$-B-L$^3$-Q as described herein. In some embodiments, R is as described in Table 2.

In some embodiments, compounds described herein have the following structure:

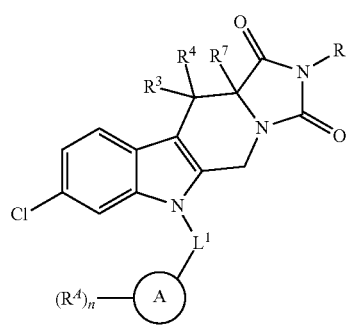

or a pharmaceutically acceptable salt, or solvate thereof.

In some embodiments, compounds described herein have the following structure:

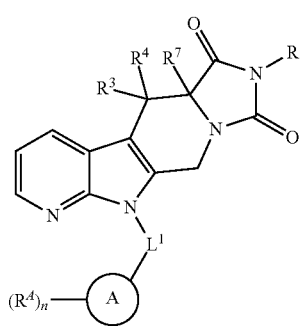

wherein,
L$^1$ is —CH$_2$—, —CH$_2$CH$_2$— or —CH$_2$CH$_2$CH$_2$—;

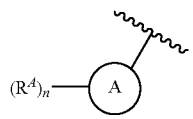

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl;

R$^3$, R$^4$, R$^7$, are as described in Table 2;
or a pharmaceutically acceptable salt, or solvate thereof.

In some embodiments, R is -L$^2$-B-L$^3$-Q as described herein. In some embodiments, R is as described in Table 2.

In some embodiments, compounds described herein have the following structure:

or a pharmaceutically acceptable salt, or solvate thereof.

In some embodiments, compounds described herein have the following structure:

wherein, $L^1$ is —CH$_2$—, —CH$_2$CH$_2$— or —CH$_2$CH$_2$CH$_2$—;

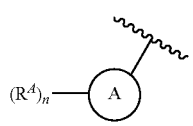

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl;

$R^3$, $R^4$, $R^7$, are as described in Table 2;

or a pharmaceutically acceptable salt, or solvate thereof.

In some embodiments, R is -L$^2$-B-L$^3$-Q as described herein. In some embodiments, R is as described in Table 2.

In some embodiments, compounds described herein have the following structure:

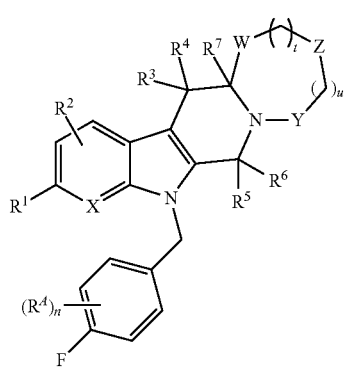

wherein n is 0, 1, 2, or 3;

or a pharmaceutically acceptable salt, or solvate thereof.

In some embodiments, compounds described herein have the following structure:

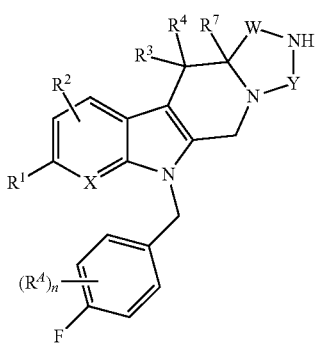

or a pharmaceutically acceptable salt, or solvate thereof.

In some embodiments, compounds described herein have the following structure:

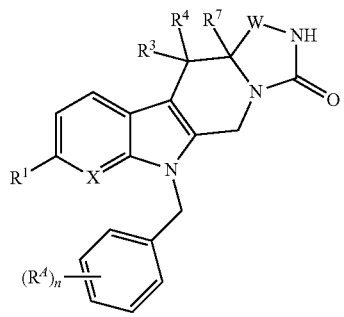

wherein,
$R^1$ is H, halogen, —CN, C$_1$-C$_4$alkyl, —CF$_3$, or C$_1$-C$_4$deuteroalkyl;
$R^3$ is H, F, C$_1$-C$_4$alkyl, or C$_1$-C$_4$fluoroalkyl;
$R^4$ is H, F, C$_1$-C$_4$alkyl, or C$_1$-C$_4$fluoroalkyl;
$R^7$ is H, or F;
each $R^A$ substituent is independently H, halogen, OH, —O—C$_1$-C$_4$alkyl, —CN, C$_1$-C$_6$alkyl, C$_1$-C$_6$fluoroalkyl, or C$_1$-C$_6$deuteroalkyl;
n is 0, 1, 2, or 3;
$L^1$ is substituted or unsubstituted C$_1$-C$_4$alkylene;
X is —CH=, —N=, or —CF=; and
W is —C(=O)—, —C(=S)—, or —CH$_2$—.
In some embodiments, $L^1$ is —CH$_2$—.
In some embodiments, $R^1$ is H, F, Cl, —CN, —CH$_3$, —CF$_3$, —CD$_3$, —OCH$_3$, or —OCF$_3$.
In some embodiments, $R^1$ is H or Cl.
In some embodiments, $R^3$ is H or —CH$_3$.
In some embodiments, $R^4$ is H or —CH$_3$.
In some embodiments, n is 1 and $R^A$ is 4-F and $L^1$ is —CH$_2$—.
In some embodiments, X is —CH= or —N=.
In some embodiments, W is —C(=O)—, or —CH$_2$—.
In some embodiments, $R^1$ is H or Cl; $R^3$ is H or —CH$_3$; $R^4$ is H or —CH$_3$; $R^7$ is H, or F; n is 1; $R^A$ is 4-F; $L^1$ is —CH$_2$—; X is —CH= or —N=; W is —C(=O)—, or —CH$_2$—.

In some embodiments, compounds described herein have the structure of Formula (VI):

Formula (VI)

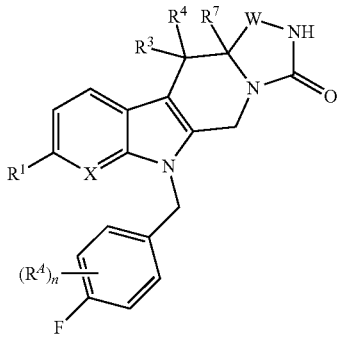

or a pharmaceutically acceptable salt, or solvate thereof.

In one aspect, described herein is a compound of Formula (VI), or a pharmaceutically acceptable salt, or solvate thereof:

Formula (VI)

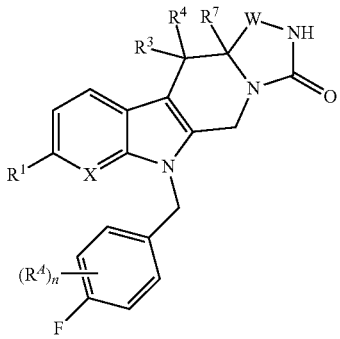

wherein,
R¹ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl;

R³ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

R⁴ is H, F, Cl, Br, CN, —OH, $C_1$-$C_4$alkyl, —O—$C_1$-$C_4$alkyl, —S—$C_1$-$C_4$alkyl, —S(=O)—$C_1$-$C_4$alkyl, —S(=O)$_2$—$C_1$-$C_4$alkyl, or $C_1$-$C_4$fluoroalkyl;

R⁷ is H, or F;

each $R^A$ substituent is independently H, halogen, OH, —O—$C_1$-$C_4$alkyl, —CN, $C_1$-$C_6$alkyl, $C_1$-$C_6$fluoroalkyl, or $C_1$-$C_6$deuteroalkyl;

n is 0, or 1;

X is —CH=, —N=, or —CF=; and

W is —C(=O)—, —C(=S)—, or —CH$_2$—.

In one aspect, described herein is a compound of Formula (VI), or a pharmaceutically acceptable salt, or solvate thereof:

Formula (VI)

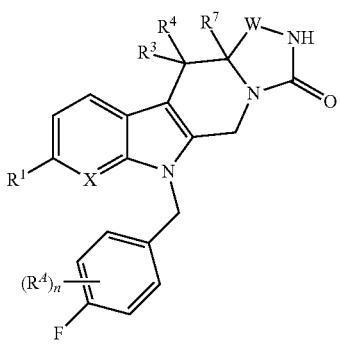

wherein,
R¹ is H, halogen, —CN, —OH, $C_1$-$C_4$alkyl, $C_1$-$C_4$fluoroalkyl, or $C_1$-$C_4$deuteroalkyl;

R³ is H, F, $C_1$-$C_4$alkyl, or $C_1$-$C_4$fluoroalkyl;

R⁴ is H, F, $C_1$-$C_4$alkyl, or $C_1$-$C_4$fluoroalkyl;

R⁷ is H, or F;

each $R^A$ substituent is independently H, halogen, OH, —O—$C_1$-$C_4$alkyl, —CN, $C_1$-$C_6$alkyl, $C_1$-$C_6$fluoroalkyl, or $C_1$-$C_6$deuteroalkyl;

n is 0, or 1;

X is —CH=, —N=, or —CF=; and

W is —C(=O)—, —C(=S)—, or —CH$_2$—.

In some embodiments, R¹ is H, F, Cl, Br, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH. In some embodiments, R¹ is H or Cl. In some embodiments, R¹ is H. In some embodiments, R¹ is Cl.

In some embodiments, R³ is H or —CH$_3$. In some embodiments, R³ is H. In some embodiments, R³ is —CH$_3$.

In some embodiments, R⁴ is H or —CH$_3$. In some embodiments, R⁴ is H. In some embodiments, R⁴ is —CH$_3$.

In some embodiments, n is 0.

In some embodiments, X is —CH= or —N=. In some embodiments, X is —CH=. In some embodiments, X is —N=. In some embodiments, X is —CF=.

In some embodiments, W is —C(=O)—, or —CH$_2$—. In some embodiments, W is —C(=O)—. In some embodiments, W is —CH$_2$—.

In some embodiments, compounds of Formula (VI) have the following structure:

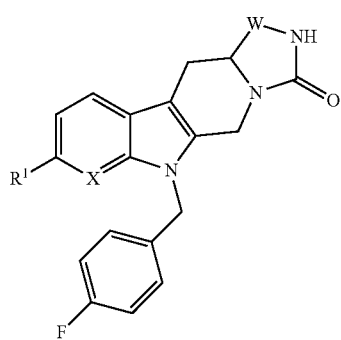

or a pharmaceutically acceptable salt, or solvate thereof.

In some embodiments, compounds described herein have the following structure:

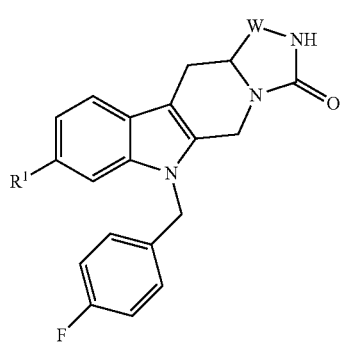

or a pharmaceutically acceptable salt, or solvate thereof.

In some embodiments, compounds described herein have the following structure:

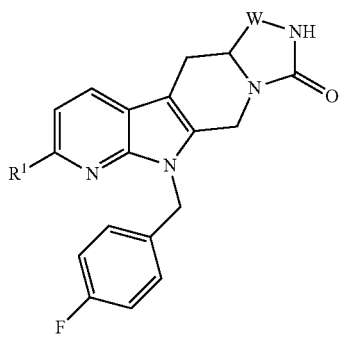

or a pharmaceutically acceptable salt, or solvate thereof.

In some embodiments, compounds described herein have the following structure:

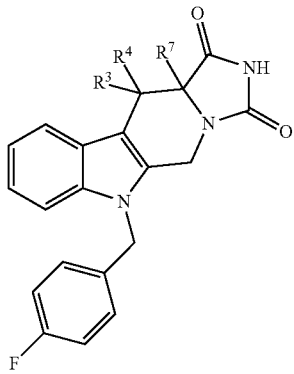

or a pharmaceutically acceptable salt, or solvate thereof.

In some embodiments, compounds described herein have the following structure:

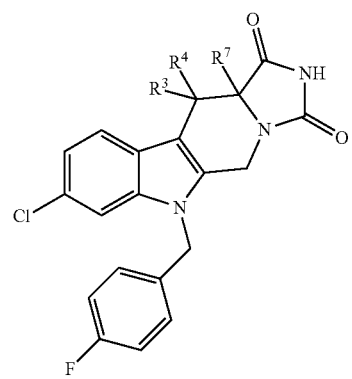

or a pharmaceutically acceptable salt, or solvate thereof.

In some embodiments, compounds described herein have the following structure:

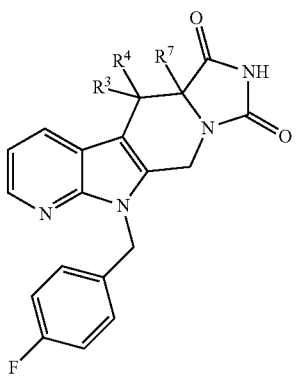

or a pharmaceutically acceptable salt, or solvate thereof.

Any combination of the groups described above for the various variables is contemplated herein. Throughout the specification, groups and substituents thereof are chosen by one skilled in the field to provide stable moieties and compounds.

Exemplary compounds include the following compounds of Table 1, Table 2, and Table 3:

TABLE 1

| Cmpd no. | $R^1$ | | $L^1$ | | W | Z |
|---|---|---|---|---|---|---|
| 1-1 | Rac | H | —CH$_2$— | 4-fluorophenyl | —C(=O)— | >NCH$_2$CH$_2$CH$_2$CO$_2$H |
| 1-2 | S-Ent | H | —CH$_2$— | 4-fluorophenyl | —C(=O)— | >NCH$_2$CH$_2$CH$_2$CO$_2$H |

TABLE 1-continued

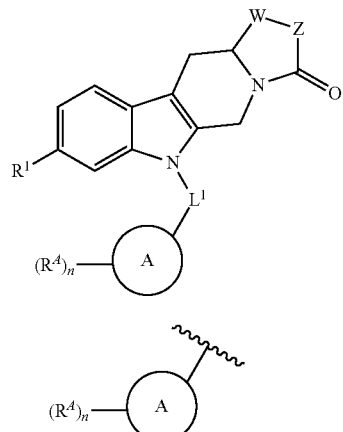

| Cmpd no. | | R¹ | L¹ | | W | Z |
|---|---|---|---|---|---|---|
| 1-3 | R-Ent | H | —CH₂— | 4-fluorophenyl | —C(=O)— | >NCH₂CH₂CH₂CO₂H |
| 1-4 | Rac | H | —CH₂— | 4-fluorophenyl | —C(=O)— | >NCH₂CH₂CO₂H |
| 1-5 | S-Ent | H | —CH₂— | 4-fluorophenyl | —C(=O)— | >NCH₂CH₂CO₂H |
| 1-6 | R-Ent | H | —CH₂— | 4-fluorophenyl | —C(=O)— | >NCH₂CH₂CO₂H |
| 1-7 | Rac | H | —CH₂CH₂CH₂— | phenyl | —C(=O)— | >NCH₂CH₂CH₂CO₂H |
| 1-8 | | H | —CH₂— | 4-fluorophenyl | —CH₂— | O |
| 1-9 | S-Ent | H | —CH₂— | 4-fluorophenyl | —CH₂— | O |
| 1-10 | R-Ent | H | —CH₂— | 4-fluorophenyl | —CH₂— | O |
| 1-11 | S-Ent | H | —CH₂— | 2-Methoxypyridin-5-yl | —C(=O)— | >NCH₂CH₂CH₂CO₂H |
| 1-12 | S-Ent | H | —CH₂— | 2-methoxypyridin-5-yl | —C(=O)— | >NCH₂CH₂CO₂H |
| 1-13 | Rac | H | —CH₂— | 4-fluorophenyl | —CH₂— | >NH |
| 1-14 | Rac | H | —CH₂— | 4-fluorophenyl | —C(=O)— | >NMe |
| 1-15 | Rac | H | —CH₂— | 4-fluorophenyl | —C(=O)— | >NH |
| 1-16 | Rac | H | —CH₂— | 4-fluorophenyl | —C(=O)— | —NHCH₂— |
| 1-17 | | H | —CH₂— | 2-methoxypyridin-5-yl | —C(=O)— | >NCH₂C(CH₃)₂CO₂H |
| 1-18 | S-Ent | H | —CH₂— | 2-methoxypyridin-5-yl | —C(=O)— | >NCH₂C(—CH₂CH₂—)CO₂H |
| 1-19 | | H | —CH₂— | 4-fluorophenyl | —C(=O)— | >NCH₂CO₂H |
| 1-20 | Rac | H | —CH₂— | 4-fluorophenyl | —CH₂— | >NCH₂CO₂H |
| 1-21 | | H | —CH₂— | 4-fluorophenyl | —CH₂— | >NCH₂CH₂CO₂H |
| 1-22 | | H | —CH₂— | 4-fluorophenyl | —CH₂— | >NCH₂CH₂CH₂CO₂H |
| 1-23 | Rac | H | —CH₂— | 4-fluorophenyl | —C(=O)— | —N(CH₂CO₂H)CH₂— |
| 1-24 | | H | —CH₂— | 4-fluorophenyl | —C(=O)— | —N(CH₂CH₂CO₂H)CH₂— |
| 1-25 | | H | —CH₂— | 4-fluorophenyl | —C(=O)— | —NCH₂CH₂CO₂H)CH₂— |
| 1-26 | | Cl | —CH₂— | 4-fluorophenyl | —CH₂— | O |
| 1-27 | | Cl | —CH₂— | 4-fluorophenyl | —C(=O)— | >NCH₂CH₂CH₂CO₂H |
| 1-28 | | Cl | —CH₂— | 4-fluorophenyl | —C(=O)— | >NCH₂CH₂CO₂H |
| 1-29 | | Cl | —CH₂— | 4-fluorophenyl | —C(=O)— | >NCH₂CO₂H |
| 1-30 | | Cl | —CH₂— | 4-fluorophenyl | —C(=O)— | >NCH₂C(CH₃)₂CO₂H |
| 1-31 | | Cl | —CH₂— | 4-fluorophenyl | —C(=O)— | >NCH₂CH₂C(CH₃)₂CO₂H |
| 1-32 | | H | —CH₂— | 4-fluorophenyl | —C(=O)— | >NCH₂CH(CH₃)CO₂H |
| 1-33 | | H | —CH₂— | 4-fluorophenyl | —C(=O)— | >NCH₂C(CH₃)₂CO₂H |
| 1-34 | S-Ent | H | —CH₂— | 4-fluorophenyl | —C(=O)— | >NCH₂C(—CH₂CH₂—)CO₂H |
| 1-35 | | H | —CH₂— | 4-fluorophenyl | —C(=O)— | >NCH₂CH(Et)CO₂H |
| 1-36 | | H | —CH₂— | 4-fluorophenyl | —C(=O)— | >NCH₂C(Et)₂CO₂H |
| 1-37 | | H | —CH₂— | 4-fluorophenyl | —C(=O)— | >NCH₂C(—(CH₂)₃—)CO₂H |
| 1-38 | | H | —CH₂— | 4-fluorophenyl | —C(=O)— | >NCH₂CH₂CH(CH₃)CO₂H |
| 1-39 | | H | —CH₂— | 4-fluorophenyl | —C(=O)— | >NCH₂CH₂C(CH₃)₂CO₂H |
| 1-40 | | H | —CH₂— | 4-fluorophenyl | —C(=O)— | >NCH₂CH₂C(—CH₂CH₂—)CO₂H |
| 1-41 | | H | —CH₂— | 4-fluorophenyl | —C(=O)— | >NCH₂CH(CH₃)CH₂CO₂H |
| 1-42 | | H | —CH₂— | 4-fluorophenyl | —C(=O)— | >NCH₂C(CH₃)₂CH₂CO₂H |
| 1-43 | | H | —CH₂— | 4-fluorophenyl | —C(=O)— | >NCH₂C(—CH₂CH₂—)CH₂CO₂H |
| 1-44 | | H | —CH₂— | 4-fluorophenyl | —C(=O)— | >NCH₂C(—(CH₂)₃—)CH₂CO₂H |
| 1-45 | | Cl | —CH₂— | 4-fluorophenyl | —C(=O)— | >NCH₂CH(CH₃)CO₂H |
| 1-46 | | Cl | —CH₂— | 4-fluorophenyl | —C(=O)— | >NCH₂C(CH₃)₂CO₂H |
| 1-47 | | Cl | —CH₂— | 4-fluorophenyl | —C(=O)— | >NCH₂C(—CH₂CH₂—)CO₂H |
| 1-48 | | Cl | —CH₂— | 4-fluorophenyl | —C(=O)— | >NCH₂CH(Et)CO₂H |
| 1-49 | | Cl | —CH₂— | 4-fluorophenyl | —C(=O)— | >NCH₂C(Et)₂CO₂H |
| 1-50 | | Cl | —CH₂— | 4-fluorophenyl | —C(=O)— | >NCH₂C(—(CH₂)₃—)CO₂H |
| 1-51 | | Cl | —CH₂— | 4-fluorophenyl | —C(=O)— | >NCH₂CH₂CH(CH₃)CO₂H |
| 1-52 | | Cl | —CH₂— | 4-fluorophenyl | —C(=O)— | >NCH₂CH₂C(CH₃)₂CO₂H |
| 1-53 | | Cl | —CH₂— | 4-fluorophenyl | —C(=O)— | >NCH₂CH₂C(—CH₂CH₂—)CO₂H |
| 1-54 | | Cl | —CH₂— | 4-fluorophenyl | —C(=O)— | >NCH₂CH(CH₃)CH₂CO₂H |
| 1-55 | | Cl | —CH₂— | 4-fluorophenyl | —C(=O)— | >NCH₂C(CH₃)₂CH₂CO₂H |
| 1-56 | | Cl | —CH₂— | 4-fluorophenyl | —C(=O)— | >NCH₂C(—CH₂CH₂—)CH₂CO₂H |
| 1-57 | | Cl | —CH₂— | 4-fluorophenyl | —C(=O)— | >NCH₂C(—(CH₂)₃—CH₂CO₂H) |
| 1-58 | | H | —CH₂— | 4-chlorophenyl | —C(=O)— | >NCH₂CH(CH₃)CO₂H |
| 1-59 | | H | —CH₂— | 4-chlorophenyl | —C(=O)— | >NCH₂C(CH₃)₂CO₂H |
| 1-60 | | H | —CH₂— | 4-chlorophenyl | —C(=O)— | >NCH₂C(—CH₂CH₂—)CO₂H |

TABLE 1-continued

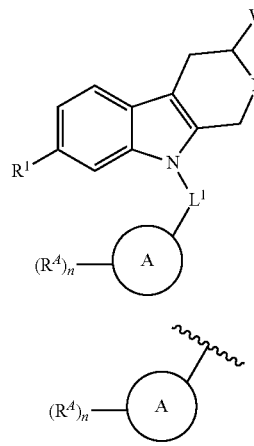

| Cmpd no. | R¹ | L¹ | (Rᴬ)ₙ—A | W | Z |
|---|---|---|---|---|---|
| 1-61 | | H | —CH₂— | 4-chlorophenyl | —C(=O)— | >NCH₂CH(Et)CO₂H |
| 1-62 | | H | —CH₂— | 4-chlorophenyl | —C(=O)— | >NCH₂C(Et)₂CO₂H |
| 1-63 | | H | —CH₂— | 4-chlorophenyl | —C(=O)— | >NCH₂C(—(CH₂)₃—)CO₂H |
| 1-64 | | H | —CH₂— | 4-chlorophenyl | —C(=O)— | >NCH₂CH₂CH(CH₃)CO₂H |
| 1-65 | | H | —CH₂— | 4-chlorophenyl | —C(=O)— | >NCH₂CH₂C(CH₃)₂CO₂H |
| 1-66 | | H | —CH₂— | 4-chlorophenyl | —C(=O)— | >NCH₂CH₂C(—CH₂CH₂—)CO₂H |
| 1-67 | | H | —CH₂— | 4-chlorophenyl | —C(=O)— | >NCH₂CH(CH₃)CH₂CO₂H |
| 1-68 | | H | —CH₂— | 4-chlorophenyl | —C(=O)— | >NCH₂C(CH₃)₂CH₂CO₂H |
| 1-69 | | H | —CH₂— | 4-chlorophenyl | —C(=O)— | >NCH₂C(—CH₂CH₂—)CH₂CO₂H |
| 1-70 | | H | —CH₂— | 4-chlorophenyl | —C(=O)— | >NCH₂C(—(CH₂)₃—)CH₂CO₂H |
| 1-71 | | Cl | —CH₂— | 4-chlorophenyl | —C(=O)— | >NCH₂CH(CH₃)CO₂H |
| 1-72 | | Cl | —CH₂— | 4-chlorophenyl | —C(=O)— | >NCH₂C(CH₃)₂CO₂H |
| 1-73 | | Cl | —CH₂— | 4-chlorophenyl | —C(=O)— | >NCH₂C(—CH₂CH₂—)CO₂H |
| 1-74 | | Cl | —CH₂— | 4-chlorophenyl | —C(=O)— | >NCH₂CH(Et)CO₂H |
| 1-75 | | Cl | —CH₂— | 4-chlorophenyl | —C(=O)— | >NCH₂C(Et)₂CO₂H |
| 1-76 | | Cl | —CH₂— | 4-chlorophenyl | —C(=O)— | >NCH₂C(—(CH₂)₃—)CO₂H |
| 1-77 | | Cl | —CH₂— | 4-chlorophenyl | —C(=O)— | >NCH₂CH₂CH(CH₃)CO₂H |
| 1-78 | | Cl | —CH₂— | 4-chlorophenyl | —C(=O)— | >NCH₂CH₂C(CH₃)₂CO₂H |
| 1-79 | | Cl | —CH₂— | 4-chlorophenyl | —C(=O)— | >NCH₂CH₂C(—CH₂CH₂—)CO₂H |
| 1-80 | | Cl | —CH₂— | 4-chlorophenyl | —C(=O)— | >NCH₂CH(CH₃)CH₂CO₂H |
| 1-81 | | Cl | —CH₂— | 4-chlorophenyl | —C(=O)— | >NCH₂C(CH₃)₂CH₂CO₂H |
| 1-82 | | Cl | —CH₂— | 4-chlorophenyl | —C(=O)— | >NCH₂C(—CH₂CH₂—)CH₂CO₂H |
| 1-83 | | Cl | —CH₂— | 4-chlorophenyl | —C(=O)— | >NCH₂C(—(CH₂)₃—)CH₂CO₂H |
| 1-84 | S-Ent | H | —CH₂— | 2-chloropyridin-5-yl | —C(=O)— | >NCH₂CO₂H |
| 1-85 | | H | —CH₂— | 2-chloropyridin-5-yl | —C(=O)— | >NCH₂CH₂CO₂H |
| 1-86 | | H | —CH₂— | 2-chloropyridin-5-yl | —C(=O)— | >NCH₂CH(CH₃)CO₂H |
| 1-87 | | H | —CH₂— | 2-chloropyridin-5-yl | —C(=O)— | >NCH₂C(CH₃)₂CO₂H |
| 1-88 | | H | —CH₂— | 2-chloropyridin-5-yl | —C(=O)— | >NCH₂C(—CH₂CH₂—)CO₂H |
| 1-89 | | H | —CH₂— | 2-chloropyridin-5-yl | —C(=O)— | >NCH₂CH₂C(CH₃)₂CO₂H |
| 1-90 | | H | —CH₂— | 2-chloropyridin-5-yl | —C(=O)— | >NCH₂CH₂C(—CH₂CH₂—)CO₂H |
| 1-91 | | H | —CH₂— | 2-chloropyridin-5-yl | —C(=O)— | >NCH₂C(CH₃)₂CH₂CO₂H |
| 1-92 | | H | —CH₂— | 2-chloropyridin-5-yl | —C(=O)— | >NCH₂C(—CH₂CH₂—)CH₂CO₂H |
| 1-93 | | Cl | —CH₂— | 2-chloropyridin-5-yl | —C(=O)— | >NCH₂CO₂H |
| 1-94 | | Cl | —CH₂— | 2-chloropyridin-5-yl | —C(=O)— | >NCH₂CH₂CO₂H |
| 1-95 | | Cl | —CH₂— | 2-chloropyridin-5-yl | —C(=O)— | >NCH₂CH(CH₃)CO₂H |
| 1-96 | | Cl | —CH₂— | 2-chloropyridin-5-yl | —C(=O)— | >NCH₂C(CH₃)₂CO₂H |
| 1-97 | | Cl | —CH₂— | 2-chloropyridin-5-yl | —C(=O)— | >NCH₂C(—CH₂CH₂—)CO₂H |
| 1-98 | | Cl | —CH₂— | 2-chloropyridin-5-yl | —C(=O)— | >NCH₂CH₂C(CH₃)₂CO₂H |
| 1-99 | | Cl | —CH₂— | 2-chloropyridin-5-yl | —C(=O)— | >NCH₂CH₂C(—CH₂CH₂—)CO₂H |
| 1-100 | | Cl | —CH₂— | 2-chloropyridin-5-yl | —C(=O)— | >NCH₂C(CH₃)₂CH₂CO₂H |
| 1-101 | | Cl | —CH₂— | 2-chloropyridin-5-yl | —C(=O)— | >NCH₂C(—CH₂CH₂—)CH₂CO₂H |
| 1-102 | | H | —CH₂— | 2-trifluoromethyl thiazol-5-yl | —C(=O)— | >NCH₂CO₂H |
| 1-103 | | H | —CH₂— | 2-trifluoromethyl thiazol-5-yl | —C(=O)— | >NCH₂CH₂CO₂H |
| 1-104 | | H | —CH₂— | 2-trifluoromethyl thiazol-5-yl | —C(=O)— | >NCH₂CH(CH₃)CO₂H |
| 1-105 | | H | —CH₂— | 2-trifluoromethyl thiazol-5-yl | —C(=O)— | >NCH₂C(CH₃)₂CO₂H |
| 1-106 | | H | —CH₂— | 2-trifluoromethyl thiazol-5-yl | —C(=O)— | >NCH₂C(—CH₂CH₂—)CO₂H |
| 1-107 | | H | —CH₂— | 2-trifluoromethyl thiazol-5-yl | —C(=O)— | >NCH₂CH₂C(CH₃)₂CO₂H |
| 1-108 | | H | —CH₂— | 2-trifluoromethyl thiazol-5-yl | —C(=O)— | >NCH₂CH₂C(—CH₂CH₂—)CO₂H |
| 1-109 | | H | —CH₂— | 2-trifluoromethyl thiazol-5-yl | —C(=O)— | >NCH₂C(CH₃)₂CH₂CO₂H |

TABLE 1-continued

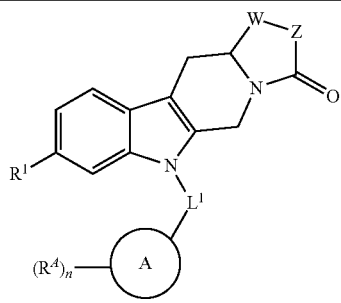

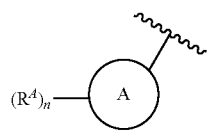

| Cmpd no. | | R¹ | L¹ | | W | Z |
|---|---|---|---|---|---|---|
| 1-110 | | H | —CH$_2$— | 2-trifluoromethyl thiazol-5-yl | —C(=O)— | >NCH$_2$C(—CH$_2$CH$_2$—)CH$_2$CO$_2$H |
| 1-111 | | Cl | —CH$_2$— | 2-trifluoromethyl thiazol-5-yl | —C(=O)— | >NCH$_2$CH$_2$CO$_2$H |
| 1-112 | | Cl | —CH$_2$— | 2-trifluoromethyl thiazol-5-yl | —C(=O)— | >NCH$_2$CH$_2$CH$_2$CO$_2$H |
| 1-113 | | Cl | —CH$_2$— | 2-trifluoromethyl thiazol-5-yl | —C(=O)— | >NCH$_2$CH(CH$_3$)CO$_2$H |
| 1-114 | | Cl | —CH$_2$— | 2-trifluoromethyl thiazol-5-yl | —C(=O)— | >NCH$_2$C(CH$_3$)$_2$CO$_2$H |
| 1-115 | | Cl | —CH$_2$— | 2-trifluoromethyl thiazol-5-yl | —C(=O)— | >NCH$_2$C(—CH$_2$CH$_2$—)CO$_2$H |
| 1-116 | | Cl | —CH$_2$— | 2-trifluoromethyl thiazol-5-yl | —C(=O)— | >NCH$_2$CH$_2$C(CH$_3$)$_2$CO$_2$H |
| 1-117 | | Cl | —CH$_2$— | 2-trifluoromethyl thiazol-5-yl | —C(=O)— | >NCH$_2$CH$_2$C(—CH$_2$CH$_2$—)CO$_2$H |
| 1-118 | | Cl | —CH$_2$— | 2-trifluoromethyl thiazol-5-yl | —C(=O)— | >NCH$_2$C(CH$_3$)$_2$CH$_2$CO$_2$H |
| 1-119 | | Cl | —CH$_2$— | 2-trifluoromethyl thiazol-5-yl | —C(=O)— | >NCH$_2$C(—CH$_2$CH$_2$—)CH$_2$CO$_2$H |
| 1-120 | Rac | H | —CH$_2$— | 4-fluorophenyl | —C(=O)— | >NCH$_2$CN |
| 1-121 | S-Ent | H | —CH$_2$— | 4-fluorophenyl | —C(=O)— | >NCH$_2$CH$_2$OH |
| 1-122 | S-Ent | H | —CH$_2$— | 4-fluorophenyl | —C(=O)— | >NCH$_2$CH$_2$CONH$_2$ |
| 1-123 | Rac | H | —CH$_2$— | 4-fluorophenyl | —C(=O)— | >NCH$_2$CH$_2$CONHCH$_2$Ph |
| 1-124 | Rac | H | —CH$_2$— | 4-fluorophenyl | —C(=O)— | >NCH$_2$CH$_2$CO-[3-hydroxy-3-trifluoromethyl pyrrolidin-1-yl) |
| 1-125 | Rac | H | —CH$_2$— | 4-fluorophenyl | —C(=O)— | >NCH$_2$CH$_2$CO-(3-cyanoazetidin-1-yl) |
| 1-126 | Rac | H | —CH$_2$— | 4-fluorophenyl | —C(=O)— | >NCH$_2$CH$_2$CONHCH$_2$ (4-(tetrazol-5-yl)phenyl) |
| 1-127 | Rac | H | —CH$_2$— | 4-fluorophenyl | —C(=O)— | >NCH$_2$CH$_2$CONHCH$_2$CH$_2$-(Pyridin-4-yl) |
| 1-128 | Rac | H | —CH$_2$— | 4-fluorophenyl | —C(=O)— | >NCH$_2$CH$_2$CONHCH$_2$-(pyrazin-2-yl) |
| 1-129 | Rac | H | —CH$_2$— | 4-fluorophenyl | —C(=O)— | >NCH$_3$ |
| 1-130 | S-Ent | H | —CH$_2$— | 4-fluorophenyl | —C(=O)— | >NH |
| 1-131 | Rac | H | —CH$_2$— | 4-methoxyphenyl | —C(=O)— | >NCH$_2$CH$_2$CO$_2$H |
| 1-132 | S-Ent | H | —CH$_2$— | 2,4-dichlorophenyl | —C(=O)— | >NCH$_2$CH$_2$CO$_2$H |
| 1-133 | S-Ent | H | —CH$_2$— | 4-chloro-2-fluorophenyl | —C(=O)— | >NCH$_2$CH$_2$CO$_2$H |
| 1-134 | S-Ent | H | —CH$_2$— | 2,4-difluorophenyl | —C(=O)— | >NCH$_2$CH$_2$CO$_2$H |
| 1-135 | S-Ent | H | —CH$_2$— | 2-fluoropyridin-5-yl | —C(=O)— | >NCH$_2$CH$_2$CO$_2$H |
| 1-136 | Rac | H | —CH$_2$— | 2-fluoropyridin-5-yl | —CH$_2$— | >NCH$_2$CH$_2$CO$_2$H |
| 1-137 | S-Ent | H | —CH$_2$— | 4-fluorophenyl | —C(=O)— | >NCH$_2$CH$_2$CONHCH$_2$CH$_2$SO$_3$H |
| 1-138 | S-Ent | H | —CH$_2$— | 4-fluorophenyl | —C(=O)— | >NCH$_2$CH$_2$CO$_2$-acylglucuronide |
| 1-139 | Rac | H | —CH$_2$— | 4-fluorophenyl | —C(=O)— | >NCH$_2$CN |
| 1-140 | Rac | H | —CH$_2$— | 4-fluorophenyl | —C(=O)— | >NCH$_2$CN$_4$H |
| 1-141 | S-Ent | H | —CH$_2$— | 4-fluorophenyl | —C(=O)— | >NCH$_2$CH$_2$CO$_2$H |
| 1-142 | S-Ent | H | —CH$_2$— | 4-fluorophenyl | —C(=O)— | >NCH$_2$CH$_2$CONHSO$_2$CH$_3$ |
| 1-143 | S-Ent | H | —CH$_2$— | 4-fluorophenyl | —C(=O)— | >NCH$_2$CH$_2$CONHSO$_2$Ph |

Rac = racemic; S-Ent = S-enantiomer; R-Ent = enantiomer

In some embodiments, the

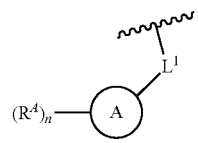

group of any on the compounds described in Table 1 is replaced with 4-chlorobenzyl; 3-chlorobenzyl; 3-fluorobenzyl; 3,5-difluorobenzyl; 2,4-difluorobenzyl; 3,5-dichlorobenzyl; phenylprop-3-yl; thien-2-ylmethyl; or 5-chlorothien-2-ylmethyl.

TABLE 2

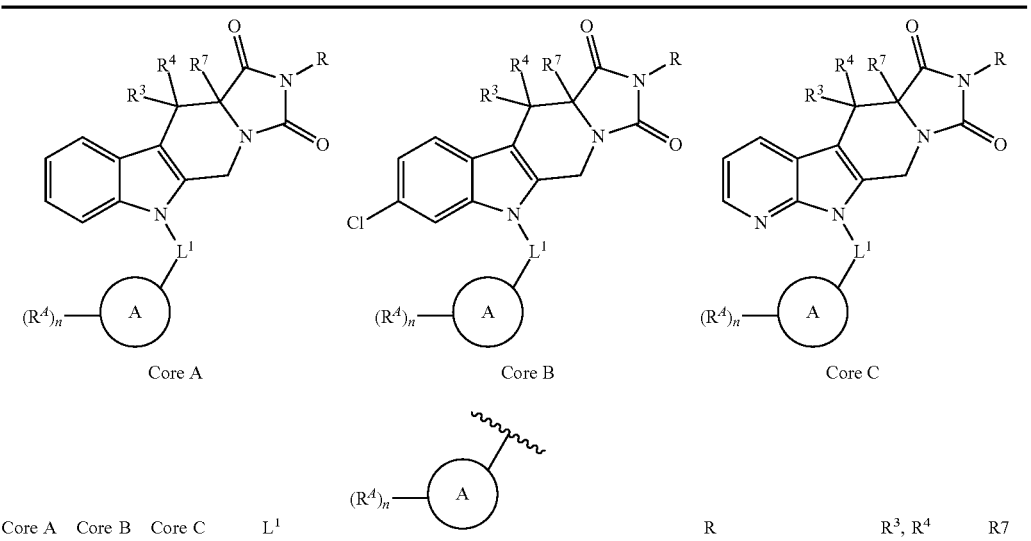

| Core A | Core B | Core C | L¹ | (R⁴)ₙ—A | R | R³, R⁴ | R7 |
|---|---|---|---|---|---|---|---|
| A1 | B1 | C1 | —CH₂— | 4-fluorophenyl | —CH₂CO₂H | F, F | H |
| A2 | B2 | C2 | —CH₂— | 4-fluorophenyl | —CH₂CH₂CO₂H | F, F | H |
| A3 | B3 | C3 | —CH₂— | 4-fluorophenyl | —CH₂CH₂CH₂CO₂H | F, F | H |
| A4 | B4 | C4 | —CH₂— | 4-fluorophenyl | —CH₂C(CH₃)₂CO₂H | F, F | H |
| A5 | B5 | C5 | —CH₂— | 4-fluorophenyl | —CH₂C(—CH₂CH₂—)CO₂H | F, F | H |
| A6 | B6 | C6 | —CH₂— | 4-fluorophenyl | —CH₂CH₂C(CH₃)₂CO₂H | F, F | H |
| A7 | B7 | C7 | —CH₂— | 4-fluorophenyl | —CH₂CH₂C(—CH₂CH₂—)CO₂H | F, F | H |
| A8 | B8 | C8 | —CH₂— | 4-fluorophenyl | —CH₂C(CH₃)₂CH₂CO₂H | F, F | H |
| A9 | B9 | C9 | —CH₂— | 4-fluorophenyl | —CH₂C(—CH₂CH₂—)CH₂CO₂H | F, F | H |
| A10 | B10 | C10 | —CH₂— | 4-fluorophenyl | —CH₂CO₂H | CH₃, CH₃ | H |
| A11 | B11 | C11 | —CH₂— | 4-fluorophenyl | —CH₂CH₂CO₂H | CH₃, CH₃ | H |
| A12 | B12 | C12 | —CH₂— | 4-fluorophenyl | —CH₂CH₂CH₂CO₂H | CH₃, CH₃ | H |
| A13 | B13 | C13 | —CH₂— | 4-fluorophenyl | —CH₂C(CH₃)₂CO₂H | CH₃, CH₃ | H |
| A14 | B14 | C14 | —CH₂— | 4-fluorophenyl | —CH₂C(—CH₂CH₂—)CO₂H | CH₃, CH₃ | H |
| A15 | B15 | C15 | —CH₂— | 4-fluorophenyl | —CH₂CH₂C(CH₃)₂CO₂H | CH₃, CH₃ | H |
| A16 | B16 | C16 | —CH₂— | 4-fluorophenyl | —CH₂CH₂C(—CH₂CH₂—)CO₂H | CH₃, CH₃ | H |
| A17 | B17 | C17 | —CH₂— | 4-fluorophenyl | —CH₂C(CH₃)₂CH₂CO₂H | CH₃, CH₃ | H |
| A18 | B18 | C18 | —CH₂— | 4-fluorophenyl | —CH₂C(—CH₂CH₂—)CH₂CO₂H | CH₃, CH₃ | H |
| A19 | B19 | C19 | —CH₂— | 4-fluorophenyl | —CH₂CO₂H | H, CH₃ | H |
| A20 | B20 | C20 | —CH₂— | 4-fluorophenyl | —CH₂CH₂CO₂H | H, CH₃ | H |
| A21 | B21 | C21 | —CH₂— | 4-fluorophenyl | —CH₂CH₂CH₂CO₂H | H, CH₃ | H |
| A22 | B22 | C22 | —CH₂— | 4-fluorophenyl | —CH₂C(CH₃)₂CO₂H | H, CH₃ | H |
| A23 | B23 | C23 | —CH₂— | 4-fluorophenyl | —CH₂C(—CH₂CH₂—)CO₂H | H, CH₃ | H |
| A24 | B24 | C24 | —CH₂— | 4-fluorophenyl | —CH₂CH₂C(CH₃)₂CO₂H | H, CH₃ | H |
| A25 | B25 | C25 | —CH₂— | 4-fluorophenyl | —CH₂CH₂C(—CH₂CH₂—)CO₂H | H, CH₃ | H |
| A26 | B26 | C26 | —CH₂— | 4-fluorophenyl | —CH₂C(CH₃)₂CH₂CO₂H | H, CH₃ | H |
| A27 | B27 | C27 | —CH₂— | 4-fluorophenyl | —CH₂C(—CH₂CH₂—)CH₂CO₂H | H, CH₃ | H |

TABLE 2-continued

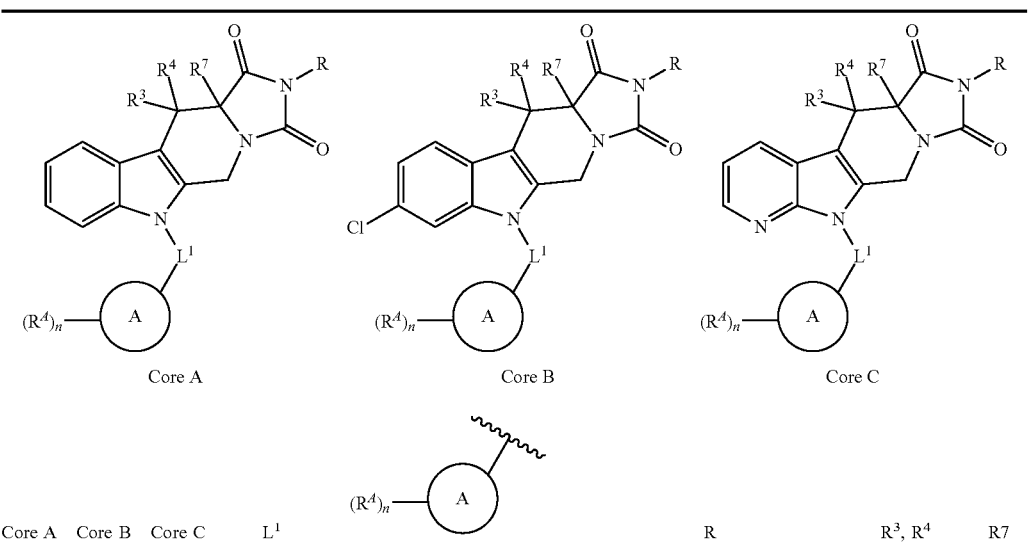

Core A  Core B  Core C

| Core A | Core B | Core C | L¹ | | R | R³, R⁴ | R7 |
|---|---|---|---|---|---|---|---|
| A28 | B28 | C28 | —CH$_2$— | 4-fluorophenyl | —CH$_2$CO$_2$H | —CH$_2$CH$_{23}$— | H |
| A29 | B29 | C29 | —CH$_2$— | 4-fluorophenyl | —CH$_2$CH$_2$CO$_2$H | —CH$_2$CH$_2$— | H |
| A30 | B30 | C30 | —CH$_2$— | 4-fluorophenyl | —CH$_2$CH$_2$CH$_2$CO$_2$H | —CH$_2$CH$_2$— | H |
| A31 | B31 | C31 | —CH$_2$— | 4-fluorophenyl | —CH$_2$C(CH$_3$)$_2$CO$_2$H | —CH$_2$CH$_2$— | H |
| A32 | B32 | C32 | —CH$_2$— | 4-fluorophenyl | —CH$_2$C(—CH$_2$CH$_2$—)CO$_2$H | —CH$_2$CH$_2$— | H |
| A33 | B33 | C33 | —CH$_2$— | 4-fluorophenyl | —CH$_2$CH$_2$C(CH$_3$)$_2$CO$_2$H | —CH$_2$CH$_2$— | H |
| A34 | B34 | C34 | —CH$_2$— | 4-fluorophenyl | —CH$_2$CH$_2$C(—CH$_2$CH$_2$—)CO$_2$H | —CH$_2$CH$_2$— | H |
| A35 | B35 | C35 | —CH$_2$— | 4-fluorophenyl | —CH$_2$C(CH$_3$)$_2$CH$_2$CO$_2$H | —CH$_2$CH$_2$— | H |
| A36 | B36 | C36 | —CH$_2$— | 4-fluorophenyl | —CH$_2$C(—CH$_2$CH$_2$—)CH$_2$CO$_2$H | —CH$_2$CH$_2$— | H |
| A37 | B37 | C37 | —CH$_2$— | 4-fluorophenyl | —CH$_2$CO$_2$H | =O | H |
| A38 | B38 | C38 | —CH$_2$— | 4-fluorophenyl | —CH$_2$CH$_2$CO$_2$H | =O | H |
| A39 | B39 | C39 | —CH$_2$— | 4-fluorophenyl | —CH$_2$CH$_2$CH$_2$CO$_2$H | =O | H |
| A40 | B40 | C40 | —CH$_2$— | 4-fluorophenyl | —CH$_2$C(CH$_3$)$_2$CO$_2$H | =O | H |
| A41 | B41 | C41 | —CH$_2$— | 4-fluorophenyl | —CH$_2$C(—CH$_2$CH$_2$—)CO$_2$H | =O | H |
| A42 | B42 | C42 | —CH$_2$— | 4-fluorophenyl | —CH$_2$CH$_2$C(CH$_3$)$_2$CO$_2$H | =O | H |
| A43 | B43 | C43 | —CH$_2$— | 4-fluorophenyl | —CH$_2$CH$_2$C(—CH$_2$CH$_2$—)CO$_2$H | =O | H |
| A44 | B44 | C44 | —CH$_2$— | 4-fluorophenyl | —CH$_2$C(CH$_3$)$_2$CH$_2$CO$_2$H | =O | H |
| A45 | B45 | C45 | —CH$_2$— | 4-fluorophenyl | —CH$_2$C(—CH$_2$CH$_2$—)CH$_2$CO$_2$H | =O | H |
| A46 | B46 | C46 | —CH$_2$— | 4-fluorophenyl | —CH$_2$CO$_2$H | H, OH | H |
| A47 | B47 | C47 | —CH$_2$— | 4-fluorophenyl | —CH$_2$CH$_2$CO$_2$H | H, OH | H |
| A48 | B48 | C48 | —CH$_2$— | 4-fluorophenyl | —CH$_2$CH$_2$CH$_2$CO$_2$H | H, OH | H |
| A49 | B49 | C49 | —CH$_2$— | 4-fluorophenyl | —CH$_2$C(CH$_3$)$_2$CO$_2$H | H, OH | H |
| A50 | B50 | C50 | —CH$_2$— | 4-fluorophenyl | —CH$_2$C(—CH$_2$CH$_2$—)CO$_2$H | H, OH | H |
| A51 | B51 | C51 | —CH$_2$— | 4-fluorophenyl | —CH$_2$CH$_2$C(CH$_3$)$_2$CO$_2$H | H, OH | H |
| A52 | B52 | C52 | —CH$_2$— | 4-fluorophenyl | —CH$_2$CH$_2$C(—CH$_2$CH$_2$—)CO$_2$H | H, OH | H |
| A53 | B53 | C53 | —CH$_2$— | 4-fluorophenyl | —CH$_2$C(CH$_3$)$_2$CH$_2$CO$_2$H | H, OH | H |
| A54 | B54 | C54 | —CH$_2$— | 4-fluorophenyl | —CH$_2$C(—CH$_2$CH$_2$—)CH$_2$CO$_2$H | H, OH | H |
| A55 | B55 | C55 | —CH$_2$— | 4-fluorophenyl | —CH$_2$CO$_2$H | F, F | CH$_3$ |
| A56 | B56 | C56 | —CH$_2$— | 4-fluorophenyl | —CH$_2$CH$_2$CO$_2$H | F, F | CH$_3$ |
| A57 | B57 | C57 | —CH$_2$— | 4-fluorophenyl | —CH$_2$CH$_2$CH$_2$CO$_2$H | F, F | CH$_3$ |
| A58 | B58 | C58 | —CH$_2$— | 4-fluorophenyl | —CH$_2$C(CH$_3$)$_2$CO$_2$H | F, F | CH$_3$ |
| A59 | B59 | C59 | —CH$_2$— | 4-fluorophenyl | —CH$_2$C(—CH$_2$CH$_2$—)CO$_2$H | F, F | CH$_3$ |
| A60 | B60 | C60 | —CH$_2$— | 4-fluorophenyl | —CH$_2$CH$_2$C(CH$_3$)$_2$CO$_2$H | F, F | CH$_3$ |
| A61 | B61 | C61 | —CH$_2$— | 4-fluorophenyl | —CH$_2$CH$_2$C(—CH$_2$CH$_2$—)CO$_2$H | F, F | CH$_3$ |
| A62 | B62 | C62 | —CH$_2$— | 4-fluorophenyl | —CH$_2$C(CH$_3$)$_2$CH$_2$CO$_2$H | F, F | CH$_3$ |
| A63 | B63 | C63 | —CH$_2$— | 4-fluorophenyl | —CH$_2$C(—CH$_2$CH$_2$—)CH$_2$CO$_2$H | F, F | CH$_3$ |
| A64 | B64 | C64 | —CH$_2$— | 4-fluorophenyl | —CH$_2$CO$_2$H | CH$_3$, CH$_3$ | CH$_3$ |
| A65 | B65 | C65 | —CH$_2$— | 4-fluorophenyl | —CH$_2$CH$_2$CO$_2$H | CH$_3$, CH$_3$ | CH$_3$ |
| A66 | B66 | C66 | —CH$_2$— | 4-fluorophenyl | —CH$_2$CH$_2$CH$_2$CO$_2$H | CH$_3$, CH$_3$ | CH$_3$ |
| A67 | B67 | C67 | —CH$_2$— | 4-fluorophenyl | —CH$_2$C(CH$_3$)$_2$CO$_2$H | CH$_3$, CH$_3$ | CH$_3$ |
| A68 | B68 | C68 | —CH$_2$— | 4-fluorophenyl | —CH$_2$C(—CH$_2$CH$_2$—)CO$_2$H | CH$_3$, CH$_3$ | CH$_3$ |
| A69 | B69 | C69 | —CH$_2$— | 4-fluorophenyl | —CH$_2$CH$_2$C(CH$_3$)$_2$CO$_2$H | CH$_3$, CH$_3$ | CH$_3$ |
| A70 | B70 | C70 | —CH$_2$— | 4-fluorophenyl | —CH$_2$CH$_2$C(—CH$_2$CH$_2$—)CO$_2$H | CH$_3$, CH$_3$ | CH$_3$ |
| A71 | B71 | C71 | —CH$_2$— | 4-fluorophenyl | —CH$_2$C(CH$_3$)$_2$CH$_2$CO$_2$H | CH$_3$, CH$_3$ | CH$_3$ |
| A72 | B72 | C72 | —CH$_2$— | 4-fluorophenyl | —CH$_2$C(—CH$_2$CH$_2$—)CH$_2$CO$_2$H | CH$_3$, CH$_3$ | CH$_3$ |

TABLE 2-continued

| Core A | Core B | Core C | L¹ | (R^A)_n-A | R | R³, R⁴ | R⁷ |
|---|---|---|---|---|---|---|---|
| A73 | B73 | C73 | —CH₂— | 4-fluorophenyl | —CH₂CO₂H | H, CH₃ | CH₃ |
| A74 | B74 | C74 | —CH₂— | 4-fluorophenyl | —CH₂CH₂CO₂H | H, CH₃ | CH₃ |
| A75 | B75 | C75 | —CH₂— | 4-fluorophenyl | —CH₂CH₂CH₂CO₂H | H, CH₃ | CH₃ |
| A76 | B76 | C76 | —CH₂— | 4-fluorophenyl | —CH₂C(CH₃)₂CO₂H | H, CH₃ | CH₃ |
| A77 | B77 | C77 | —CH₂— | 4-fluorophenyl | —CH₂C(—CH₂CH₂—)CO₂H | H, CH₃ | CH₃ |
| A78 | B78 | C78 | —CH₂— | 4-fluorophenyl | —CH₂CH₂C(CH₃)₂CO₂H | H, CH₃ | CH₃ |
| A79 | B79 | C79 | —CH₂— | 4-fluorophenyl | —CH₂CH₂C(—CH₂CH₂—)CO₂H | H, CH₃ | CH₃ |
| A80 | B80 | C80 | —CH₂— | 4-fluorophenyl | —CH₂C(CH₃)₂CH₂CO₂H | H, CH₃ | CH₃ |
| A81 | B81 | C81 | —CH₂— | 4-fluorophenyl | —CH₂C(—CH₂CH₂—)CH₂CO₂H | H, CH₃ | CH₃ |
| A82 | B82 | C82 | —CH₂— | 4-fluorophenyl | —CH₂CO₂H | —CH₂CH₂— | CH₃ |
| A83 | B83 | C83 | —CH₂— | 4-fluorophenyl | —CH₂CH₂CO₂H | —CH₂CH₂— | CH₃ |
| A84 | B84 | C84 | —CH₂— | 4-fluorophenyl | —CH₂CH₂CH₂CO₂H | —CH₂CH₂— | CH₃ |
| A85 | B85 | C85 | —CH₂— | 4-fluorophenyl | —CH₂C(CH₃)₂CO₂H | —CH₂CH₂— | CH₃ |
| A86 | B86 | C86 | —CH₂— | 4-fluorophenyl | —CH₂C(—CH₂CH₂—)CO₂H | —CH₂CH₂— | CH₃ |
| A87 | B87 | C87 | —CH₂— | 4-fluorophenyl | —CH₂CH₂C(CH₃)₂CO₂H | —CH₂CH₂— | CH₃ |
| A88 | B88 | C88 | —CH₂— | 4-fluorophenyl | —CH₂CH₂C(—CH₂CH₂—)CO₂H | —CH₂CH₂— | CH₃ |
| A89 | B89 | C89 | —CH₂— | 4-fluorophenyl | —CH₂C(CH₃)₂CH₂CO₂H | —CH₂CH₂— | CH₃ |
| A90 | B90 | C90 | —CH₂— | 4-fluorophenyl | —CH₂C(—CH₂CH₂—)CH₂CO₂H | —CH₂CH₂— | CH₃ |
| A91 | B91 | C91 | —CH₂— | 4-fluorophenyl | —CH₂CO₂H | =O | CH₃ |
| A92 | B92 | C92 | —CH₂— | 4-fluorophenyl | —CH₂CH₂CO₂H | =O | CH₃ |
| A93 | B93 | C93 | —CH₂— | 4-fluorophenyl | —CH₂CH₂CH₂CO₂H | =O | CH₃ |
| A94 | B94 | C94 | —CH₂— | 4-fluorophenyl | —CH₂C(CH₃)₂CO₂H | =O | CH₃ |
| A95 | B95 | C95 | —CH₂— | 4-fluorophenyl | —CH₂C(—CH₂CH₂—)CO₂H | =O | CH₃ |
| A96 | B96 | C96 | —CH₂— | 4-fluorophenyl | —CH₂CH₂C(CH₃)₂CO₂H | =O | CH₃ |
| A97 | B97 | C97 | —CH₂— | 4-fluorophenyl | —CH₂CH₂C(—CH₂CH₂—)CO₂H | =O | CH₃ |
| A98 | B98 | C98 | —CH₂— | 4-fluorophenyl | —CH₂C(CH₃)₂CH₂CO₂H | =O | CH₃ |
| A99 | B99 | C99 | —CH₂— | 4-fluorophenyl | —CH₂C(—CH₂CH₂—)CH₂CO₂H | =O | CH₃ |
| A100 | B100 | C100 | —CH₂— | 4-fluorophenyl | —CH₂CO₂H | H, OH | CH₃ |
| A101 | B101 | C101 | —CH₂— | 4-fluorophenyl | —CH₂CH₂CO₂H | H, OH | CH₃ |
| A102 | B102 | C102 | —CH₂— | 4-fluorophenyl | —CH₂CH₂CH₂CO₂H | H, OH | CH₃ |
| A103 | B103 | C103 | —CH₂— | 4-fluorophenyl | —CH₂C(CH₃)₂CO₂H | H, OH | CH₃ |
| A104 | B104 | C104 | —CH₂— | 4-fluorophenyl | —CH₂C(—CH₂CH₂—)CO₂H | H, OH | CH₃ |
| A105 | B105 | C105 | —CH₂— | 4-fluorophenyl | —CH₂CH₂C(CH₃)₂CO₂H | H, OH | CH₃ |
| A106 | B106 | C106 | —CH₂— | 4-fluorophenyl | —CH₂CH₂C(—CH₂CH₂—)CO₂H | H, OH | CH₃ |
| A107 | B107 | C107 | —CH₂— | 4-fluorophenyl | —CH₂C(CH₃)₂CH₂CO₂H | H, OH | CH₃ |
| A108 | B108 | C108 | —CH₂— | 4-fluorophenyl | —CH₂C(—CH₂CH₂—)CH₂CO₂H | H, OH | CH₃ |
| A109 | B109 | C109 | —CH₂— | 4-fluorophenyl | H | H, H | H |
| A110 | B110 | C110 | —CH₂— | 4-fluorophenyl | H | CH₃, CH₃ | H |
| A111 | B111 | C111 | —CH₂— | 4-fluorophenyl | —CH₂C(CH₃)₂CO₂H | H, H | H |
| A112 | B112 | C112 | —CH₂— | 4-fluorophenyl | —CH₂CH₂CO₂H | CH₃, CH₃ | H |
| A113 | B113 | C113 | —CH₂— | 4-fluorophenyl | —CH₂CH₂CO₂H | H, H | CH₃ |
| A114 | B114 | C114 | —CH₂— | 4-fluorophenyl | —CH₂CH₂CO₂H | H, H | H Rac |
| A115 | B115 | C115 | —CH₂— | 4-fluorophenyl | —CH₂CH₂CO₂H | H, H | H S-Ent |
| A116 | B116 | C116 | —CH₂— | 4-fluorophenyl | —CH₂CH₂CO₂H | H, H | H R-Ent |

In some embodiments, the

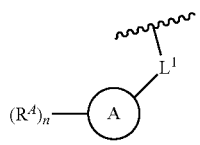

group of any on the compounds described in Table 2 for Core A and Core B is replaced with 4-chlorobenzyl; 3-chlorobenzyl; 3-fluorobenzyl; 3,5-difluorobenzyl; 2,4-difluorobenzyl; 3,5-dichlorobenzyl; 2-chloropyridin-5-ylmethyl; 2-methoxypyridin-5-ylmethyl; 2-trifluoromethylthiazol-5-ylmethyl; phenylprop-3-yl; thien-2-ylmethyl; or 5-chlorothien-2-ylmethyl.

TABLE 3

Core E

| Compound | X | R |
|---|---|---|
| E1 | CH | —CH$_2$CH$_2$CO$_2$H |
| E2 | CH | H |
| E3 | N | H |

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyamino acid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds described herein are synthesized using standard synthetic techniques or using methods known in the art in combination with methods described herein. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Tryptophan and substituted tryptophans are commercially available. In some embodiments, substituted tryptophans are synthesized in racemic form. In some embodiments, individual enantiomers of tryptophan and substituted tryptophans are obtained by resolution (c.f. Coker et al, J. Org. Chem., 1962, 27, p 850) of racemic tryptophan and substituted tryptophans. In other embodiments, individual enantiomers of tryptophan and substituted tryptophans are prepared enantioselectively (see Ma et al, J. Med. Chem., 2001, 66, p 4525 and Pavlov et al, J. Org. Chem., 2011, 76, p 6116 and references cited therein). Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources.

In some embodiments, compounds described herein are prepared as outlined in Scheme 1.

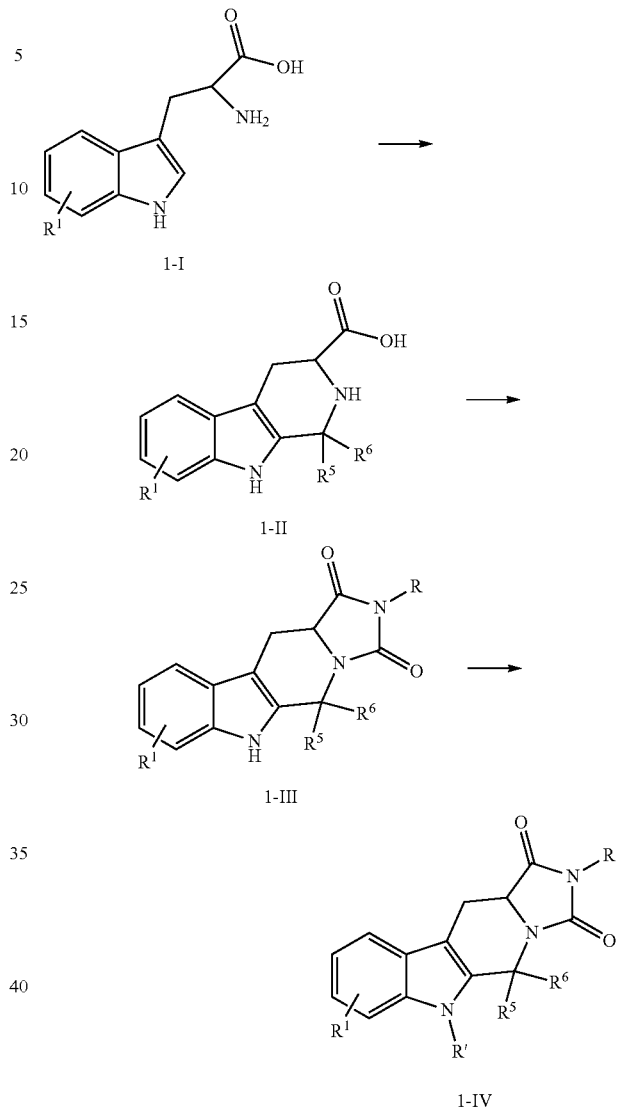

In some embodiments, the preparation of compounds described herein begins with the appropriately substituted tryptophan 1-I. In some embodiments, the tryptoline analog 1-II is prepared by a Pictet-Spengler reaction of 1-I with formaldehyde ($R^5$=$R^6$=H; Scheme 1). Using aldehydes or ketones, substituted tryptoline derivatives ($R^5$ and $R^6$ are H and/or alkyl) are prepared. In some embodiments, the amino acid of 1-II is coupled with an amine R—NH$_2$ (where R is -L$^2$-B-L$^3$-Q as described herein) in the presence of triphosgene followed by heating in a solvent such as DMSO to yield 1-III. In some embodiments, the indole NH is alkylated by treatment of 1-III with, for example Cs$_2$CO$_3$ and an alkylating agent in a solvent such as DMF. In some further embodiments, the resulting N-alkylated analog (1-IV) is further modified using standard chemical transformations. Racemic compounds synthesized using this route may be resolved into the corresponding enantiomers using standard procedures, for example, using chiral phase HPLC.

An alternative route to preparing compounds described herein is shown in Scheme 2.

Scheme 2

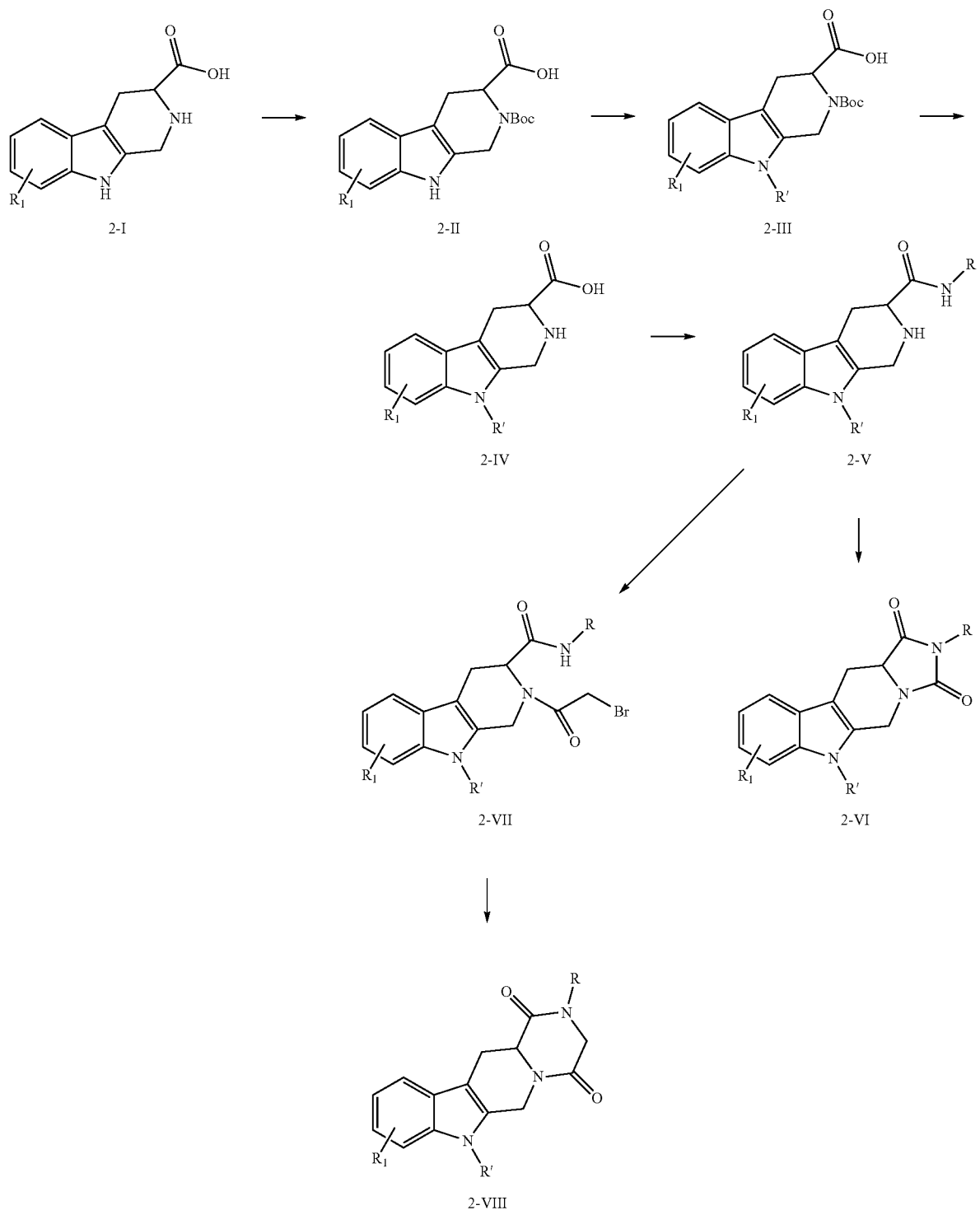

In some embodiments, the basic nitrogen of the tricyclic tryptoline 2-I is protected as the N-Boc derivative 2-II using $Boc_2O$ under standard conditions. In some embodiments, alkylation of the indole N—H of 2-II to give 2-III is achieved using the procedures described for Scheme 1. Deprotection under acidic conditions (e.g. with TFA) yields 2-IV. This sequence allows for the asymmetric preparation of substituted tryptophan derivatives 2-IV starting from optically active tryptophans in which racemization of the chiral center has been substantially reduced. In some embodiments, compound 2-IV is converted in one step to 2-VI as described for Scheme 1. In some other embodiments, compound 2-IV is converted to 2-VI in 2 steps consisting of amide bond formation with an amine R—$NH_2$ (to give 2-V) followed by cyclization in the presence of triphosgene to afford 2-VI. In some embodiments, 6-membered ring analogs of general structure 2-VIII are synthesized from 2-V by treatment with bromoacetyl bromide in the presence of a base such as Et₃N in a solvent such as THF. In some embodiments, the resulting bromo-containing compound 2-VII undergoes an intramolecular cyclization to give 2-VIII.

Scheme 3 describes tetracyclic analogs containing an oxazolidinone ring such as 3-IV.

Scheme 3

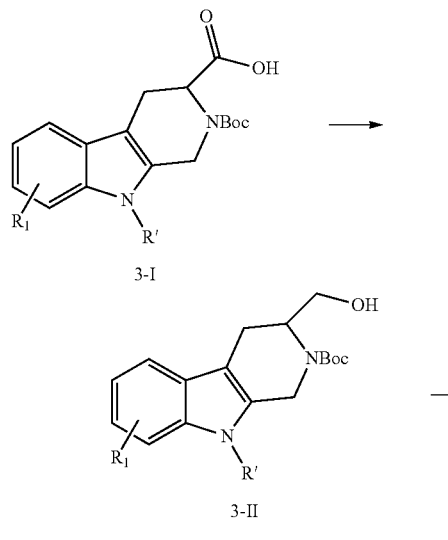

3-I

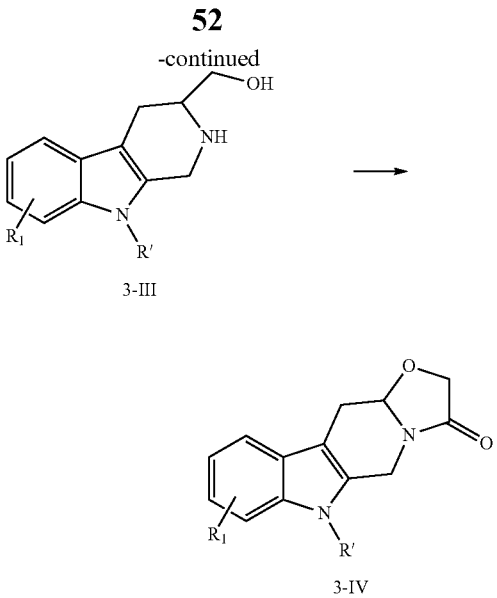

3-III

3-IV

In some embodiments, starting with the, chemoselective reduction of the acid group of tryptoline 3-1 using, for example, BH₃ in THF results in the alcohol 3-II. Deprotection of the Boc-amine using e.g. TFA provides 3-III which may then be cyclized in the presence of CDI and a base such as Et₃N to give 3-IV.

The route to prepare tetracyclic analogs containing a cyclic urea ring such as 4-VIII and 4-IX are described in Scheme 4.

Scheme 4

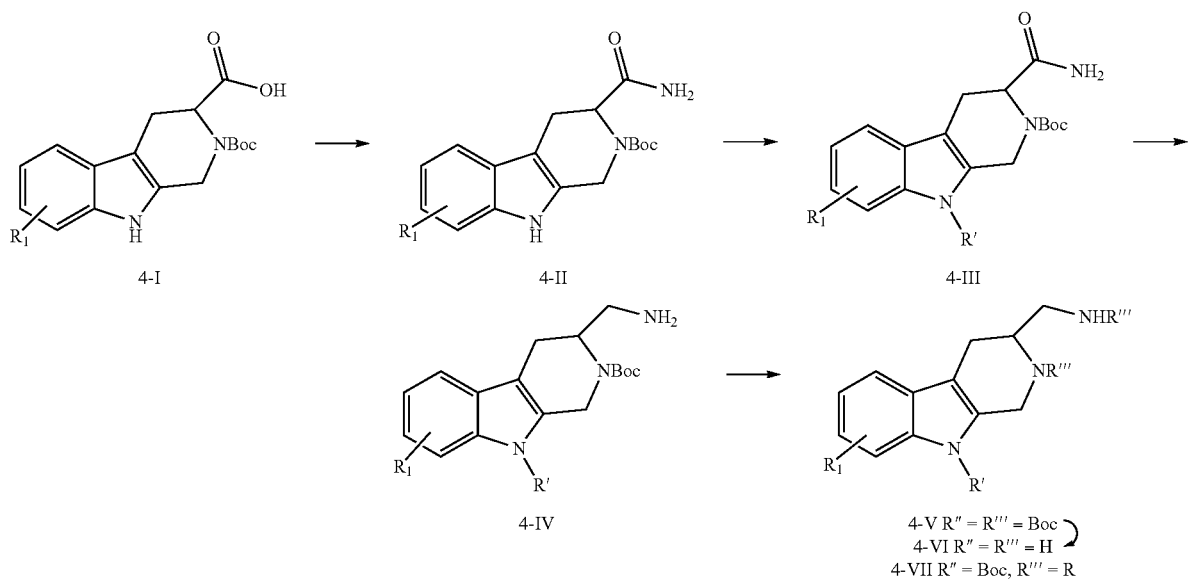

4-I        4-II        4-III

4-IV        4-V R″ = R‴ = Boc
            4-VI R″ = R‴ = H
            4-VII R″ = Boc, R‴ = R

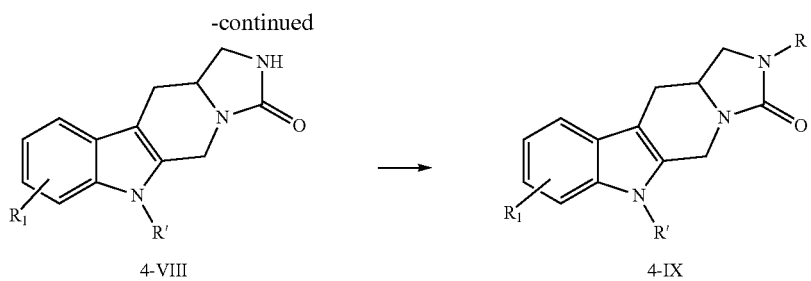

4-VIII → 4-IX

In some embodiments, the acid of the N-Boc derivative 4-I is converted into the primary amide 4-II using, for example EDCI, HOBt and NH$_4$Cl in a suitable solvent such as THF. N-alkylation as described for Scheme 1 then affords 4-III. In some embodiments, the sequence of reactions is reversed such that the N-alkylation precedes the primary amide formation. Reduction of the primary amide using BH$_3$.DMS in THF yields the primary amine 4-IV and cyclization then yields the unsubstituted oxazolidinone 4-VIII. Alternatively, the Boc group of 4-IV is removed under acidic conditions to give 4-VI or the primary amine of 4-IV is Boc-protected (to yield 4-V) and then both Boc groups are removed to give 4-VI. In some embodiments, reductive amination of an aldehyde with 4-IV is used to introduce a substituent on the primary amine (to give 4-VII). Cyclization of 4-VI using, for example, CDI and Et$_3$N in THF yields the tetracycle 4-VIII and N-alkylation using a base such as NaH in THF followed by reaction with an electrophile then provides compounds of general structure 4-IX. An alternate procedure involves intermediate 4-VII that can be deprotected under acidic conditions to remove the Boc group and the diamine cyclize with CDI as above to generate 4-IX.

In some embodiments, substituted tryptophans such as compounds 5-I are used to prepare compounds described herein.

Scheme 5

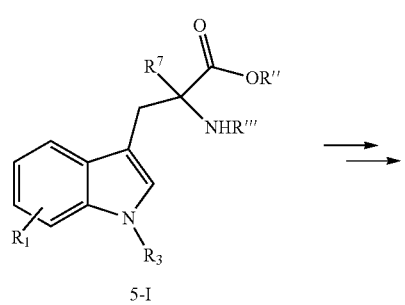

5-I

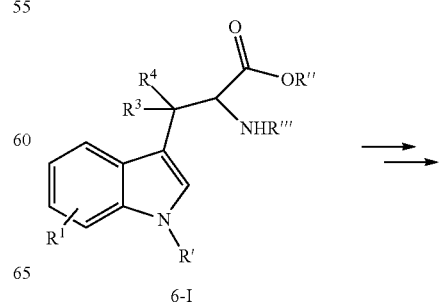

5-II

Procedures to introduce substituents α- to the amino acid to give compounds such as 5-I have been described (Scheme 5; see for example Schirlin et al, J. Med. Chem., 1988, 31, p 30 and Zembower et al J. Med. Chem., 1993, 36, p 305). Using the chemistry described in the schemes 1-4 above, compounds such as 5-II, 5-III and 5-IV may be synthesized.

In some embodiments, substituted tryptophans such as compounds 6-I are used to prepare compounds described herein.

Scheme 6

6-I

-continued

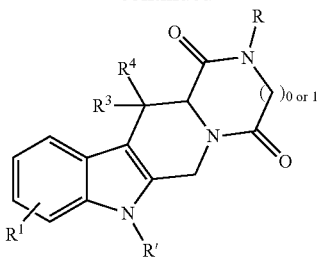

6-II

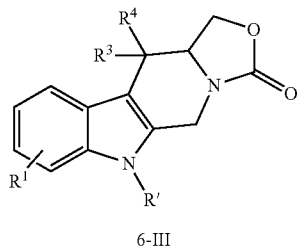

6-III

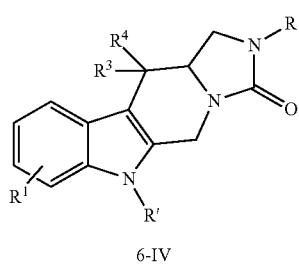

6-IV

Tryptophan derivatives (e.g. Scheme 6, 6-I) containing substituents in the benzylic position may be prepared by alkylation of 3-indole acetic acid esters or nitrile derivatives (Anderson et al, Tet Lett., 1997, 38, 317) or they can be prepared directly from 3-H indoles (Reddy et al, org. Letts., 2002, 4, 695). Procedures to introduce substituents at the benzylic position of the amino acid side-chain to give compounds such as 6-I have been described (X=OH; see for example Crich and Banerjee, J. Org. Chem., 2006, 71, p 7106). Using the chemistry described in the schemes 1-4 above, compounds such as 6-II, 6-III and 6-IV may be synthesized. When the substituent $R^3$ is OH it can be oxidized to produce a carbonyl and then further reacted e.g. with an alkyl lithium or Grignard reagent to introduce a tertiary alcohol ($R^3$=OH; $R^4$=alkyl).

In some embodiments, the synthesis of compounds described herein includes the steps outlined in Scheme 7.

Scheme 7

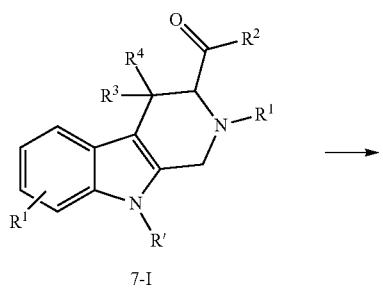

7-I

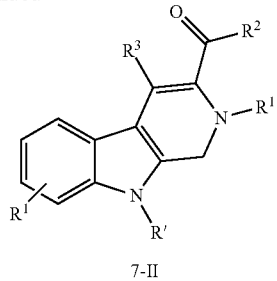

7-II

In some embodiments, introduction of a double bond in the tetrahydro-b-carboline derivatives 7-I is achieved by oxidation using, for example, selenium dioxide to afford compounds of general structure 7-II (Scheme 7; c.f. Gatta, J. Heterocyclic Chem., 1987, 24, p 1183). Alternative methods to achieve this transformation involve dehydration of the hydroxyl derivative ($R^3$=OH), or benzylic bromination (to give $R^3$=Br) followed by elimination using a base such as DBU.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, male reproductive tissue toxicity can be assessed in suitable in vivo models. In some embodiments, male reproductive tissue toxicity is assessed by monitoring any decreases in the testes weight and/or epididymis weight. For example, in a suitable rat male reproductive tissue toxicity study, Compounds (1-5), racemic (1-30) and racemic (1-33) exhibited undesired decreases in testes weight whereas Compounds (1-1) and (1-15) did not exhibit the same effects. In some embodiments, no decreases in the testes weight (as a percentage of body weight) were observed for Compounds (1-1) and (1-15) when dosed at 300 mpk PO for 5 days In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, hormone blocking therapy, radiation therapy, monoclonal antibodies, or combinations thereof.

Chemotherapy includes the use of anti-cancer agents.

In one aspect, the compound described herein, or a pharmaceutically acceptable salt thereof, is administered or formulated in combination with one or more anti-cancer agents.

EXAMPLES

The following examples are provided for illustrative purposes only and not to limit the scope of the claims provided herein.

Example 1: Synthesis of 4-(6-(4-fluorobenzyl)-1,3-dioxo-11,11a-dihydro-1H-imidazol[1',5':1,6]pyrido[3,4-b]indol-2(3H,5H,6H)-yl)butanoic acid (1-1)

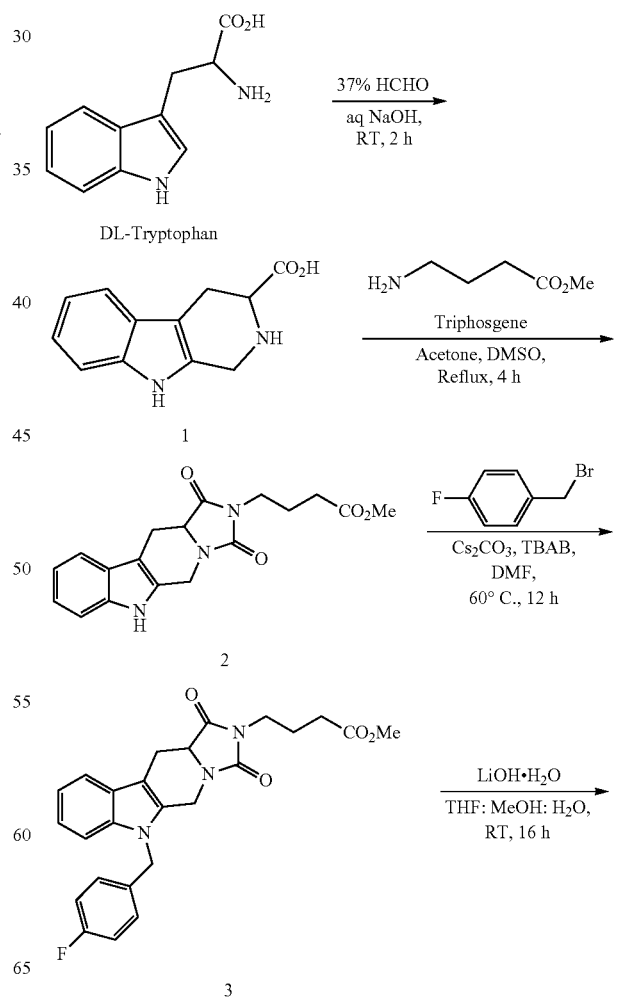

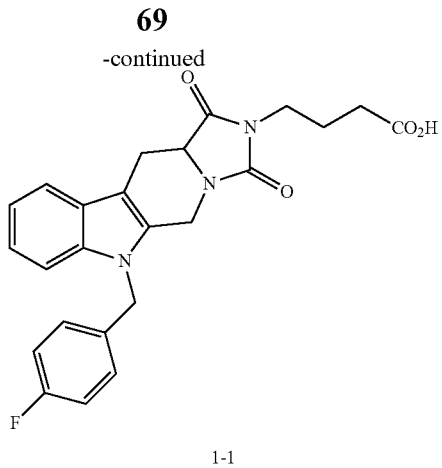

1-1

Step 1. Synthesis of 2,3,4,9-tetrahydro-1H-pyrido[3,4-b]indole-3-carboxylic acid (1)

To a stirred solution of DL-Tryptophan 1 (5.0 g, 24.5 mmol) in aqueous NaOH solution (0.98 g in 10 mL of $H_2O$) under inert atmosphere was added 37% formalin (735 mg, 24.5 mmol) at RT and stirred for 2 h; heated to reflux and stirred for 3 h. The reaction was monitored by TLC; after completion of the reaction, the reaction mixture was neutralized with 6N aq. HCl solution (4 mL) to pH~5. The obtained precipitate was filtered, washed with water, triturated with MeOH (2×10 mL), $CH_2Cl_2$ (2×10 mL) and dried under reduced pressure to afford compound 1 (2.72 g, 51%) as a pale yellow solid. $^1$H NMR (400 MHz, DMSO-$d_6$): δ 10.96 (s, 1H), 9.02 (br s, 1H), 7.43 (d, J=8.0 Hz, 1H), 7.32 (d, J=8.0 Hz, 1H), 7.08 (d, J=8.0 Hz, 1H), 6.96 (t, J=8.0 Hz, 1H), 4.25-4.15 (m, 2H), 3.90 (br s, 1H), 3.64-3.60 (m, 1H), 3.16-3.11 (m, 1H), 2.85-2.79 (m, 1H).

Step 2: Synthesis of methyl 4-(1,3-dioxo-5,6,11,11-tetrahydro-1H-imidazo[1',5':1,6]pyrido[3,4-b]indol-2(3H)-yl)butanoate (2)

To a stirred solution of methyl 4-aminobutanoate (300 mg, 1.95 mmol) in $CH_2Cl_2$ and aq. saturated $NaHCO_3$ solution (1:1; 20 mL) was added triphosgene (231 mg, 0.78 mmol) at 0° C. and stirred for 30 min. The reaction solution was warmed to RT and stirred for 30 min. The reaction mixture was then diluted with aq. saturated $NaHCO_3$ solution (10 mL) and extracted with $CH_2Cl_2$ (3×10 mL). The combined organic extracts were washed with brine (20 mL), dried over $Na_2SO_4$, filtered and concentrated under reduced pressure to obtain the crude isocyanate.

The crude isocyanate (225 mg) was dissolved in acetone and DMSO (2.5:1, 14 mL) under inert atmosphere and added compound 1 (340 mg, 1.57 mmol) at RT; heated to reflux and stirred for 4 h. The reaction was monitored by TLC; after completion of the reaction, the reaction mixture was diluted with water (20 mL) and extracted with $CH_2Cl_2$ (2×20 mL). The combined organic extracts were washed with brine (20 mL), dried over $Na_2SO_4$, filtered and concentrated under reduced pressure to obtain the crude. The crude was purified through silica gel column chromatography using 3-5% MeOH/$CH_2Cl_2$ to afford compound 2 (314 mg, 58%) as a pale yellow solid. $^1$H NMR (400 MHz, DMSO-$d_6$): δ 11.01 (s, 1H), 7.47 (d, J=7.6 Hz, 1H), 7.34 (d, J=7.6 Hz, 1H), 7.07 (t, J=7.6 Hz, 1H), 6.99 (t, J=7.6 Hz, 1H), 4.89 (d, J=16.0 Hz, 1H), 4.41-4.37 (m, 2H), 3.56 (s, 3H), 3.47 (t, J=6.4 Hz, 2H), 3.24-3.19 (m, 1H), 2.76-2.70 (m, 1H), 2.36 (t, J=7.6 Hz, 2H), 1.85-1.78 (m, 2H); LC-MS (ESI): 97.8%; m/z 340.4 (M–H$^-$); (column: X Select C-18, 50×3.0 mm, 3.5 m); RT 3.25 min; 5 mM $NH_4$OAc: ACN; 0.8 mL/min).

Step 3: Synthesis of methyl 4-(6-(4-fluorobenzyl)-1,3-dioxo-5,6,11,11a-tetrahydro-1H-imidazo[1',5':1,6]pyrido[3,4-b]indol-2(3H)-yl)butanoate (3)

To a stirred solution of compound 2 (150 mg, 0.44 mmol) in DMF (10 mL) under inert atmosphere was added 4-fluorobenzyl bromide (0.08 mL, 0.66 mmol), $Cs_2CO_3$ (286 mg, 0.88 mmol), TBAB (7 mg, 0.02 mmol) at RT; heated to 60° C. and stirred for 12 h. The reaction was monitored by TLC; after completion of the reaction, the reaction mixture was diluted with water (20 mL) and extracted with EtOAc (2×25 mL). The combined organic extracts were washed with brine (20 mL), dried over $Na_2SO_4$, filtered and concentrated under reduced pressure to obtain the crude. The crude was purified through silica gel column chromatography using 30-40% EtOAc/Hexanes to afford compound 3 (151 mg) as pale yellow solid. $^1$H NMR (400 MHz, DMSO-$d_6$): δ 7.54 (d, J=7.6 Hz, 1H), 7.49 (d, J=8.4 Hz, 1H), 7.16-7.06 (m, 6H), 5.42 (q, J=17.2 Hz, 2H), 4.89 (d, J=16.0 Hz, 1H), 4.40-4.30 (m, 2H), 3.55 (s, 3H), 3.46 (t, J=6.8 Hz, 2H), 3.27-3.23 (m, 1H), 2.78-2.71 (m, 1H), 2.35 (t, J=7.6 Hz, 2H), 1.83-1.76 (m, 2H); LC-MS (ESI): δ 7.5%; m/z 450.5 (M+H$^+$); (column: X Select C-18, 50×3.0 mm, 3.5 μm); RT 3.71 min; 5 mM $NH_4$OAc: ACN; 0.8 mL/min).

Step 4: Synthesis of 4-(6-(4-fluorobenzyl)-1,3-dioxo-11,11a-dihydro-1H-imidazo[1',5':1,6]pyrido[3,4-b]indol-2(3H,5H,6H)-yl)butanoic acid To a stirred solution of compound 3 (35 mg, 0.077 mmol) in THF:MeOH:$H_2O$ (3:1:1, 5 mL) under inert atmosphere was added LiOH.$H_2O$ (9 mg, 0.22 mmol) at RT and stirred for 12 h. The reaction was monitored by TLC; after completion of the reaction, the reaction mixture was concentrated under reduced pressure. The residue was diluted with water (20 mL), acidified with 1N aq. HCl solution to pH~3 and extracted with $CH_2Cl_2$ (2×20 mL). The combined organic extracts were dried over sodium sulphate, filtered and concentrated under reduced pressure to obtain the crude. The crude was purified through silica gel column chromatography using 50-60% EtOAc/Hexanes to afford the title compound 1-1 (8 mg, 23%) as a pale yellow solid. $^1$H NMR (400 MHz, DMSO-$d_6$): δ 12.06 (br s, 1H), 7.54 (d, J=7.6 Hz, 1H), 7.48 (d, J=8.0 Hz, 1H), 7.16-7.04 (m, 6H), 5.42 (q, J=16.8 Hz, 2H; ABX pattern), 4.91 (d, J=16.0 Hz, 1H), 4.40-4.30 (m, 2H), 3.46 (t, J=6.8 Hz, 2H), 3.31-3.24 (m, 1H), 2.81-2.74 (m, 1H), 2.25 (t, J=7.2 Hz, 2H), 1.80-1.73 (m, 2H); MS (ESI): m/z 436.8 (M+H$^+$); UPLC: 85.6%; (column: Acquity BEH C-18 (50×2.1 mm, 1.7μ); RT 2.42 min; ACN: 0.025% TFA (aq); 0.5 mL/min.

Example 2: Synthesis of (S)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid (1-2)

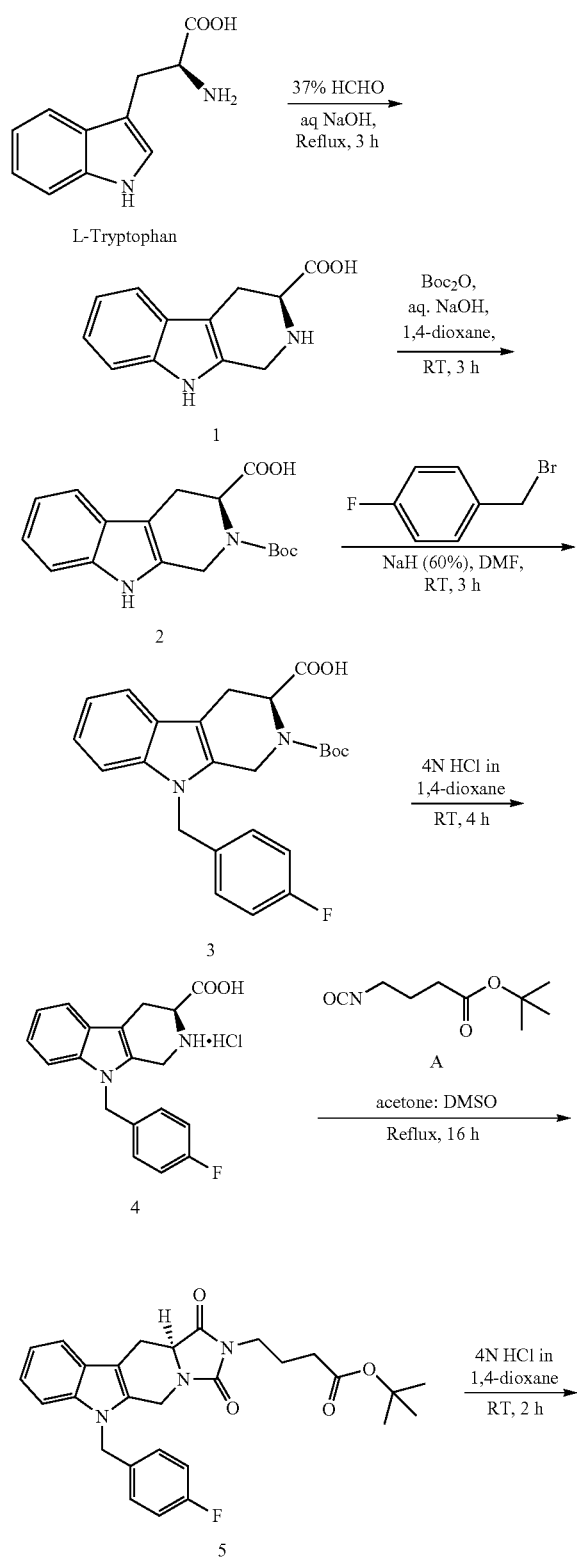

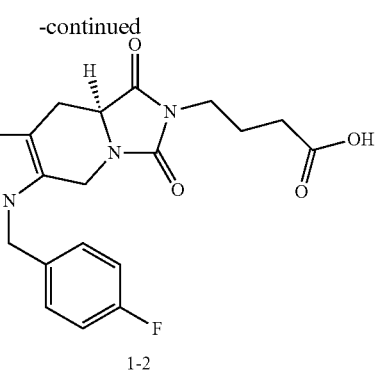

Step 1: Synthesis of (S)-2,3,4,9-tetrahydro-1H-pyrido[3,4-b]indole-3-carboxylic acid (1)

Following the procedure of Example 1, step 1, but using L-tryptophan as starting material in place of DL-tryptophan, the title compound was obtained. $^1$H NMR (400 MHz, DMSO-$d_6$): δ 10.90 (s, 1H), 9.02 (br s, 1H), 7.42 (d, J=8.0 Hz, 1H), 7.30 (d, J=8.0 Hz, 1H), 7.08 (t, J=8.0 Hz, 1H), 6.96 (t, J=8.0 Hz, 1H), 4.20 (q, J=16.0 Hz, 2H), 3.62 (t, J=7.2 Hz, 1H), 3.16-3.11 (m, 1H), 2.82-2.78 (m, 1H); LC-MS (ESI): 95.3%; m/z 217.2 (M+H$^+$); (column: X Select CSH C-18, 50×3.0 mm, 3.5 μm); RT 1.68 min; 5 mM NH$_4$OAc: ACN; 0.8 mL/min).

Step 2: Synthesis of (S)-2-(tert-butoxycarbonyl)-2,3,4,9-tetrahydro-1H-pyrido[3,4-b]indole-3-carboxylic acid (2)

To a stirred solution of compound 1 (9.0 g, 41.6 mmol) in 1,4-dioxane (150 mL) under inert atmosphere were added NaOH solution (3.4 g, 83.3 mmol) in water (75 mL), Boc-anhydride (11.0 g, 49.99 mmol) at RT and stirred for 3 h. The reaction was monitored by TLC; after completion of the reaction, the reaction mixture was diluted with water (40 mL), acidified with citric acid solution. The obtained solid was filtered, washed with water (2×15 mL), triturated with n-pentane (2×10 mL) and dried under reduced pressure to afford compound 2 (8.0 g, 61%) as an off-white solid. $^1$H NMR (500 MHz, DMSO-$d_6$): δ 12.75 (br s, 1H), 10.87 (s, 1/2H), 10.82 (s, 1/2H), 7.41 (d, J=8.0 Hz, 1H), 7.29-7.27 (m, 1H), 7.04 (t, J=7.5 Hz, 1H), 6.95 (t, J=7.5 Hz, 1H), 5.15-5.03 (m, 1H), 4.71 (t, J=16.5 Hz, 1H), 4.46-4.32 (m, 1H), 3.29-3.26 (m, 1H), 2.99-2.92 (m, 1H), 1.47 (s, 9×1/2H), 1.44 (s, 9×1/2H); LC-MS (ESI): 99.4%; m/z 315.3 (M–H$^-$); (column: X Select CSH C-18, 50×3.0 mm, 3.5 μm); RT 2.56 min; 5 mM NH$_4$OAc: ACN; 0.8 mL/min).

Step 3: Synthesis of (S)-2-(tert-butoxycarbonyl)-9-(4-fluorobenzyl)-2,3,4,9-tetrahydro-1H-pyrido[3,4-b]indole-3-carboxylic acid (3)

To a stirred solution of compound 2 (4.0 g, 12.65 mmol) in DMF (150 mL) under inert atmosphere was added NaH (60% in mineral oil; 1.1 g, 27.84 mmol) slowly for 30 min followed by 4-fluorobenzyl bromide (2.9 g, 15.34 mmol) at 0° C.; warmed to RT and stirred for 3 h. The reaction was monitored by TLC; after completion of the reaction, the reaction mixture was diluted with water (40 mL), acidified with citric acid and extracted with EtOAc (2×50 mL). The combined organic extracts were washed with brine (60 mL), dried over Na$_2$SO$_4$, filtered and concentrated under reduced pressure to obtain the crude. The crude was purified through silica gel column chromatography using 15-20% EtOAc/Hexanes to afford compound 3 (2.3 g, 43%) as a pale brown solid. $^1$H NMR (500 MHz, DMSO-d$_6$): δ 12.80 (br s, 1H), 7.50-7.44 (m, 2H), 7.13-7.00 (m, 6H), 5.41-5.28 (m, 2H), 5.16-5.06 (m, 1H), 4.68-4.61 (m, 1H), 4.44-4.29 (m, 1H), 3.34-3.31 (m, 1H), 3.06-2.98 (m, 1H), 1.43 (s, 9×1/2H), 1.41 (s, 9×1/2H); LC-MS (ESI): 95.7%; m/z 423.5 (M–H$^−$); (column: X Select CSH C-18, 50×3.0 mm, 3.5 μm); RT 3.10 min; 5 mM NH$_4$OAc (aq.): ACN; 0.8 mL/min; UPLC: 96.5%; (column: Acquity BEH C-18 (50×2.1 mm, 1.7); RT 2.80 min; ACN: 0.025% TFA (aq); 0.5 mL/min; Chiral HPLC: 98.6%, R$_t$=4.35 min (Chiralpak IA, 250×4.6 mm, 5 μm); mobile phase (A) 0.1% TFA in n-Hexane, (B) THF:MeOH (80:20), (A:B=75:25); flow rate: 1.0 mL/min; ee: 100%

Step 4: Synthesis of (S)-9-(4-fluorobenzyl)-2,3,4,9-tetrahydro-1H-pyrido[3,4-b]indole-3-carboxylic acid hydrochloride (4)

Compound 3 (1.0 g, 2.35 mmol) was added to 4M HCl in 1,4-dioxane solution (20 mL) under inert atmosphere at RT and stirred for 4 h. The reaction was monitored by TLC; after completion of the reaction, the reaction mixture was basified with triethyl amine and extracted with EtOAc (2×30 mL). The combined organic extracts were washed with brine (20 mL), dried over Na$_2$SO$_4$, filtered and concentrated under reduced pressure to obtain the crude. The crude was triturated with n-pentane (2×5 mL) to afford compound 4 (500 mg, 59%) as a pale brown solid. $^1$H NMR (500 MHz, DMSO-d$_6$): δ 7.49 (d, J=7.5 Hz, 1H), 7.41 (d, J=8.5 Hz, 1H), 7.11-7.02 (m, 6H), 5.33 (s, 2H), 4.25 (d, J=15.5 Hz, 1H), 4.09 (d, J=15.5 Hz, 1H), 3.62-3.61 (m, 1H), 3.15-3.12 (m, 1H), 2.86-2.81 (m, 1H); LC-MS (ESI): 94.0%; m/z 325.4 (M+H$^+$); (column: X Select CSH C-18, 50×3.0 mm, 3.5 μm); RT 2.68 min; 5 mM NH$_4$OAc (aq.): ACN; 0.8 mL/min).

Step 5: Synthesis of tert-butyl 4-isocyanatobutanoate (A)

To a stirred solution of tert-butyl 4-aminobutanoate hydrochloride (300 mg, 1.53 mmol) in CH$_2$Cl$_2$ (10 mL) and saturated NaHCO$_3$ solution (10 mL) under inert atmosphere was added triphosgene (182 mg, 0.61 mmol) at 0° C.; warmed to RT and stirred for 1 h. The reaction was monitored by TLC; after completion of the reaction, the reaction mixture was diluted with water (25 mL) and extracted with CH$_2$Cl$_2$ (2×30 mL). The combined organic extracts were washed with brine (30 mL), dried over Na$_2$SO$_4$, filtered and concentrated under reduced pressure to obtain crude A (250 mg) as a pale green liquid. This crude material was directly used for next reaction without purification.

Step 6: Synthesis of tert-butyl (S)-4-(6-(4-fluorobenzyl)-1,3-dioxo-5,6,11,11a-tetrahydro-1H-imidazo[1',5':1,6]pyrido[3,4-b]indol-2(3H)-yl)butanoate (5)

To a stirred solution of compound 4 (300 mg, 0.92 mmol) in acetone: DMSO (2:1, 24 mL) under inert atmosphere was added A (171 mg) at RT; heated to reflux and stirred for 16 h. The reaction was monitored by TLC; after completion of the reaction, the reaction mixture was diluted with water (25 mL) and extracted with EtOAc (2×30 mL). The combined organic extracts were washed with water (20 mL), brine (20 mL), dried over Na$_2$SO$_4$, filtered and concentrated under reduced pressure to obtain the crude. The crude was purified through silica gel column chromatography using 10% EtOAc/Hexanes to afford compound 5 (110 mg, 24%) as pale green thick syrup. $^1$H NMR (500 MHz, DMSO-d$_6$): δ 7.55 (d, J=7.5 Hz, 1H), 7.49 (d, J=8.0 Hz, 1H), 7.16-7.05 (m, 6H), 5.43 (q, J=14.0 Hz, 2H), 4.99 (d, J=16.5 Hz, 1H), 4.40-4.31 (m, 2H), 3.45 (t, J=7.0 Hz, 2H), 3.29-3.25 (m, 1H), 2.81-2.77 (m, 1H), 2.24 (t, J=7.0 Hz, 2H), 1.77-1.74 (m, 2H), 1.39 (s, 9H); LC-MS (ESI): 98.4%; m/z 435.9 (M$^+$-(—CMe$_3$)); (column: X Select CSH C-18, 50×3.0 mm, 3.5 μm); RT 4.41 min; 0.05% TFA (aq.): ACN; 0.8 mL/min).

Step 7: Synthesis of (S)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid Compound 5 (90 mg, 0.18 mmol) was added to a solution of 4N HCl in 1,4-dioxane (4 mL) under inert atmosphere at RT and stirred for 2 h. The reaction was monitored by TLC; after completion of the reaction, the reaction mixture was diluted with ice-cold water (15 mL) and extracted with EtOAc (2×20 mL). The combined organic extracts were washed with water (15 mL), brine (15 mL), dried over Na$_2$SO$_4$, filtered and concentrated under reduced pressure to obtain the crude. The crude was triturated with n-hexane (2×5 mL) to afford the title compound 1-2 (60 mg, 75%) as an off-white solid. $^1$H NMR (400 MHz, CD$_3$OD): δ 7.54 (d, J=7.4 Hz, 1H), 7.36 (d, J=7.8 Hz, 1H), 7.16-6.98 (m, 6H), 5.35 (s, 2H), 4.95 (d, J=16.0 Hz, 1H), 4.36-4.31 (m, 2H), 3.61 (t, J=7.0 Hz, 2H), 3.37-3.33 (m, 1H), 2.88-2.81 (m, 1H), 2.33 (t, J=7.4 Hz, 2H), 1.96-1.90 (m, 2H); MS (ESI): m/z 434.2 (M–H$^−$); UPLC: 95.8%; (column: Acquity BEH C-18 (50×2.1 mm, 1.7); RT 2.40 min; ACN: 0.025% TFA (aq); 0.5 mL/min; Chiral HPLC: 93.9%, R$_t$=14.21 min (Chiralpak IA, 250×4.6 mm, 5 μm); mobile phase (A) 0.1% TFA in n-Hexane, (B) THF:MeOH (80:20), (A:B=75:25); flow rate: 1.0 mL/min; ee: 94.2%

Example 3: Synthesis of (R)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid (1-3)

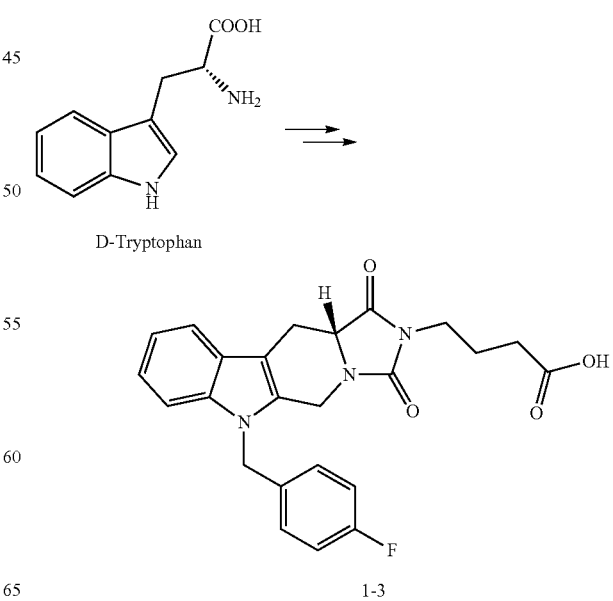

1-3

Following the procedure of Example 2 but using D-tryptophan in place of L-tryptophan, the title compound 1-3 was prepared as an off-white solid. 1H NMR data is identical with 1-2 data; MS (ESI): m/z 436.3 (M+H$^+$); UPLC: 95.7%; (column: Acquity BEH C-18 (50×2.1 mm, 1.7); RT 2.39 min; ACN: 0.025% TFA (aq); 0.5 mL/min; Chiral HPLC: 96.5%, R$_t$=12.81 min (Chiralpak IA, 250×4.6 mm, 5 μm); mobile phase (A) 0.1% TFA in n-Hexane, (B) THF:MeOH (80:20), (A:B=75:25); flow rate: 1.0 mL/min); ee: 100%

Example 4: Synthesis of 3-(6-(4-fluorobenzyl)-1,3-dioxo-11,11a-dihydro-1H-imidazo[1',5':1,6]pyrido[3,4-b]indol-2(3H,5H,6H)-yl)propanoic acid (1-4)

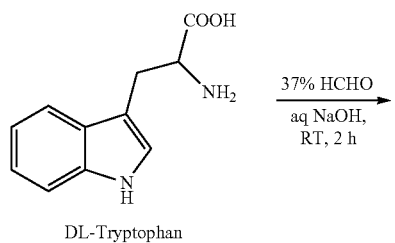

DL-Tryptophan

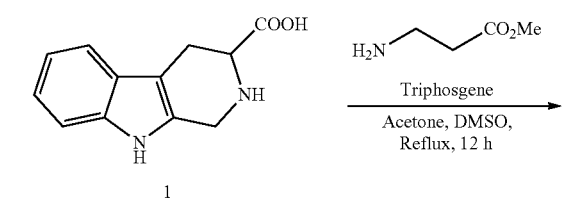

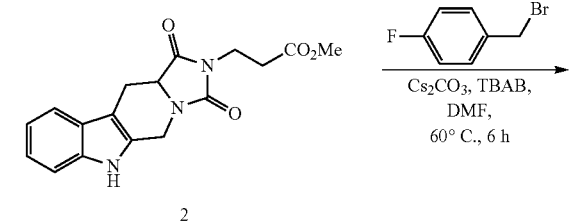

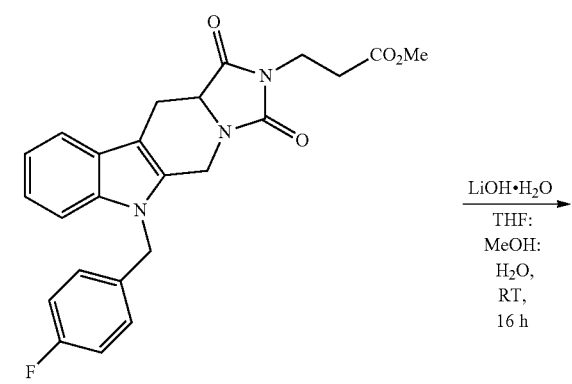

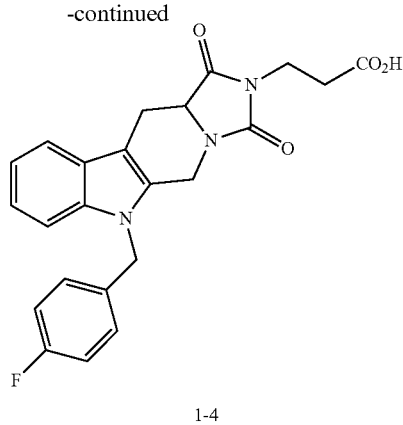

1-4

Following the procedure for Example 1 but using methyl 3-aminopropanoate in place of methyl 4-aminobutanoate in step 2, the title compound 1-4 was prepared as a pale yellow solid. 1H NMR (400 MHz, CD$_3$OD): δ 7.52 (d, J=8.0 Hz, 1H), 7.35 (d, J=8.0 Hz, 1H), 7.18-7.01 (m, 6H), 5.34 (s, 2H), 4.95 (d, J=16.0 Hz, 1H), 4.36-4.30 (m, 2H), 3.81 (d, J=7.2 Hz, 2H), 3.38-3.31 (m, 1H), 2.84-2.77 (m, 1H), 2.67 (d, J=7.2 Hz, 2H); MS (ESI): m/z 422.6 (M+H$^+$); HPLC: 85.5%; (column: Acquity BEH C-18 (50×2.1 mm, 1.7μ); RT 2.37 min; ACN: 0.025% TFA (aq); 0.5 mL/min.

Example 5: Synthesis of 3-(6-(4-fluorobenzyl)-1,3-dioxo-11,11a-dihydro-1H-imidazo[1',5':1,6]pyrido[3,4-b]indol-2(3H,5H,6H)-yl)propanoic acid (1-5; Enantiomer A) and 3-(6-(4-fluorobenzyl)-1,3-dioxo-11,11-a-dihydro-1H-imidazo[1',5':1,6]pyrido[3,4-b]indol-2(3H,5H,6H)-yl)propanoic acid (1-6; Enantiomer B)

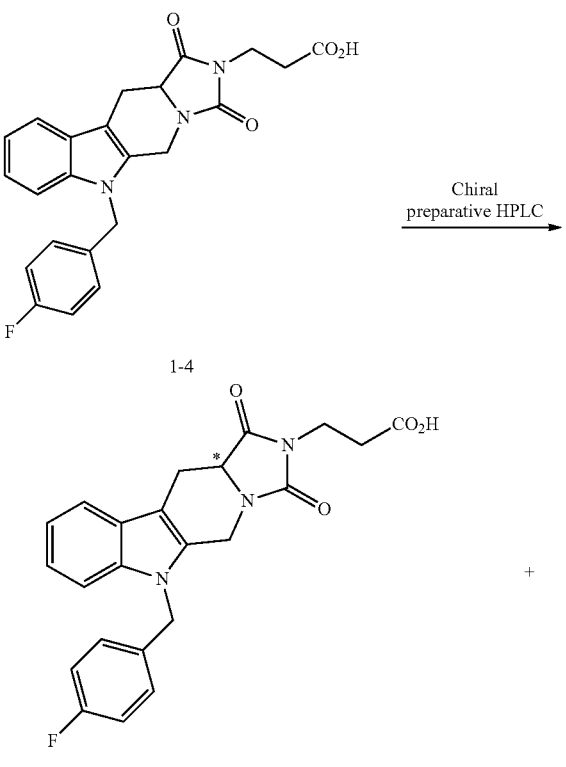

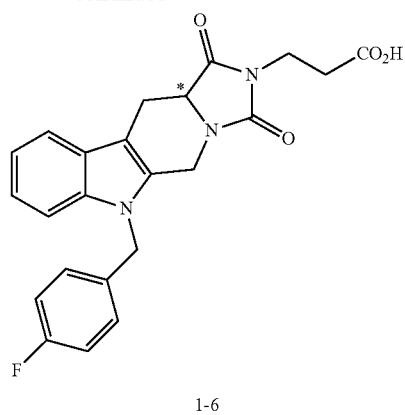

1-6

Separation of Two Enantiomers from Racemate 1-4:

120 mg of compound 1-4 (Example 4) with 97% HPLC purity was subjected to chiral preparative HPLC purification (column: Chiralpak IB, 250×20 mm; mobile phase (A): 0.1% TFA in n-Hexane; mobile phase (B): $CH_2Cl_2$: MeOH (50:50); eluent (A:B)=80:20; flow rate: 15 mL/min) to afford Enantiomer A 1-5 (15 mg) and Enantiomer B 1-6 (13 mg).

Enantiomer A 1-5: $^1$H NMR (400 MHz, $CD_3OD$): Data is identical with the racemate 1-4; MS (ESI): m/z 422.3 (M+H$^+$); HPLC: 80.1%; (column: Acquity BEH C-18 (50× 2.1 mm, 1.7µ); RT 2.37 min; ACN: 0.025% TFA (Aq); 0.5 mL/min; Chiral HPLC: 83.0%; $R_f$=14.18 min (Chiralpak IB, 250×4.6 mm, 5 µm); mobile phase (A) 0.1% TFA in n-Hexane (B) $CH_2Cl_2$:MeOH (50:50) (A:B=80:20); flow rate: 1.0 mL/min); ee: 100%.

This material is identical to the compound prepared from L-tryptophan following the procedure described in Example 2 but using tert-butyl β-alanine ester.HCl in place of tert-butyl 4-aminobutanoate hydrochloride in step 5.

Enantiomer B 1-6: $^1$H NMR (400 MHz, $CD_3OD$): Data is identical with the racemate 1-4; MS (ESI): m/z 422.3 (M+H$^+$); UPLC: 98.8%; (column: Acquity BEH C-18 (50× 2.1 mm, 1.7µ); RT 2.38 min; ACN: 0.025% TFA (Aq); 0.5 mL/min; Chiral HPLC: 98.9%, $R_f$=16.74 min (Chiralpak IB, 250×4.6 mm, 5 µm); mobile phase (A) 0.1% TFA in n-Hexane (B) $CH_2Cl_2$:MeOH (50:50) (A:B=80:20); flow rate: 1.0 mL/min); ee: 97.9%

Alternative preparation of (S)-3-(6-(4-fluorobenzyl)-1,3-dioxo-5,6,11,11a-tetrahydro-1H-imidazo[1′,5′:1,6]pyrido[3,4-b]indol-2(3H)-yl)propanoic acid (1-5; Enantiomer A)

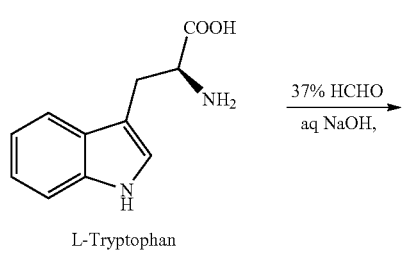

L-Tryptophan

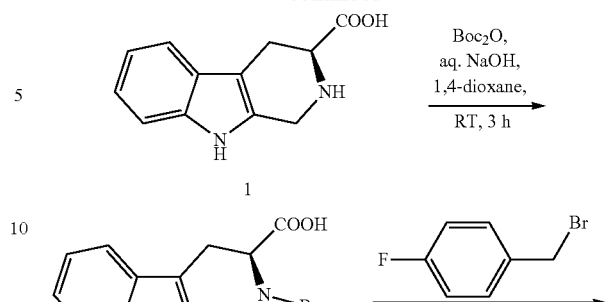

1-5 Enantiomer A

-continued

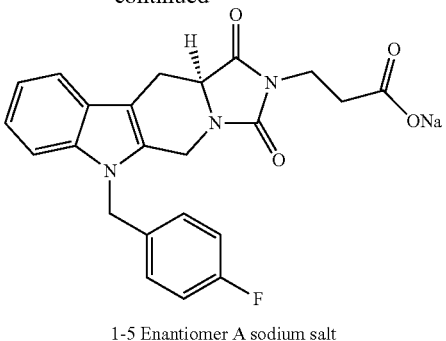

1-5 Enantiomer A sodium salt

Step 1: Synthesis of (S)-2,3,4,9-tetrahydro-1H-pyrido[3,4-b]indole-3-carboxylic acid (1)

Formaldehyde (37% aq. solution, 39.7 mL, 490 mmol) was added to a stirred solution of L-tryptophan (100.0 g, 490 mmol) in aqueous NaOH (19.6 g in 200 mL of $H_2O$, 490 mmol) and stirred for 2 hr. The mixture was heated to reflux and stirred for 3.5 hr. The mixture was cooled to 50° C. and carefully acidified to pH 5-6 with 6.0 M $HCl_{(aq)}$ solution. The mixture was diluted with water (200 mL). The flask was removed from heat and cooled to room temperature. The precipitates filtered off and washed with water. The solids were resuspended in THF (800 mL), stirred at RT for 1 hr, and filtered to afford compound 1 (101.3 g, 95%) as beige solid. $^1$H NMR (300 MHz, DMSO-$d_6$): δ 10.93 (s, 1H), 8.88 (br s, 1H), 7.43 (d, 1H), 7.31 (d, 1H), 7.02 (t, 1H), 6.97 (t, 1H), 4.18 (q, 2H), 3.61-3.56 (m, 1H), 3.12 (dd, 1H), 2.83-2.75 (m, 1H); LC-MS [M+H$^+$ 217].

Step 2: Synthesis of (S)-2-(tert-butoxycarbonyl)-2,3,4,9-tetrahydro-1H-pyrido[3,4-b]indole-3-carboxylic acid (2)

$K_2CO_3$ (129.5 g, 937 mmol) dissolved in water (470 mL) was poured into a stirred solution of (S)-2,3,4,9-tetrahydro-1H-pyrido[3,4-b]indole-3-carboxylic acid (1; 101.3 g, 468 mmol) and di-tert-butyl dicarbonate (122.7 g, 562 mmol) in THF (470 mL) at 0° C. The reaction was stirred at room temperature overnight. The next day the THF was removed under reduced pressure and the remaining residue was carefully acidified to pH 3-4 with saturated citric acid solution. The precipitants filtered off and washed with water to afford compound 2 (143.5 g, 97%) as a beige powder. $^1$H NMR (300 MHz, DMSO-$d_6$): δ 12.75 (br s, 1H), 10.88 (s, 1/2H), 10.83 (s, 1/2H), 7.40 (d, 1H), 7.28-7.25 (m, 1H), 7.05 (t, 1H), 6.92 (t, 1H), 5.15-5.10 (m, 1H), 4.69 (t, 1H), 4.45-4.29 (m, 1H), 3.30-3.23 (m, 1H), 2.98-2.88 (m, 1H), 1.46 (s, 9×1/2H), 1.42 (s, 9×1/2H); LC-MS [M+H$^+$317].

Step 3: Synthesis of (S)-2-(tert-butoxycarbonyl)-9-(4-fluorobenzyl)-2,3,4,9-tetrahydro-1H-pyrido[3,4-b]indole-3-carboxylic acid (3)

The acid 2 (20.0 g, 63.2 mmol) in DMF (630 mL) was degassed and the flask was cooled in ice water bath. NaH (60% in mineral oil; 7.8 g, 196.0 mmol) was slowly added portionwise over 45 min at 0° C. and stirred for 1 hr. 4-fluorobenzyl bromide (8.7 mL, 69.5 mmol) was added dropwise over 45 min at 0° C. and stirred for 1.5 hr. The reaction quenched with water.

The mixture diluted with water (1.8 L) and washed with EtOAc (1 L). The aqueous layer was acidified to pH 3-4 with solid citric acid. The mixture extracted with EtOAc (3×300 mL). The combined organic extracts were washed with water (900 mL), brine (200 mL), dried over $Na_2SO_4$, filtered, and concentrated under reduced pressure. The crude was purified by silica gel column chromatography using 0-30% EtOAc/Hexane to give a solid. The solid was washed with 10% $CH_2Cl_2$/hexane to afford the acid 3 (19.5 g, 72%) as a white powder. $^1$H NMR (300 MHz, DMSO-$d_6$): δ 12.81 (br s, 1H), 7.48-7.42 (m, 2H), 7.13-6.97 (m, 6H), 5.41-5.28 (m, 2H), 5.14-5.03 (m, 1H), 4.66-4.58 (m, 1H), 4.42-4.27 (m, 1H), 3.32-3.28 (m, 1H), 3.06-2.96 (m, 1H), 1.40 (s, 9×1/2H), 1.39 (s, 9×1/2H); LC-MS [M+H$^+$425].

Step 4: Synthesis of (S)-9-(4-fluorobenzyl)-2,3,4,9-tetrahydro-1H-pyrido[3,4-b]indole-3-carboxylic acid (4)

The acid 3 (18.9 g, 44.5 mmol), 4M HCl in 1,4-dioxane solution (56 mL, 222.7 mmol), and 1,4-dioxane (85 mL) stirred at RT overnight. The reaction diluted with water (200 mL) and neutralized to pH 7 with $Et_3N$. Water (400 mL) was added and the mixture stirred for 30 min. The solid was collected by filtration and washed with water (300 mL) to afford the amino acid 4 (13.0 g, 90%) as a pale yellow powder. $^1$H NMR (300 MHz, DMSO-$d_6$): δ 8.95 (br s, 1H), 7.48 (d, 1H), 7.39 (d, 1H), 7.14-6.99 (m, 6H), 5.33 (s, 2H), 4.24 (d, 1H), 4.08 (d, 1H), 3.63-3.58 (m, 1H), 3.17-3.10 (m, 1H), 2.86-2.81 (m, 1H); LC-MS [M+H$^+$325].

Step 5: Synthesis of tert-butyl 3-isocyanatopropionate (5)

β-Alanine tert-butyl ester hydrochloride (13.0, 71.6 mmol) in $CH_2Cl_2$ (240 mL) and saturated $NaHCO_{3(aq)}$ solution (240 mL) was degassed and the flask was cooled in ice water bath. Triphosgene (21.2 g, 71.6 mmol) was added in one portion under inert atmosphere at 0° C. The reaction stirred at 0° C. to RT over 2.5 hr. The reaction was diluted with water (500 mL) and poured into separatory funnel. The layers separated and the aqueous layer was extracted with $CH_2Cl_2$. The combined organic extracts were washed with brine, dried over $Na_2SO_4$, filtered, and concentrated under reduced pressure to obtain crude 5 (11.5 g) as a yellow liquid. This crude material was directly used for next reaction without purification. $^1$H NMR (300 MHz, $CDCl_3$): δ 3.53 (t, 2H), 2.52 (t, 2H), 1.47 (s, 9H).

Step 6: Synthesis of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate (6)

The amino acid 4 (21.0 g, 64.7 mmol) and anhydrous DMA (260 mL) in 1 L round bottom flask equipped with condenser was degassed. tert-Butyl 3-isocyanatopropionate (5) (11.1 g, 64.7 mmol) was added and the mixture was heated to 100° C. overnight. The reaction cooled to room temperature and diluted with water (1.25 L) and brine (50 mL). The mixture extracted with EtOAc (3×300 mL). The combined organic extracts were washed with water (900 mL), brine (200 mL), dried over $Na_2SO_4$, filtered, and concentrated under reduced pressure. The crude material was purified through a silica gel column with 10% EtOAc/$CH_2Cl_2$. The fractions concentrated under reduce pressure to provide a solid. The solid was washed with 10% $CH_2Cl_2$/Hexane to afford the ester 6 (25.9 g, 84%). $^1$H NMR (300 MHz, DMSO-$d_6$): δ 7.54 (d, 1H), 7.47 (d, 1H), 7.16-7.02 (m, 6H), 5.42 (q, 2H), 4.88 (d, 1H), 4.41-4.30 (m, 2H), 3.62 (t, 2H), 3.31-3.23 (m, 1H), 2.77-2.68 (m, 1H), 1.34 (s, 9H); LC-MS [M+H$^+$478].

Step 7: Synthesis of (S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid (1-5; Enantiomer A)

The tert-butyl ester 6 (20.0 g, 41.9 mmol) was added to a solution of 4N HCl in 1,4-dioxane (100 mL) at RT and stirred for 6 hr. The reaction was diluted with ice-cold water (1 L) and extracted with EtOAc (2×150 mL). The combined organic extracts were washed with Na$_2$SO$_4$, filtered, and concentrated under reduced pressure to obtain the crude. The crude was purified by silica gel column chromatography using 0-70% EtOAc/Hexane. The combined fractions were concentrated under reduced pressure to afford pale yellow foam (16.4 g). The foam was dissolved in isopropyl acetate (75 mL) and then ether (75 mL) was added. Pentane (10 mL) was added to the solution and sonicated until a precipitate formed. Pentane (100 mL) was added. The mixture stirred at RT for 1.5 hr. The solids filtered off and washed with isopropyl acetate: ether: pentane (150 mL, 1:1:1.5) to afford (S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid (1-5) (12.8 g, 72%) as a white solid. $^1$H NMR (300 MHz, DMSO-d$_6$): δ 12.37 (s, 1H), 7.54 (d, 1H), 7.48 (d, 1H), 7.15-7.02 (m, 6H), 5.42 (q, 2H), 4.89 (d, 1H), 4.40-4.30 (m, 2H), 3.65 (d, 2H), 3.32-3.22 (m, 1H), 2.79-2.70 (m, 1H), 2.56-2.54 (m, 2H); LC-MS [M+H$^+$422].

Step 8: Synthesis of (S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid sodium salt (1-5 sodium salt)

(S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid (1-5) (40.35 g, 95.7 mmol) dissolved in tetrahydrofuran (960 mL) in 2 L round bottom flask equipped with addition funnel was degassed and cooled in ice water bath. 1M NaOH (86.2 mL, 86.2 mmol) was added dropwise over 3 hr at 0° C. The solvent removed under reduce pressure to afford (S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid sodium salt (1-5 sodium salt; 42.4 g, 100%) as a pale yellow solid. $^1$H NMR (300 MHz, DMSO-d$_6$): δ 7.53 (d, 1H), 7.47 (d, 1H), 7.16-7.02 (m, 6H), 5.40 (q, 2H), 4.89 (d, 1H), 4.36-4.28 (m, 2H), 3.56-3.49 (m, 2H), 3.27-3.20 (m, 1H), 2.76-2.67 (m, 1H), 2.17-2.11 (m, 2H); LC-MS [M+H$^+$422].

Example 6: Synthesis of 4-(1,3-dioxo-6-(3-phenylpropyl)-11,11a-dihydro-1H-imidazo[1',5':1,6]pyrido[3,4-b]indol-2(3H,5H,6H)-yl)butanoic acid (1-7)

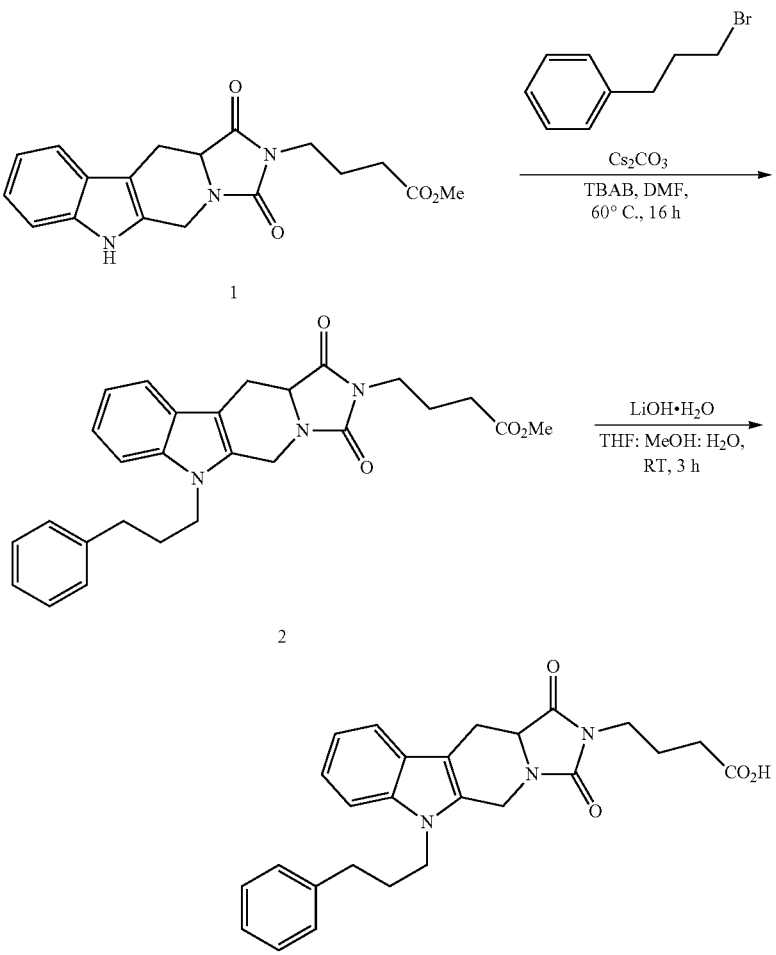

Step 1: Synthesis of methyl 4-(1,3-dioxo-6-(3-phenylpropyl)-5,6,11,11a-tetrahydro-1H-imidazo[1',5':1,6]pyrido[3,4-b]indol-2(3H)-yl)butanoate (2)

To a stirred solution of methyl 4-(1,3-dioxo-5,6,11,11a-tetrahydro-1H-imidazo[1',5':1,6]pyrido[3,4-b]indol-2(3H)-yl)butanoate 1 (Example 1, step 2; 100 mg, 0.29 mmol) in DMF (1 mL) under inert atmosphere were added Cs$_2$CO$_3$ (190 mg, 0.58 mmol), TBAB (4 mg, 0.014 mmol) and (3-bromopropyl)benzene (0.05 mL, 0.35 mmol) at RT; heated to 60° C. and stirred for 16 h. The reaction was monitored by TLC; after completion of the reaction, the reaction mixture was allowed to cool to RT, diluted with water (20 mL) and extracted with EtOAc (2×20 mL). The combined organic extracts were dried over Na$_2$SO$_4$, filtered and concentrated under reduced pressure to obtain the crude. The crude was purified through silica gel column chromatography using 7-10% EtOAc/Hexanes to afford compound 2 (22 mg, 16%) as yellow thick syrup. $^1$H NMR (400 MHz, DMSO-d$_6$): δ 7.50 (d, J=7.6 Hz, 1H), 7.37 (d, J=7.6 Hz, 1H), 7.29-7.26 (m, 2H), 7.20-7.17 (m, 3H), 7.12 (t, J=7.6 Hz, 1H), 7.02 (t, J=7.6 Hz, 1H), 4.99 (d, J=16.0 Hz, 1H), 4.44-4.37 (m, 2H), 4.13 (t, J=7.2 Hz, 2H), 3.58 (s, 3H), 3.49 (t, J=7.6 Hz, 2H), 3.29-3.24 (m, 1H), 2.77-2.75 (m, 1H), 2.65 (t, J=7.6 Hz, 2H), 2.34 (t, J=7.6 Hz, 2H), 2.01-1.97 (m, 2H), 1.82-1.78 (m, 2H); LC-MS (ESI): 89.2%; m/z 460.6 (M+H$^+$); (column: X Select C-18, 50×3.0 mm, 3.5 μm); RT 4.04 min; 5 mM NH$_4$OAc: ACN; 0.8 mL/min).

Step 2: Synthesis of 4-(1,3-dioxo-6-(3-phenylpropyl)-11,11a-dihydro-1H-imidazo[1',5':1,6]pyrido[3,4-b]indol-2(3H,5H,6H)-yl)butanoic acid To a stirred solution of compound 2 (21 mg, 0.045 mmol) in THF:MeOH:H$_2$O (3:1:1, 2.5 mL) under inert atmosphere were added LiOH.H$_2$O (6 mg, 0.14 mmol) at 0° C.; warmed to RT and stirred for 3 h. The reaction was monitored by TLC; after completion of the reaction, the reaction mixture was diluted with water (15 mL), acidified with 1N aqueous HCl solution to pH~2 and extracted with CH$_2$Cl$_2$ (2×20 mL). The combined organic extracts were dried over Na$_2$SO$_4$, filtered and concentrated under reduced pressure to obtain the crude. The crude was triturated with n-pentane (2×5 mL) to afford the title compound 1-7 (8 mg, 40%) as pale yellow solid. 1H NMR (400 MHz, DMSO-d$_6$): δ 12.05 (br s, 1H), 7.50 (d, J=7.6 Hz, 1H), 7.37 (d, J=7.6 Hz, 1H), 7.28-7.26 (m, 2H), 7.23-7.13 (m, 4H), 7.03 (t, J=7.6 Hz, 1H), 5.00 (d, J=16.0 Hz, 1H), 4.44-4.36 (m, 2H), 4.13 (t, J=6.8 Hz, 2H), 3.48 (t, J=7.2 Hz, 2H), 3.27-3.23 (m, 1H), 2.77-2.73 (m, 1H), 2.65 (t, J=7.2 Hz, 2H), 2.24 (t, J=7.2 Hz, 2H), 1.97-1.94 (m, 2H), 1.80-1.76 (m, 2H); LC-MS (ESI): 85.71%; m/z 446.5 (M+H$^+$); (column: X Select CSH C-18, 50×3.0 mm, 3.5 μm); RT 3.00 min; 5 mM NH$_4$OAc: ACN; 0.8 mL/min); UPLC: 88.2%; (column: Acquity BEH C-18 (50×2.1 mm, 1.7μ); RT 2.59 min; ACN: 0.025% TFA (aq); 0.5 mL/min.

Example 7: Synthesis of 6-(4-fluorobenzyl)-5,6,11,11a-tetrahydrooxazolo[3',4':1,6]pyrido[3,4-b]indol-3(1H)-one (1-8)

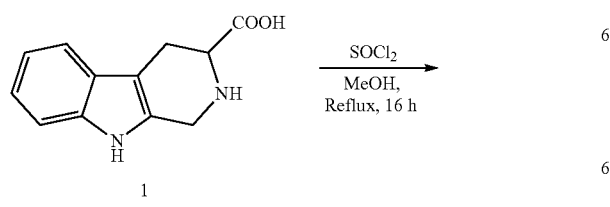

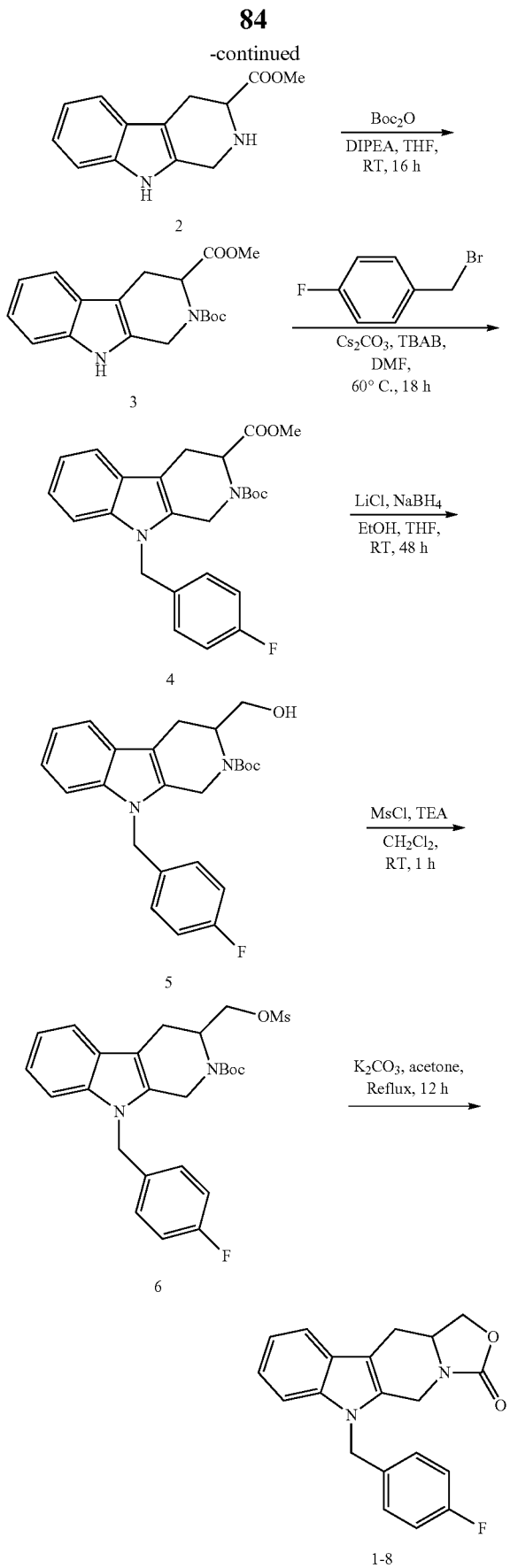

Step 1: Synthesis of methyl 2,3,4,9-tetrahydro-1H-pyrido[3,4-b]indole-3-carboxylate (2)

To a stirred solution of 2,3,4,9-tetrahydro-1H-pyrido[3,4-b]indole-3-carboxylic acid 1 (Example 1, step 1; 4.0 g, 18.5 mmol) in MeOH (50 mL) under inert atmosphere was added thionyl chloride (10 mL) at RT; heated to reflux and stirred for 16 h. The reaction was monitored by TLC; after completion of the reaction, the volatiles were removed under reduced pressure. The residue was diluted with water (40 mL), pH was adjusted to ~9 using saturated aq. NaHCO$_3$ solution and extracted with EtOAc (2×40 mL). The combined organic extracts were washed with brine (35 mL), dried over Na$_2$SO$_4$, filtered and concentrated under reduced pressure to obtain compound 2 (4.2 g, 99%) as a colorless syrup.

Step 2; Synthesis of 2-(tert-butyl) 3-methyl 1,3,4,9-tetrahydro-2H-pyrido[3,4-b]indole-2,3-dicarboxylate (3)

To a stirred solution of compound 2 (4.2 g, 18.3 mmol) in THF (30 mL) under inert atmosphere were added diisopropyl ethyl amine (3.18 mL, 18.3 mmol) and Boc-anhydride (3.58 mg, 16.4 mmol) at RT and stirred for 16 h. The reaction was monitored by TLC; after completion of the reaction, the reaction mixture was diluted with water (40 mL) and extracted with EtOAc (2×35 mL). The combined organic extracts were washed with brine (20 mL), dried over Na$_2$SO$_4$, filtered and concentrated under reduced pressure to obtain the crude. The crude was purified through silica gel column chromatography using 10-15% EtOAc/Hexanes to afford compound 3 (3.7 g, 61%) as a pale yellow oil. $^1$H NMR (500 MHz, DMSO-d$_6$): δ 10.89 (s, 1/2H), 10.84 (s, 1/2H), 7.41 (d, J=7.5 Hz, 1H), 7.29-7.27 (m, 1H), 7.04 (t, J=7.5 Hz, 1H), 6.96 (t, J=7.5 Hz, 1H), 5.27-5.14 (m, 1H), 4.77-4.70 (m, 1H), 4.44-4.30 (m, 1H), 3.57 (s, 3/2H), 3.56 (m, 3/2H), 3.28-3.26 (m, 1H), 3.03-2.97 (m, 1H), 1.48-1.43 (m, 9H); LC-MS (ESI): 94.6%; m/z 329.3 (M−H$^-$); (column: X Select C-18, 50×3.0 mm, 3.5 μm); RT 3.80 min; 5 mM NH$_4$OAc: ACN; 0.8 mL/min).

Step 3: Synthesis of 2-(tert-butyl) 3-methyl 9-(4-fluorobenzyl)-1,3,4,9-tetrahydro-2H-pyrido[3,4-b]indole-2,3-dicarboxylate (4)

To a stirred solution of compound 3 (3.7 g, 11.2 mmol) in DMF (25 mL) under inert atmosphere were added 4-fluorobenzyl bromide (2.1 mL, 16.8 mmol), Cs$_2$CO$_3$ (7.28 g, 22.4 mmol) and TBAB (181 mg, 0.56 mmol) at RT; heated to 60° C. and stirred for 18 h. The reaction was monitored by TLC; after completion of the reaction, the reaction mixture was cooled to rt, diluted with cold water (40 mL) and extracted with EtOAc (2×30 mL). The combined organic extracts were washed with brine (30 mL), dried over Na$_2$SO$_4$, filtered and concentrated under reduced pressure to obtain the crude. The crude was purified through silica gel column chromatography using 10-15% EtOAc/Hexanes to afford 3.65 g of compound 4 with 63% purity. This material was directly taken for next step without further purification.

Step 4: Synthesis of tert-butyl 9-(4-fluorobenzyl)-3-(hydroxymethyl)-1,3,4,9-tetrahydro-2H-pyrido[3,4-b]indole-2-carboxylate (5)

To a stirred solution of anhydrous LiCl (767 mg, 18.26 mmol) in EtOH (15 mL) under inert atmosphere was added NaBH$_4$ (694 mg, 18.26 mmol) at 0° C.; warmed to RT and stirred for 1 h. To this, compound 4 (1.6 g) in anhydrous THF (20 mL) was added at 0° C.; warmed to RT and stirred for 48 h. The reaction was monitored by TLC; after completion of the reaction, the volatiles were removed under reduced pressure. The residue was diluted with water (30 mL) and extracted with EtOAc (3×20 mL). The combined organic extracts were washed with brine (25 mL), dried over Na$_2$SO$_4$, filtered and concentrated under reduced pressure to obtain the crude. The crude was purified through silica gel column chromatography using 15-20% EtOAc/Hexanes to afford compound 5 (997 mg) as colorless viscous oil. $^1$H NMR (500 MHz, DMSO-d$_6$): δ 7.45 (d, J=7.5 Hz, 2H), 7.14-7.01 (m, 6H), 5.36-5.29 (m, 2H), 4.79 (t, J=5.5 Hz, 2H), 4.56-4.51 (m, 1H), 4.04-4.01 (m, 2H), 2.85-2.81 (m, 2H), 1.43-1.36 (m, 9H); LC-MS (ESI): 97.02%; m/z 411.5 (M+H$^+$); (column: X Select C-18, 50×3.0 mm, 3.5 μm); RT 4.33 min; 5 mM NH$_4$OAc: ACN; 0.8 mL/min).

Step 5: Synthesis of tert-butyl 9-(4-fluorobenzyl)-3-(((methylsulfonyl)oxy)methyl)-1,3,4,9-tetrahydro-2H-pyrido[3,4-b]indole-2-carboxylate (6)

To a stirred solution of compound 5 (150 mg, 0.36 mmol) in CH$_2$Cl$_2$ (8 mL) under inert atmosphere were added Et$_3$N (0.13 mL, 0.91 mmol), methane sulfonyl chloride (0.03 mL, 0.36 mmol) drop wise for 2 min at RT and stirred for 1 h. The reaction was monitored by TLC; after completion of the reaction, the reaction mixture was diluted with water (20 mL) and extracted with CH$_2$Cl$_2$ (2×20 mL). The combined organic extracts were washed with brine (20 mL), dried over Na$_2$SO$_4$, filtered and concentrated under reduced pressure to obtain the crude compound 6 (130 mg, crude) as pale yellow semi-solid. The crude was carried to the next step without further purification.

Step 6: Synthesis of 6-(4-fluorobenzyl)-5,6,11,11a-tetrahydrooxazolo[3',4':1,6]pyrido[3,4-b]indol-3(1H)-one To a stirred solution of compound 6 (130 mg, 0.26 mmol) in acetone (10 mL) under inert atmosphere were added potassium carbonate (220 mg, 1.59 mmol) at RT; heated to reflux and stirred for 12 h. The reaction was monitored by TLC; after completion of the reaction, the volatiles were removed under reduced pressure. The residue was diluted with water (20 mL) and extracted with EtOAc (2×20 mL). The combined organic extracts were dried over Na$_2$SO$_4$, filtered and concentrated under reduced pressure to obtain the crude. The crude was purified through silica gel column chromatography using 20-30% EtOAc/Hexanes to afford the title compound 1-8 (40 mg, 45%) as an off-white solid. $^1$H NMR (400 MHz, CD$_3$OD): δ 7.49 (d, J=7.6 Hz, 1H), 7.33 (d, J=8.4 Hz, 1H), 7.16-7.12 (m, 1H), 7.09-6.98 (m, 5H), 5.33 (s, 2H), 4.74-4.64 (m, 2H), 4.32-4.27 (m, 2H), 4.18-4.10 (m, 1H), 3.17-3.12 (m, 1H), 2.79-2.72 (m, 1H); MS (ESI): m/z 336.9 (M+); UPLC: 99.2%; (column: Acquity BEH C-18 (50×2.1 mm, 1.7μ); RT 2.53 min; ACN: 0.025% TFA (aq); 0.5 mL/min.

Example 8: Synthesis of (S)-6-(4-fluorobenzyl)-5,6,11,11a-tetrahydrooxazolo[3',4':1,6]pyrido[3,4-b]indol-3(1H)-one (1-9)

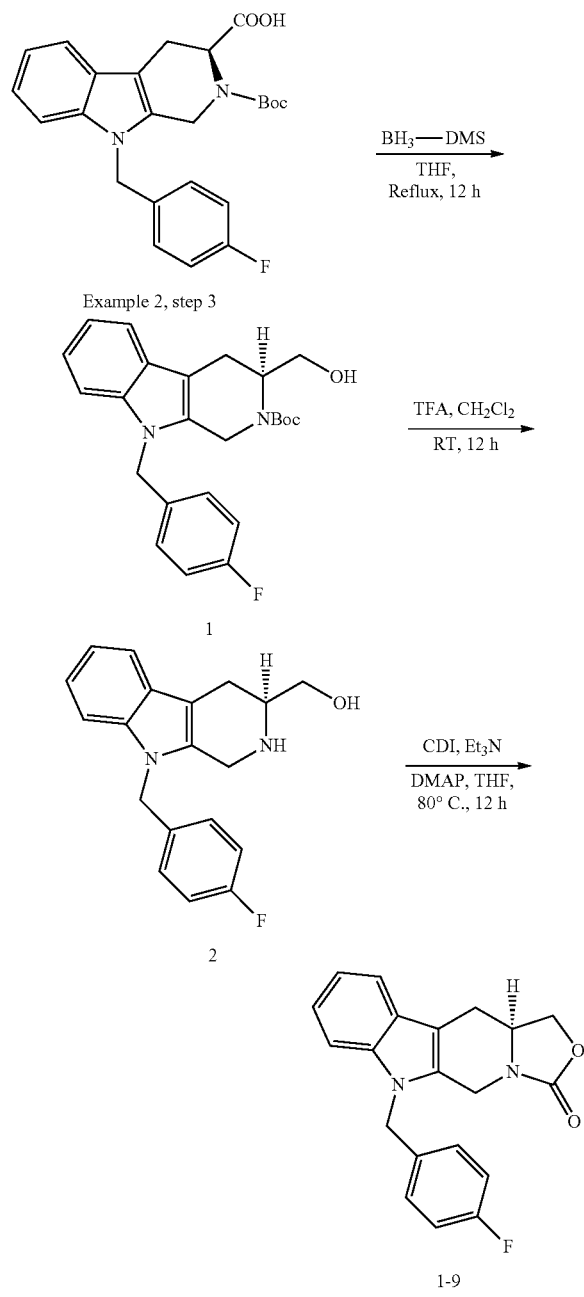

Step 1: Synthesis of tert-butyl (S)-9-(4-fluorobenzyl)-3-(hydroxymethyl)-1,3,4,9-tetrahydro-2H-pyrido[3,4-b]indole-2-carboxylate (1)

To a stirred solution of (S)-2-(tert-butoxycarbonyl)-9-(4-fluorobenzyl)-2,3,4,9-tetrahydro-1H-pyrido[3,4-b]indole-3-carboxylic acid (Example 2, step 3; 500 mg, 1.17 mmol) in dry THF (20 mL) under inert atmosphere was added BH$_3$.DMS (5M in ether, 0.75 mL, 3.53 mmol) at 0° C.; heated to 80° C. and stirred for 12 h. The reaction was monitored by TLC; after completion of the reaction, the reaction mixture was quenched with ice-cold water (20 mL) and extracted with EtOAc (2×30 mL). The combined organic extracts were dried over Na$_2$SO$_4$, filtered and concentrated under reduced pressure to obtain the crude. The crude was purified through silica gel column chromatography using 10-15% EtOAc/Hexanes to afford 1 (370 mg, 77%) as an off-white solid. $^1$H NMR (400 MHz, CDCl$_3$): δ 7.51 (d, J=7.2 Hz, 1H), 7.16 (d, J=7.6 Hz, 1H), 7.12-7.10 (m, 2H), 6.99-6.95 (m, 4H), 5.20 (br s, 2H), 4.82-4.76 (m, 2H), 4.14-4.09 (m, 1H), 3.60-3.58 (m, 2H), 3.06-3.00 (m, 1H), 2.82-2.78 (m, 1H), 1.47 (s, 9H); LC-MS (ESI): 95.8%; m/z 411.3 (M+H$^+$); (column: X Select CSH C-18, 50×3.0 mm, 3.5 μm); RT 4.10 min; 5 mM NH$_4$OAc: ACN; 0.8 mL/min); UPLC: 93.4%; (column: Eclipse-XDB-C18 (150×4.6 mm, 5 μm); RT 11.69 min; ACN: 5 mM NH$_4$OAc; 1.0 mL/min; Chiral HPLC: 95.6%, R$_t$=5.13 min (Chiralpak IA, 250×4.6 mm, 5 μm); mobile phase (A) 0.1% DEA in n-Hexane (B) CH$_2$Cl$_2$:MeOH (50:50); (A:B=80:20); flow Rate: 1.0 mL/min).

Step 2: Synthesis of (S)-(9-(4-fluorobenzyl)-2,3,4,9-tetrahydro-1H-pyrido[3,4-b]indol-3-yl) methanol (2)

To a stirred solution of 1 (130 mg, 0.31 mmol) in CH$_2$Cl$_2$ (10 mL) under inert atmosphere was added TFA (0.5 mL) at 0° C.; warmed to RT and stirred for 12 h. The reaction was monitored by TLC; after completion of the reaction, the volatiles were removed under reduced pressure to afford compound 1 (150 mg) as yellow oil. The obtained material was taken for next reaction without purification.

Step 3: Synthesis of (S)-6-(4-fluorobenzyl)-5,6,11,11a-tetrahydrooxazolo[3',4':1,6]pyrido[3,4-b]indol-3(1H)-one (1-9)

To a stirred solution of compound 2 (75 mg, 0.24 mmol) in dry THF (20 mL) were added CDI (39 mg, 0.24 mmol), Et$_3$N (73 mg, 0.72 mmol) and DMAP (5.9 mg, 0.04 mmol) at 0° C. under inert atmosphere; heated to 80° C. and stirred for 12 h. The reaction was monitored by TLC; after completion of the reaction, the reaction mixture was diluted with water (15 mL) and extracted with EtOAc (2×20 mL). The combined organic extracts were dried over Na$_2$SO$_4$, filtered and concentrated under reduced pressure to obtain the crude. The crude was purified through silica gel column chromatography using 15-20% EtOAc/Hexanes to afford the title compound 1-9 (12 mg, 15%) as colorless oil. $^1$H NMR (400 MHz, CDCl$_3$): δ 7.51 (d, J=7.6 Hz, 1H), 7.28 (d, J=8.0 Hz, 1H), 7.23-7.13 (m, 2H), 6.98-6.96 (m, 4H), 5.26 (q, J=16.8 Hz, 2H), 4.80 (d, J=16.0 Hz, 1H), 4.65 (t, J=8.0 Hz, 1H), 4.27-4.20 (m, 2H), 4.11-4.04 (m, 1H), 3.16-3.11 (m, 1H), 2.85-2.79 (m, 1H); LC-MS (ESI): 99.0%; m/z 337.3 (M+H$^+$); (column: X Select CSH C-18, 50×3.0 mm, 3.5 μm); RT 4.47 min; 5 mM NH$_4$OAc: ACN; 0.8 mL/min); UPLC: 94.2%; (column: Acquity BEH C-18 (50×2.1 mm, 1.7μ); RT 2.53 min; ACN: 0.025% TFA (aq); 0.5 mL/min; Chiral HPLC: 85.1%, R$_t$=10.47 min (Chiralpak IA, 250×4.6 mm, 5μ); mobile phase (A) 0.1% DEA in n-Hexane, (B) CH$_2$Cl$_2$:MeOH (50:50); (A:B=80:20); flow Rate: 1.0 mL/min); ee=100%.

Example 9: Synthesis of (R)-6-(4-fluorobenzyl)-5,6,11,11a-tetrahydrooxazolo[3',4':1,6]pyrido[3,4-b]indol-3(1H)-one (1-10)

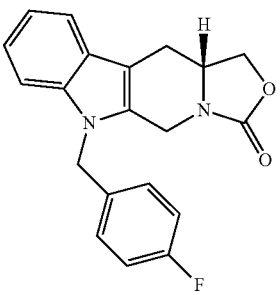

Following the procedure of Example 8 but using (R)-2-(tert-butoxycarbonyl)-9-(4-fluorobenzyl)-2,3,4,9-tetrahydro-1H-pyrido[3,4-b]indole-3-carboxylic acid in place of (S)-2-(tert-butoxycarbonyl)-9-(4-fluorobenzyl)-2,3,4,9-tetrahydro-1H-pyrido[3,4-b]indole-3-carboxylic acid in Step 1, the title compound 1-10 was prepared as an off-white solid. $^1$H NMR (400 MHz, CD$_3$OD): δ 7.49 (d, J=8.0 Hz, 1H), 7.33 (d, J=8.0 Hz, 1H), 7.16-7.12 (m, 1H), 7.09-6.97 (m, 5H), 5.32 (s, 2H), 4.73-4.63 (m, 2H), 4.31-4.25 (m, 2H), 4.16-4.09 (m, 1H), 3.16-3.11 (m, 1H), 2.77-2.70 (m, 1H); LC-MS (ESI): 95.0%; m/z 337.3 (M+H$^+$); (column: X Select CSH C-18, 50×3.0 mm, 3.5 µm); RT 4.47 min; 5 mM NH$_4$OAc: ACN; 0.8 mL/min); HPLC: 97.4%; (column: Eclipse-XDB-C18 (150×4.6 mm, 5 µm); RT 10.83 min; ACN: 5 mM NH$_4$OAc (aq); 1.0 mL/min; Chiral HPLC: 96.3%, Rt=11.17 min (Chiralpak IA, 250×4.6 mm, 5 pt); mobile phase (A) 0.1% DEA in n-Hexane (B) CH$_2$Cl$_2$: MeOH (50:50); (A:B=80:20); flow Rate: 1.0 mL/min); ee=100%.

Example 10: Synthesis of (S)-4-(6-((6-methoxypyridin-3-yl)methyl)-1,3-dioxo-11,11a-dihydro-1H-imidazo[1',5':1,6]pyrido[3,4-b]indol-2(3H,5H,6H)-yl)butanoic acid (1-11)

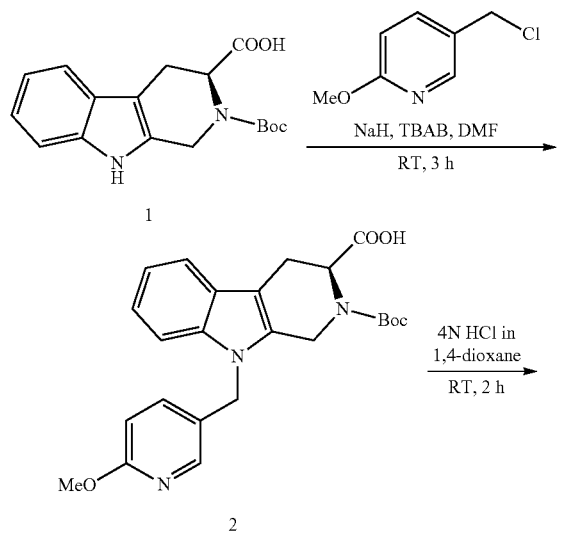

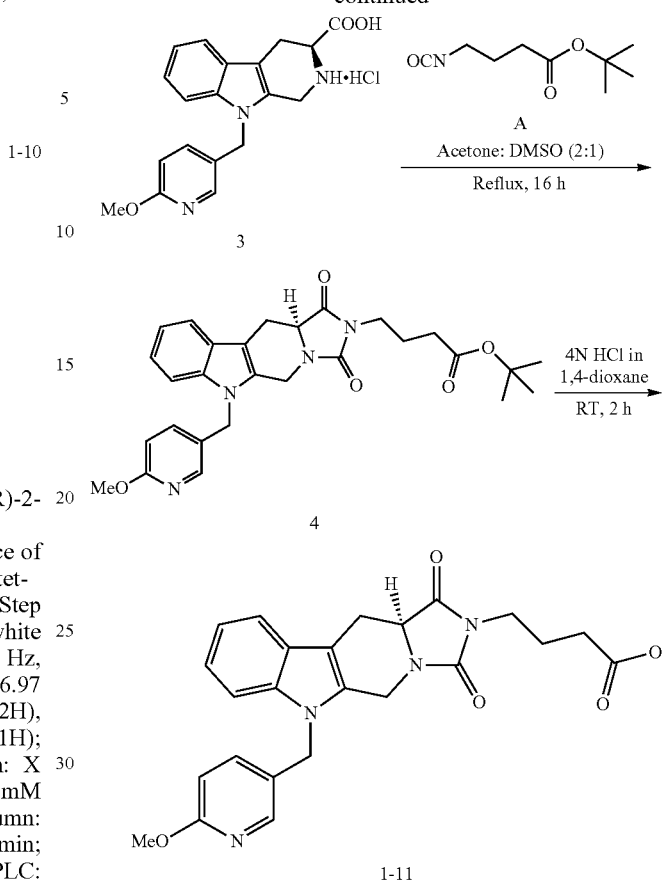

Step 1: Synthesis of (S)-2-(tert-butoxycarbonyl)-9-((6-methoxypyridin-3-yl)methyl)-2,3,4,9-tetrahydro-1H-pyrido[3,4-b]indole-3-carboxylic acid (2)

A solution of (S)-2-(tert-butoxycarbonyl)-2,3,4,9-tetrahydro-1H-pyrido[3,4-b]indole-3-carboxylic acid (1) (Example 2, step 2; 1.0 g, 3.16 mmol) in DMF (5 mL) was added to NaH (60% in mineral oil; 278 mg, 6.95 mmol) in DMF (15 mL) at 0° C. under inert atmosphere and stirred for 30 min. To this, 5-(chloromethyl)-2-methoxypyridine (596 mg, 3.79 mmol) was added at 0° C.; warmed to RT, added TBAB (25 mg) and stirred for 3 h. The reaction was monitored by TLC; after completion of the reaction, the reaction mixture was quenched with ice-cold water (20 mL) and extracted with EtOAc (2×30 mL). The combined organic extracts were dried over Na$_2$SO$_4$, filtered and concentrated under reduced pressure to obtain the crude. The crude was purified through silica gel column chromatography using 30-40% EtOAc/Hexanes to afford compound 2 (1.2 g, 86%) as pale brown oil. $^1$H NMR (500 MHz, DMSO-d$_6$): δ 12.83 (br s, 1H), 7.95 (s, 1/2H), 7.91 (s, 1/2H), 7.52-7.47 (m, 2H), 7.34-7.30 (m, 1H), 7.11 (t, J=7.5 Hz, 1H), 7.03 (t, J=7.5 Hz, 1H), 6.73 (d, J=8.0 Hz, 1H), 5.37-5.25 (m, 2H), 5.14-5.05 (m, 1H), 4.75-6.68 (m, 1H), 4.49-4.36 (m, 1H), 3.79 (s, 3H), 3.39-3.35 (m, 1H), 3.00-2.94 (m, 1H), 1.43 (s, 9H); MS (ESI): m/z 436.2 (M−H$^−$); HPLC: 99.0%; (column: Eclipse-XDB-C18 (150×4.6 mm, 5 µm); RT 7.95 min; ACN: 5 mM NH$_4$OAc (aq); 1.0 mL/min).

Step 2: Synthesis of (S)-9-((6-methoxypyridin-3-yl) methyl)-2,3,4,9-tetrahydro-1H-pyrido[3,4-b]indole-3-carboxylic acid hydrochloride (3)

Compound 2 (150 mg, 0.34 mmol) was dissolved in 4N HCl in 1,4-dioxane solution (4 mL) under inert atmosphere and stirred at RT for 2 h. The reaction was monitored by TLC; after completion of the reaction, the reaction mixture was diluted with EtOAc (20 mL). The obtained solid was filtered, washed with EtOAc (2×10 mL) and dried under reduced pressure to afford compound 2 (100 mg, 78%) as pale brown solid. $^1$H NMR (400 MHz, DMSO-$d_6$): δ 14.20 (br s, 1H), 10.03 (br s, 2H), 7.98 (s, 1H), 7.57-7.54 (m, 2H), 7.41 (d, J=7.2 Hz, 1H), 7.18 (t, J=7.2 Hz, 1H), 7.07 (d, J=7.2 Hz, 1H), 6.75 (d, J=8.0 Hz, 1H), 5.36 (s, 2H), 4.56-4.51 (m, 2H), 4.38-4.34 (m, 1H), 3.79 (s, 3H), 3.37-3.32 (m, 1H), 3.08-3.05 (m, 1H); LC-MS (ESI): 95.8%; m/z 338.3 (M+H$^+$); (column: X Select C-18, 50×3.0 mm, 3.5 µm); RT 3.02 min; 5 mM Aq. NH$_4$OAc: ACN; 0.8 mL/min).

Step 3: Synthesis of tert-butyl (S)-4-(6-((6-methoxypyridin-3-yl)methyl)-1,3-dioxo-5,6,11,11a-tetrahydro-1H-imidazo[1',5':1,6]pyrido[3,4-b]indol-2(3H)-yl)butanoate (4)

To a stirred solution of compound 3 (100 mg, 0.26 mmol) in acetone:DMSO (2:1, 7.5 mL) under inert atmosphere was added tert-butyl 4-isocyanatobutanoate (A) (100 mg) at RT; heated to reflux and stirred for 16 h. The reaction was monitored by TLC; after completion of the reaction, the reaction mixture was diluted with water (10 mL) and extracted with EtOAc (2×25 mL). The combined organic extracts were washed with saturated bicarbonate solution (20 ml), brine (20 mL), dried over Na$_2$SO$_4$, filtered and concentrated under reduced pressure to obtain the crude. The crude was purified through silica gel column chromatography using 20-30% EtOAc/Hexanes to afford compound 4 (50 mg, 38%) as pale brown solid. $^1$H NMR (500 MHz, DMSO-$d_6$): δ 8.02 (s, 1H), 7.58-7.56 (m, 2H), 7.39 (d, J=8.0 Hz, 1H), 7.16 (t, J=8.0 Hz, 1H), 7.04 (t, J=8.0 Hz, 1H), 6.76 (d, J=8.5 Hz, 1H), 5.39 (q, J=14.5 Hz, 2H), 4.98 (d, J=16.0 Hz, 1H), 4.39-4.37 (m, 2H), 3.78 (s, 3H), 3.45 (t, J=7.0 Hz, 2H), 3.26-3.21 (m, 1H), 2.78-2.76 (m, 1H), 2.23 (t, J=7.5 Hz, 2H), 1.77-1.73 (m, 2H), 1.37 (s, 9H); LC-MS (ESI): 97.2%; m/z 505.6 (M+H$^+$); (column: X Select CSH C-18, 50×3.0 mm, 3.5 µm); RT 4.13 min; 5 mM Aq. NH$_4$OAc: ACN; 0.8 mL/min); Chiral HPLC: 89.9%, (Chiralpak IA, 250×4.6 mm, 5 µm); mobile phase (A) 0.1% TFA in n-Hexane, (B) THF:MeOH (80:20), (A:B=75:25); flow rate: 1.0 mL/min).

Step 4: Synthesis of (S)-4-(6-((6-methoxypyridin-3-yl)methyl)-1,3-dioxo-11,11a-dihydro-1H-imidazo[1',5':1,6]pyrido[3,4-b]indol-2(3H,5H,6H)-yl)butanoic acid (1-11)

Compound 3 (50 mg, 0.09 mmol) was dissolved in a solution of 4N HCl in 1,4-dioxane (2 mL) under inert atmosphere and stirred at RT for 2 h. The reaction was monitored by TLC; after completion of the reaction, the reaction mixture was diluted with ice-cold water (15 mL) and extracted with EtOAc (2×15 mL). The combined organic extracts were dried over Na$_2$SO$_4$, filtered and concentrated under reduced pressure to obtain the crude. The crude was triturated with n-hexane (2×5 mL) to afford the title compound 1-11 (30 mg, 74%) as pale brown solid. $^1$H NMR (500 MHz, CD$_3$OD): δ 7.98 (s, 1H), 7.86 (d, J=8.0 Hz, 1H), 7.58 (d, J=7.5 Hz, 1H), 7.41 (d, J=8.0 Hz, 1H), 7.28 (d, J=8.0 Hz, 1H), 7.22 (t, J=7.5 Hz, 1H), 7.15 (t, J=8.0 Hz, 1H), 5.46-5.43 (m, 2H), 5.04 (d, J=16.0 Hz, 1H), 4.46-4.37 (m, 2H), 4.08 (s, 3H), 3.64-3.62 (m, 2H), 3.39-3.36 (m, 1H), 2.86-2.82 (m, 1H), 2.40-2.37 (t, J=7.5 Hz, 2H), 1.97-1.95 (m, 2H); MS (ESI): m/z 449.4 (M+H$^+$); UPLC: 88.3%; (column: Acquity BEH C-18 (50×2.1 mm, 1.7); RT 2.18 min; ACN: 0.025% TFA (aq); 0.5 mL/min; Chiral HPLC: 80.6%, R$_t$=15.68 min (Chiralpak IA, 250×4.6 mm, 5 µm); mobile phase (A) 0.1% TFA in n-Hexane, (B) THF:MeOH (80:20), (A:B=75:25); flow rate: 1.0 mL/min).

Example 11: Synthesis of (S)-3-(6-((6-methoxypyridin-3-yl)methyl)-1,3-dioxo-11,11a-dihydro-1H-imidazo[1',5':1,6]pyrido[3,4-b]indol-2(3H,5H,6H)-yl)propanoic acid (1-12)

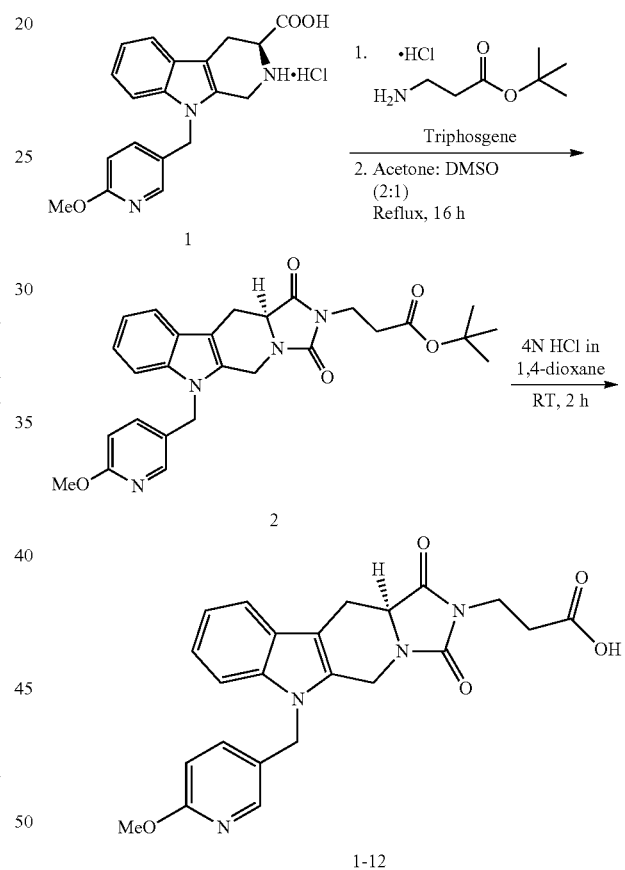

Step 1: Synthesis of tert-butyl (S)-3-(6-((6-methoxypyridin-3-yl)methyl)-1,3-dioxo-5,6,11,11a-tetrahydro-1H-imidazo[1',5':1,6]pyrido[3,4-b]indol-2(3H)-yl)propanoate (2)

To a stirred solution of tert-butyl 3-aminopropanoate hydrochloride (200 mg, 1.10 mmol) in CH$_2$Cl$_2$ (10 mL), saturated NaHCO$_3$ solution (10 mL) under inert atmosphere was added triphosgene (130 mg, 0.44 mmol) at 0° C. and stirred for 1 h. The reaction was monitored by TLC; after completion of the reaction, the reaction mixture was diluted with water (25 mL) and extracted with CH$_2$Cl$_2$ (2×25 mL). The combined organic extracts were washed with brine (20 mL), dried over Na₂SO₄, filtered and concentrated under reduced pressure to obtain 150 mg of isocyanate compound as pale brown syrup. ¹H NMR (500 MHz, DMSO-d₆): δ 3.48 (t, J=6.5 Hz, 2H), 2.54 (t, J=6.5 Hz, 2H), 1.40 (s, 9H).

To a stirred solution of compound 1 (Example 11, step 2; 150 mg, 0.40 mmol) in acetone:DMSO (2:1, 10.5 mL) under inert atmosphere was added the isocyanate (150 mg) at RT; heated to reflux and stirred for 16 h. The reaction was monitored by TLC; after completion of the reaction, the reaction mixture was diluted with water (25 mL) and extracted with EtOAc (2×30 mL). The combined organic extracts were washed with brine (20 mL), dried over Na₂SO₄, filtered and concentrated under reduced pressure to obtain the crude. The crude was purified through silica gel column chromatography using 20% EtOAc/Hexanes to afford compound 2 (40 mg, 20%) as an off-white solid. ¹H NMR (500 MHz, DMSO-d₆): δ 8.00 (s, 1H), 7.55-7.53 (m, 2H), 7.38 (d, J=8.0 Hz, 1H), 7.15 (t, J=7.5 Hz, 1H), 7.07 (t, J=8.5 Hz, 1H), 6.75 (d, J=8.5 Hz, 1H), 5.38 (q, J=14.5 Hz, 2H), 4.98 (d, J=16.5 Hz, 1H), 4.42-4.39 (m, 2H), 3.80 (s, 3H), 3.65 (t, J=7.0 Hz, 2H), 3.36-3.32 (m, 1H), 2.76-2.72 (m, 1H), 2.56-2.54 (m, 2H), 1.36 (m, 9H); LC-MS (ESI): 98.2%; m/z 491.6 (M+H⁺); (column: X Select CSH C-18, 50×3.0 mm, 3.5 μm); RT 4.02 min; 5 mM NH₄OAc: ACN; 0.8 mL/min).

Step 2: Synthesis of (S)-3-(6-((6-methoxypyridin-3-yl)methyl)-1,3-dioxo-11,11a-dihydro-1H-imidazo[1',5':1,6]pyrido[3,4-b]indol-2(3H,5H,6H)-yl)propanoic acid (1-12)

A solution of compound 2 (40 mg, 0.08 mmol) in 4N HCl in 1,4-dioxane (2 mL) was stirred at RT for 2 h under inert atmosphere. The reaction was monitored by TLC; after completion of the reaction, the reaction mixture was diluted with ice-cold water (10 mL) and extracted with EtOAc (2×15 mL). The combined organic extracts were washed with water (10 mL), brine (10 mL), dried over Na₂SO₄, filtered and concentrated under reduced pressure to obtain the crude. The crude was triturated with n-pentane (2×5 mL) to afford the title compound 1-12 (20 mg, 57%) as an off-white solid. 1H NMR (400 MHz, CD₃OD): δ 7.90 (s, 1H), 7.53 (d, J=7.6 Hz, 1H), 7.42 (d, J=8.0 Hz, 1H), 7.39 (d, J=7.6 Hz, 1H), 7.17 (t, J=7.6 Hz, 1H), 7.09 (t, J=7.6 Hz, 1H), 6.70 (d, J=8.0 Hz, 1H), 5.32 (s, 2H), 5.03 (d, J=16.0 Hz, 1H), 4.39-4.34 (m, 2H), 3.85 (s, 3H), 3.81 (t, J=7.2 Hz, 2H), 3.37-3.32 (m, 1H), 2.84-2.79 (m, 1H), 2.67 (t, J=7.2 Hz, 2H); MS (ESI): m/z 435.3 (M+H⁺); UPLC: 97.7%; (column: Acquity BEH C-18 (50×2.1 mm, 1.7); RT 2.15 min; ACN: 0.025% TFA (aq); 0.5 mL/min; Chiral HPLC: 94.7%, R_t=15.84 min (Chiralpak IA, 250×4.6 mm, 5 μm); mobile phase (A) 0.1% TFA in n-Hexane, (B) THF:MeOH (80:20), (A:B=75:25); flow rate: 1.0 mL/min).

Example 12: Synthesis of 6-(4-fluorobenzyl)-5,6,11,11a-tetrahydro-1H-imidazo[1',5':1,6]pyrido[3,4-b]indol-3(2H)-one (1-13)

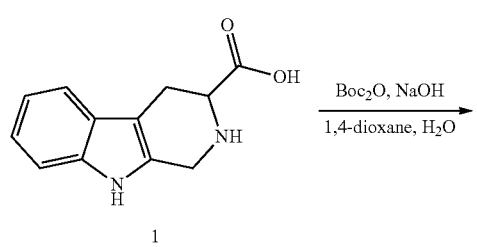

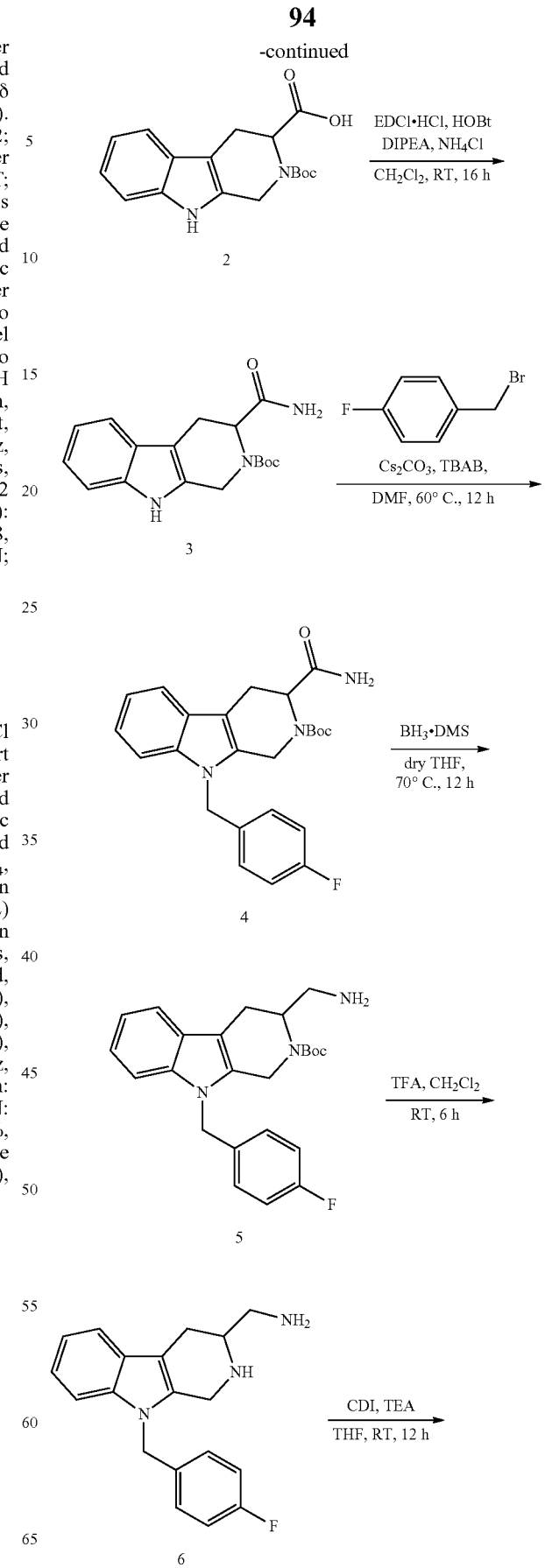

-continued

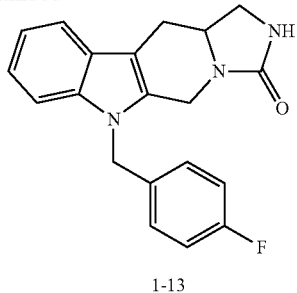

1-13

Step 1: Synthesis of 2-(tert-butoxycarbonyl)-2,3,4,9-tetrahydro-1H-pyrido[3,4-b]indole-3-carboxylic acid (2)

To a stirred solution of 2,3,4,9-tetrahydro-1H-pyrido[3,4-b]indole-3-carboxylic acid 1 (15.0 g, 69.44 mmol) in 1,4-dioxane (350 mL) under inert atmosphere were added aqueous NaOH solution (5.7 g in 180 mL of $H_2O$) and Boc-anhydride (15.5 g, 71.42 mmol) at 0° C.; warmed to RT and stirred for 4 h. The reaction was monitored by TLC; after completion of the reaction, the reaction mixture was acidified with citric acid. The obtained solid was diluted with water (100 mL) and extracted with EtOAc (3×80 mL). The combined organic extracts were washed with brine (70 mL), dried over $Na_2SO_4$, filtered and concentrated under reduced pressure to obtain compound 2 (17.0 g, 77%) as an off-white solid. $^1$H NMR (400 MHz, DMSO-$d_6$): Data suggested as 1:1 rotameric mixture; δ 12.72 (br s, 1H), 10.87 (s, 1/2H), 10.82 (s, 1/2H), 7.40 (d, J=8.0 Hz, 1H), 7.29-7.26 (m, 1H), 7.06-7.02 (m, 1H), 6.98-6.94 (m, 1H), 5.14-5.02 (m, 1H), 4.75-4.67 (m, 1H), 4.47-4.32 (m, 1H), 3.31-3.26 (m, 1H), 2.98-2.90 (m, 1H), 1.47 (s, 9/2H), 1.44 (s, 9/2H); LC-MS (ESI): 99.06%; m/z 315.3 (M−H$^-$); (column: X Select CSH C-18, 50×3.0 mm, 3.5 μm); RT 2.53 min; 5 mM NH$_4$OAc: ACN; 0.8 mL/min).

Step 2: Synthesis of tert-butyl 3-carbamoyl-1,3,4,9-tetrahydro-2H-pyrido[3,4-b]indole-2-carboxylate (3)

To a stirred solution of compound 2 (15.0 g, 47.40 mmol) in $CH_2Cl_2$ (500 mL) under inert atmosphere were added EDCI.HCl (55.45 g, 290.32 mmol), HOBt (39.19 g, 290.32 mmol), DIEA (37.45 g, 290.32 mmol), NH$_4$Cl (2.56 g, 48.38 mmol) at 0° C.; warmed to RT and stirred for 16 h. The reaction was monitored by TLC; after completion of the reaction, the reaction mixture was diluted with water (100 mL) and extracted with EtOAc (3×80 mL). The combined organic extracts were washed with brine (2×70 mL), dried over $Na_2SO_4$, filtered and concentrated under reduced pressure to obtain the crude. The crude was purified through silica gel column chromatography using 20-25% EtOAc/Hexanes to afford compound 3 (10.0 g, 67%) as an off-white solid. $^1$H NMR (500 MHz, DMSO-$d_6$): δ 10.82 (s, 1/2H), 10.77 (s, 1/2H), 7.39-7.35 (m, 2H), 7.27-7.25 (m, 1H), 7.02 (t, J=8.0 Hz, 1H), 6.97-6.92 (m, 2H), 5.04-4.92 (m, 1H), 4.73-4.70 (m, 1H), 4.59-4.56 (m, 1/2H), 4.47-4.43 (m, 1/2H), 3.31-3.29 (m, 1H), 2.91-2.89 (m, 1H), 1.46 (s, 9/2H), 1.43 (m, 9/2H); LC-MS (ESI): 84.4%; m/z 314.3 (M−H$^-$) (column: X Select CSH C-18, 50×3.0 mm, 3.5 μm); RT 3.16 min; 5 mM NH$_4$OAc: ACN; 0.8 mL/min).

Step 3: Synthesis of tert-butyl 3-carbamoyl-9-(4-fluorobenzyl)-1,3,4,9-tetrahydro-2H-pyrido[3,4-b]indole-2-carboxylate (4)

To a stirred solution of compound 3 (1.0 g, 3.17 mmol) in DMF (20 mL) under inert atmosphere were added $Cs_2CO_3$ (2.06 g, 6.34 mmol), TBAB (51 mg, 0.15 mmol), 4-fluorobenzyl bromide (0.89 g, 4.76 mmol) at RT; heated to 60° C. and stirred for 12 h. The reaction was monitored by TLC; after completion of the reaction, the reaction mixture was diluted with water (40 mL) and extracted with EtOAc (2×40 mL). The combined organic extracts were dried over $Na_2SO_4$, filtered and concentrated under reduced pressure to obtain the crude. The crude was purified through silica gel column chromatography using 15-20% EtOAc/Hexanes to afford compound 4 (430 mg, 32%) as an off-white solid. $^1$H NMR (400 MHz, DMSO-$d_6$): δ 7.44-7.40 (m, 3H), 7.14-7.00 (m, 6H), 6.95 (br s, 1H), 5.46-5.22 (m, 2H), 5.06-4.94 (m, 1H), 4.69-4.43 (m, 2H), 3.29-3.20 (m, 1H), 3.03-2.90 (m, 1H), 1.42-1.39 (s, 9/2H), 1.39 (s, 9/2H); LC-MS (ESI): 86.3%; m/z 424.2 (M+H$^+$); (column: X Select CSH C-18, 50×3.0 mm, 3.5 μm); RT 3.97 min; 5 mM NH$_4$OAc: ACN; 0.8 mL/min); HPLC: 85.4%; (column: Acquity BEH C-18 (50×2.1 mm, 1.7μ); RT 2.62 min. ACN: 0.025% TFA (aq); 0.5 mL/min.

Step 4: Synthesis of tert-butyl 3-(aminomethyl)-9-(4-fluorobenzyl)-1,3,4,9-tetrahydro-2H-pyrido[3,4-b]indole-2-carboxylate (5)

To a stirred solution of compound 4 (5.0 g, 11.82 mmol) in dry THF (150 mL) under inert atmosphere was added BH$_3$.DMS (5M in ether; 5.39 g, 70.92 mmol) drop wise for 10 min at 0° C.; heated to 70° C. and stirred for 12 h. The reaction was monitored by TLC; after completion of the reaction, the reaction mixture was quenched with ice-cold water (50 mL) and extracted with EtOAc (2×50 mL). The combined organic extracts were dried over $Na_2SO_4$, filtered and concentrated under reduced pressure to obtain the crude. The crude was triturated with n-pentane (2×10 mL), ether (2×10 mL) to afford compound 5 (3.0 g, 62%) as an off-white solid. $^1$H NMR (400 MHz, CD$_3$OD): δ 7.45 (d, J=7.6 Hz, 1H), 7.32-7.29 (m, 1H), 7.14-6.98 (m, 6H), 5.33-5.29 (m, 2H), 4.66-4.64 (m, 1H), 4.15-4.11 (m, 1H), 3.63-3.61 (m, 1H), 2.99-2.95 (m, 1H), 2.82-2.79 (m, 1H), 2.68-2.64 (m, 2H), 1.47 (br s, 9H); LC-MS (ESI): 85.5%; m/z 410.5 (M+H$^+$); (column: X Select CSH C-18, 50×3.0 mm, 3.5 μm); RT 4.01 min; 5 mM NH$_4$OAc: ACN; 0.8 mL/min); HPLC: 80.6%; (column: Acquity BEH C-18 (50×2.1 mm, 1.7μ); RT 2.21 min; ACN: 0.025% TFA (aq); 0.5 mL/min.

Step 5: Synthesis of (9-(4-fluorobenzyl)-2,3,4,9-tetrahydro-1H-pyrido[3,4-b]indol-3-yl) methanamine (6)

To a stirred solution of compound 5 (250 mg, 0.61 mmol) in $CH_2Cl_2$ (10 mL) under inert atmosphere was added TFA (1 mL) at 0° C.; warmed to RT and stirred for 6 h. The reaction was monitored by TLC; after completion of the reaction, the volatiles were removed under reduced pressure to afford crude compound 6 (270 mg) as an off-white solid. The crude material was directly taken for next reaction.

Step 6: Synthesis of 6-(4-fluorobenzyl)-5,6,11,11a-tetrahydro-1H-imidazo[1',5':1,6]pyrido[3,4-b]indol-3(2H)-one (1-13)

To a stirred solution of compound 6 (270 mg, crude) in dry THF (20 mL) under inert atmosphere were added CDI (141.5 mg, 0.87 mmol), Et₃N (529.5 mg, 5.24 mmol) at 0° C.; warmed to RT and stirred for 12 h. The reaction was monitored by TLC; after completion of the reaction, the reaction mixture was diluted with water (20 mL) and extracted with EtOAc (2×30 mL). The combined organic extracts were dried over Na₂SO₄, filtered and concentrated under reduced pressure to obtain the crude. The crude was purified by preparative HPLC to afford the title compound 1-13 (40 mg, 19% in two steps) as pale brown syrup. ¹H NMR (400 MHz, CD₃OD): δ 7.48 (d, J=7.6 Hz, 1H), 7.31 (d, J=8.0 Hz, 1H), 7.14-7.10 (m, 1H), 7.07-6.97 (m, 5H), 5.32 (s, 2H), 4.72 (d, J=16.4 Hz, 1H), 4.12 (d, J=16.4 Hz, 1H), 3.98-3.92 (m, 1H), 3.74 (t, J=8.4 Hz, 1H), 3.32-3.30 (m, 1H), 3.08-3.03 (m, 1H), 2.80-2.74 (m, 1H); LC-MS (MS): 99.7%; m/z 336.1 (M+H⁺); (column: X Select CSH C-18, 50×3.0 mm, 3.5 μm); RT 3.61 min; 5 mM NH₄OAc: ACN; 0.8 mL/min); HPLC: 97.1%; (column: Eclipse-XDB-C18 (150×4.6 mm, 5 μm); RT 10.29 min; ACN: 5 mM aq. NH₄OAc; 1.0 mL/min.

Example 13: Synthesis of 6-(4-fluorobenzyl)-2-methyl-5,6,11,11a-tetrahydro-1H-imidazo[1',5':1,6]pyrido[3,4-b]indol-3(2H)-one (1-14)

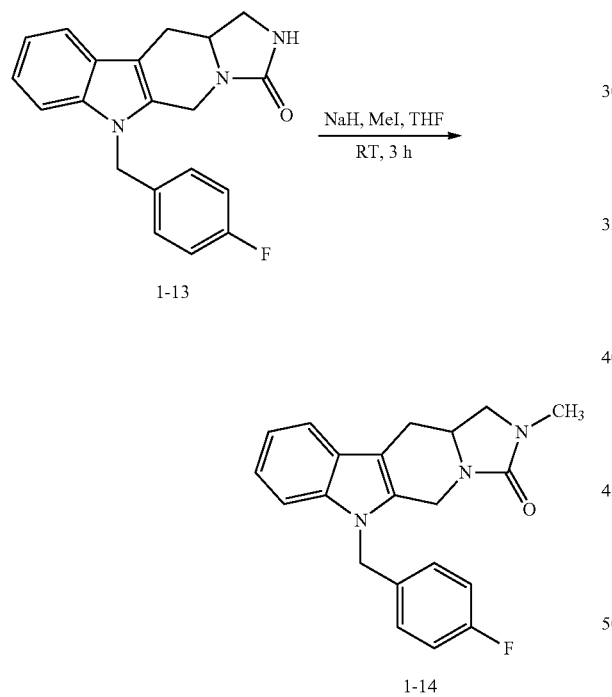

To a stirred solution of 1-13 (Example 12; 20 mg, 0.06 mmol) in dry THF (10 mL) under inert atmosphere was added NaH (60% in mineral oil; 3.6 mg, 0.089 mmol) at 0° C.; warmed to RT and stirred for 30 min. To this, methyl iodide (8.47 mg, 0.06 mmol) was added at 0° C.; warmed to RT and stirred for 3 h. The reaction was monitored by TLC; after completion of the reaction, the reaction mixture was diluted with water (10 mL) and extracted with CH₂Cl₂ (2×20 mL). The combined organic extracts were dried over Na₂SO₄, filtered and concentrated under reduced pressure to afford the title compound 1-14 (8 mg, 38%) as colorless semisolid. ¹H NMR (400 MHz, CD₃OD): δ 7.48 (d, J=7.6 Hz, 1H), 7.31 (d, J=8.0 Hz, 1H), 7.12 (t, J=7.6 Hz, 1H), 7.07-6.97 (m, 5H), 5.32 (s, 2H), 4.72 (d, J=16.0 Hz, 1H), 4.13 (d, J=16.0 Hz, 1H), 3.90-3.82 (m, 1H), 3.69 (t, J=8.4 Hz, 1H), 3.28-3.26 (m, 1H), 3.10-3.05 (m, 1H), 2.83 (s, 3H), 2.74-2.68 (m, 1H); LC-MS (MS): 90.5%; m/z 350.3 (M+H⁺); (column: X Select C-18, 50×3.0 mm, 3.5 μm); RT 4.50 min; 5 mM NH₄OAc: ACN; 0.8 mL/min); HPLC: 90.1%; (column: Eclipse-XDB-C18 (150×4.6 mm, 5 μm); RT 10.96 min; ACN: 5 mM NH₄OAc; 1.0 mL/min.

Example 14: Synthesis of compound 6-(4-fluorobenzyl)-5,6,11,11a-tetrahydro-1H-imidazo[1',5':1,6]pyrido[3,4-b]indole-1,3(2H)-dione (1-15)

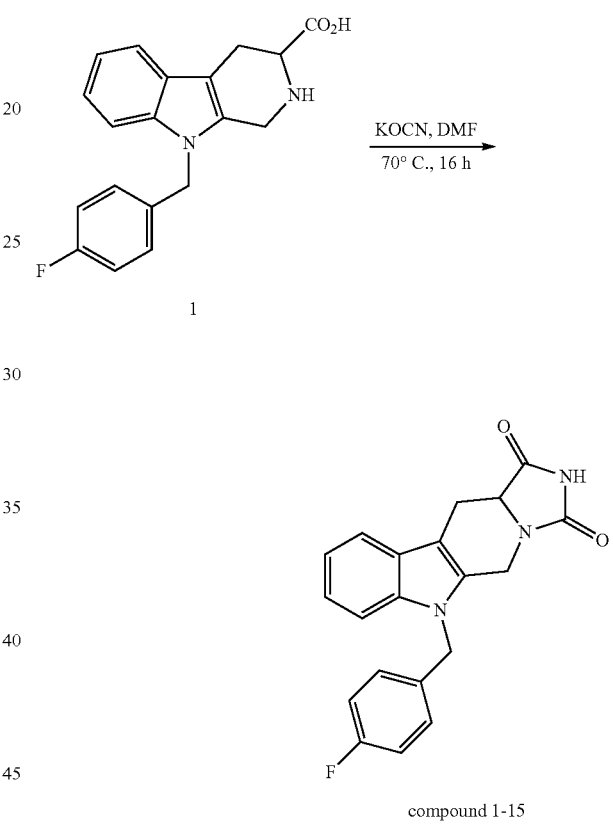

compound 1-15

To a stirred solution of compound 1 (Example 2, step 4 but using racemic starting material in step 1; 1.0 g, 88% pure) in DMF (10 mL) was added KOCN (750 mg, 9.25 mmol) at RT under inert atmosphere. The reaction mixture was heated to 70° C. for 16 h. After completion of the reaction by TLC, the reaction mixture was diluted with water (20 mL) and extracted with EtOAc (2×30 mL). The combined organic extracts were washed with brine (20 mL), dried over Na₂SO₄, filtered and dried under reduced pressure to obtain the crude. The crude was purified (silica gel chromatography; 40-50% EtOAc/hexanes) to afford the title compound 1-15 (178 mg, ~19% for two steps) as an off-white solid. ¹H NMR (500 MHz, DMSO-d₆): δ 10.93 (s, 1H), 7.54 (d, J=8.0 Hz, 1H), 7.49 (d, J=8.0 Hz, 1H), 7.16-7.05 (m, 6H), 5.44 (d, J=16.5 Hz, 1H), 5.38 (d, J=16.5 Hz, 1H), 4.85 (d, J=17.0 Hz, 1H), 4.36-4.33 (m, 1H), 4.28 (d, J=17.0 Hz, 1H), 3.25-3.21 (m, 1H), 2.79-2.74 (m, 1H); LC-MS (ESI): 97.0%; m/z 347.9 (M−H⁺).

Example 15: Synthesis of (S)-6-(4-fluorobenzyl)-5,6,11,11a-tetrahydro-1H-imidazo[1',5':1,6]pyrido[3,4-b]indole-1,3(2H)-dione (1-130)

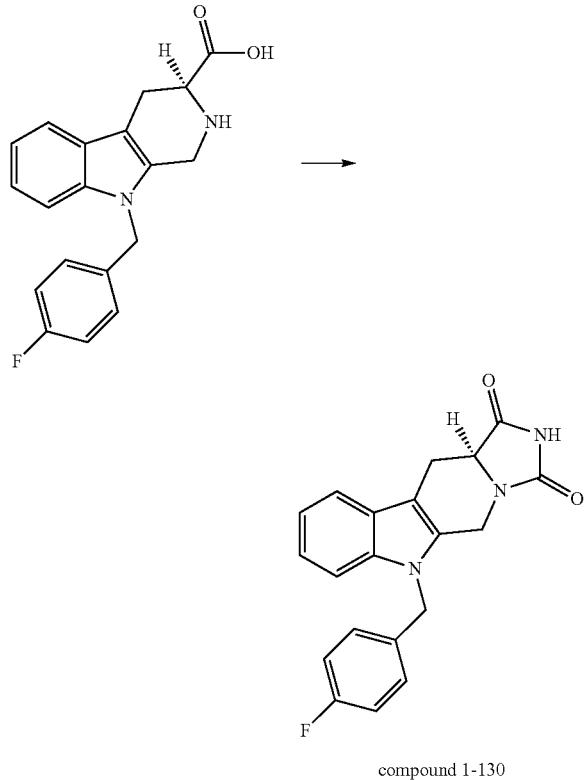

compound 1-130

Following the procedure of Example 14 but using (S)-9-(4-fluorobenzyl)-2,3,4,9-tetrahydro-1H-pyrido[3,4-b]indole-3-carboxylic acid (Example 2, Step 4) as starting material, the title compound 1-130 was prepared as a white solid. ¹H NMR (300 MHz, DMSO-d₆): δ 10.93 (s, 1H), 7.46-7.54 (m, 2H), 7.01-7.16 (m, 6H), 5.43 (d, 1H), 5.36 (d, 1H), 4.83 (d, 1H), 4.33 (dd, 1H), 4.25 (d, 1H), 3.21 (dd, 1H), 2.75 (m, 1H); LC-MS (ESI): m/z 350 (M+H⁺).

Example 16: Synthesis of 6-(4-fluorobenzyl)-2-methyl-5,6,11,11a-tetrahydro-1H-imidazo[1',5':1,6]pyrido[3,4-b]indole-1,3(2H)-dione (1-129)

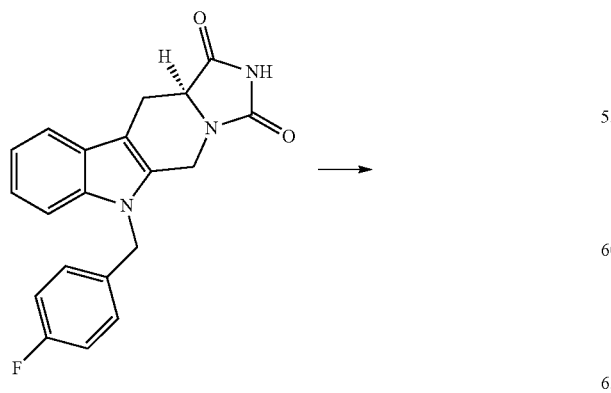

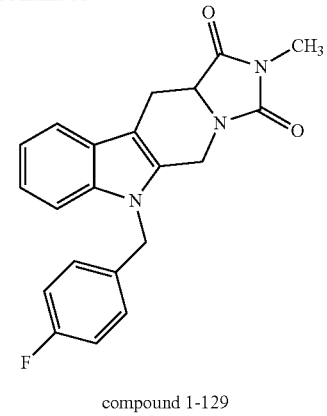

compound 1-129

A mixture of the dione 1 (Example 15; 50 mg, 0.143 mmol), K₂CO₃ (30 mg, 0.22 mmol), and DMF (1 mL) stirred at RT for 10 min. Methyl iodide (41 mg, 0.29 mmol) was added and the mixture stirred at RT for 15 h. Reaction mixture was partitioned between water and 10:1 EtOAc:MeOH. The organic layer was separated, dried over MgSO₄, filtered and concentrated under reduced pressure. The crude was purified via silica gel column chromatography (eluting with 0-60% EtOAc in hexanes) to afford the title compound 1-129 (33 mg, 63%) as a solid. ¹H NMR (300 MHz, DMSO-d₆): δ 7.40-7.60 (m, 2H), 7.02-7.13 (m, 6H), 5.45 (d, 1H), 5.38 (d, 1H), 4.89 (d, 1H), 4.30-4.40 (m, 2H), 3.24 (dd, 1H), 2.89 (s, 3H), 2.76 (m, 1H); LC-MS (ESI): m/z 364 (M+H⁺).

Example 17: Synthesis of 6-(4-fluorobenzyl)-2-(2-hydroxyethyl)-5,6,11,11a-tetrahydro-1H-imidazo[1',5':1,6]pyrido[3,4-b]indole-1,3(2H)-dione (1-121)

compound 1-121

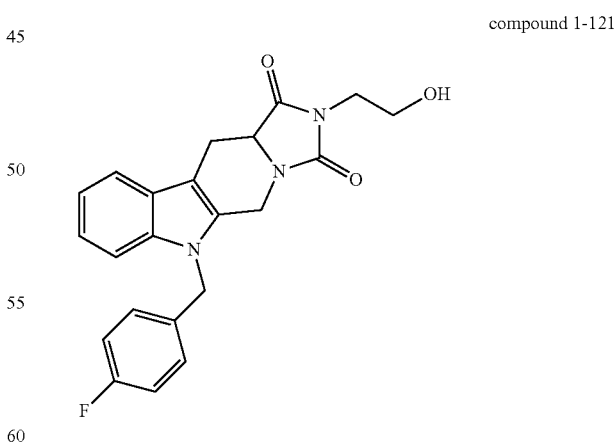

Following the procedure of Example 16 but using 2-bromoethanol in place of methyl iodide, the title compound was obtained. ¹H NMR (300 MHz, DMSO-d₆): δ 7.47-7.55 (m, 2H), 7.02-7.14 (m, 6H), 5.46 (d, 1H), 5.38 (d, 1H), 4.79-4.91 (m, 2H), 4.30-4.40 (m, 2H), 3.47-3.53 (m, 4H), 3.25 (dd, 1H), 2.77 (m, 1H); LC-MS (ESI): m/z 394 (M+H⁺).

Example 18: Synthesis of 2-(6-(4-fluorobenzyl)-1,3-dioxo-5,6,11,11a-tetrahydro-1H-imidazo[1',5':1,6]pyrido[3,4-b]indol-2(3H)-yl)acetonitrile (1-139)

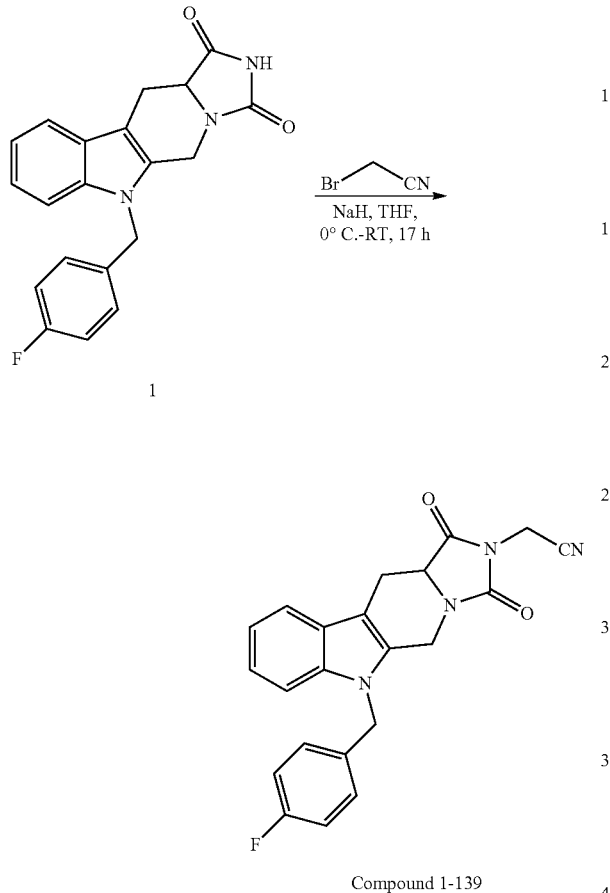

Compound 1-139

To a stirred solution of the dione 1 (Example 14; 400 mg, 1.04 mmol) in anhydrous THF (30 mL) was added NaH (60% in mineral oil, 98 mg, 2.07 mmol) at 0° C. under inert atmosphere. The reaction mixture was warmed to RT and stirred for 45 min. To this was added 2-bromoacetonitrile (247 mg, 2.07 mmol) in THF (10 mL) drop wise at 0° C.; warmed to RT and stirred for 16 h. After completion of the reaction (TLC), the mixture was quenched with ice-cold water (50 mL) and extracted with EtOAc (3×30 mL). The combined organic extracts were washed with brine (30 mL), dried over $Na_2SO_4$, filtered and dried under reduced pressure. The crude was purified (silica gel chromatography; 25% EtOAc/hexanes) to afford the title compound 1-139 (270 mg, 66%) as an off-white solid. $^1$H NMR (500 MHz, DMSO-$d_6$): 7.55 (d, J=7.5 Hz, 1H), 7.49 (d, J=8.0 Hz, 1H), 7.16-7.05 (m, 6H), 5.43 (q, 2H), 4.92 (d, J=16.5 Hz, 1H), 4.59 (s, 2H), 4.55-4.52 (m, 1H), 4.38 (d, J=17.0 Hz, 1H), 3.28-3.27 (m, 1H), 2.84 (t, J=12.5 Hz, 1H); LC-MS (ESI): 99.6%; m/z 387.9 (M–H$^+$).

Example 19: Synthesis of 2-(6-(4-fluorobenzyl)-1,3-dioxo-5,6,11,11a-tetrahydro-1H-imidazo[1',5':1,6]pyrido[3,4-b]indol-2(3H)-yl)acetic acid (1-19)

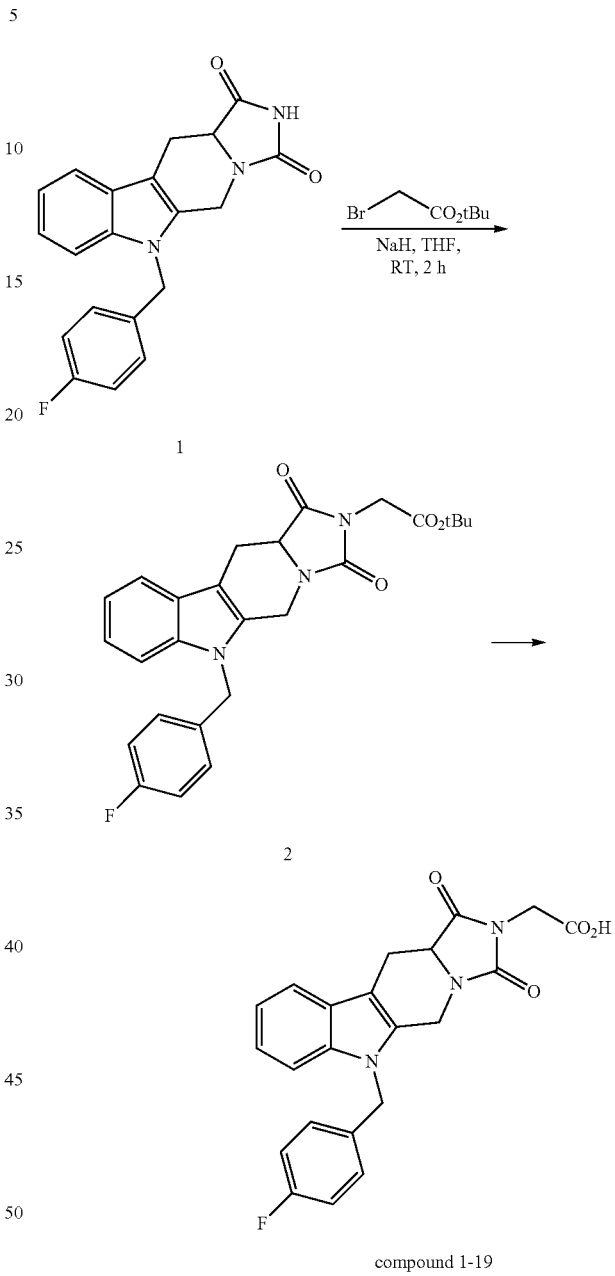

compound 1-19

Step 1: Synthesis of tert-butyl 2-(6-(4-fluorobenzyl)-1,3-dioxo-5,6,11,11a-tetrahydro-1H-imidazo[1',5':1,6]pyrido[3,4-b]indol-2(3H)-yl)acetate Following the procedure of Example 18, but using tert-butyl 2-bromoacetate in place of 2-bromoacetonitrile, ester 2 was obtained as a pale yellow solid. $^1$H NMR (400 MHz, DMSO-$d_6$): δ 7.56 (d, J=7.6 Hz, 1H), 7.48 (d, J=7.6 Hz, 1H), 7.16-7.05 (m, 6H), 5.42 (d, J=16.8 Hz, 1H), 5.39 (d, J=16.8 Hz, 1H), 4.95 (d, J=16.0 Hz, 1H), 4.56-4.52 (m, 1H), 4.38 (d, J=16.0 Hz, 1H), 4.13 (s, 2H), 3.36-3.34 (m, 1H), 2.77-2.73 (m, 1H), 1.40 (s, 9H); LC-MS (ESI): 93.8%; m/z 408.4 ([M-tBu]+H$^+$).

Step 2: Synthesis of 2-(6-(4-fluorobenzyl)-1,3-di-oxo-5,6,11,11a-tetrahydro-1H-imidazo[1',5':1,6]pyrido[3,4-b]indol-2(3H)-yl)acetic acid (1-19)

Following the procedure of Example 5, Step 7 but using ester 2 in place of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate, the title compound 1-19 was obtained as an off-white solid. LC-MS (ESI): m/z 408 (M+H$^+$).

Example 20: Synthesis of 7-(4-fluorobenzyl)-2,3,6,7,12,12a-hexahydropyrazino[1',2':1,6]pyrido[3,4-b]indole-1,4-dione (1-16)

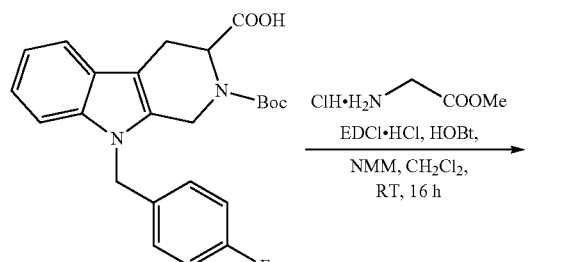

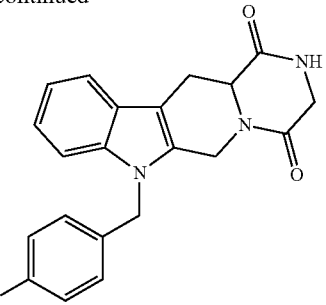

compound 1-16

Step 1: Synthesis of tert-butyl 9-(4-fluorobenzyl)-3-((2-methoxy-2-oxoethyl)carbamoyl)-1,3,4,9-tetrahydro-2H-pyrido[3,4-b]indole-2-carboxylate (2)

To a stirred solution of the acid 1 (Example 2, Step 3 but using racemic starting material in Step 1; 800 mg, 1.88 mmol) in CH$_2$Cl$_2$ (15 mL) under inert atmosphere were added EDCI.HCl (540 mg, 2.83 mmol), HOBt (382 mg, 2.83 mmol), NMM (0.62 mL, 5.66 mmol) at RT and stirred for 10 min. To this, glycine methyl ester.HCl (353 mg, 2.83 mmol) was added at RT and stirred for 16 h. After completion of the reaction by TLC, the reaction mixture was diluted with water (30 mL) and extracted with EtOAc (2×30 mL). The combined organic extracts were washed with brine (20 mL), dried over Na$_2$SO$_4$, filtered and dried under reduced pressure to obtain the crude. The crude was purified (silica gel chromatography; 30-40% EtOAc/hexanes) to afford compound 2 (578 mg, 62%) as a viscous oil. $^1$H NMR (500 MHz, DMSO-d$_6$): data suggested as a 1:1 rotamers; δ 8.41-8.38 (m, 1H), 7.44-7.39 (m, 2H), 7.11-7.01 (m, 6H), 5.42-5.06 (m, 3H), 4.77-4.69 (m, 1H), 4.56-4.46 (m, 1H), 3.81-3.70 (m, 2H), 3.47 (s, 3H), 3.34-3.30 (m, 1H), 3.01-2.92 (m, 1H), 1.43-1.39 (m, 9H); LC-MS (ESI): 97.6%; m/z 396.4 ([M-Boc]+H$^+$).

Step 2: Synthesis of methyl (9-(4-fluorobenzyl)-2,3,4,9-tetrahydro-1H-pyrido[3,4-b]indole-3-carbonyl)glycinate (3)

To a stirred solution of compound 2 (570 mg, 1.14 mmol) in CH$_2$Cl$_2$ (10 mL) was added TFA (0.5 mL) at 0° C. under inert atmosphere. The reaction was warmed to RT and maintained at same temperature for 4 h. The volatiles were removed under reduced pressure. The residue was diluted with saturated NaHCO$_3$ (20 mL) and extracted with CH$_2$Cl$_2$ (2×30 mL). The combined organic extracts were washed with brine (20 mL), dried over Na$_2$SO$_4$, filtered and dried under reduced pressure to obtain 450 mg of compound 3 as a thick syrup, which was used without further purification.

Step 3: Synthesis of 7-(4-fluorobenzyl)-2,3,6,7,12,12a-hexahydropyrazino[1',2':1,6]pyrido[3,4-b]indole-1,4-dione (compound 1-16)

To a stirred solution of crude compound 3 (450 mg) in DMF (10 mL) were added CDI (185 mg, 1.13 mmol), Et$_3$N (0.15 mL) and DMAP (27 mg, 0.22 mmol) at RT under inert atmosphere. The reaction mixture was heated to 100° C. and stirred for 20 h. The reaction mixture was diluted with water (20 mL) and extracted with EtOAc (2×30 mL). The combined organic extracts were washed with brine (20 mL), dried over Na₂SO₄, filtered and dried under reduced pressure to obtain the crude. The crude was purified (silica gel chromatography; 70-80% EtOAc/hexanes) to afford the title compound 1-16 (160 mg, ~39% for two steps) as a pale yellow solid. ¹H NMR (500 MHz, DMSO-d₆): δ 8.26 (s, 1H), 7.51 (d, J=8.0 Hz, 1H), 7.44 (d, J=8.0 Hz, 1H), 7.15-7.03 (m, 6H), 5.45-5.36 (m, 3H), 4.27-4.24 (m, 1H), 4.13 (d, J=16.5 Hz, 1H), 4.05 (d, J=16.5 Hz, 1H), 3.88-3.84 (m, 1H), 3.25-3.21 (m, 1H), 2.95-2.89 (m, 1H); MS(ESI): m/z 364.3 (M+H⁺); HPLC: 96.9%.

Example 21: Synthesis of 2-(7-(4-fluorobenzyl)-1,4-dioxo-3,4,6,7,12,12a-hexahydropyrazino[1',2':1,6]pyrido[3,4-b]indol-2(1H)-yl)acetic acid (1-23)

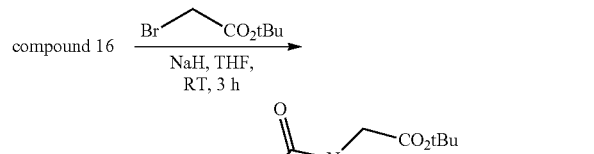

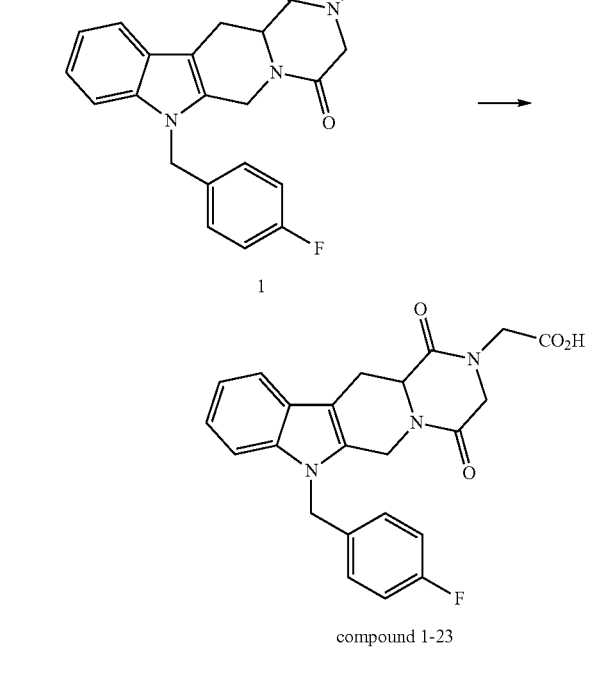

compound 1-23

Step 1: Synthesis of tert-butyl 2-(7-(4-fluorobenzyl)-1,4-dioxo-3,4,6,7,12,12a-hexahydro pyrazino[1',2':1,6]pyrido[3,4-b]indol-2(1H)-yl)acetate To a stirred solution of compound 1-16 (Example 20; 100 mg, 0.27 mmol) in THF (10 mL) under inert atmosphere was added NaH (13 mg, 0.55 mmol) at 0° C.; warmed to RT and stirred for 45 min. To this, tert-butyl 2-bromoacetate (0.04 mL, 0.27 mmol) was added at 0° C.; warmed to RT and stirred for 3 h. The reaction mixture was diluted with water (20 mL) and extracted with EtOAc (2×25 mL). The combined organic extracts were washed with brine (20 mL), dried over Na₂SO₄, filtered and dried under reduced pressure to obtain the crude. The crude was purified (silica gel chromatography; 40-50% EtOAc/hexanes) to afford ester 1 (90 mg, 69%) as a pale yellow solid. ¹H NMR (400 MHz, DMSO-d₆): δ 7.52 (d, J=8.0 Hz, 1H), 7.45 (d, J=8.0 Hz, 1H), 7.16-7.10 (m, 5H), 7.05 (t, J=7.5 Hz, 1H), 5.46-5.35 (m, 3H), 4.46-4.43 (m, 1H), 4.22-4.01 (m, 5H), 3.26-3.23 (m, 1H), 2.93-2.88 (m, 1H), 1.45 (s, 9H); LC-MS (ESI): 98.2%; m/z 478.5 (M+H⁺).

Step 2: Synthesis of 2-(7-(4-fluorobenzyl)-1,4-dioxo-3,4,6,7,12,12a-hexahydropyrazino[1',2':1,6]pyrido[3,4-b]indol-2(1H)-yl)acetic acid (1-23)

Following the procedure of Example 5, Step 7 but using ester 1 in place of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate, the title compound 1-23 was obtained. LC-MS (ESI): m/z 422 (M+H⁺).

Example 22: Synthesis of 3-(7-(4-fluorobenzyl)-1,4-dioxo-3,4,6,7,12,12a-hexahydropyrazino[1',2':1,6]pyrido[3,4-b]indol-2(1H)-yl)propanoic acid (1-24)

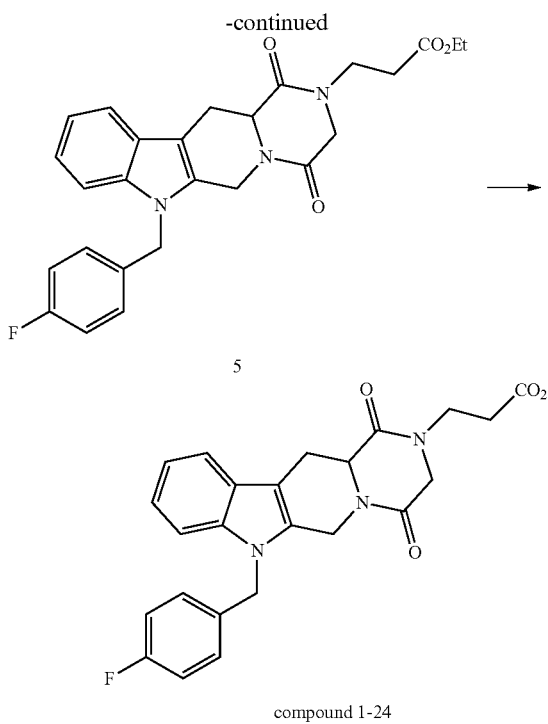

compound 1-24

Step 1: Synthesis of ethyl 3-((2-methoxy-2-oxoethyl)amino)propanoate (2)

To a stirred solution of methyl glycinate.HCl (5.0 g, 39.8 mmol) in 2-propanol:$H_2O$ (3:1, 40 mL) was added $Et_3N$ (5.69 mL, 42.2 mmol) at 60° C. under inert atmosphere. To this, ethyl acrylate (2.8 mL, 26.2 mmol) was added in two portions with an interval of 2 h and stirred for 5 h; then stirred at RT for 16 h. The reaction mixture was diluted with 3% aq. $NaHCO_3$ (30 mL) and extracted with EtOAc (2×30 mL). The combined organic extracts were washed with brine (20 mL), dried over $Na_2SO_4$, filtered and dried in vacuo to obtain the crude. The crude was purified (silica gel chromatography; 30-50% EtOAc/hexanes) to afford compound 2 (720 mg, 10%) as a colorless liquid. $^1$H NMR (500 MHz, DMSO-$d_6$): δ 4.05 (q, J=7.0 Hz, 2H), 3.62 (s, 3H), 3.33-3.32 (m, 2H), 2.74 (t, J=6.5 Hz, 2H), 2.40 (t, J=6.5 Hz, 2H), 2.09 (br s, 1H), 1.18 (t, J=7.0 Hz, 3H).

Step 2: Synthesis of tert-butyl 3-((3-ethoxy-3-oxo-propyl)(2-methoxy-2-oxoethyl)carbamoyl)-9-(4-fluorobenzyl)-1,3,4,9-tetrahydro-2H-pyrido[3,4-b]indole-2-carboxylate (3)

To a stirred solution of the acid 1 (Example 2, Step 3 but using racemic starting material in Step 1; 400 mg, 0.94 mmol) in DMF (10 mL) were added diisopropylethylamine (0.41 mL, 2.35 mmol), HATU (537 mg, 1.40 mmol), HOBt (191 mg, 1.40 mmol) and stirred under inert atmosphere for 15 min. To this, compound 2 (178 mg, 0.94 mmol) was added at RT and stirred for 16 h. The reaction mixture was diluted with water (30 mL) and extracted with EtOAc (2×30 mL). The combined organic extracts were washed with brine (30 mL), dried over $Na_2SO_4$, filtered and dried under reduced pressure to obtain the crude. The crude was purified (silica gel chromatography; 15-20% EtOAc/hexanes) to afford compound 3 (350 mg, 62%) as an off-white solid. $^1$H NMR (500 MHz, DMSO-$d_6$): (1:1 rotamers) δ 7.47-7.39 (m, 2H), 7.11-7.00 (m, 6H), 5.46-5.26 (m, 3H), 4.81-4.74 (m, 1H), 4.46-4.32 (m, 2H), 4.18-3.92 (m, 5H), 3.69 (s, 3/2H), 3.47 (s, 3/2 H), 3.05-3.02 (m, 2H), 2.81-2.79 (m, 2H), 1.44-1.41 (m, 9H), 1.22 (t, J=7.0 Hz, 3/2H), 1.11 (t, J=7.0 Hz, 3/2H); LC-MS (ESI): 97.9%; m/z 496.6 ([M-Boc]+$H^+$).

Step 3: Synthesis of ethyl 3-(9-(4-fluorobenzyl)-N-(2-methoxy-2-oxoethyl)-2,3,4,9-tetrahydro-1H-pyrido[3,4-b]indole-3-carboxamido)propanoate (4)

To a stirred solution of diester 3 (350 mg, 0.71 mmol) in $CH_2Cl_2$ (3 mL) was added TFA (3 mL) at RT under inert atmosphere and stirred for 4 h. The volatiles were removed under reduced pressure. The residue was diluted with saturated $NaHCO_3$ (30 mL) and extracted with EtOAc (2×30 mL). The combined organic extracts were washed with brine (20 mL), dried over $Na_2SO_4$, filtered and dried under reduced pressure to obtain 250 mg of compound 4 as a pale yellow solid, which was used without further purification.

Step 4: Synthesis of ethyl 3-(7-(4-fluorobenzyl)-1,4-dioxo-3,4,6,7,12,12a-hexahydropyrazino[1',2':1,6]pyrido[3,4-b]indol-2(1H)-yl)propanoate (5)

To a stirred solution of crude amine 4 (250 mg) in DMF (5 mL) were added CDI (82 mg, 0.51 mmol), $Et_3N$ (0.14 mL, 1.04 mmol) and DMAP (12 mg, 0.10 mmol) at RT under inert atmosphere. The reaction mixture was heated to 100° C. in a sealed tube for 12 h. The reaction mixture was diluted with water (20 mL) and extracted with EtOAc (2×30 mL). The combined organic extracts were washed with brine (20 mL), dried over $Na_2SO_4$, filtered and dried under reduced pressure to obtain the crude. The crude was purified (silica gel chromatography; 40-60% EtOAc/hexanes) to afford 5 (95 mg, 41%) as an off-white solid. $^1$H NMR (400 MHz, DMSO-$d_6$): δ 7.50 (d, J=8.0 Hz, 1H), 7.43 (d, J=8.0 Hz, 1H), 7.15-7.02 (m, 6H), 5.45-5.35 (m, 3H), 4.33 (dd, J=11.6, 4.0 Hz, 1H), 4.31-4.05 (m, 5H), 3.63-3.50 (m, 2H), 3.25-3.20 (m, 1H), 2.92-2.86 (m, 1H), 2.63 (t, J=7.2 Hz, 2H), 1.19 (t, J=6.8 Hz, 3H); LC-MS (ESI): 99.9%; m/z 464.5 (M+$H^+$).

Step 5: Synthesis of 3-(7-(4-fluorobenzyl)-1,4-dioxo-3,4,6,7,12,12a-hexahydropyrazino[1',2':1,6]pyrido[3,4-b]indol-2(1H)-yl)propanoic acid (1-24)

To a stirred solution of 5 in a mixture of 2 mL of THF, 1 mL of MeOH, and 1 mL of water was added 1 eq of 0.1 N NaOH. The mixture was stirred at room temperature for 5-7 hours. After the reaction completion, the mixture was evaporated to dryness to afford the title compound 1-24. LC-MS (ESI): m/z 436 (M+$H^+$).

Example 23: Synthesis of (S)-4-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylbutanoic acid (1-39)

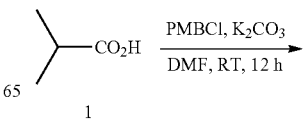

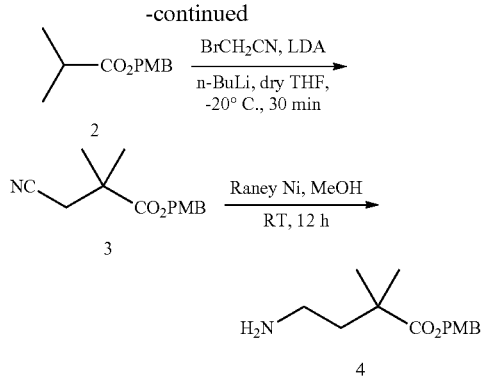

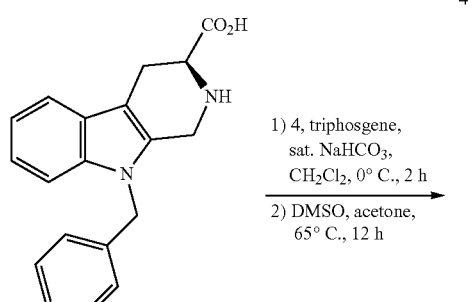

mmol), PMB-chloride (8.86 g, 56.8 mmol) at 0° C. under inert atmosphere. The reaction mixture was warmed to RT and stirred for 12 h. The reaction mixture was diluted with water (120 mL) and extracted with EtOAc (3×30 mL). The combined organic extracts were dried over $Na_2SO_4$, filtered and concentrated under reduced pressure to obtain the crude. This was purified (silica gel chromatography; 3-5% EtOAc/hexanes) to afford compound 2 (7.5 g, 63%) as a colorless liquid. $^1$H NMR (500 MHz, $CDCl_3$): δ 7.28 (d, J=9.0 Hz, 2H), 6.88 (d, J=9.0 Hz, 2H), 5.04 (s, 2H), 3.80 (s, 3H), 2.58-2.55 (m, 1H), 1.16 (t, J=7.0 Hz, 6H).

Step 2: Synthesis of 4-methoxybenzyl 3-cyano-2,2-dimethylpropanoate (3)

To a stirred solution of diisopropylamine (13.26 g, 131.31 mmol) in dry THF (200 mL) under inert atmosphere was added n-BuLi (2.5 M, 4.61 g, 72.11 mmol) at −78° C.; warmed to −20° C. and stirred for 30 min. To this, compound 2 (7.5 g, 36.05 mmol) was added at −78° C.; warmed to −20° C. and stirred for 30 min. The reaction mixture was again cooled to −78° C. and bromoacetonitrile (5.19 g, 43.2 mmol) added. The reaction mixture was then slowly warmed to −20° C. and stirred for 3 h. The reaction mixture was quenched with ice-cold water (50 mL) and extracted with EtOAc (3×70 mL). The combined organic extracts were dried over anhydrous $Na_2SO_4$, filtered and concentrated under reduced pressure to obtain the crude. This was purified (silica gel chromatography; 5-7% EtOAc/hexanes) to afford compound 3 (4.5 g, 50%) as a yellow oil. $^1$H NMR (500 MHz, $CDCl_3$): δ 7.28 (d, J=8.0 Hz, 2H), 6.89 (d, J=8.0 Hz, 2H), 5.09 (s, 2H), 3.81 (s, 3H), 2.59 (s, 2H), 1.36 (s, 6H).

Step 3: Synthesis of 4-methoxybenzyl 4-amino-2,2-dimethylbutanoate (4)

To a stirred solution of compound 3 (1.5 g, 6.07 mmol) in MeOH (20 mL) under inert atmosphere was added Raney-Ni (3.0 g) at RT and stirred under $H_2$ atmosphere (balloon pressure) for 12 h. The reaction mixture was filtered through a celite pad and the filtrate was concentrated under reduced pressure to obtain the crude compound 4 (1.7 g) as a yellow oil, which was used without further purification.

Step 4: Synthesis of 4-methoxybenzyl (S)-4-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylbutanoate (6)

To a stirred solution of compound 4 (500 mg) in $CH_2Cl_2$ (20 mL) under inert atmosphere were added saturated $NaHCO_3$ (20 mL), triphosgene (236.4 mg, 0.79 mmol) at 0° C. and stirred for 2 h. After completion of the reaction by TLC, the reaction mixture was diluted with water (20 mL) and extracted with $CH_2Cl_2$ (2×30 mL). The combined organic extracts were dried over $Na_2SO_4$, filtered and concentrated under reduced pressure to obtain the crude isocyanate (400 mg) as colorless oil, which was used without further purification.

To a stirred solution of crude isocyanate (400 mg) in acetone (20 mL) under inert atmosphere were added acid 5 (Example 2, Step 4; 185 mg, 0.57 mmol) and DMSO (5 mL) at RT; heated to 65° C. for 12 h. After completion of the reaction by TLC, the reaction mixture was diluted with water (20 mL) and extracted with EtOAc (3×30 mL). The combined organic extracts were dried over $Na_2SO_4$, filtered and concentrated under reduced pressure to obtain the crude.

Step 1: Synthesis of 4-methoxybenzyl isobutyrate (2)

To a stirred solution of isobutyric acid 1 (5.0 g, 56.8 mmol) in DMF (100 mL) were added $K_2CO_3$ (23.5 g, 170.4

The crude was purified (silica gel chromatography; 20% EtOAc/hexanes) and further purified by preparative HPLC to afford 6 (50 mg) as an off-white solid. $^1$H NMR (400 MHz, CD$_3$OD): δ 7.52 (d, J=7.6 Hz, 1H), 7.33 (d, J=7.6 Hz, 1H), 7.22 (d, J=8.8 Hz, 2H), 7.15 (t, J=8.0 Hz, 1H), 7.08 (t, J=8.0 Hz, 1H), 7.03-7.01 (m, 2H), 6.99-6.92 (m, 2H), 6.82 (d, J=8.8 Hz, 2H), 5.32 (s, 2H), 4.96-4.91 (m, 3H), 4.29 (d, J=16.0 Hz, 1H), 4.21-4.17 (m, 1H), 3.71 (s, 3H), 3.57-3.53 (m, 2H), 3.34-3.28 (m, 1H), 2.86-2.80 (m, 1H), 1.90 (t, J=7.2 Hz, 2H), 1.21 (s, 6H); LC-MS (ESI): 99.0%; m/z 584.6 (M+H$^+$); Chiral HPLC: 95.4%, R$_t$=9.56 min (Chiralpak IA, 250×4.6 mm, 5 μm); mobile phase (A) 0.1% DEA in n-Hexane (B) CH$_2$Cl$_2$: MeOH (50:50) (A:B: 75:25); flow Rate: 1.0 mL/min).

Step 5: Synthesis of (S)-4-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylbutanoic acid (1-39)

To a stirred solution of 6 in methanol (5 mL) was added ammonium formate (500 mg) under N$_2$. To the mixture was then added 10% Pd/C (10 mg). The mixture was vigorously stirred at room temperature for 2 hours. After completion, the mixture was filtered through Celite. The filtrate was evaporated to dryness. The residue was extracted with ethyl acetate (10 mL) and di water (10 mL). The organic layer was separated, washed with brine (10 mL), dried over Na$_2$SO$_4$, filtered and evaporated to dryness to afford the title compound 1-39 as a white solid. LC-MS (ESI): m/z 464 (M+H$^+$).

Example 24: Synthesis of (S)-4-(6-(4-fluorobenzyl)-1,3-dioxo-5,6,11,11a-tetrahydro-1H-imidazo[1',5':1,6]pyrido[3,4-b]indol-2(3H)-yl)-3,3-dimethylbutanoic acid (1-42)

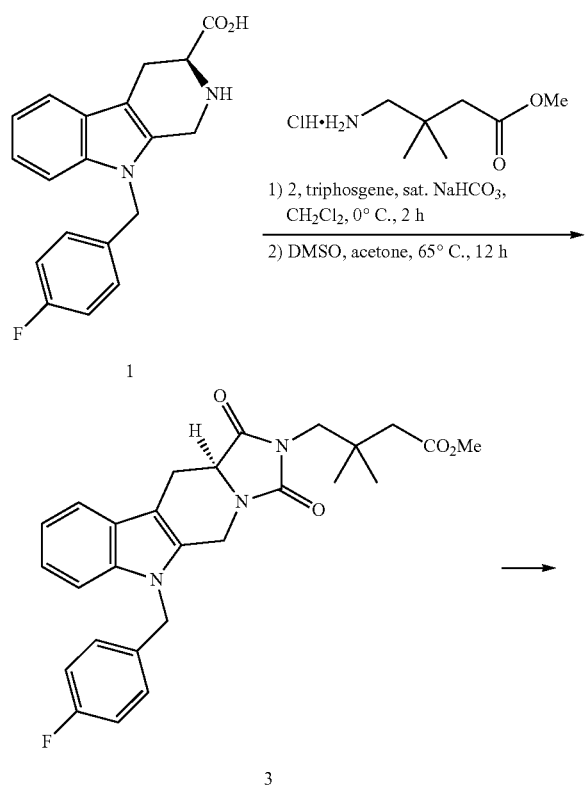

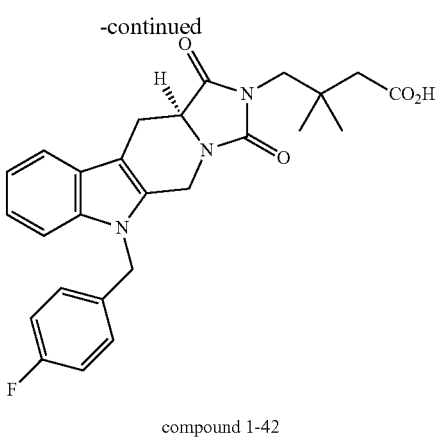

compound 1-42

Step 1: Synthesis of methyl 4-amino-3,3-dimethylbutanoate hydrochloride (2)

To a stirred solution of 4-amino-3,3-dimethylbutanoic acid hydrochloride (50 mg, 0.29 mmol) in MeOH (15 mL) under inert atmosphere was added SOCl$_2$ (42.2 mg, 0.35 mmol) at 0° C.; heated the reaction mixture to 80° C. for 12 h. The mixture was cooled to RT and the volatiles were removed to afford crude compound 2 (70 mg) as an off-white solid, which was used as such. $^1$H NMR (400 MHz, DMSO-d$_6$): δ 7.99-7.89 (br s, 3H), 3.59 (s, 3H), 2.80 (s, 2H), 2.38 (s, 2H), 1.01 (s, 6H); LC-MS (ESI): 100%; 146.3 (M+H$^+$).

Step 2: Synthesis of methyl (S)-4-(6-(4-fluorobenzyl)-1,3-dioxo-5,6,11,11a-tetrahydro-1H-imidazo[1',5':1,6]pyrido[3,4-b]indol-2(3H)-yl)-3,3-dimethylbutanoate (3)

To a stirred solution of compound 2 (70 mg) in CH$_2$Cl$_2$ (10 mL) under inert atmosphere were added saturated NaHCO$_3$ (10 mL), triphosgene (57.2 mg, 0.19 mmol) at 0° C. The reaction mixture was stirred at 0-20° C. for 2 h. After completion of the reaction by TLC, the reaction mixture was diluted with water (10 mL) and extracted with CH$_2$Cl$_2$ (2×25 mL). The combined organic extracts were dried over Na$_2$SO$_4$, filtered and concentrated under reduced pressure to obtain crude isocyante (80 mg) as colorless oil.

To a stirred solution of crude isocyanate (80 mg) in acetone (2 mL) under inert atmosphere were added acid 1 (example 2, Step 4; 151 mg, 0.46 mmol) and DMSO (2 mL) at RT; heated to 65° C. for 12 h. After completion of the reaction by TLC, the reaction mixture was diluted with water (20 mL) and extracted with EtOAc (2×30 mL). The combined organic extracts were dried over Na$_2$SO$_4$, filtered and concentrated under reduced pressure to obtain the crude. The crude was purified (silica gel chromatography; 20% EtOAc/hexanes) to afford 3 (15 mg, 10% for three steps) as an off-white solid. $^1$H NMR (400 MHz, CD$_3$OD): δ 7.54 (d, J=8.0 Hz, 1H), 7.36 (d, J=8.0 Hz, 1H), 7.16 (t, J=7.6 Hz, 1H), 7.11-6.98 (m, 5H), 5.36 (s, 2H), 4.96 (d, J=15.6 Hz, 1H), 4.39-4.34 (m, 2H), 3.63 (s, 3H), 3.53 (s, 2H), 3.41-3.36 (m, 1H), 2.86-2.81 (m, 1H), 2.32 (s, 2H), 1.05 (s, 6H); LC-MS (ESI): 97.5%; m/z 476.8 (M+H$^+$); Chiral HPLC: 95.2%, R$_t$=10.73 min (Chiralpak IB, 250×4.6 mm, 5 μm); mobile phase (A) 0.1% DEA in n-Hexane (B) CH$_2$Cl$_2$: MeOH (50:50) (A:B: 80:20); at 1.0 mL/min).

Step 3: Synthesis of (S)-4-(6-(4-fluorobenzyl)-1,3-dioxo-5,6,11,11a-tetrahydro-1H-imidazo[1',5':1,6]pyrido[3,4-b]indol-2(3H)-yl)-3,3-dimethylbutanoic acid (1-42)

To a stirred solution of 3 in a mixture of 2 mL of THF, 1 mL of MeOH, and 1 mL of water was added 1 eq of 0.1 N NaOH at 0° C. The mixture was stirred at room temperature for 24 hours then evaporated to dryness to afford the title compound 1-42. LC-MS (ESI): m/z 486 (M+Na$^+$)

Example 25: Synthesis of (S)-4-(8-chloro-6-(4-fluorobenzyl)-1,3-dioxo-5,6,11,11a-tetrahydro-1H-imidazo[1',5':1,6]pyrido[3,4-b]indol-2(3H)-yl)butanoic acid (1-27)

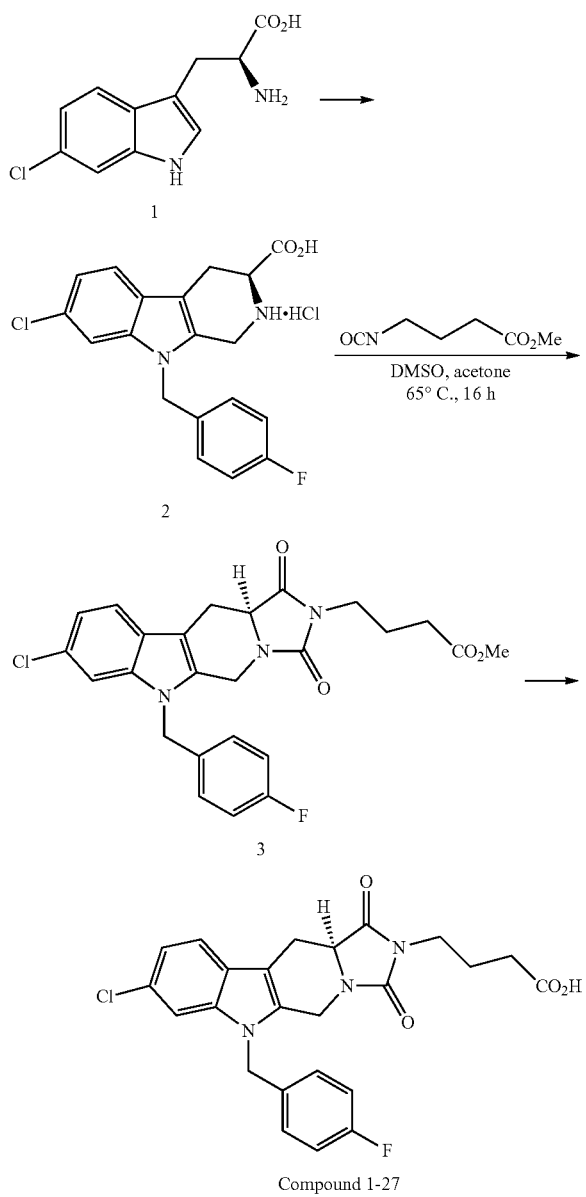

Compound 1-27

Step 1: Synthesis of (S)-7-chloro-9-(4-fluorobenzyl)-2,3,4,9-tetrahydro-1H-pyrido[3,4-b]indole-3-carboxylic acid hydrochloride (2)

Following the procedure of Example 5, Steps 1-4, but using 6-chloro-L-tryptophan as starting material in place of L-tryptophan, compound 2 was obtained. $^1$H NMR (500 MHz, DMSO-d$_6$): δ 14.20 (br s, 1H), 9.92 (br s, 1H), 7.66 (s, 1H), 7.60 (d, J=8.5 Hz, 1H), 7.18-7.09 (m, 5H), 5.48-5.40 (m, 2H), 4.54-4.51 (m, 1H), 4.47 (d, J=16.0 Hz, 1H), 4.29 (d, J=16.0 Hz, 1H), 3.37-3.33 (m, 1H), 3.08-3.05 (m, 1H).

Step 2: Synthesis of methyl 4-isocyanobutanoate

To a stirred solution of methyl 4-aminobutanoate.HCl (550 mg, 3.58 mmol) in CH$_2$Cl$_2$ and aq. sat. NaHCO$_3$ solution (1:1; 20 mL) was added triphosgene (425 mg, 1.43 mmol) at 0° C. and stirred for 30 min. The reaction solution was warmed to RT and stirred for 2 h. The reaction mixture was then diluted with aq. sat. NaHCO$_3$ (10 mL) and extracted with CH$_2$Cl$_2$ (3×15 mL). The combined organic extracts were washed with brine (20 mL), dried over Na$_2$SO$_4$, filtered and concentrated under reduced pressure to obtain the crude isocyanate (466 mg).

Step 3: Synthesis of methyl (S)-4-(8-chloro-6-(4-fluorobenzyl)-1,3-dioxo-5,6,11,11a-tetrahydro-1H-imidazo[1',5':1,6]pyrido[3,4-b]indol-2(3H)-yl)butanoate (3)

To a stirred solution of methyl 4-isocyanobutanoate (466 mg) in acetone (12 mL) under inert atmosphere were added compound 5 (100 mg, 0.27 mmol) and DMSO (6 mL) at RT; heated to 65° C. for 16 h. After completion of the reaction by TLC, the reaction mixture was extracted with EtOAc (3×30 mL). The combined organic extracts were washed with water (2×30 mL), dried over Na$_2$SO$_4$, filtered and concentrated under reduced pressure to obtain the crude. The crude was purified (silica gel chromatography; 20-30% EtOAc/hexanes) to afford 3 (13 mg, 10%) as a white solid. $^1$H NMR (400 MHz, CD$_3$OD): δ 7.50 (d, J=8.4 Hz, 1H), 7.40 (s, 1H), 7.09-7.01 (m, 5H), 5.34 (s, 2H), 4.94 (d, J=16.0 Hz, 1H), 4.35-4.30 (m, 2H), 3.61 (s, 3H), 3.60-3.58 (m, 2H), 3.31-3.30 (m, 1H), 2.85-2.78 (m, 1H), 2.39 (t, J=7.2 Hz, 2H), 1.97-1.90 (m, 2H); MS (ESI): m/z 484.5 (M+H$^+$); Chiral HPLC: 80.3%, R$_t$=24.09 min (Chiralpak IA, 250×4.6 mm, 5 μm); mobile phase (A) 0.1% DEA in n-Hexane (B) CH$_2$Cl$_2$: MeOH (50:50) (A:B: 80:20); at 1.0 mL/min).

Step 4: Synthesis of (S)-4-(8-chloro-6-(4-fluorobenzyl)-1,3-dioxo-5,6,11,11a-tetrahydro-1H-imidazo[1',5':1,6]pyrido[3,4-b]indol-2(3H)-yl)butanoic acid (1-27)

Following the procedure of Example 22, Step 5, but using ester 1 in place of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate, the title compound 1-27 was obtained. LC-MS (ESI): m/z 492 (M+Na$^+$)

Example 26: Synthesis of (S)-8-chloro-6-(4-fluorobenzyl)-5,6,11,11a-tetrahydro-1H-imidazo[1',5':1,6]pyrido[3,4-b]indole-1,3(2H)-dione (1-26)

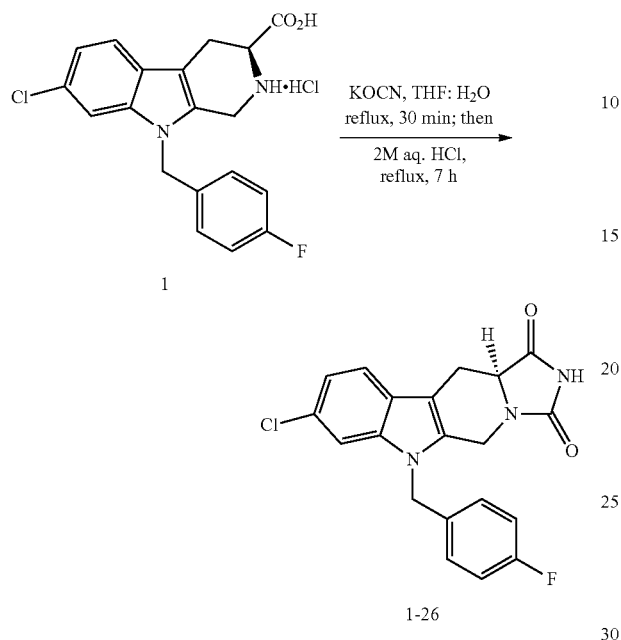

To a stirred solution of the acid 1 (Example 25, Step 1; 100 mg, 0.27 mmol) in THF:H$_2$O (1:1, 4 mL) was added KOCN (45 mg, 0.55 mmol) at RT under inert atmosphere. The reaction mixture was heated to reflux for 30 min. The reaction was cooled to RT and added 2.0M HCl (4 mL). The resultant solution was again heated to reflux for 7 h. The mixture was cooled to RT, the precipitated solid was filtered, washed with water (2×5 mL), n-pentane (2×5 mL). The obtained solid was purified (silica gel chromatography; 2-3% MeOH/CH$_2$Cl$_2$) to afford the title compound 1-26 (50 mg, 51%) as an off-white solid. $^1$H NMR (400 MHz, DMSO-d$_6$): δ 10.93 (s, 1H), 7.66 (s, 1H), 7.56 (d, J=8.4 Hz, 1H), 7.18-7.06 (m, 5H), 5.46 (d, J=16.8 Hz, 1H), 5.39 (d, J=16.8 Hz, 1H), 4.82 (d, J=16.4 Hz, 1H), 4.35-4.31 (m, 1H), 4.24 (d, J=16.4 Hz, 1H), 3.25-3.20 (m, 1H), 2.78-2.72 (m, 1H); LC-MS (ESI): 99.6%; m/z 383.2 (M–H$^+$); Chiral HPLC: 100%, R$_t$=23.40 min (Chiralpak IA, 250×4.6 mm, 5 µm); mobile phase (A) 0.1% DEA in n-Hexane (B) CH$_2$Cl$_2$: MeOH (50:50) (A:B: 80:20); at 1.0 mL/min).

Example 27: Synthesis of (S)-3-(6-((6-chloropyridin-3-yl)methyl)-1,3-dioxo-5,6,11,11a-tetrahydro-1H-imidazo[1',5':1,6]pyrido[3,4-b]indol-2(3H)-yl)propanoic acid (1-84)

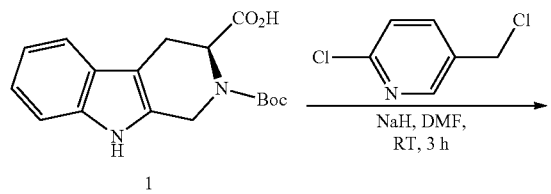

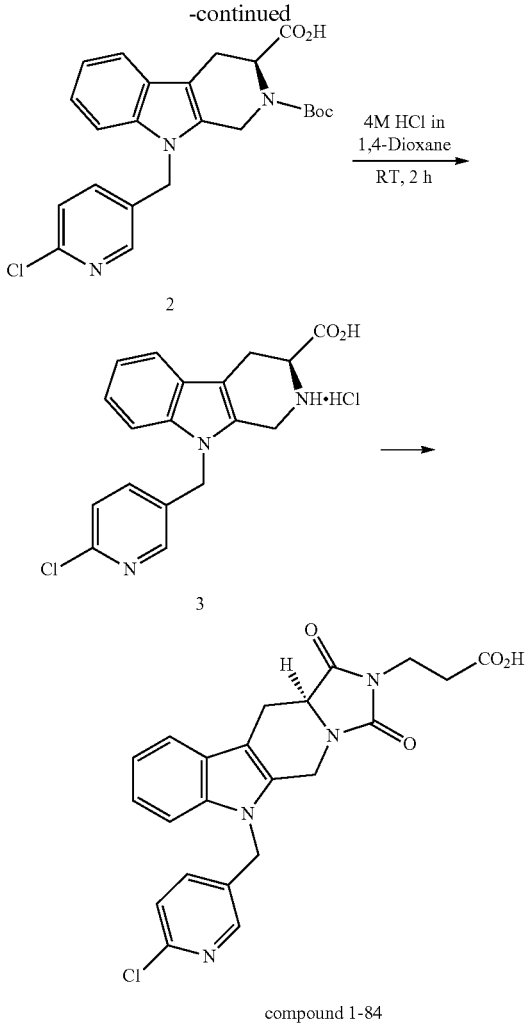

Step 1: Synthesis of (S)-2-(tert-butoxycarbonyl)-9-((6-chloropyridin-3-yl)methyl)-2,3,4,9-tetrahydro-1H-pyrido[3,4-b]indole-3-carboxylic acid (2)

To a stirred solution of acid 1 (Example 5, Step 2; 1.0 g, 3.16 mmol) in DMF (50 mL) under inert atmosphere was added NaH (278 mg, 6.96 mmol) at 0° C.; then warmed to RT for 30 min. To this, 2-chloro-5-(chloromethyl)pyridine (622 mg, 3.79 mmol) was added at RT and stirred for 3 h. The reaction mixture was quenched with water (10 mL) and acidified with citric acid to pH~5 and extracted with EtOAc (2×40 mL). The combined organic extracts were washed with water (20 mL), brine (20 mL), dried over Na$_2$SO$_4$, filtered and concentrated under reduced pressure to obtain the crude. The crude was purified (silica gel chromatography; 20% EtOAc/hexanes) to afford compound 2 (1.0 g, 72%) as an off-white solid. $^1$H NMR (500 MHz, DMSO-d$_6$): ~1:1 rotamers; δ 12.85 (br s, 1H), 8.12 (s, 1/2H), 8.08 (s, 1/2H), 7.51-7.34 (m, 4H), 7.13-7.04 (m, 2H), 5.48-5.39 (m, 2H), 5.17-5.06 (m, 1H), 4.72-4.65 (m, 1H), 4.43 (d, J=16.5 Hz, 1/2H), 4.31 (d, J=16.5 Hz, 1/2H), 3.33-3.31 (m, 1H), 3.04-2.95 (m, 1H), 1.43 (s, 9H).

Step 2: Synthesis of (S)-9-((6-chloropyridin-3-yl)methyl)-2,3,4,9-tetrahydro-1H-pyrido[3,4-b]indole-3-carboxylic acid (3)

A solution of compound 2 (300 mg, 0.68 mmol) in 4.0M HCl in 1,4-dioxane (5 mL) was stirred at RT under inert atmosphere for 2 h. The reaction mixture was diluted with EtOAc (25 mL), the solid precipitated was filtered, washed with EtOAc (5 mL), and concentrated under reduced pressure to obtain the compound 3 (150 mg, 49%) as a pale brown solid. $^1$H NMR (500 MHz, DMSO-$d_6$): δ 8.70 (br s, 1H), 8.20 (s, 1H), 7.51 (d, J=7.5 Hz, 1H), 7.45-7.41 (m, 3H), 7.12 (t, J=7.5 Hz, 1H), 7.05 (t, J=7.5 Hz, 1H), 5.42 (s, 2H), 4.29 (d, J=15.5 Hz, 1H), 4.15 (d, J=15.5 Hz, 1H), 3.65-3.62 (m, 1H), 3.17-3.13 (m, 1H), 2.86-2.81 (m, 1H).

Step 3: Synthesis of (S)-3-(6-((6-chloropyridin-3-yl)methyl)-1,3-dioxo-5,6,11,11a-tetrahydro-1H-imidazo[1',5':1,6]pyrido[3,4-b]indol-2(3H)-yl)propanoic acid (1-84)

Following the procedure of Example 5, Step 6 and 7 but using acid 3 as starting material the title compound 1-84 was obtained. $^1$H NMR (500 MHz, CD$_3$OD): δ 8.12 (s, 1H), 7.57 (d, J=8.0 Hz, 1H), 7.43-7.37 (m, 3H), 7.20 (t, J=8.0 Hz, 1H), 7.13 (t, J=8.0 Hz, 1H), 5.46 (s, 2H), 5.03 (d, J=15.5 Hz, 1H), 4.39-4.36 (m, 2H), 3.86-3.82 (m, 2H), 3.41-3.37 (m, 1H), 2.88-2.82 (m, 1H), 2.69 (t, J=7.5 Hz, 2H); MS (ESI): m/z 437.2 (M+H$^+$); Chiral HPLC: 90.4%, R$_t$=29.5 min (Chiralpak IA, 250×4.6 mm, 5 μm); mobile phase (A) 0.1% TFA in n-Hexane (B) THF: MeOH (80:20) (A:B: 75:25); at 1.0 mL/min).

Example 28: Synthesis of (S)-1-((6-((6-methoxypyridin-3-yl)methyl)-1,3-dioxo-5,6,11,11a-tetrahydro-1H-imidazo[1',5':1,6]pyrido[3,4-b]indol-2(3H)-yl)methyl)cyclopropane-1-carboxylic acid (1-18)

Step 1: Synthesis of tert-butyl 1-(isocyanatomethyl)cyclopropane-1-carboxylate (2)

To a stirred solution of tert-butyl 1-(aminomethyl)cyclopropane-1-carboxylate (150 mg, 0.87 mmol) in CH$_2$Cl$_2$ (20 mL) under inert atmosphere were added saturated aqueous NaHCO$_3$ (20 mL) and triphosgene (103 mg, 0.35 mmol) at 0° C. and stirred for 30 min. After completion of the reaction by TLC, the reaction mixture was diluted with water (20 mL) and extracted with CH$_2$Cl$_2$ (2×30 mL). The combined organic extracts were dried over Na$_2$SO$_4$, filtered and concentrated under reduced pressure to obtain crude isocyanate 2 (100 mg) as a colorless liquid, which was used without further purification. $^1$H NMR (500 MHz, DMSO-$d_6$): δ 3.39 (s, 2H), 1.41 (s, 9H), 1.11-1.09 (m, 2H), 0.93-0.90 (m, 2H).

Step 2: Synthesis of (S)-1-((6-((6-methoxypyridin-3-yl)methyl)-1,3-dioxo-5,6,11,11a-tetrahydro-1H-imidazo[1',5':1,6]pyrido[3,4-b]indol-2(3H)-yl)methyl)cyclopropane-1-carboxylic acid (1-18)

Following the procedure of Example 5, Step 6 and 7 but using acid 1 (Example 27, Step 2) and isocyanate 2 as starting materials, the title compound 1-18 was prepared. $^1$H NMR (400 MHz, CD$_3$OD): δ 7.93 (s, 1H), 7.61 (d, J=8.8 Hz, 1H), 7.54 (d, J=8.0 Hz, 1H), 7.39 (d, J=8.0 Hz, 1H), 7.18 (t, J=8.0 Hz, 1H), 7.11 (t, J=8.0 Hz, 1H), 6.99 (d, J=8.8 Hz, 1H), 5.39 (s, 2H), 5.02 (d, J=16.4 Hz, 1H), 4.43-4.33 (m, 2H), 3.90 (d, J=14.4 Hz, 1H), 3.83 (d, J=14.4 Hz, 1H), 3.66 (s, 3H), 3.40-3.39 (m, 1H), 2.84-2.78 (m, 1H), 1.24-1.21 (m, 2H), 1.04-1.01 (m, 2H); MS (ESI): m/z 461.4 (M+H$^+$); Chiral HPLC: 83.8%, R$_t$=22.59 min (Chiralpak IA, 250×4.6 mm, 5 μm); mobile phase (A) 0.1% TFA in n-Hexane (B) THF: MeOH (80:20) (A:B: 75:25); at 1.0 mL/min).

Example 29: Synthesis of (S)-3-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylpropanoic acid (1-30)

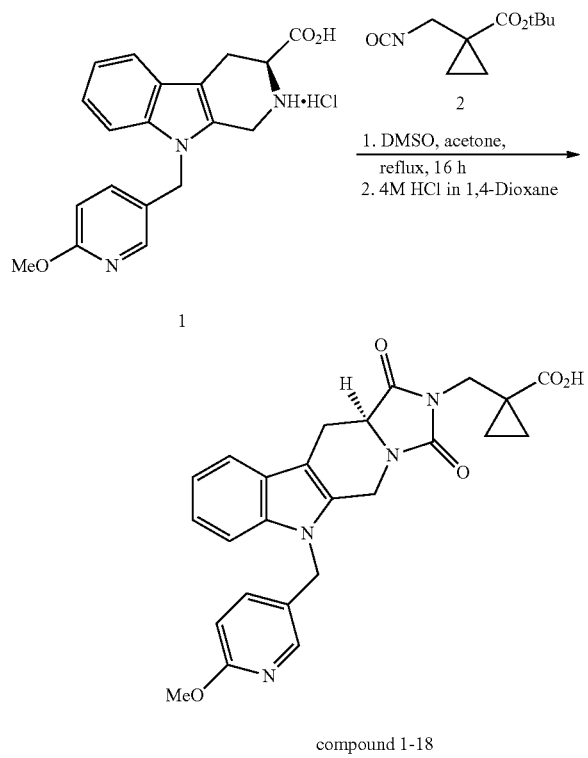

compound 1-18

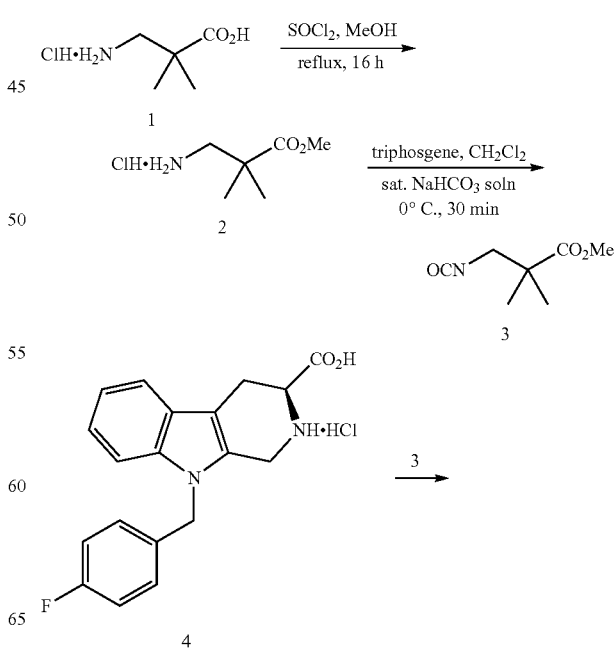

119

-continued

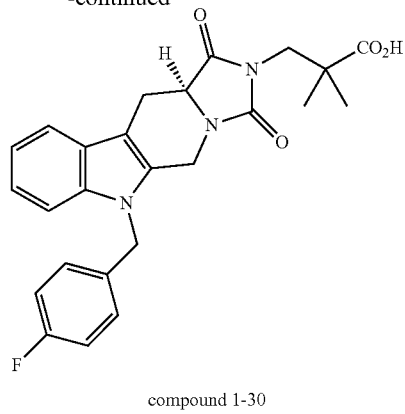

compound 1-30

Step 1: Synthesis of methyl 3-amino-2,2-dimethylpropanoate hydrochloride (2)

To a stirred solution of 3-amino-2,2-dimethylpropanoic acid HCl 1 (300 mg, 1.97 mmol) in MeOH (10 mL) was added $SOCl_2$ (1.5 mL) at 0° C. under inert atmosphere. The mixture was heated to reflux for 16 h then the volatiles were removed under reduced pressure, triturated with EtOAc (2×5 mL), n-pentane (2×5 mL) and dried under reduced pressure to obtain compound 2 (310 mg, 94%) as an off-white solid. $^1$H NMR (500 MHz, DMSO-$d_6$): δ 8.10 (br s, 3H), 3.65 (s, 3H), 2.94 (s, 2H), 1.20 (s, 6H).

Step 2: Synthesis of methyl 3-isocyanato-2,2-dimethylpropanoate (3)

To a stirred solution of compound 2 (300 mg, 1.79 mmol) in $CH_2Cl_2$ (25 mL) under inert atmosphere were added saturated $NaHCO_3$ solution (25 mL) and triphosgene (241 mg, 0.81 mmol) at 0° C. and stirred for 2 h. After completion of the reaction by TLC, the mixture was diluted with water (20 mL) and extracted with $CH_2Cl_2$ (2×30 mL). The combined organic extracts were washed with water (20 mL), brine (20 mL), dried over $Na_2SO_4$, filtered and concentrated under reduced pressure to obtain crude isocyanate 3 (250 mg) as a pale brown liquid, which was used without purification. $^1$H NMR (500 MHz, DMSO-$d_6$): δ 3.65 (s, 3H), 3.46 (s, 2H), 1.16 (s, 6H).

Step 3: Synthesis of (S)-3-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylpropanoic acid (1-30)

Following the procedure of Example 5, Step 6 and 7, but using isocyanate 3 as starting material,
the title compound 1-30 was obtained. LC-MS (ESI): m/z 472 (M+Na$^+$)

120

Example 30: Synthesis of (S)-1-((6-(4-fluorobenzyl)-1,3-dioxo-5,6,11,11a-tetrahydro-1H-imidazo[1',5':1,6]pyrido[3,4-b]indol-2(3H)-yl)methyl)cyclopropane-1-carboxylic acid (1-34)

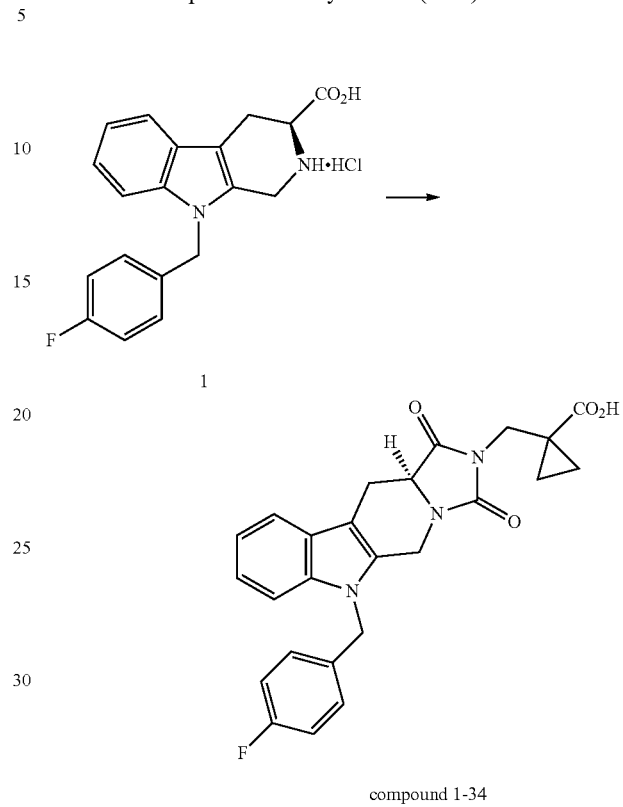

compound 1-34

Following the procedure of Example 5, Step 6 and 7, but using tert-butyl 1-(isocyanatomethyl) cyclopropane-1-carboxylate as starting material, the title compound 1-34 was obtained. LC-MS (ESI): m/z 470 (M+Na$^+$).

Example 31: Synthesis of 3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (C114)

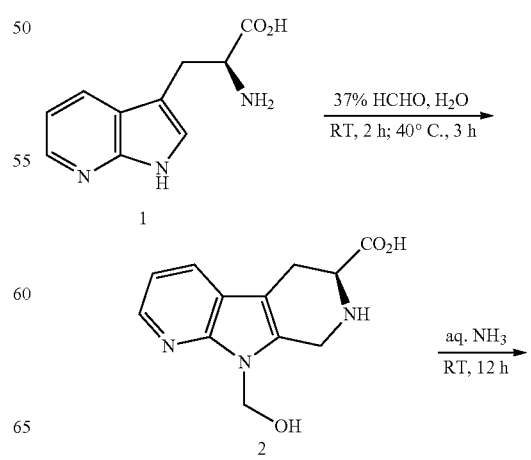

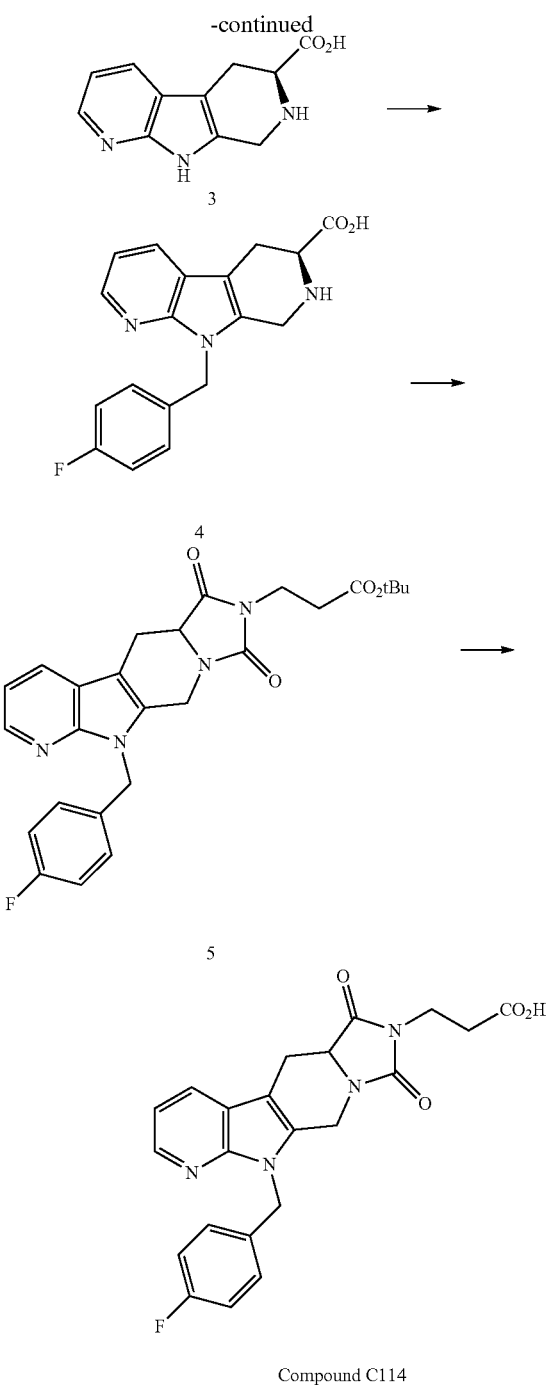

Step 1: Synthesis of (S)-9-(hydroxymethyl)-6,7,8,9-tetrahydro-5H-pyrrolo[2,3-b:5,4-c']dipyridine-6-carboxylic acid (2)

To a stirred solution of (S)-2-amino-3-(1H-pyrrolo[2,3-b]pyridin-3-yl)propanoic acid 1 (500 mg, 2.43 mmol) in water (1 mL) was added 37% aq. formaldehyde (73.2 mg, 2.43 mmol) at RT under inert atmosphere and stirred for 2 h. The reaction mixture was then heated to 40° C. for 3 h. The reaction mixture was cooled to RT, filtered and the solid obtained was dried under reduced pressure to afford compound 2 (220 mg, 36%) as an off-white solid. $^1$H NMR (400 MHz, DMSO-d$_6$): δ 8.23-8.21 (n, 1H), 7.92 (d, J=8.8 Hz, 1H), 7.12-7.09 (m, 1H), 6.41 (br s, 1H), 5.59-5.52 (m, 2H), 4.42 (d, J=16.0 Hz, 1H), 4.28 (d, J=16.0 Hz, 1H), 3.62-3.58 (m, 1H), 3.16-3.12 (m, 1H), 2.85-2.79 (m, 1H).

Step 2: Synthesis of (S)-6,7,8,9-tetrahydro-5H-pyrrolo[2,3-b:5,4-c']dipyridine-6-carboxylic acid (3)

A solution of compound 2 (220 mg, 0.89 mmol) in aqueous ammonia solution (2 mL) was stirred at RT under inert atmosphere for 12 h. The mixture was concentrated under reduced pressure to afford compound 3 (190 mg) as an off-white solid. $^1$H NMR (400 MHz, DMSO-d$_6$): δ 11.40 (br s, 1H), 8.14 (dd, J=4.8, 1.6 Hz, 1H), 7.86 (d, J=7.6 Hz, 1H), 7.04-7.01 (m, 1H), 4.21 (d, J=16.0 Hz, 1H), 4.16 (d, J=16.0 Hz, 1H), 3.61-3.57 (m, 1H), 3.13-3.08 (m, 1H), 2.81-2.75 (m, 1H); LC-MS (ESI): 96.9%; m/z 218.1 (M+H$^+$).

Step 3: Synthesis of (S)-9-(4-fluorobenzyl)-6,7,8,9-tetrahydro-5H-pyrrolo[2,3-b:5,4-c']dipyridine-6-carboxylic acid (4)

Following the procedure of Example 5, Step 3-5, but using acid 3 as starting material the acid 4 was prepared and used without purification.

Step 4: Synthesis of tert-butyl 3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionate (5)

Following the procedure of Example 5, Step 6, but using acid 4 as starting material, the title compound 5 was obtained. $^1$H NMR (400 MHz, CD$_3$OD): δ 8.26 (d, J=6.4 Hz, 1H), 8.00 (d, J=8.0 Hz, 1H), 7.19-7.12 (m, 3H), 7.04-7.00 (m, 2H), 5.56-5.46 (m, 2H), 4.94 (d, J=16.4 Hz, 1H), 4.35-4.31 (m, 2H), 3.77 (t, J=6.8 Hz, 2H), 3.40-3.35 (m, 1H), 2.84-2.78 (m, 1H), 2.61-2.56 (m, 2H), 1.40 (s, 9H); LC-MS (ESI): 98.7%; m/z 479.5 (M+H$^+$); Chiral HPLC: R$_t$=23.22 min (51.65%); 24.66 min (48.35%) (Chiralpak IA, 250×4.6 mm, 5 μm); mobile phase (A) 0.1% TFA in n-Hexane (B) THF: MeOH (80:20) (A:B: 85:15); at 1.0 mL/min).

Step 5: Synthesis of 3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (C114)

Following the procedure of Example 5, Step 7 but using ester 5 in place of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate, the title compound C114 was obtained. LC-MS (ESI): m/z 423 (M+H$^+$).

Example 32: Synthesis of 3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (C114 Enantiomer A) and 3-{8-[(4-fluorophenyl)methyl]-12,14-dioxo-6.8.11.13-tetraazatetracyclo[7.7.0.02, 7.011,15]hexadeca-1(9),2(7),3,5-tetraen-13-yl}propionic acid (C114 Enantiomer B)

Compound 5 from Example 31 (racemate) was separated by Chiral HPLC (Chiralpak IC, 250×4.6 mm, 5 μm; mobile phase (A) 0.1% DEA in n-Hexane (B) EtOH (A:B: 80:20); at 1.0 mL/min).

First eluted was compound 5 Enantiomer A: $^1$H-NMR is identical with racemate 5 data; MS (ESI): m/z 479.6 (M+H$^+$); Chiral HPLC: 98.4%; R$_t$=25.14 min. This material was deprotected according to Example 31, Step 4 to give C114 Enantiomer A Second eluted was compound 5 Enantiomer B: $^1$H-NMR is identical with racemate 5 data; MS (ESI): m/z 479.6 (M+H$^+$); Chiral HPLC: 97.4%; R$_t$=31.72 min. This material was deprotected according to Example 31, Step 4 to give C114 Enantiomer B Example 33: Synthesis of (S)-3-(6-(4-fluorobenzyl)-1-oxo-3-thioxo-5,6,11,11a-tetrahydro-1H-imidazo[1',5':1,6]pyrido[3,4-b]indol-2(3H)-yl)propanoic acid (E1)

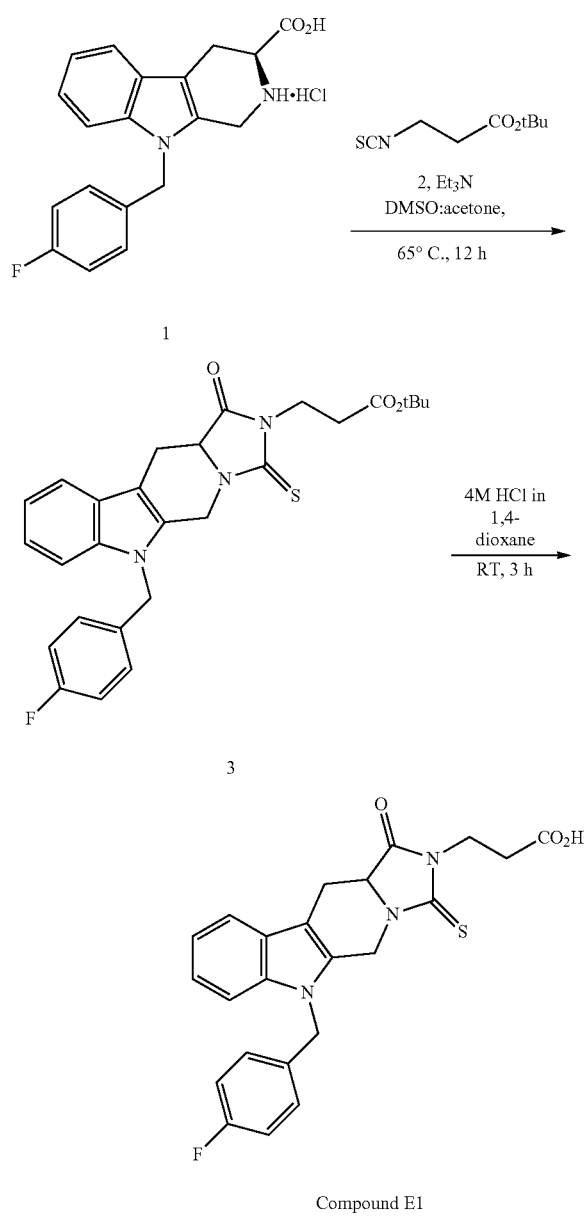

Step 1: Synthesis of tert-butyl 3-isothiocyanatopropanoate (2)

To a stirred solution of β-alanine tert-butyl ester.HCl (200 mg, 1.10 mmol) in CH$_2$Cl$_2$ (20 mL) under inert atmosphere were added thiophosgene (38.11 mg, 0.33 mmol) and aq. NaHCO$_3$ (20 mL) at 0° C. and stirred for 2 h. After completion of the reaction by TLC, the mixture was diluted with water (25 mL) and extracted with CH$_2$Cl$_2$ (3×25 mL). The combined organic extracts were dried Na$_2$SO$_4$, filtered and concentrated under reduced pressure to obtain crude thioisocyanate 2 (200 mg) as a yellow oil, which was used without further purification.

Step 2: Synthesis of tert-butyl (S)-3-(6-(4-fluorobenzyl)-1-oxo-3-thioxo-5,6,11,11a-tetrahydro-1H-imidazo[1',5':1,6]pyrido[3,4-b]indol-2(3H)-yl)propanoate (3)

To a stirred solution of acid 1 (Example 2, Step 4; 346.5 mg, 1.07 mmol) in acetone (20 mL) under inert atmosphere were added crude thioisocyanate 2 (200 mg), Et$_3$N (108 mg, 1.06 mmol) and DMSO (5 mL) at RT under inert atmosphere. The reaction was heated to 65° C. and stirred for 12 h. The mixture was diluted with water (20 mL) and extracted with EtOAc (2×30 mL). The combined organic extracts were dried over Na$_2$SO$_4$, filtered and concentrated under reduced pressure to obtain the crude. The crude was purified (silica gel chromatography; 10-15% EtOAc/hexanes) to afford compound 3 (250 mg, 47%) as a yellow solid. $^1$H NMR (500 MHz, CDCl$_3$): δ 7.54 (d, J=8.0 Hz, 1H), 7.29-7.17 (m, 3H), 7.03-6.98 (m, 4H), 5.54 (d, J=16.0 Hz, 1H), 5.33 (d, J=16.5 Hz, 1H), 5.22 (d, J=16.5 Hz, 1H), 4.43 (d, J=16.0 Hz, 1H), 4.31-4.30 (m, 1H), 4.17-4.13 (m, 2H), 3.47-3.46 (m, 1H), 2.91-2.89 (m, 1H), 2.71-2.67 (m, 2H), 1.44 (s, 9H); LC-MS (ESI): 89.9%; m/z 492.6 (M−H$^+$).

Step 3: Synthesis of (S)-3-(6-(4-fluorobenzyl)-1-oxo-3-thioxo-5,6,11,11a-tetrahydro-1H-imidazo[1',5':1,6]pyrido[3,4-b]indol-2(3H)-yl)propanoic acid (E1)

A solution of compound 3 (100 mg, 0.20 mmol) in 4.0 M HCl in 1,4-dioxane (2 mL) was stirred at 0° C.-RT for 3 h under inert atmosphere. The volatiles were removed under reduced pressure. The residue was diluted with water (10 mL) and extracted with EtOAc (2×20 mL). The combined organic extracts were dried over Na$_2$SO$_4$, filtered and concentrated under reduced pressure. The residue was triturated with n-pentane (8 mL) to afford 50 mg of the title compound E1 (57%) with 90% HPLC purity as a brown solid. $^1$H NMR (500 MHz, CD$_3$OD): δ 7.54 (d, J=7.5 Hz, 1H), 7.37 (d, J=8.0 Hz, 1H), 7.18 (t, J=7.5 Hz, 1H), 7.12-7.01 (m, 5H), 5.49 (d, J=16.5 Hz, 1H), 5.38 (s, 2H), 4.52-4.49 (m, 2H), 4.16-4.12 (m, 2H), 3.44-3.40 (m, 1H), 2.90-2.85 (m, 1H), 2.76-2.71 (m, 2H); MS (ESI): m/z 436.2 (M−H$^+$); Chiral HPLC: R$_t$=11.70 min (42.2%); 14.52 min (40.79%) (Chiralpak IB, 250×4.6 mm, 5 μm); mobile phase (A) 0.1% TFA in n-Hexane (B) CH$_2$Cl$_2$:MeOH (50:50) (A:B: 80:20); at 1.0 mL/min).

Example 34: Synthesis of 3-(6-(4-fluorobenzyl)-11,11-dimethyl-1,3-dioxo-5,6,11,11a-tetrahydro-1H-imidazo[1',5':1,6]pyrido[3,4-b]indol-2(3H)-yl)propanoic acid (A11)
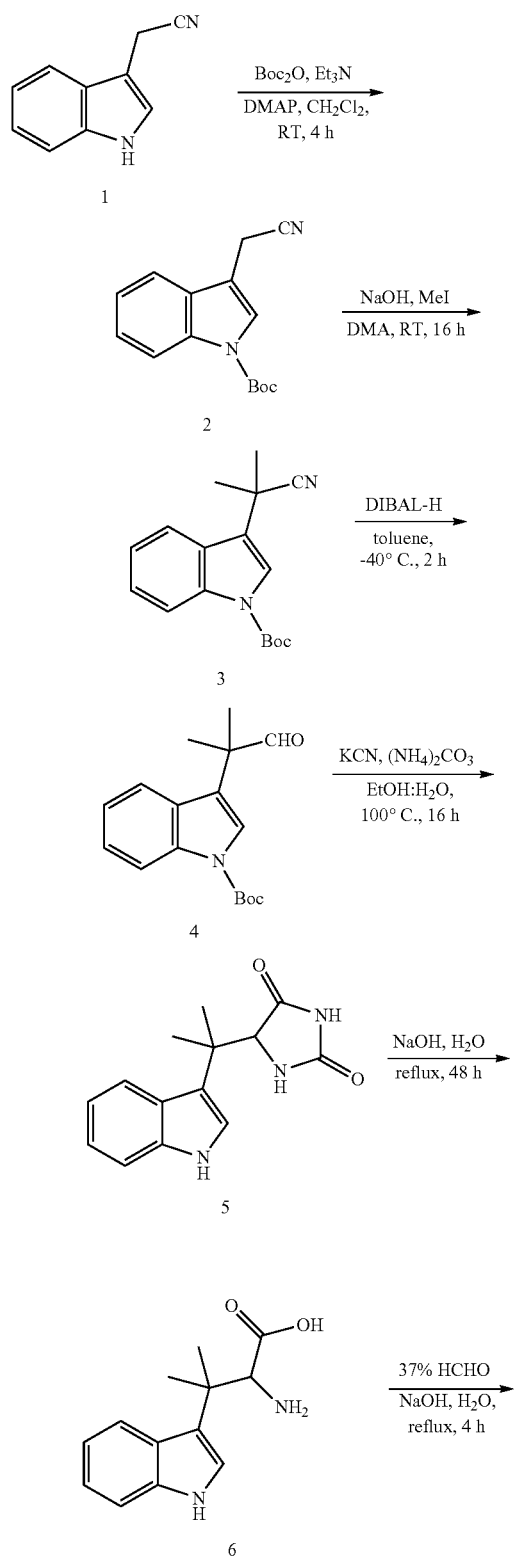
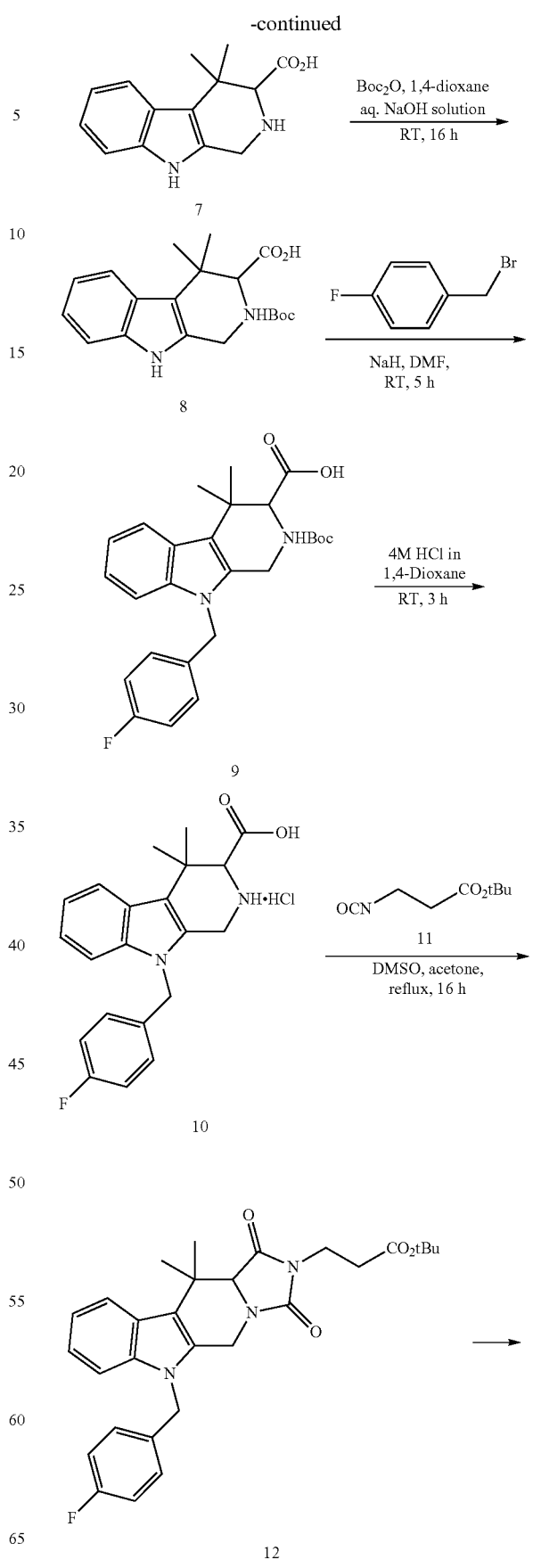

127

-continued

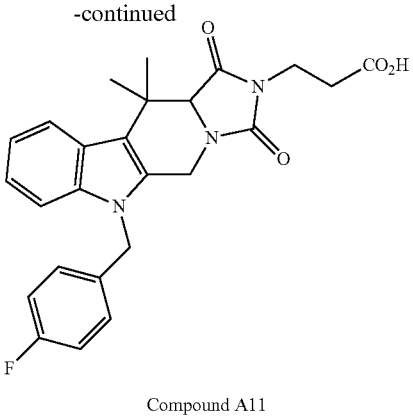

Compound A11

Step 1: Synthesis of tert-butyl 3-(cyanomethyl)-1H-indole-1-carboxylate (2)

To a stirred solution of 2-(1H-indol-3-yl)acetonitrile 1 (5.0 g, 32.0 mmol) in $CH_2Cl_2$ (100 mL) were added $Et_3N$ (5.8 g, 57.6 mmol), DMAP (234 mg, 1.92 mmol) and Boc-anhydride (8.3 g, 38.4 mmol) at RT under inert atmosphere. The reaction was stirred for 4 h and monitored by TLC. The reaction mixture was diluted with water (100 mL) and extracted with $CH_2Cl_2$ (3×75 mL). The combined organic extracts were dried over $Na_2SO_4$, filtered and concentrated under reduced pressure to obtain the crude. The crude product was triturated with n-pentane (2×20 mL) and dried under reduced pressure to afford compound 2 (7.0 g, 85%) as an off-white solid. $^1H$ NMR (500 MHz, DMSO-$d_6$): δ 8.08 (d, J=8.0 Hz, 1H), 7.70-7.67 (m, 2H), 7.40 (t, J=8.0 Hz, 1H), 7.32 (t, J=8.0 Hz, 1H), 4.12 (s, 2H), 1.63 (s, 9H).

Step 2: Synthesis of tert-butyl 3-(2-cyanopropan-2-yl)-1H-indole-1-carboxylate (3)

To a stirred solution of compound 2 (7.0 g, 27.31 mmol) in N,N-dimethylacetamide (75 mL) was added NaOH (3.2 g, 80.0 mmol) at 0° C. under inert atmosphere and stirred for 30 min. To this, MeI (11.5 g, 81.56 mmol) was added at 0° C. and the reaction was warmed to RT and stirred for 16 h. The reaction mixture was diluted with water (50 mL) and extracted with EtOAc (2×75 mL). The combined organic extracts were washed with water (40 mL), brine (40 mL), dried over $Na_2SO_4$, filtered and concentrated under reduced pressure to obtain the crude. The crude product was purified (silica gel chromatography; 5% EtOAc/hexanes) to afford compound 3 (4.5 g, 58%) as an off-white solid. $^1H$ NMR (500 MHz, DMSO-$d_6$): δ 8.12 (d, J=8.0 Hz, 1H), 7.84 (d, J=7.5 Hz, 1H), 7.60 (s, 1H), 7.42-7.39 (m, 1H), 7.36-7.33 (m, 1H), 1.80 (s, 6H), 1.64 (s, 9H).

Step 3: Synthesis of tert-butyl 3-(2-methyl-1-oxopropan-2-yl)-1H-indole-1-carboxylate (4)

To a stirred solution of compound 3 (4.5 g, 15.82 mmol) in toluene (150 mL) under inert atmosphere was added DIBAL-H (2.3 g, 16.17 mmol) drop wise at −40° C. for 10 min. The reaction was stirred for 2 h. The reaction mixture was quenched with a mixture of ether (40 mL), aqueous $NH_4Cl$ solution (40 mL) and extracted with ether (3×75 mL). The combined organic extracts were washed with water (50 mL), brine (50 mL), dried over $Na_2SO_4$, filtered

128 and concentrated under reduced pressure to obtain the crude. The crude was purified (silica gel chromatography; 3% EtOAc/hexanes) to afford compound 4 (2.5 g, 55%) as an off-white solid. $^1H$ NMR (500 MHz, DMSO-$d_6$): δ 9.52 (s, 1H), 8.09 (d, J=8.0 Hz, 1H), 7.57 (s, 1H), 7.43 (d, J=8.0 Hz, 1H), 7.34 (t, J=8.0 Hz, 1H), 7.23 (t, J=8.0 Hz, 1H), 1.64 (s, 9H), 1.49 (s, 6H).

Step 4: Synthesis of 5-(2-(1H-indol-3-yl)propan-2-yl)imidazolidine-2,4-dione (5)

To a stirred solution of compound 4 (2.0 g, 6.96 mmol) in EtOH: $H_2O$ (1:1, 40 mL) under inert atmosphere were added KCN (779 mg, 11.98 mmol), $(NH_4)_2CO_3$ (2.67 g, 27.81 mmol) at RT; heated to 100° C. and stirred for 16 h in sealed tube. The mixture was cooled to RT, diluted with water (60 mL) and extracted with EtOAc (3×70 mL). The combined organic extracts were washed with water (60 mL), brine (60 mL), dried over $Na_2SO_4$, filtered and concentrated under reduced pressure to obtain the crude compound 5 (1.6 g) as an off-white solid, which was used without further purification. $^1H$ NMR (500 MHz, DMSO-$d_6$): δ 10.87 (s, 1H), 10.27 (s, 1H), 7.75-7.74 (m, 2H), 7.32 (d, J=8.5 Hz, 1H), 7.06-7.01 (m, 2H), 6.92 (t, J=8.0 Hz, 1H), 4.30 (s, 1H), 1.48 (s, 6H); LC-MS (ESI): 92.6%; m/z 258.0 (M+H$^+$).

Step 5: Synthesis of 2-amino-3-(1H-indol-3-yl)-3-methylbutanoic acid (6)

To a stirred solution of compound 5 (1.6 g, 6.22 mmol) in $H_2O$ (3.6 mL) under inert atmosphere was added NaOH (2.76 g, 68.48 mmol) at RT; heated to reflux for 48 h. The mixture was cooled to RT, the solution was filtered, washed with water (2×20 mL) and the filtrate was concentrated under reduced pressure to obtain the crude compound 6 (2.1 g) as an off-white solid, which was used without further purification. $^1H$ NMR (500 MHz, DMSO-$d_6$): δ 10.84 (s, 1H), 7.73 (d, J=8.0 Hz, 1H), 7.34 (d, J=7.5 Hz, 1H), 7.05-7.02 (m, 2H), 6.94 (t, J=8.0 Hz, 1H), 3.68 (s, 1H), 1.51 (s, 3H), 1.31 (s, 3H).

Step 6: Synthesis of 4,4-dimethyl-2,3,4,9-tetrahydro-1H-pyrido[3,4-b]indole-3-carboxylic acid (7)

To a stirred solution of crude compound 6 (1.3 g) in $H_2O$ (3.3 mL) under inert atmosphere were added NaOH (224 mg, 5.60 mmol), 37% formalin (0.45 mL, 5.60 mmol) at RT; heated to reflux and stirred for 4 h. The mixture was cooled to RT, acidified with 10% aq. HCl solution (to pH~4). The precipitated solid was filtered, washed with water (2×10 mL) and n-pentane (2×10 mL). The obtained solid was triturated with $CH_2Cl_2$ (2×5 mL), n-pentane (2×5 mL) and dried under reduced pressure to obtain 7 (750 mg, ~58%) as a pale yellow solid. $^1H$ NMR (400 MHz, DMSO-$d_6$): δ 11.05 (s, 1H), 9.55 (br s, 1H), 7.61 (d, J=8.0 Hz, 1H), 7.34 (d, J=8.0 Hz, 1H), 7.06 (t, J=8.0 Hz, 1H), 6.97 (t, J=8.0 Hz, 1H), 4.25 (d, J=15.6 Hz, 1H), 4.08 (d, J=15.6 Hz, 1H), 3.69-3.67 (m, 1H), 1.71 (s, 3H), 1.35 (s, 3H); LC-MS (ESI): 85.7%; m/z 245.2 (M+H$^+$).

Step 7: Synthesis of 2-(tert-butoxycarbonyl)-4,4-dimethyl-2,3,4,9-tetrahydro-1H-pyrido[3,4-b]indole-3-carboxylic acid (8)

To a stirred solution of compound 7 (700 mg, 2.86 mmol) in 1,4-dioxane:$H_2O$ (2:1, 19.8 mL) under inert atmosphere was added NaOH (229 mg, 5.73 mmol) at 0° C. To this Boc-anhydride (938 mg, 4.30 mmol) was added at 0° C.; warmed to RT and stirred for 16 h. The mixture was acidified with saturated citric acid solution (up to pH~4) and extracted with EtOAc (2×30 mL). The combined organic extracts were dried over $Na_2SO_4$, filtered and concentrated under reduced pressure to obtain the crude. The crude was purified (silica gel chromatography; 1-2% $MeOH/CH_2Cl_2$) to afford compound 8 (350 mg, 35%) as an off-white solid. $^1$H NMR (500 MHz, DMSO-$d_6$): (1:1 rotemeric mixture) δ 12.53 (br s, 1H), 10.86 (br s, 2H), 10.83 (br s, 1/2H), 7.56 (d, J=8.0 Hz, 1H), 7.28-7.27 (m, 1H), 7.00 (t, J=8.0 Hz, 1H), 6.92 (t, J=8.0 Hz, 1H), 4.74 (d, J=17.5 Hz, 1H), 4.64-4.52 (m, 2H), 1.62 (s, 3H), 1.46 (s, 9/2H), 1.44 (s, 9/2 H), 1.28 (s, 3H).

Step 8: Synthesis of 2-(tert-butoxycarbonyl)-9-(4-fluorobenzyl)-4,4-dimethyl-2,3,4,9-tetrahydro-1H-pyrido[3,4-b]indole-3-carboxylic acid (9)

To a stirred solution of compound 8 (350 mg, 1.01 mmol) in DMF (5 mL) under inert atmosphere was added NaH (107 mg, 60% in mineral oil; 2.67 mmol) at 0° C.; warmed to RT and stirred for 1 h. To this, 4-fluorobenzyl bromide (230 mg, 1.22 mmol) in DMF (1 mL) was added at 0° C. The reaction was warmed to RT and stirred for 5 h. The mixture was quenched with water (5 mL) and acidified with saturated citric acid solution (to pH~5-6) and extracted with EtOAc (2×40 mL). The combined organic extracts were washed with water (20 mL), dried over $Na_2SO_4$, filtered and concentrated under reduced pressure to obtain the crude. The crude was purified (silica gel chromatography; 1% MeOH/ $CH_2Cl_2$) to afford compound 9 (360 mg, 78%) as an off-white solid. $^1$H NMR (400 MHz, $CDCl_3$): δ 7.69 (d, J=7.6 Hz, 1H), 7.18 (d, J=7.6 Hz, 1H), 7.12-7.04 (m, 2H), 6.91-6.89 (m, 4H), 5.26-5.13 (m, 2H), 4.90-4.81 (m, 1H), 4.69-4.66 (m, 1H), 4.57-4.44 (m, 1H), 1.76 (s, 3H), 1.46 (s, 9H), 1.41 (s, 3H).

Step 9: Synthesis of 9-(4-fluorobenzyl)-4,4-dimethyl-2,3,4,9-tetrahydro-1H-pyrido[3,4-b]indole-3-carboxylic acid hydrochloride (10)

A solution of compound 9 (360 mg, 0.79 mmol) in 4.0 M HCl in 1,4-dioxane (6 mL) was stirred at 0° C.-RT under inert atmosphere for 3 h. The volatiles were removed under reduced pressure and the obtained solid was washed with ether (2×8 mL) to afford compound 10 (250 mg, 81%) as an off-white solid. $^1$H NMR (400 MHz, DMSO-$d_6$): δ 14.21 (br s, 1H), 10.39 (br s, 1H), 7.71 (d, J=7.6 Hz, 1H), 7.44 (d, J=7.6 Hz, 1H), 7.15-7.04 (m, 6H), 5.40 (s, 2H), 4.41-4.33 (m, 2H), 4.25 (s, 1H), 1.72 (s, 3H), 1.43 (s, 3H).

Step 10: Synthesis of tert-butyl 3-(6-(4-fluorobenzyl)-11,11-dimethyl-1,3-dioxo-5,6,11,11a-tetrahydro-H-imidazo[1',5':1,6]pyrido[3,4-b]indol-2(3H)-yl)propanoate (12)

To a stirred solution of compound 10 (100 mg, 0.28 mmol) in acetone (20 mL) under inert atmosphere was added crude isocyanate 11 (228 mg) and DMSO (3 mL) at RT; heated to reflux and stirred for 16 h. The mixture was diluted with water (20 mL) and extracted with EtOAc (2×30 mL). The combined organic extracts were washed with water (20 mL), dried over $Na_2SO_4$, filtered and concentrated under reduced pressure to obtain the crude. The crude was purified (silica gel chromatography; 15% EtOAc/hexanes) to afford 12 (22 mg, 15%) as an off-white solid. $^1$H NMR (400 MHz, $CDCl_3$): δ 7.78 (d, J=8.0 Hz, 1H), 7.30 (d, J=8.0 Hz, 1H), 7.24 (t, J=8.0 Hz, 1H), 7.12 (t, J=8.0 Hz, 1H), 7.01-6.96 (m, 4H), 5.28 (d, J=16.0 Hz, 1H), 5.14 (d, J=16.0 Hz, 1H), 5.02 (d, J=16.8 Hz, 1H), 4.24 (d, J=16.8 Hz, 1H), 3.92 (s, 1H), 3.84-3.82 (m, 2H), 2.60 (t, J=7.2 Hz, 2H), 1.94 (s, 3H), 1.40 (s, 9H), 1.26 (s, 3H); LC-MS (ESI): 98.9%; m/z 504.7 (M−H$^+$).

Step 11: Synthesis of 3-(6-(4-fluorobenzyl)-11,11-dimethyl-1,3-dioxo-5,6,11,11a-tetrahydro-1H-imidazo[1',5':1,6]pyrido[3,4-b]indol-2(3H)-yl)propanoic acid (A11)

Following the procedure of Example 5, Step 7 but using ester 12 in place of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate, the title compound A11 was obtained. LC-MS (ESI): m/z 450 (M+H$^+$).

Example 35: Synthesis of 6-(4-fluorobenzyl)-11,11-dimethyl-5,6,11,11a-tetrahydro-1H-imidazo[1',5':1,6]pyrido[3,4-b]indole-1,3(2H)-dione (A110)

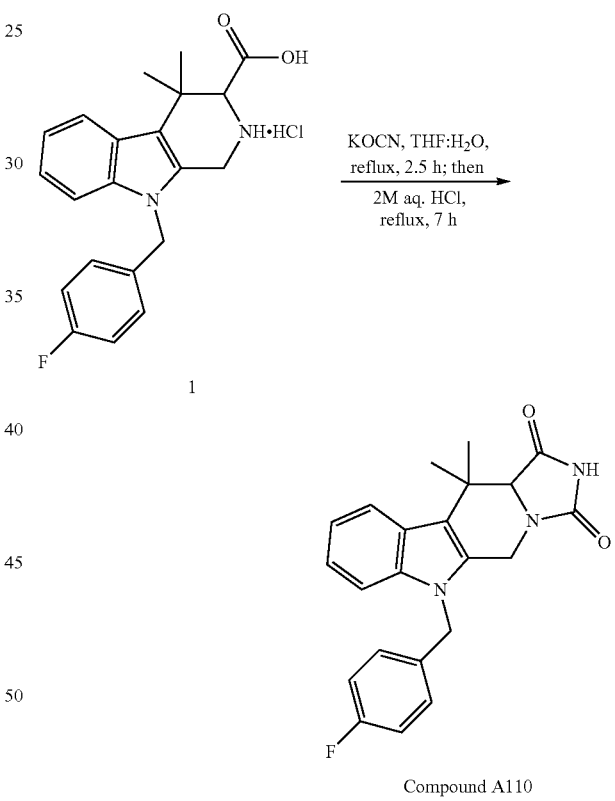

Compound A110

To a stirred solution of compound 1 (Example 34, Step 9; 100 mg, 0.25 mmol) in THF:$H_2O$ (1:1, 4 mL) under inert atmosphere was added KOCN (45.8 mg, 0.56 mmol) at RT; heated to reflux and stirred for 2.5 h. The reaction mixture was cooled to RT and was added 2.0 M aqueous HCl (4 mL). The reaction mixture was heated to reflux and stirred for 7 h. The mixture was cooled to RT, the precipitated solid was filtered, washed with water (2×10 mL), n-pentane (2×5 mL) and dissolved in 10% $MeOH/CH_2Cl_2$ (20 mL) and concentrated under reduced pressure to obtain the crude. The crude was purified (silica gel chromatography; 1-2% MeOH/ $CH_2Cl_2$) to afford the title compound A110 (40 mg, 42%) as an off-white solid. $^1$H NMR (500 MHz, DMSO-$d_6$): δ 10.95 (s, 1H), 7.72 (d, J=8.0 Hz, 1H), 7.47 (d, J=8.0 Hz, 1H), 7.15-7.08 (m, 4H), 7.03 (t, J=8.0 Hz, 2H), 5.38 (s, 2H), 4.84 (d, J=16.5 Hz, 1H), 4.24 (d, J=16.5 Hz, 1H), 4.12 (s, 1H), 1.76 (s, 3H), 1.17 (s, 3H); LC-MS (ESI): 99.4%; m/z 376.4 (M–H$^+$).

Example 36: Synthesis of 6-(4-fluorobenzyl)-11,11-dimethyl-5,6,11,11a-tetrahydro-1H-imidazo[1',5':1,6]pyrido[3,4-b]indole-1,3(2H)-dione (A110 Enantiomer A) & 6-(4-fluorobenzyl)-11,11-dimethyl-5,6,11,11a-tetrahydro-1H-imidazo[1',5':1,6]pyrido[3,4-b]indole-1,3(2H)-dione (A110 Enantiomer B)

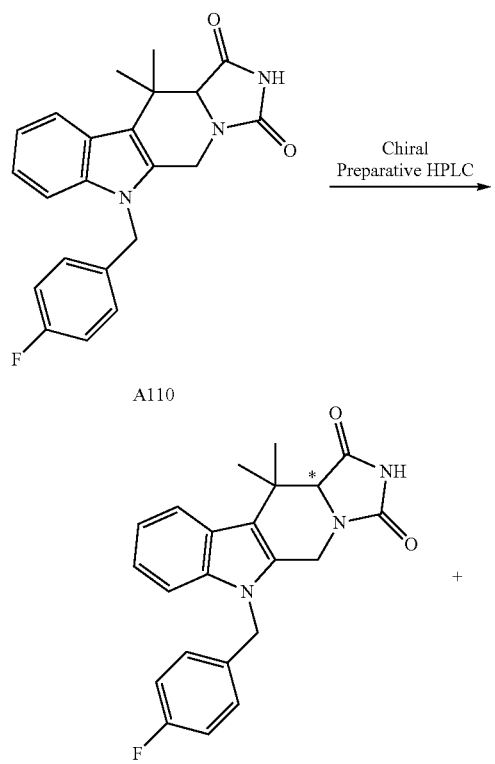

Enantiomer A as the first eluted compound: $^1$H NMR (400 MHz, DMSO-$d_6$): Data is identical with the racemate; Chiral HPLC: 100%; R$_t$=16.91 min (Chiralpak-IC, 250×4.6 mm, 5μ); mobile phase (A) 0.1% DEA in n-Hexane (B) CH$_2$Cl$_2$:CH$_3$OH (50:50) (A:B=85:15); at 1.0 mL/min).

And A110 Enantiomer B as the second eluted compound: $^1$H NMR (400 MHz, DMSO-$d_6$): Data is identical with the racemate; Chiral HPLC: 100%; R$_t$=24.50 min.

Example 37: Synthesis of 2-(6-(4-fluorobenzyl)-3-oxo-11,11a-dihydro-1H-imidazo[1',5':1,6]pyrido[3,4-b]indol-2(3H,5H,6H)-yl)acetic acid (1-20)

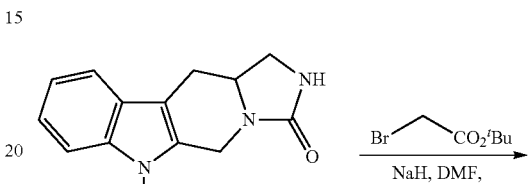

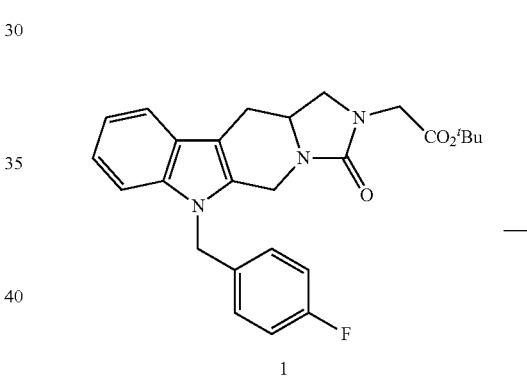

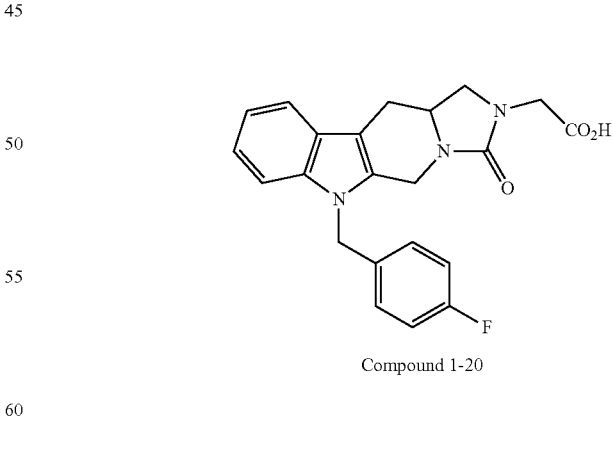

The racemic hydantoin A110 (Example 35) was separated by chiral preparative HPLC (Chiralpak-IC, 250×4.6 mm, 5μ; (A): 0.1% DEA in n-Hexane; (B): CH$_2$Cl$_2$: CH$_3$OH (50:50); eluent (A:B)=85:15; flow rate: 1.0 mL/min.) to afford A110

Following the procedure of Example 21, Steps 1 and 2, but using Compound 1-13 (Example 12) as starting material, the title compound 1-20 was obtained. LC-MS (ESI): m/z 394 (M+H$^+$).

133

Example 38: Synthesis of 3-(6-(4-fluorobenzyl)-3-oxo-11,11a-dihydro-1H-imidazo[1',5':1,6]pyrido[3,4-b]indol-2(3H,5H,6H)-yl)propanoic acid (1-21)

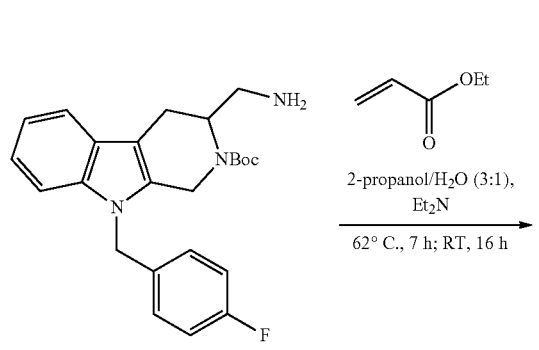

1

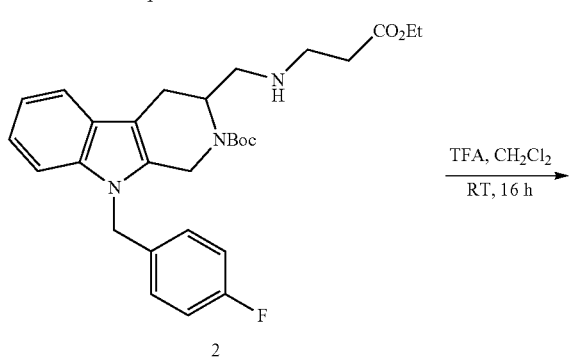

2

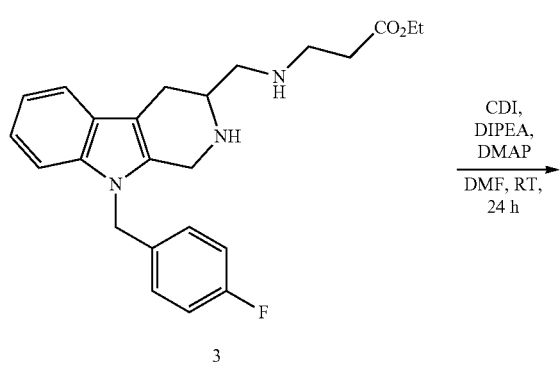

3

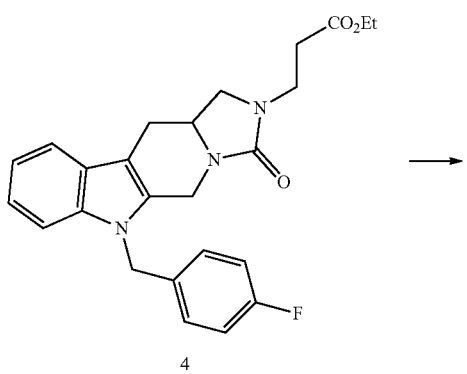

4

134

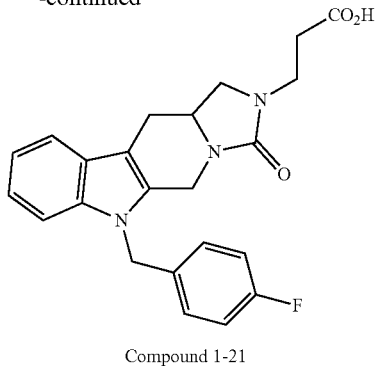

Compound 1-21

Step 1: Synthesis of tert-butyl 3-(((3-ethoxy-3-oxo-propyl)amino)methyl)-9-(4-fluorobenzyl)-3,4-dihydro-1H-pyrido[3,4-b]indole-2(9H)-carboxylate (2)

To a stirred solution of the amine 1 (Example 12, Step 4; 3.0 g, 7.33 mmol) in 2-propanol/H$_2$O (3:1, 20 mL) was added Et$_3$N (1.05 mL, 7.77 mmol) at 60° C. To this was added ethyl acrylate (0.26 mL, 2.42 mmol) at an internal temperature of 62-63° C. and stirred for 2 h. Additional ethyl acrylate (0.26 mL, 2.42 mmol) was added at 62° C. and stirred for 5 h. The reaction mixture was cooled to RT and allowed to stand for overnight. The mixture was diluted with 3% aqueous NaHCO$_3$ solution (80 mL) and extracted with EtOAc (3×40 mL). The combined organic extracts were washed with brine (50 mL), dried over Na$_2$SO$_4$, filtered and dried under reduced pressure. The crude was purified (silica gel chromatography; 40-50% EtOAc/hexanes) to afford compound 2 (425 mg, 11%) as a colorless liquid. $^1$H NMR (400 MHz, DMSO-d$_6$): δ 7.44-7.40 (m, 2H), 7.15-7.00 (m, 6H), 5.36-5.31 (m, 2H), 5.04-4.94 (m, 1H), 4.77-4.48 (m, 2H), 4.05-3.99 (m, 2H), 2.78-2.66 (m, 2H), 2.34 (t, J=6.8 Hz, 2H), 1.41 (s, 9H), 1.23-1.12 (m, 3H); LC-MS (ESI): 59.8%; m/z 510.7 (M+H$^+$).

Step 2: Synthesis of ethyl 3-(((9-(4-fluorobenzyl)-2,3,4,9-tetrahydro-1H-pyrido[3,4-b]indol-3-yl)methyl)amino)propanoate (3)

To a stirred solution of compound 2 (700 mg, 1.37 mmol) in CH$_2$Cl$_2$ (3 mL) was added TFA (4 mL) at RT under inert atmosphere and stirred for 16 h. The volatiles were removed under reduced pressure. The residue was quenched with aq. NaHCO$_3$ solution (30 mL) and extracted with EtOAc (3×30 mL). The combined organic extracts were washed with brine (30 mL), dried over Na$_2$SO$_4$, filtered and dried under reduced pressure to obtain crude compound 3 (708 mg) as an off-white solid, which was used as such. LC-MS (ESI): 46.4%; m/z 410.5 (M+H$^+$).

Step 3: Synthesis of ethyl 3-(6-(4-fluorobenzyl)-3-oxo-11,11a-dihydro-1H-imidazo[1',5':1,6]pyrido[3,4-b]indol-2(3H,5H,6H)-yl)propanoate (4)

To a stirred solution of the compound 3 (320 mg, crude) in DMF (10 mL) were added CDI (127 mg, 0.78 mmol), N,N-diisopropylethylamine (0.29 mL, 1.56 mmol) followed by DMAP (19 mg, 0.15 mmol) at RT under inert atmosphere and stirred for 24 h. The mixture was diluted with water (20 mL) and extracted with EtOAc (3×20 mL). The combined organic extracts were washed with brine (20 mL), dried over Na$_2$SO$_4$, filtered and dried under reduced pressure. The crude was purified (silica gel chromatography; 60%-70% EtOAc/hexanes) to afford 4 (26 mg, 8%) as an off-white sticky solid. $^1$H NMR (400 MHz, CDCl$_3$): δ 7.49 (d, J=7.6 Hz, 1H), 7.19-7.17 (m, 1H), 7.15-7.10 (m, 2H), 6.99-6.92 (m, 4H), 5.21 (q, 2H), 4.80 (d, J=16.0 Hz, 1H), 4.13 (q, 2H), 4.10-4.06 (m, 1H), 3.83-3.76 (m, 1H), 3.69 (t, J=8.0 Hz, 1H), 3.56 (t, J=6.8 Hz, 2H), 3.30-3.26 (m, 1H), 3.06-3.01 (m, 1H), 2.78-2.70 (m, 1H), 2.58 (t, J=6.8 Hz, 2H), 1.26 (t, J=7.2 Hz, 3H); LC-MS (ESI): 97.5%; m/z 436.4 (M+H$^+$).

Step 4: Synthesis of 3-(6-(4-fluorobenzyl)-3-oxo-11,11a-dihydro-1H-imidazo[1',5':1,6]pyrido[3,4-b]indol-2(3H,5H,6H)-yl)propanoic acid (1-21)

To a stirred ice cold solution of 4 in a mixture of 0.750 mL of THF and 0.250 mL of MeOH was added 1 eq of 0.1 N NaOH over 10 minutes. The mixture was stirred at room temperature for 24 hours then the mixture was evaporated to dryness to afford the title compound 1-21. LC-MS (ESI): m/z 408 (M+H$^+$)

Example 39: Synthesis of (S)-3-(1,3-dioxo-6-((2-(trifluoromethyl)thiazol-5-yl)methyl)-11,11a-dihydro-1H-imidazo[1',5':1,6]pyrido[3,4-b]indol-2(3H,5H,6H)-yl)propanoic acid (1-102)

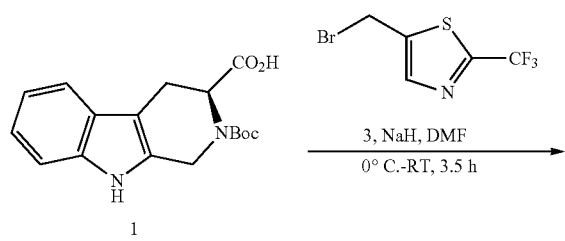

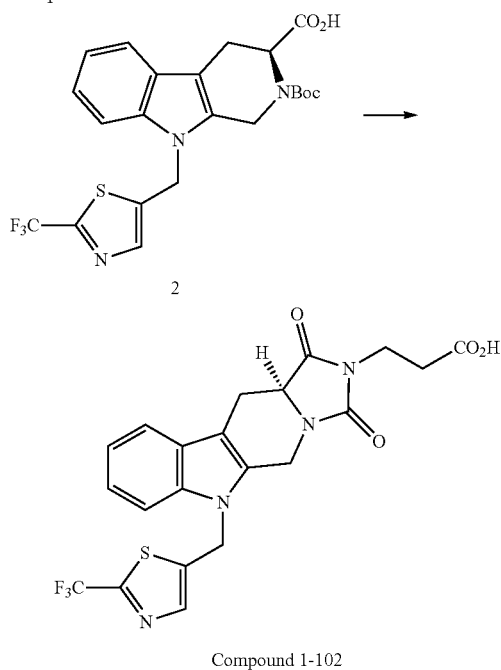

Step 1: Synthesis of (S)-2-(tert-butoxycarbonyl)-9-((2-(trifluoromethyl)thiazol-5-yl)methyl)-2,3,4,9-tetrahydro-1H-pyrido[3,4-b]indole-3-carboxylic acid (2)

To a stirred solution of acid 1 (Example 5, Step 2; 600 mg, 1.86 mmol) in DMF (20 mL) was added NaH (60% in mineral oil, 89.4 mg, 3.73 mmol) at 0° C. under inert atmosphere; warmed to RT and stirred for 30 min. To this was added 5-(bromomethyl)-2-(trifluoromethyl)thiazole 3 (458 mg, 1.86 mmol) in DMF (5 mL) at 0° C.; warmed to RT and stirred for 3 h. The mixture was quenched with ice cold water (40 mL) and extracted with EtOAc (3×30 mL). The combined organic extracts were washed with brine (25 mL), dried over Na$_2$SO$_4$, filtered and dried under reduced pressure. The crude was purified (silica gel chromatography; 2% CH$_3$OH/CH$_2$Cl$_2$) to afford compound 2 (300 mg, 33%) as a brown solid. $^1$H NMR (500 MHz, CDCl$_3$): δ 7.69-7.63 (m, 1H), 7.52 (d, J=8.0 Hz, 1H), 7.25-7.14 (m, 3H), 5.39 (s, 2H), 5.29-5.24 (m, 1H), 4.88-4.74 (m, 1H), 4.59-4.49 (m, 1H), 3.44-3.41 (m, 1H), 3.14-3.11 (m, 1H), 1.51 (s, 9H); LC-MS (ESI): 72.0%; m/z 480.8 (M−H$^+$).

Step 2: Synthesis of (S)-3-(1,3-dioxo-6-((2-(trifluoromethyl)thiazol-5-yl)methyl)-11,11a-dihydro-1H-imidazo[1',5':1,6]pyrido[3,4-b]indol-2(3H,5H,6H)-yl)propanoic acid (1-102)

Following the procedure of example 5, Steps 4-6, but using the acid 2 as starting material, the title compound 1-102 was obtained. LC-MS (ESI): m/z 479 (M+H$^+$).

Example 40: Synthesis of (S)-3-(6-(4-methoxybenzyl)-1,3-dioxo-11,11a-dihydro-1H-imidazo[1',5':1,6]pyrido[3,4-b]indol-2(3H,5H,6H)-yl)propanoic acid (1-131)

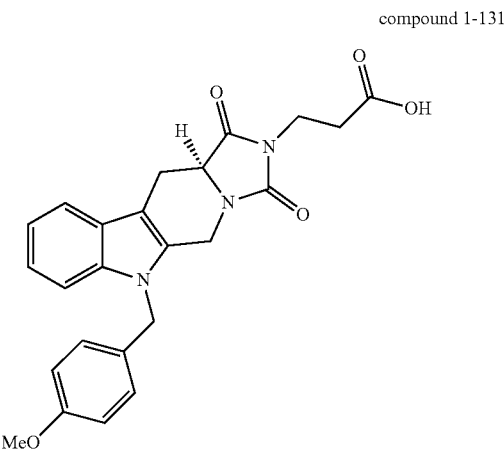 [SMILES: COc1ccc(Cn2c3c(c4ccccc42)C[C@H]2C(=O)N(CCC(=O)O)C(=O)N2C3)cc1]

compound 1-131

Following the procedure of Example 39, but using of 4-methoxybenzyl chloride as the alkylating agent in Step 1, the title compound 1-131 was obtained as a tan solid. $^1$H NMR (300 MHz, DMSO-d$_6$): δ 12.36 (br s, 1H), 7.48-7.53 (m, 2H), 7.00-7.15 (m, 4H), 6.84-6.86 (m, 2H), 5.38 (d, 1H), 5.29 (d, 1H), 4.89 (d, 1H), 4.30-4.39 (m, 2H), 3.68 (s, 3H), 3.61-3.68 (m, 2H), 3.20-3.38 (m, 2H), 2.73 (m, 1H), 2.53 (m, 1H); LC-MS (ESI): m/z 432 (M−H; negative ionization).

Example 41: Synthesis of (S)-3-(6-(2,4-dichlorobenzyl)-1,3-dioxo-11,11a-dihydro-1H-imidazo[1',5':1,6]pyrido[3,4-b]indol-2(3H,5H,6H)-yl)propanoic acid (1-132)

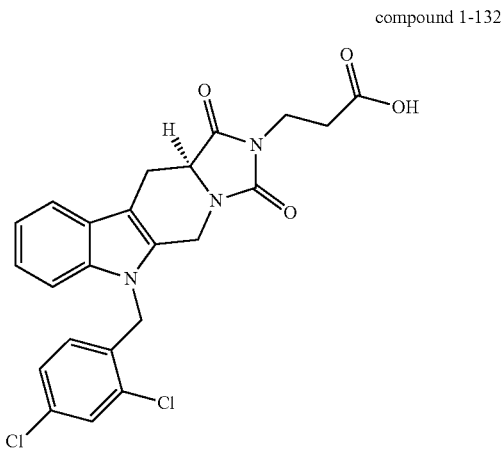 [SMILES: O=C(O)CCN1C(=O)[C@@H]2Cc3c(n(Cc4ccc(Cl)cc4Cl)c4ccccc34)CN2C1=O]

compound 1-132

Following the procedure for Example 39, but using 2,4-dichlorobenzyl chloride as the alkylating agent in Step 1, the title compound 1-132 was obtained. $^1$H NMR (300 MHz, DMSO-$d_6$): δ 12.37 (br s, 1H), 7.71 (d, 1H), 7.57 (d, 1H), 7.34 (d, 1H), 7.27 (dd, 1H), 7.04-7.14 (m, 2H), 6.31 (d, 1H), 5.50 (d, 1H), 5.43 (d, 1H), 4.85 (d, 1H), 4.38 (m, 1H), 4.30 (d, 1H), 3.63 (t, 2H), 3.27 (m, 1H), 2.77 (m, 1H), 2.54 (t, 2H); LC-MS (ESI): m/z 472 (M−H; negative ionization).

Example 42: Synthesis of (S)-3-(6-(4-chloro-2-fluorobenzyl)-1,3-dioxo-11,11a-dihydro-1H-imidazo[1',5':1,6]pyrido[3,4-b]indol-2(3H,5H,6H)-yl)propanoic acid (1-133)

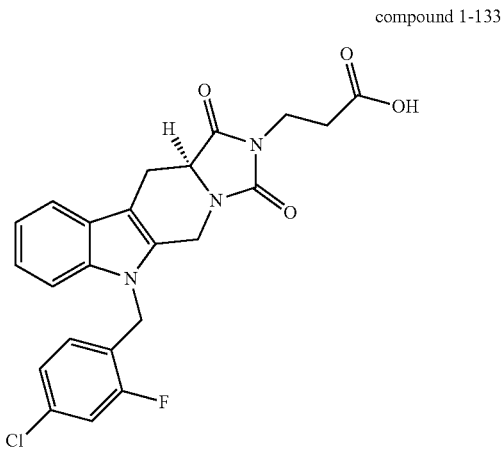 [SMILES: O=C(O)CCN1C(=O)[C@@H]2Cc3c(n(Cc4ccc(Cl)cc4F)c4ccccc34)CN2C1=O]

compound 1-133

Following the procedure for Example 39, but using 4-chloro-2-fluorobenzyl bromide as the alkylating agent in Step 1, the title compound 1-133 was obtained. 1H NMR (300 MHz, DMSO-$d_6$): δ 12.36 (br s, 1H), 7.42-7.55 (m, 3H), 7.03-7.21 (m, 3H), 6.78 (t, 1H), 5.47 (s, 2H), 4.94 (d, 1H), 4.31-4.40 (m, 2H), 3.59-3.69 (m, 2H), 3.26 (m, 1H), 2.72 (m, 1H), 2.54 (t, 2H); LC-MS (ESI): m/z 456 (M+H$^+$).

Example 43: Synthesis of (S)-3-(6-(2,4-difluorobenzyl)-1,3-dioxo-11,11a-dihydro-1H-imidazo[1',5':1,6]pyrido[3,4-b]indol-2(3H,5H,6H)-yl)propanoic acid (1-134)

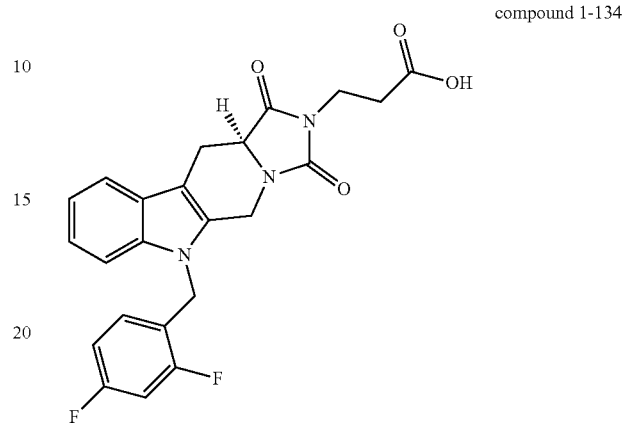

compound 1-134

Following the procedure for Example 39, but using 2,4-difluorobenzyl bromide as the alkylating agent in Step 1, the title compound 1-134 was obtained. 1H NMR (300 MHz, DMSO-$d_6$): δ 12.37 (br s, 1H), 7.53 (d, 1H), 7.46 (d, 1H), 7.28 (m, 1H), 6.96-7.14 (m, 3H), 6.86 (m, 1H), 5.46 (d, 1H), 5.43 (d, 1H), 4.94 (d, 1H), 4.32-4.40 (m, 2H), 3.62 (t, 2H), 3.24 (m, 1H), 2.74 (m, 1H), 2.54 (t, 2H); LC-MS (ESI): m/z 440 (M+H$^+$).

Example 44: Synthesis of (S)-3-(6-((6-fluoropyridin-3-yl)methyl)-1,3-dioxo-11,11a-dihydro-1H-imidazo[1',5':1,6]pyrido[3,4-b]indol-2(3H,5H,6H)-yl)propanoic acid (1-135)

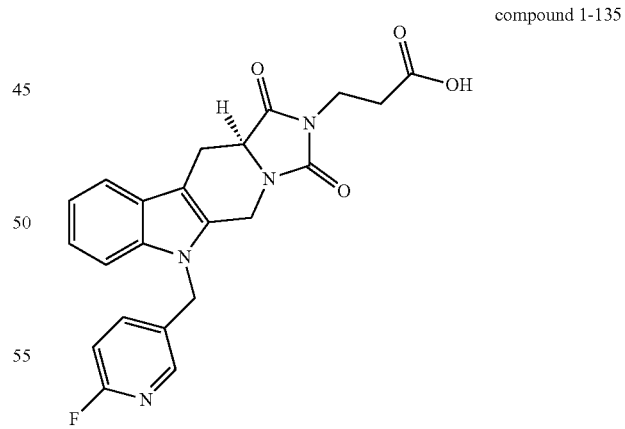

compound 1-135

Following the procedure for Example 39, but using 5-(chloromethyl)-2-fluoropyridine as the alkylating agent in Step 1, the title compound 1-135 was obtained. $^1$H NMR (300 MHz, DMSO-$d_6$): δ 12.36 (br s, 1H), 8.04 (d, 1H), 7.43-7.63 (m, 3H), 7.06-7.16 (m, 3H), 5.48 (s, 2H), 4.98 (d, 1H), 4.34-4.41 (m, 2H), 3.64 (t, 2H), 3.24 (dd, 1H), 2.74 (m, 1H), 2.54 (t, 2H); LC-MS (ESI): m/z 421 (M−H, negative ionisation).

Example 45: Synthesis of (S)-6-(4-fluorobenzyl)-3-thioxo-2,3,5,6,11,11a-hexahydro-1H-imidazo[1',5':1,6]pyrido[3,4-b]indol-1-one (E2)

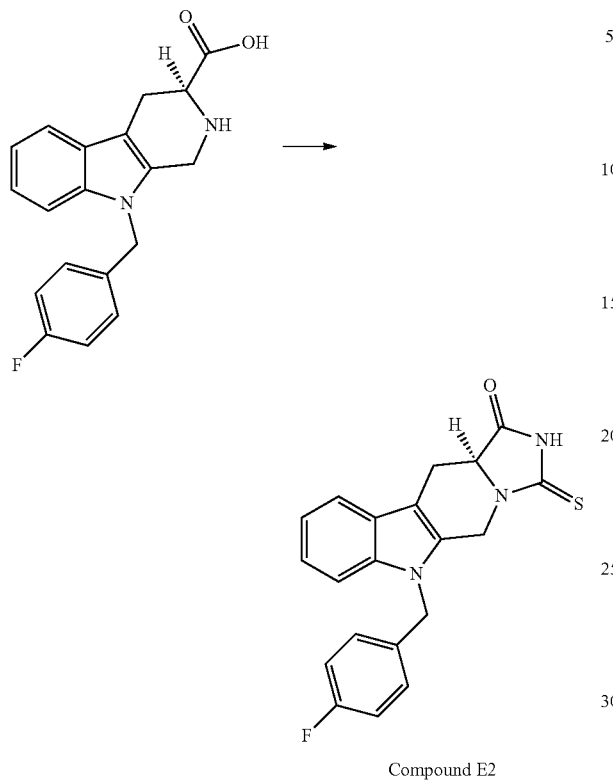

Compound E2

A mixture of the acid 1 (Example 2, Step 4; 200 mg, 0.62 mmol), KSCN (598 mg, 6.17 mmol), THF (2 mL), and water (2 mL) was heated in a Biotage Microwave Synthesizer at 160° C. for 2 h. The mixture was cooled to RT and partitioned between EtOAc and aq. 2M HCl. The organic layer was separated, dried over MgSO₄, filtered, and concentrated under reduced pressure. The crude was purified via silica gel column chromatography (eluting with 0-100% EtOAc in hexanes) to afford the title compound E2 (41 mg, 18%) as a solid. $^1$H NMR (300 MHz, DMSO-d$_6$): δ 12.01 (s, 1H), 7.55 (d, 1H), 7.49 (d, 1H), 7.03-7.17 (m, 6H), 5.50 (d, 1H), 5.40 (d, 1H), 5.28 (d, 1H), 4.60 (dd, 1H), 4.58 (d, 1H), 3.29 (dd, 1H), 2.85 (dd, 1H); LC-MS (ESI): m/z 366 (M+H⁺).

Example 46: Synthesis of (S)-3(6-(4-fluorobenzyl)-3-oxo-1-thioxo-5,6,11,11a-tetrahydro-1H-imidazo[1',5':1,6]pyrido[3,4-b]indol-2(3H)-yl)propanoic acid (1-141)

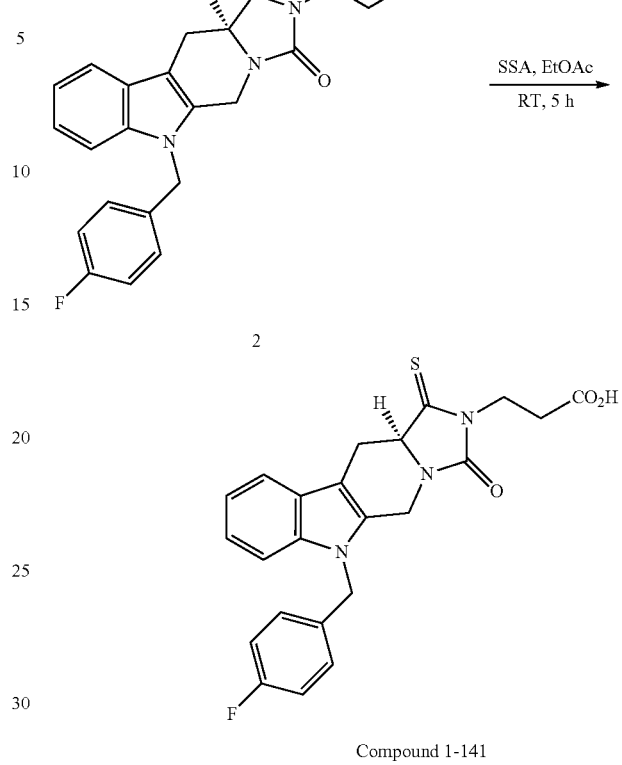

Compound 1-141

Step 1: Synthesis of tert-butyl (S)-3(6-(4-fluorobenzyl)-3-oxo-1-thioxo-5,6,11,11a-tetrahydro-1H-imidazo[1',5':1,6]pyrido[3,4-b]indol-2(3H)-yl)propanoate (2)

To a stirred solution of the ester 1 (Example 5, Step 5; 50 mg, 0.1 mmol) in toluene (5 mL) was added Lawesson's reagent (42 mg, 0.1 mmol) at RT under inert atmosphere; heated to below 60° C. and stirred for 16 h. After completion of the reaction (TLC), the volatiles were removed under reduced pressure. The crude was purified (silica gel chromatography; 10% EtOAc/hexanes) to afford compound 2 (16 mg, 31%) as a red sticky solid. $^1$H NMR (400 MHz, CDCl$_3$): δ 7.56 (d, J=7.2 Hz, 1H), 7.29-7.24 (m, 1H), 7.23-7.15 (m, 2H), 6.97 (d, J=6.8 Hz, 4H), 5.24 (q, 2H), 4.99 (d, J=16.4 Hz, 1H), 4.47-4.43 (m, 1H), 4.31 (d, J=16.0 Hz, 1H), 4.18 (t, J=7.2 Hz, 2H), 3.68-3.63 (m, 1H), 2.80-2.69 (m, 3H), 1.43 (s, 9H); LC-MS (ESI): 95.1%; m/z 492.5 (M−H⁺).

Step 2: Synthesis of (S)-3(6-(4-fluorobenzyl)-3-oxo-1-thioxo-5,6,11,11a-tetrahydro-1H-imidazo[1',5':1,6]pyrido[3,4-b]indol-2(3H)-yl)propanoic acid (1-141)

To a stirred solution of compound 2 (50 mg, 0.1 mmol) in ethylacetate (20 mL) was added silica sulfuric acid (500 mg) at RT under inert atmosphere and stirred for 5 h. After completion of the reaction (TLC), the mixture was filtered, washed with EtOAC (20 mL). The filtrate was washed with water (10 mL), brine (10 mL), dried over Na₂SO₄, filtered and concentrated under reduced pressure. The crude was purified (silica gel chromatography; 50% EtOAc/hexanes) to afford the title compound 1-141 (15 mg, 34%) as a red solid. ¹H NMR (400 MHz, DMSO-d₆): δ 12.40 (br s, 1H), 7.56 (d, J=7.6 Hz, 1H), 7.49 (d, J=8.4 Hz, 1H), 7.16-7.04 (m, 6H), 5.43 (q, 2H), 4.92 (d, J=15.6 Hz, 1H), 4.70-4.66 (m, 1H), 4.43 (d, J=16.0 Hz, 1H), 4.05-4.00 (m, 2H), 3.47-3.42 (m, 1H), 2.75-2.68 (m, 1H), 2.66-2.62 (m, 2H); LC-MS (ESI): 93.3%; m/z 436.4 (M–H⁺).

Example 47: Synthesis of 3-{8-[(p-fluorophenyl)methyl]-12,14-dioxo-6.8.11.13-tetrazatetracyclo [7.7.0.02,7.011,15]hexadeca-1(9),2(7),3,5-tetraene-13-yl}-2,2-dimethyl propionic acid (C111)

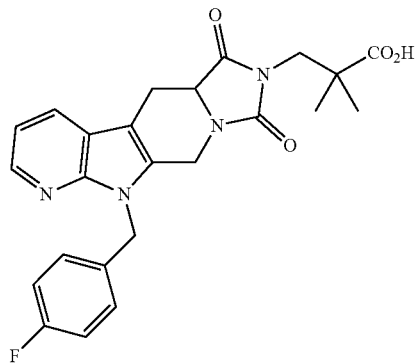

Compound C111

Step 1: Synthesis of tert butyl 3-isocyanato-2,2-dimethylpropanoate

To a stirred solution of tert-butyl 3-amino-2,2dimethyl-propanoate hydrochloride (100 mg, 0.48 mmol) in CH₂Cl₂ (20 mL) were added aqueous NaHCO₃ solution (20 mL) and triphosgene (42 mg, 0.14 mmol) at 0° C. and stirred for 2 h at 0° C. After completion of the reaction (TLC), the mixture was diluted with water (20 mL) and extracted with CH₂Cl₂ (3×20 mL). The combined organic extracts were dried over Na₂SO₄, filtered and concentrated under reduced pressure to obtain crude isocyanate (30 mg) as a colorless oil which was used without further purification.

Step 2: Synthesis of 3-{8-[(p-fluorophenyl)methyl]-12,14-dioxo-6.8.11.13-tetrazatetracyclo[7.7.0.02, 7.011,15]hexadeca-1(9),2(7),3,5-tetraene-13-yl}2,2dimethyl propionic acid (C111)

Following the procedure of Example 31, but using tert butyl 3-isocyanato-2,2-dimethylpropanoate as the isocyanate from Step 1 above in place of tert butyl 3-isocyanatopropanoate, the title compound C111 was obtained. LC-MS [M+H⁺451].

Example 48: Synthesis of 8-[p-fluorophenyl)methyl]-6.8.11.13-tetrazatetracyclo[7.7.0.02, 7.011, 15]hexadeca-1(9),2(7),3,5-tetraen-12,14-dione (C109)

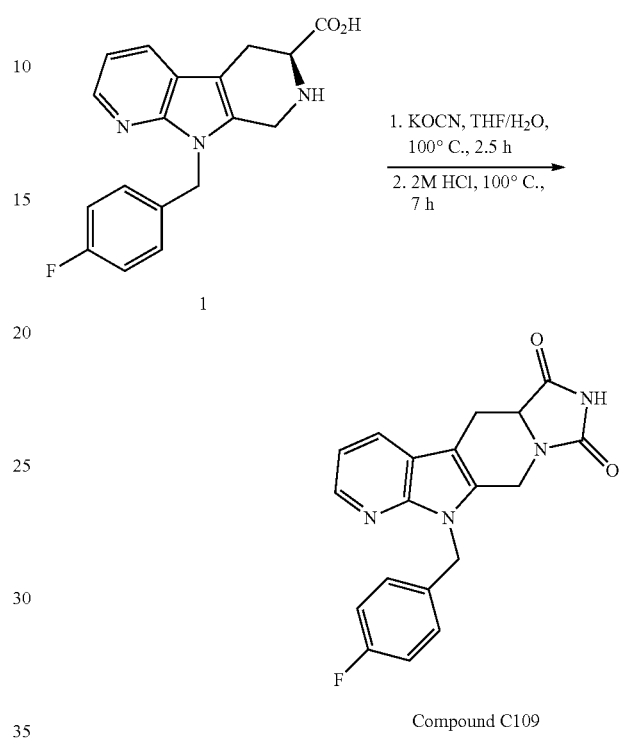

Compound C109

Following the procedure of Example 14 but using the acid 1 (Example 31, Step 3) as starting material, the title compound C109 was obtained as an off-white solid. ¹H NMR (400 MHz, CD₃OD): δ 8.26-8.25 (m, 1H), 8.00 (d, J=8.0 Hz, 1H), 7.19-7.13 (m, 3H), 7.05-6.99 (m, 2H), 5.50 (s, 2H), 4.93-4.89 (m, 1H), 4.36-4.26 (m, 2H), 3.39-3.34 (m, 1H), 2.88-2.81 (m, 1H);

LC-MS (ESI): 96.2%; m/z 351.3 (M+H⁺).

Example 49: Synthesis of 8-[p-fluorophenyl)methyl]-12-thioxo-6.8.11.13-tetrazatetracyclo [7.7.0.02,7.011,15]hexadeca-1(9),2(7),3,5-tetraen-14-one (E3)

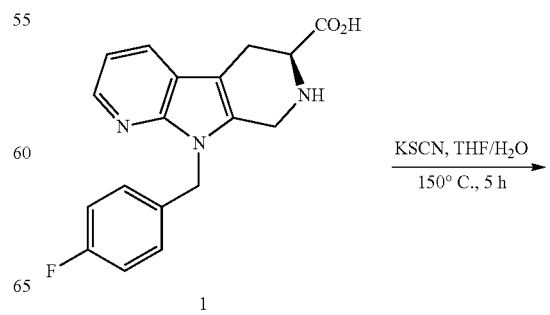

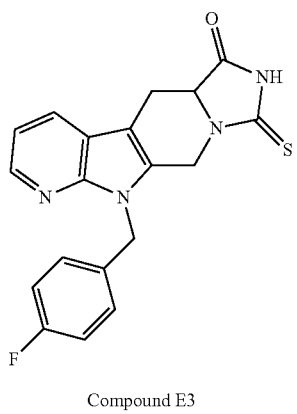

Compound E3

Following the procedure of Example 45 but using the acid 1 (Example 31, Step 3) as starting material, the title compound E3 was obtained as yellow sticky oil. $^1$H NMR (400 MHz, CD$_3$OD): δ 8.27 (dd, J=4.8, 1.6 Hz, 1H), 8.00 (dd, J=7.6, 1.2 Hz, 1H), 7.20-7.14 (m, 3H), 7.06-7.00 (m, 2H), 5.52 (s, 2H), 5.44 (d, J=17.2 Hz, 1H), 4.51-4.47 (m, 1H), 4.44-4.40 (m, 1H), 3.44-3.38 (m, 1H), 2.92-2.84 (m, 1H); MS (Agilent 6310 Ion Trap): m/z 365.1 (M−H$^+$).

Example 50: Synthesis of 3-{8-[(p-fluorophenyl)methyl]-16,16-dimethyl-12,14-dioxo-6.8.11.13-tetrazatetracyclo[7.7.0.0$^{2,7}$.0$^{11,15}$]hexadeca-1(9),2(7),3,5-tetraene-13-yl}propionic acid (C11)

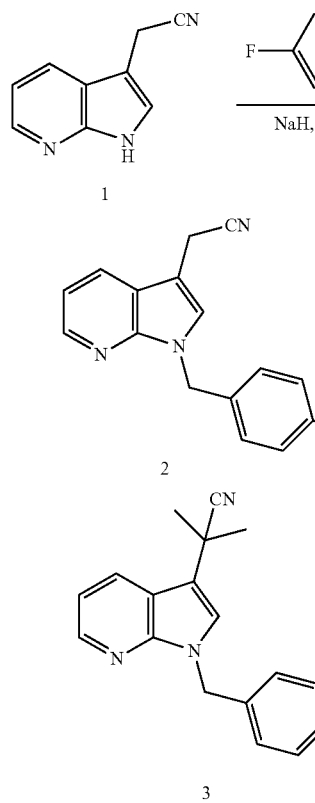

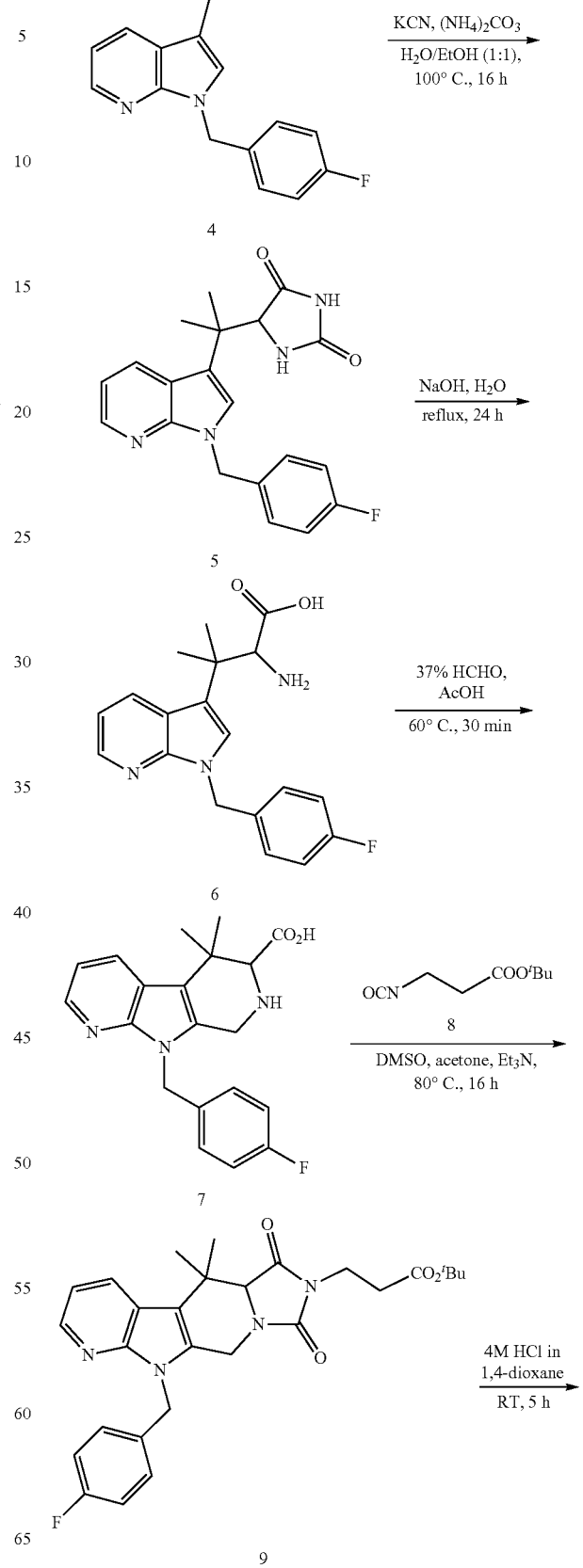

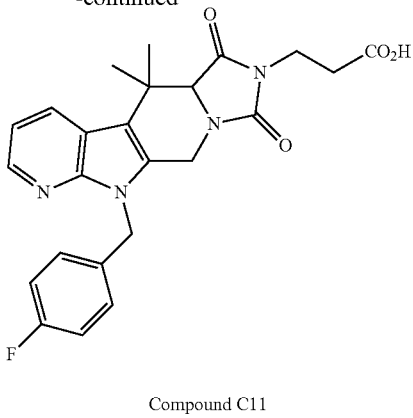

Compound C11

Step 1: Synthesis of 2-(1-(4-fluorobenzyl)-1H-pyrrolo[2,3-b]pyridin-3-yl)acetonitrile (2)

To a stirred solution of NaH (60% in mineral oil, 1.34 g, 28.02 mmol) in DMF (15 mL) was added 2-(1H-pyrrolo[2,3-b]pyrindin-3-yl)acetonitrile 1 (2.0 g, 12.73 mmol) in DMF (10 mL) drop wise at 0° C. under inert atmosphere. The reaction mixture was warmed to RT and stirred for 1 h. To this was added 1-(bromomethyl)-4-fluorobenzene (2.05 g, 10.83 mmol) in DMF (10 mL) drop wise at 0° C.; warmed to RT and stirred for 8 h. After completion of the reaction (TLC), the mixture was quenched with ice-cold water (100 mL) and extracted with EtOAc (3×40 mL). The combined organic extracts were washed with brine (40 mL), dried over Na$_2$SO$_4$, filtered and dried under reduced pressure. The crude was purified (silica gel chromatography; 10-15% EtOAc/hexanes) to afford compound 2 (1.2 g, 36%) as a pale brown semi solid. $^1$H NMR (500 MHz, DMSO-d$_6$): δ 8.33-8.32 (m, 1H), 8.06 (d, J=8.0 Hz, 1H), 7.64 (s, 1H), 7.33-7.31 (m, 2H), 7.19-7.11 (m, 3H), 5.45 (s, 2H), 4.09 (s, 2H); LC-MS (ESI): 80.6%; m/z 266.2 (M+H$^+$).

Step 2: Synthesis of 2-(1-(4-fluorobenzyl)-1H-pyrrolo[2,3-b]pyridin-3-yl)-2-methyl propanenitrile (3)

To a stirred solution of NaH (60% in mineral oil, 652 mg, 13.5 mmol) in anhydrous THF (15 mL) was added compound 2 (1.2 g, 4.53 mmol) in THF (5 mL) drop wise at 0° C. under inert atmosphere. The reaction mixture was warmed to RT and stirred for 1 h. To this was added MeI (1.16 mL, 18.11 mmol) in THF (5 mL) at 0° C.; stirred at 0° C. for 2 h and at RT for 16 h. After completion of the reaction (TLC), the mixture was quenched with ice-cold water (100 mL) and extracted with EtOAc (3×30 mL). The combined organic extracts were washed with brine (30 mL), dried over Na$_2$SO$_4$, filtered and dried under reduced pressure. The crude was purified (silica gel chromatography; 10% EtOAc/hexanes) to afford compound 3 (800 mg, 61%) as a pale yellow semi solid. $^1$H NMR (400 MHz, DMSO-d$_6$): δ 8.34-8.32 (m, 1H), 8.19 (d, J=8.0 Hz, 1H), 7.70 (s, 1H), 7.37-7.33 (m, 2H), 7.20-7.11 (m, 3H), 5.44 (s, 2H), 1.77 (s, 6H); LC-MS (ESI): 89.0%; m/z 294.2 (M+H$^+$).

Step 3: Synthesis of 2-(1-(4-fluorobenzyl)-1H-pyrrolo[2,3-b]pyridin-3-yl)-2-methylpropanal (4)

To a stirred solution of compound 3 (1.06 g, 3.62 mmol) in toluene (15 mL) was added DIBAL-H (1 M in toluene, 4.3 mL, 4.34 mmol) drop wise at −40° C. under inert atmosphere; stirred at −40° C. for 2 h. After completion of the reaction (TLC), the mixture was quenched with aq. sat.NH$_4$Cl solution (40 mL). Diethyl ether (20 mL) was added and the resulting suspension was filtered through a pad of celite and washed with ether (20 mL). The organic layer was separated and aqueous layer was extracted with ether (3×20 mL). The combined organic extracts were washed with brine (30 mL), dried over Na$_2$SO$_4$, filtered and dried under reduced pressure. The crude was purified (silica gel chromatography; 2%-7% EtOAc/hexanes) to afford compound 4 (600 mg, 56%) as a semi solid. $^1$H NMR (400 MHz, DMSO-d$_6$): δ 9.46 (s, 1H), 8.28-8.26 (m, 1H), 7.86 (d, J=8.0 Hz, 1H), 7.65 (s, 1H), 7.36-7.33 (m, 2H), 7.16-7.07 (m, 3H), 5.44 (s, 2H), 1.47 (s, 6H); LC-MS (ESI): 95.0%; m/z 297.2 (M+H$^+$).

Step 4: Synthesis of 5-(2-(1-(4-fluorobenzyl)-1H-pyrrolo[2,3-b]pyridin-3-yl)propan-2-yl)imidazolidine-2,4-dione (5)

To a stirred solution of compound 4 (500 mg, 1.68 mmol) in EtOH/H$_2$O (1:1, 20 mL) were added KCN (164 mg, 2.53 mmol) and (NH$_4$)$_2$CO$_3$ (648 mg, 6.75 mmol) in a sealed tube at RT; heated to 100° C. and stirred for 16 h. After completion of the reaction (TLC), the mixture was cooled to RT, diluted with water (40 mL) and extracted with EtOAc (3×30 mL). The combined organic extracts were washed with brine (20 mL), dried over Na$_2$SO$_4$, filtered and concentrated under reduced pressure. The crude was triturated with n-pentane (2×5 mL) and dried under vacuum to afford compound 5 (400 mg, 65%) as a colorless solid, which was used without further purification. $^1$H NMR (500 MHz, DMSO-d$_6$): δ 10.26 (s, 1H), 8.19-8.17 (m, 2H), 7.97 (s, 1H) 7.39 (s, 1H), 7.24-7.21 (m, 2H), 7.11-7.02 (m, 3H), 5.44 (q, 2H), 4.25 (s, 1H), 1.51 (s, 3H), 1.47 (S, 3H); LC-MS (ESI): 90.6%; m/z 367.4 (M+H$^+$).

Step 5: Synthesis of 2-amino-3-(1-(4-fluorobenzyl)-1H-pyrrolo[2,3-b]pyridin-3-yl)-3-methylbutanoic acid (6)

To a stirred solution of compound 5 (400 mg, crude) in H$_2$O (10 mL) was added NaOH (568 mg, 14.21 mmol) at RT; heated to reflux and stirred for 24 h. After completion of the reaction (TLC), the mixture was cooled to RT and neutralized with 1 N HCl (20 mL) to pH~7. The obtained solid was filtered and the filtrate was concentrated under reduced pressure to obtain the crude compound 6 (1.1 g) as white solid, which was used without further purification. LC-MS (ESI): 92.9%; m/z 342.3 (M+H$^+$).

Step 6: Synthesis of 9-(4-fluorobenzyl)-5,5-dimethyl-6,7,8,9-tetrahydro-5H-pyrrolo[2,3-b:5,4-c']dipyridine-6-carboxylic acid (7)

To a stirred solution of compound 6 (510 mg, crude) in acetic acid (6 mL) was added 37% formalin (181 mg, 6.11 mmol) at RT; heated to 60° C. and stirred for 30 min. After completion of the reaction (TLC), the mixture was filtered, washed with acetic acid (10 mL) and the filtrate was concentrated under reduced pressure to obtain the crude. This was triturated with n-pentane (2×5 mL) and dried under vacuum to afford compound 7 (250 mg, 47%) as a pale yellow solid. $^1$H NMR (500 MHz, DMSO-d$_6$): δ 8.23-8.00 (m, 2H), 7.21-7.02 (m, 5H), 6.28 (br s, 1H), 5.50-5.36 (m, 2H), 4.54 (s, 1H), 4.17 (d, J=14.5 Hz, 1H), 3.56 (d, J=14.5 Hz, 1H), 1.66 (s, 3H), 1.31 (s, 3H); LC-MS (ESI): 93.2%; m/z 354.3 (M+H⁺).

Step 7: Synthesis of tert-butyl 3-{8-[(p-fluorophenyl)methyl]-16,16-dimethyl-12,14-dioxo-6.8.11.13-tetrazatetracyclo[7.7.0.0²,⁷.0¹¹,¹⁵]hexadeca-1(9),2(7),3,5-tetraene-13-yl}propionate (9)

To a stirred solution of compound 7 (250 mg, 0.71 mmol) in acetone (25 mL) and DMSO (6 mL) under inert atmosphere were added tert-butyl 3-isocyanatopropanoate 8 (1 g, crude) and Et₃N (0.11 mL, 0.85 mmol) at RT; heated to 80° C. and stirred for 16 h. After completion of the reaction (TLC), the mixture was diluted with water (20 mL) and extracted with EtOAc (3×30 mL). The combined organic extracts were washed with brine (20 mL), dried over Na₂SO₄, filtered and concentrated under reduced pressure. The crude was purified (silica gel chromatography; 10%-15% EtOAc/hexanes) to afford compound 9 (90 mg, 21%) as a pale yellow semi solid. ¹H NMR (400 MHz, DMSO-d₆): δ 8.33-8.32 (m, 1H), 8.02 (d, J=8.0 Hz, 1H), 7.14-7.08 (m, 3H), 7.00-6.95 (m, 2H), 5.61 (d, J=16.0 Hz, 1H), 5.22 (d, J=16.0 Hz, 1H), 4.98 (d, J=16.4 Hz, 1H), 4.19 (d, J=16.4 Hz, 1H), 3.90 (s, 1H), 3.81 (t, J=7.2 Hz, 2H), 2.60 (t, J=7.2 Hz, 2H), 1.87 (s, 3H), 1.45 (s, 9H), (1.19 (s, 3H); LC-MS: 97.9%; m/z 507.5 (M+H⁺).

Step 8: Synthesis of 3-{8-[(p-fluorophenyl)methyl]-16,16-dimethyl-12,14-dioxo-6.8.11.13-tetrazatetracyclo[7.7.0.0²,⁷.0¹¹,¹⁵]hexadeca-1(9),2(7),3,5-tetraene-13-yl}propionic acid (C11)

A solution of compound 9 (50 mg, 0.1 mmol) in 4 M HCl in 1,4-dioxane (5 mL) was stirred at RT under inert atmosphere for 5 h. After completion of the reaction (TLC), the volatiles were removed under reduced pressure and the obtained solid was triturated with diethyl ether (2×5 mL) and n-pentane (2×5 mL) and dried under vacuum to afford the title compound C11 (25 mg, 40%) as a pale pink solid. ¹H NMR (500 MHz, DMSO-d₆): 8.27-8.26 (m, 1H), 8.17 (d, J=7.5 Hz, 1H), 7.24-7.12 (m, 5H), 5.48 (q, 2H), 4.94 (d, J=16.5 Hz, 1H), 4.29 (d, J=16.5 Hz, 1H), 4.14 (s, 1H), 3.69-3.59 (m, 2H), 2.54-2.50 (m, 2H), 1.76 (s, 3H), 1.09 (s, 3H); LC-MS (ESI): 97.7%; m/z 451.5 (M+H⁺).

Example 51: Synthesis of (S)-3-(6-(4-fluorobenzyl)-1,3-dioxo-11,11a-dihydro-1H-imidazo[1',5':1,6]pyrido[3,4-b]indol-2(3H,5H,6H)-yl)-N-(methylsulfonyl)propanamide (1-142)

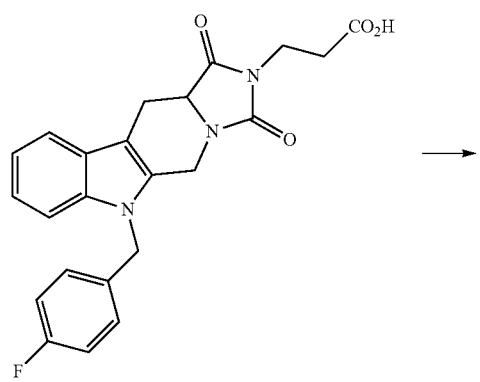

1

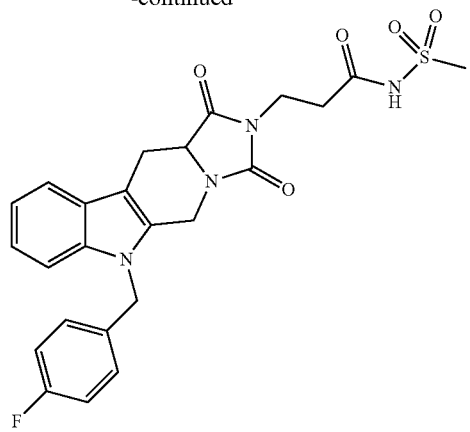

Compound 1-142

The acid 1 (Example 5; 200 mg, 0.47 mmol), HATU (271 mg, 0.71 mmol), methylsulfonamide (54 mg, 0.57 mmol), N,N-diisopropylethylamine (289 μL, 1.66 mmol), and DCM (2.0 mL) stirred at RT overnight. The mixture washed with water, brine, dried over Na₂SO₄, filtered, and concentrated under reduced pressure. The crude material was purified by silica gel column chromatography using 0-5% MeOH/DCM to afford the title compound 1-142 (36 mg, 15%) as a yellow solid. LC-MS [M+H⁺ 499].

Example 52: Synthesis of (S)-3-(6-(4-fluorobenzyl)-1,3-dioxo-11,11a-dihydro-1H-imidazo[1',5':1,6]pyrido[3,4-b]indol-2(3H,5H,6H)-yl)-N-(phenylsulfonyl)propanamide (1-143)

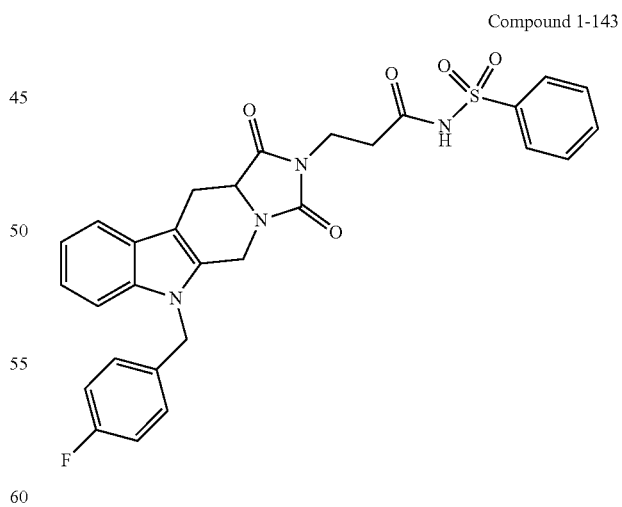

Compound 1-143

Following the procedure of Example 51 but using benzenesulfonamide in place of methanesulfonamide, the title compound 1-143 was obtained as a white solid. LC-MS [M+H⁺ 561].

Example 53: Synthesis of 3-(6-(4-fluorobenzyl)-11a-methyl-1,3-dioxo-11,11a-dihydro-1H-imidazo[1',5':1,6]pyrido[3,4-b]indol-2(3H,5H,6H)-yl)propanoic acid (A113)

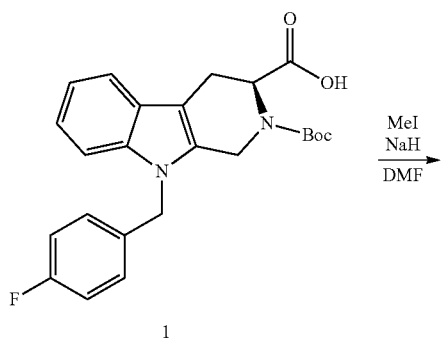

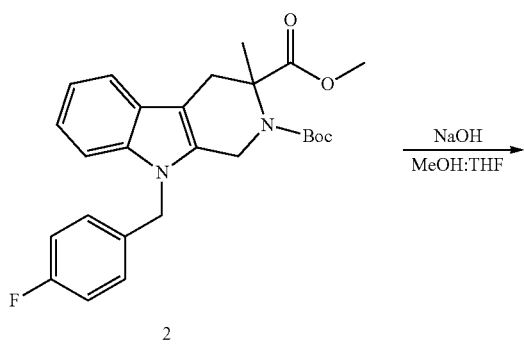

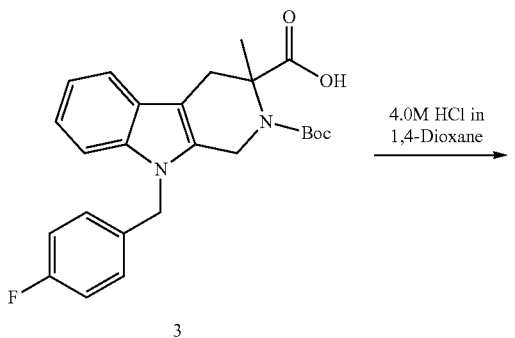

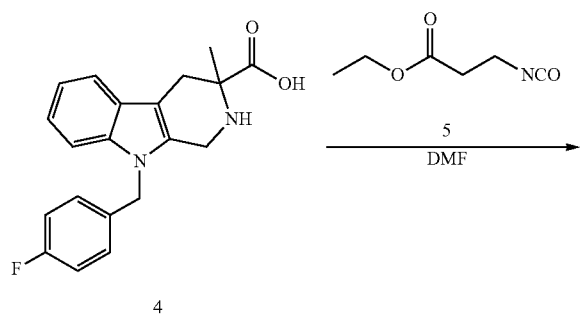

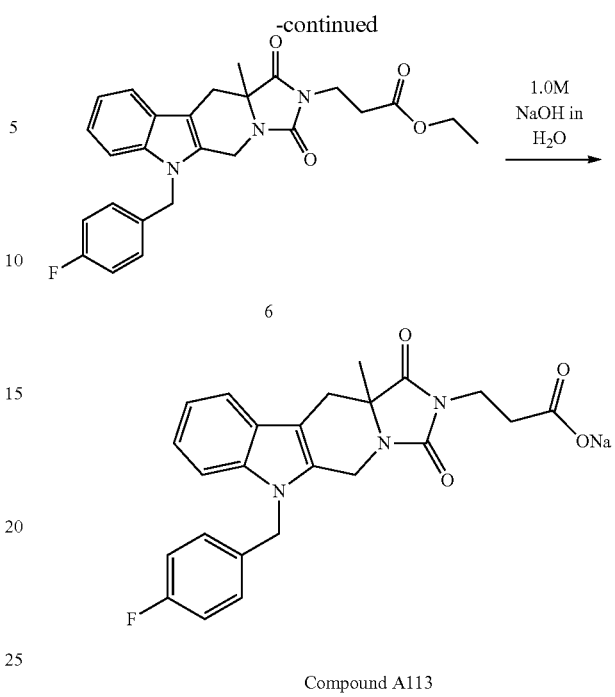

Compound A113

Step 1: 2-tert-butyl 3-methyl 9-(4-fluorobenzyl)-3-methyl-3,4-dihydro-1H-pyrido[3,4-b]indole-2,3(9H)-dicarboxylate (2)

The acid 1 (Example 5, Step 3; 1.5 g, 3.53 mmol) dissolved in DMF (14 mL) was degassed and cooled in ice water bath. 60% NaH in mineral oil (580 mg, 14.49 mmol) was added portionwise and the mixture stirred at 0° C. for 30 min. Then iodomethane (154 µL, 2.47 mmol) was added dropwise and the reaction stirred at 0° C. to RT overnight. The mixture cooled in ice water bath and quenched with water. Then it was diluted with water and extracted with EtOAc (2×). The organics extracts were combined, washed with brine, dried over $Na_2SO_4$, filtered, and concentrated under reduced pressure. The crude material was purified by silica gel column chromatography using 0-20% EtOAc/Hx to afford 2 (441 mg, 28%) as a white foam. $^1H$ NMR (300 MHz, DMSO-$d_6$): 7.50-7.42 (m, 2H), 7.14-6.98 (m, 6H), 5.37 (q, 2H), 4.77 (d, 1H), 4.29 (d, 1H), 3.65 (s, 3H), 3.19 (d, 1H), 2.82 (d, 1H), 1.33 (s, 3H), 1.25 (s, 9H); LC-MS [M+H$^+$ 453].

Step 2: 2-(tert-butoxycarbonyl)-9-(4-fluorobenzyl)-3-methyl-2,3,4,9-tetrahydro-1H-pyrido[3,4-b]indole-3-carboxylic acid (3)

NaOH (780 mg, 19.49 mmol) in water (4 mL) was added to 2 (441 mg, 0.97 mmol) in MeOH:THF (2:1) (6 mL). The reaction heated at 90° C. overnight. The next day the mixture concentrated and diluted with water (20 mL). The solution was acidified with 6.0 M aq HCl. The solids filtered off to afford the acid 3 (439 mg, 98%) as an off white powder. $^1H$ NMR (300 MHz, DMSO-$d_6$): 7.45-7.38 (m, 2H), 7.13-6.98 (m, 6H), 5.33 (m, 2H), 4.69 (d, 1H), 4.32 (d, 1H), 3.19 (d, 1H), 2.70 (d, 1H), 1.37 (s, 3H), 1.27 (s, 9H); LC-MS [M+H$^+$439].

Step 3: 9-(4-fluorobenzyl)-3-methyl-2,3,4,9-tetrahydro-1H-pyrido[3,4-b]indole-3-carboxylic acid (4)

Acid 3 (438 mg, 0.95 mmol) and 4M HCl in 1,4-dioxane solution (2 mL) stirred at RT overnight. The reaction diluted with water (200 mL) and neutralized to pH 7 with triethylamine. The precipitants filtered off and washed with water to afford 4 (275 mg, 85%) as a beige powder. $^1$H NMR (300 MHz, DMSO-$d_6$): δ 8.95 (br s, 1H), 7.47-7.39 (m, 2H), 7.14-6.99 (m, 6H), 5.33 (m, 2H), 4.33 (d, 1H), 3.96 (d, 1H), 3.18 (d, 1H), 2.74 (d, 1H), 1.34 (s, 3H); LC-MS [M+H$^+$339].

Step 4: ethyl 3-isocyanatopropanoate (5)

β-Alanine ethyl ester HCl (263 mg, 1.71 mmol) in CH$_2$Cl$_2$ (8 mL) and saturated NaHCO$_3$ solution (8 mL) was degassed and the vial was cooled in ice water bath. Triphosgene (508 mg, 1.71 mmol) was added in one portion under inert atmosphere at 0° C. The reaction stirred at 0° C. to RT over 3 hr. The reaction was diluted with water (15 mL), the layers separated and the aqueous layer was extracted with CH$_2$Cl$_2$. The combined organic extracts were washed with brine, dried over Na$_2$SO$_4$, filtered, and concentrated under reduced pressure to obtain crude 5 (216 mg) as a white crystalline solid. This crude material was directly used for next reaction without purification. $^1$H NMR (300 MHz, CDCl$_3$): δ 4.20 (q, 2H), 3.59 (t, 2H), 2.60 (t, 2H), 1.28 (t, 3H).

Step 5: Ethyl 3-(6-(4-fluorobenzyl)-11a-methyl-1,3-dioxo-11,11a-dihydro-1H-imidazo[1',5':1,6]pyrido[3,4-b]indol-2(3H,5H,6H)-yl)propanoate (6)

Acid 4 (100 mg, 0.30 mmol) in anhydrous DMF (2 mL) was degassed. To this was added the isocyanate 5 (43 mg, 0.30 mmol) and the mixture heated to 100° C. overnight. The reaction cooled to RT and diluted with water. The mixture extracted with EtOAc (3×). The combined organic extracts were washed with water, brine, dried over Na$_2$SO$_4$, filtered, and concentrated under reduced pressure. The crude material was purified by silica gel column chromatography using 0-50% EtOAc/Hx to afford the ester 6 (69 mg, 51%) as a white foam. $^1$H NMR (300 MHz, DMSO-$d_6$): δ 7.52-7.44 (m, 2H), 7.16-7.01 (m, 6H), 5.43 (q, 2H), 4.96 (d, 1H), 4.25 (d, 1H), 4.00 (q, 2H), 3.66 (t, 2H), 3.03 (d, 1H), 2.88 (d, 1H), 2.60 (t, 2H), 1.32 (s, 3H), 1.10 (t, 3H); LC-MS [M+H$^+$464].

Step 6: 3-(6-(4-fluorobenzyl)-11a-methyl-1,3-dioxo-11,11a-dihydro-1H-imidazo[1',5':1,6]pyrido[3,4-b]indol-2(3H,5H,6H)-yl)propanoic acid 1M NaOH (142 µL, 0.14 mmol) was added to the ester 6 (66 mg, 0.14 mmol) in THF:MeOH (3:1) (4 mL) at 0° C. The mixture stirred at 0° C. to RT over 6 hr. Additional 1M NaOH (14 µL, 0.014 mmol) was added at 0° C. and the mixture stirred at 0° C. to RT over 2 hr. The solvent removed under reduce pressure to afford the title compound A113 (53 mg, 81%) as an off white powder. $^1$H NMR (300 MHz, DMSO-$d_6$): δ 7.51-7.43 (m, 2H), 7.16-7.03 (m, 6H), 5.42 (q, 2H), 4.97 (d, 1H), 4.22 (d, 1H), 3.60-3.51 (m, 2H), 3.00 (d, 1H), 2.85 (d, 1H), 2.13-2.08 (m, 2H), 1.31 (s, 3H); LC-MS [M+H$^+$436].

Example 53: Synthesis of 2-((2H-tetrazol-5-yl)methyl)-6-(4-fluorobenzyl)-5,6,11,11a-tetrahydro-1H-imidazo[1',5':1,6]pyrido[3,4-b]indole-1,3(2H)-dione (1-140)

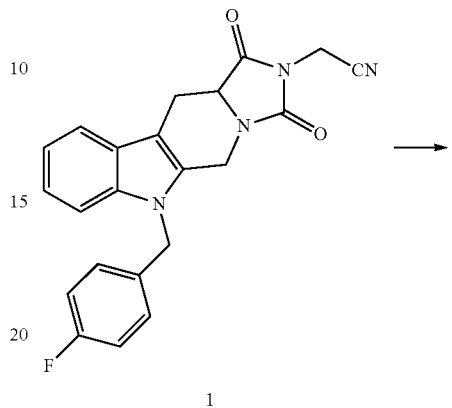

1

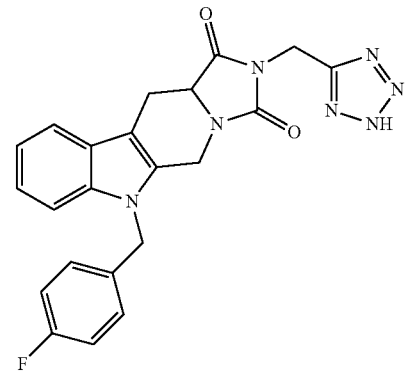

Compound 1-140

To a solution of the nitrile 1 (Example 18; 100 mg, 0.25 mmol) in anhydrous DMF (3 mL) were added NaN$_3$ (83 mg, 1.27 mmol) and NH$_4$Cl (68 mg, 1.27 mmol) at RT and heated to 130° C. for 6 h. The reaction mixture was quenched with ice-cold water (30 mL) and extracted with EtOAc (3×20 mL). The combined organic extracts were washed with brine (30 mL), dried over Na$_2$SO$_4$, filtered and dried under reduced pressure to obtain the crude. The crude was purified by preparative HPLC purification to afford the title compound 1-140 (12 mg, 11%) as an off-white solid. $^1$H NMR (400 MHz, CD$_3$OD): 7.54 (d, J=7.6 Hz, 1H), 7.35 (d, J=8.4 Hz, 1H), 7.16 (t, J=7.2 Hz, 1H), 7.11-6.98 (m, 5H), 5.36 (s, 2H), 5.01-4.97 (m, 1H), 4.94 (s, 2H), 4.45-4.41 (m, 2H), 3.37-3.36 (m, 1H), 2.98-2.94 (m, 1H); LC-MS (ESI): 99.2%; m/z 432.4 (M+H$^+$).

Example 51: Synthesis of 3-{8-[(p-fluorophenyl)
methyl]-16,16-dimethyl-12,14-dioxo-6.8.11.13-tet-
razatetracyclo[7.7.0.02,7.011,15]hexadeca-1(9),2(7),
3,5-tetraene-13-yl}-2,2-dimethylpropionic acid
(C13)

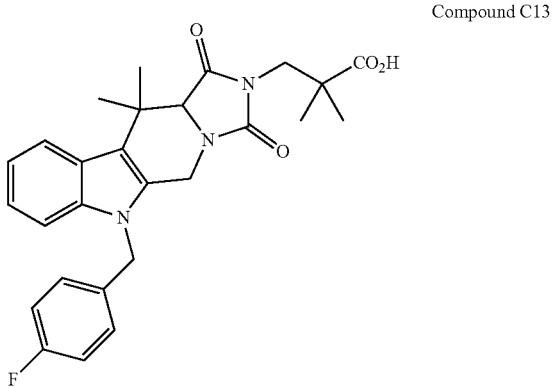 [SMILES: CC(C)(CN1C(=O)C2N(Cc3c(c4ccccc4n3Cc3ccc(F)cc3)C2(C)C)C1=O)C(=O)O]

Compound C13

Following the procedure of Example 50 but using tert butyl 3-isocyanato-2,2-dimethylpropanoate (from Example 47, Step 1) in Step 7, the title compound C13 was obtained. LCMS m/z 479 (M+H$^+$).

Example 54: Parenteral Pharmaceutical Composition

To prepare a parenteral pharmaceutical composition suitable for administration by injection (subcutaneous, intravenous), 1-100 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example 55: Oral Solution To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example 56: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 57: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example 58: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example 59: Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 20-fold using Centriprep-30 filter devices (Millipore). To assay for autotaxin inhibition, 10-20 μL of the concentrated conditioned media is incubated with 2.5 μL of a test compound in DMSO and 72.5-82.5 μL lyso-PLD buffer (100 mM Tris pH 9, 500 mM NaCl, 5 mM MgCl$_2$, 5 mM CaCl$_2$, 0.05% Triton X-100 in the presence or absence of 0.2% fatty-acid-free human serum albumin) for 15 min at 37° C. After the 15 min incubation, 5 ul of 2 mM LPC (14:0; Avanti Polar Lipids Cat#855575C) diluted in lyso-PLD buffer is added for a final concentration of 100 uM and the incubation continues for 1.5-3 hours at 37° C. 100 μl of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM MgCl$_2$ is added and the incubation continued for 15 minutes at room temperature before reading the absorbance at 555 nm.

Illustrative biological activity of representative compounds in the human autotaxin assay described herein is presented in the following table:

| Compound no. | IC$_{50}$ (μM) |
| --- | --- |
| 1-1 | A |
| 1-2 | A |
| 1-3 | A |
| 1-4 | A |
| 1-5 | A |
| 1-6 | A |
| 1-7 | A |
| 1-8 | A |
| 1-9 | A |
| 1-10 | C |
| 1-11 | A |
| 1-12 | A |
| 1-13 | A |
| 1-14 | A |
| 1-15 | A |
| 1-16 | A |
| 1-18 | A |
| 1-19 | A |
| 1-20 | B |
| 1-21 | A |
| 1-23 | A |
| 1-24 | A |
| 1-26 | C |

-continued

| Compound no. | IC$_{50}$ (μM) |
|---|---|
| 1-27 | C |
| 1-30 | A |
| 1-34 | A |
| 1-39 | A |
| 1-42 | A |
| 1-84 | A |
| 1-102 | A |
| 1-121 | A |
| 1-129 | A |
| 1-130 | A |
| 1-131 | A |
| 1-132 | A |
| 1-133 | A |
| 1-134 | A |
| 1-135 | A |
| 1-139 | A |
| 1-140 | A |
| 1-141 | C |
| 1-142 | A |
| 1-143 | A |
| A11 | A |
| A110 | A |
| A110 ent A | A |
| A110 ent B | A |
| A113 | C |
| C11 | A |
| C13 | A |
| C109 | A |
| C111 | A |
| C114 | A |
| C114 entA | A |
| C114 entB | A |
| E1 | C |
| E2 | A |
| E3 | A |

A is ≤ 0.5 μM; B is > 0.5 μM but ≤ 1 μM; C > 1 μM.
Ent = enantiomer

Example 60: Human Whole Blood Autotaxin Assay

Inhibition of ATX activity in human whole blood is assayed by measuring the concentration of 20:4 LPA in plasma after a prolonged incubation at 37° C. Blood is drawn from consenting human volunteers into heparin vacutainer tubes and 200 μl aliquots are added to 2 μl test compound in DMSO or DMSO alone. Several of the vehicle tubes are centrifuged immediately at 800×g for 10 minutes at 4° C. and the plasma removed for processing to determine the baseline concentration of 20:4 LPA. The remaining blood samples containing vehicle or test compound are incubated at 37° C. for 4 hours before centrifuging at 800×g for 10 minutes at 4° C. to obtain plasma. Plasma is processed for LCMS as follows: 40 ul plasma is removed and 5 volumes of methanol containing 125 ng/ml 17:0 LPA as an internal standard are added and the mixture incubated at −20° C. for 10 min before centrifuging at 4000×g for 10 minutes at 4° C. 150 μl of the supernatant is transferred to a 96-well plate and diluted with 100 μl of an organic solution (90:10:0.1 of water/acetonitrile/ammonium hydroxide) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MRM). The mobile phases contain 0.1% ammonium hydroxide in 90% water/10% acetonitrile (solvent A) and 0.1% ammonium hydroxide in 90% acetonitrile/10% water (solvent B). The flow rate was maintained at 0.8 mL/min and the total run time was 3 min. Analytes were separated using a linear gradient as follows: 1) mobile phase was held for 0.5 min at 10% B; 2) B was increased from 10% to 90% over the next 1 min; 3) B was held constant for 0.5 min at 90%; and 4) B was returned to the initial gradient conditions.

The examples and embodiments described herein are for illustrative purposes only and various modifications or changes suggested to persons skilled in the art are to be included within the spirit and purview of this application and scope of the appended claims.

What is claimed is:
1. A compound having the structure of Formula (II), or a pharmaceutically acceptable salt or solvate thereof:

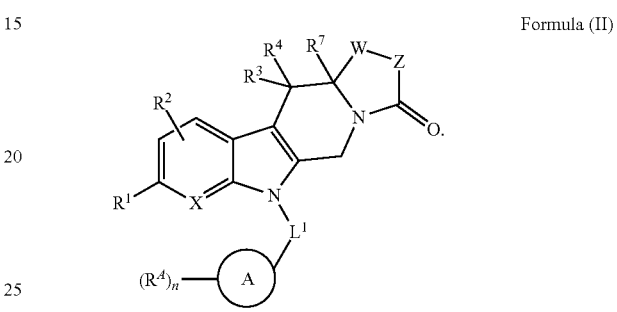

Formula (II)

wherein,
$R^1$ is H, halogen, —CN, $C_1$-$C_4$alkyl, or —CF$_3$;
$R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;
$R^3$ is H or —CH$_3$;
$R^4$ is H or —CH$_3$;
$R^7$ is H;
$L^1$ is $C_1$-$C_4$alkylene;
A is a substituted or unsubstituted phenyl or substituted or unsubstituted monocyclic heteroaryl;
each $R^A$ substituent is independently H, halogen, OH, —OR$^9$, —CN, —NO$_2$, $C_1$-$C_6$alkyl, $C_1$-$C_6$fluoroalkyl, $C_1$-$C_6$heteroalkyl, or substituted or unsubstituted $C_3$-$C_8$cycloalkyl;
n is 0, 1, 2, 3, or 4;
X is —CH═, —N═, or —CF═;
W is —C(═O)—;
Z is

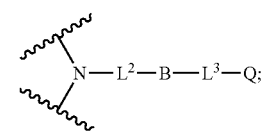

$L^2$ is $C_1$-$C_6$alkylene;
B is absent;
$L^3$ is absent or $C_3$-$C_6$cycloalkylene;
Q is —CO$_2$H, —CO$_2$($C_1$-$C_6$alkyl), —OH, —B(OH)$_2$, —C(═O)NHSO$_2$R$^9$, —C(═O)N(R$^{10}$)$_2$, —C(═O)NH—OH, —C(═O)NH—CN, —SO$_2$NHC(═O)R$^9$, —OP(═O)(OH)$_2$, —P(═O)(OH)$_2$, tetrazolyl, substituted or unsubstituted monocyclic heterocycle, —S(═O)$_2$R$^9$, —S(═O)R$^9$, —SR$^9$, —S(═O)$_2$N(R$^{10}$)$_2$, —NR$^{10}$S(═O)$_2$R$^9$, —OC(═O)R$^9$, —OCO$_2$R$^9$, —N(R$^{10}$)$_2$, —C(═O)N(R$^{10}$)$_2$, —OC(═O)N(R$^{10}$)$_2$, —NHC(═O)R$^9$, or —NHC(═O)OR$^9$;

each $R^9$ is independently $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, —$C_1$-$C_4$alkylene-substituted or unsubstituted monocyclic heteroaryl, or a substituted or unsubstituted bicyclic heteroaryl;

each $R^{10}$ is independently H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-substituted or unsubstituted aryl, a substituted or unsubstituted monocyclic heteroaryl, or —$C_1$-$C_4$alkylene-substituted or unsubstituted monocyclic heteroaryl;

or two $R^{10}$ groups attached to the same N atom are taken together with the N atom to which they are attached to form a substituted or unsubstituted heterocycle.

2. The compound of claim 1, or a pharmaceutically acceptable salt or solvate thereof, wherein:
Q is —$CO_2H$, —$CO_2(C_1$-$C_6$alkyl), —OH, —$B(OH)_2$, —C(=O)NHSO$_2R^9$, —C(=O)N($R^{10}$)$_2$, —C(=O)NH—OH, —C(=O)NH—CN, —SO$_2$NHC(=O)$R^9$, —OP(=O)(OH)$_2$, —P(=O)(OH)$_2$, or tetrazolyl.

3. The compound of claim 2, or a pharmaceutically acceptable salt or solvate thereof, wherein:
Q is —$CO_2H$, —$CO_2(C_1$-$C_6$alkyl), —$B(OH)_2$, —C(=O)NHSO$_2R^9$, —C(=O)N($R^{10}$)$_2$, or tetrazolyl.

4. The compound of claim 3, or a pharmaceutically acceptable salt, or solvate thereof, wherein:
$L^2$ is —CH$_2$—, —CH$_2$CH$_2$—, —CH$_2$CH$_2$CH$_2$—, or —CH$_2$CH$_2$CH$_2$CH$_2$—; and
Q is —$CO_2H$, or —$CO_2(C_1$-$C_6$alkyl).

5. The compound of claim 2, or a pharmaceutically acceptable salt or solvate thereof, wherein:
$L^1$ is —CH$_2$—; and
A is phenyl.

6. The compound of claim 2, or a pharmaceutically acceptable salt or solvate thereof, wherein:
$L^1$ is —CH$_2$—; and
A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

7. The compound of claim 5, or a pharmaceutically acceptable salt or solvate thereof, wherein:
$R^1$ is H, F, Cl, Br, —CN, —CH$_3$, or —CF$_3$; and
$R^2$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$.

8. The compound of claim 1, or a pharmaceutically acceptable salt or solvate thereof, wherein the compound has the following structure of Formula (III), or Formula (IV):

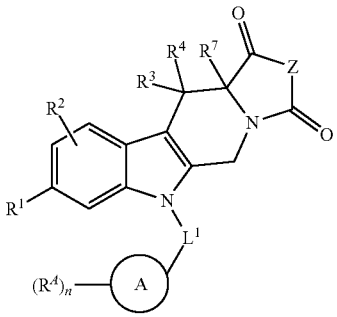

Formula (III)

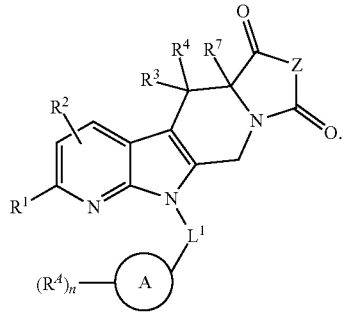

Formula (IV)

9. A compound of claim 1, wherein the compound is:
4-(6-(4-fluorobenzyl)-1,3-dioxo-11,11a-dihydro-1H-imidazo[1',5':1,6]pyrido[3,4-b]indol-2(3H,5H,6H)-yl)butanoic acid;
(S)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid;
(R)-4-(6-(4-fluorobenzyl)-1,3-dioxo-11,11a-dihydro-1H-imidazo[1',5':1,6]pyrido[3,4-b]indol-2(3H,5H,6H)-yl)butanoic acid;
3-(6-(4-fluorobenzyl)-1,3-dioxo-11,11a-dihydro-1H-imidazo[1',5':1,6]pyrido[3,4-b]indol-2(3H,5H,6H)-yl)propanoic acid;
3-(6-(4-fluorobenzyl)-1,3-dioxo-11,11a-dihydro-1H-imidazo[1',5':1,6]pyrido[3,4-b]indol-2(3H,5H,6H)-yl)propanoic acid (Enantiomer A);
3-(6-(4-fluorobenzyl)-1,3-dioxo-11,11a-dihydro-1H-imidazo[1',5':1,6]pyrido[3,4-b]indol-2(3H,5H,6H)-yl)propanoic acid (Enantiomer B);
4-(1,3-dioxo-6-(3-phenylpropyl)-11,11a-dihydro-1H-imidazo[1',5':1,6]pyrido[3,4-b]indol-2(3H,5H,6H)-yl)butanoic acid;
(S)-4-(6-((6-methoxypyridin-3-yl)methyl)-1,3-dioxo-11,11a-dihydro-1H-imidazo[1',5':1,6]pyrido[3,4-b]indol-2(3H,5H,6H)-yl)butanoic acid;
(S)-3-(6-((6-methoxypyridin-3-yl)methyl)-1,3-dioxo-11,11a-dihydro-1H-imidazo[1',5':1,6]pyrido[3,4-b]indol-2(3H,5H,6H)-yl)propanoic acid;
6-(4-fluorobenzyl)-2-(2-hydroxyethyl)-5,6,11,11a-tetrahydro-1H-imidazo[1',5':1,6]pyrido[3,4-b]indole-1,3(2H)-dione;
2-(6-(4-fluorobenzyl)-1,3-dioxo-5,6,11,11a-tetrahydro-1H-imidazo[1',5':1,6]pyrido[3,4-b]indol-2(3H)-yl)acetic acid;
(S)-4-(6-(4-fluorobenzyl)-1,3-dioxo-5,6,11,11a-tetrahydro-1H-imidazo[1',5':1,6]pyrido[3,4-b]indol-2(3H)-yl)-2,2-dimethylbutanoic acid;
(S)-4-(6-(4-fluorobenzyl)-1,3-dioxo-5,6,11,11a-tetrahydro-1H-imidazo[1',5':1,6]pyrido[3,4-b]indol-2(3H)-yl)-3,3-dimethylbutanoic acid;
(S)-4-(8-chloro-6-(4-fluorobenzyl)-1,3-dioxo-5,6,11,11a-tetrahydro-1H-imidazo[1',5':1,6]pyrido[3,4-b]indol-2(3H)-yl)butanoic acid;
(S)-3-(6-((6-chloropyridin-3-yl)methyl)-1,3-dioxo-5,6,11,11a-tetrahydro-1H-imidazo[1',5':1,6]pyrido[3,4-b]indol-2(3H)-yl)propanoic acid;
(S)-1-((6-((6-methoxypyridin-3-yl)methyl)-1,3-dioxo-5,6,11,11a-tetrahydro-1H-imidazo[1',5':1,6]pyrido[3,4-b]indol-2(3H)-yl)methyl)cyclopropane-1-carboxylic acid;

(S)-3-(6-(4-fluorobenzyl)-1,3-dioxo-5,6,11,11a-tetra-hydro-1H-imidazo[1',5':1,6]pyrido[3,4-b]indol-2(3H)-yl)-2,2-dimethylpropanoic acid;

(S)-1-((6-(4-fluorobenzyl)-1,3-dioxo-5,6,11,11a-tetra-hydro-1H-imidazo[1',5':1,6]pyrido[3,4-b]indol-2(3H)-yl)methyl)cyclopropane-1-carboxylic acid;

3-{8-[(4-fluorophenyl)methyl]-12,14-dioxo-6,8, 11,13-tetraazatetracyclo[7.7.0.0$^{2,7}$.0$^{11,15}$]hexadeca-1(9),2(7),3,5-tetraen-13-yl}propionic acid;

3-{8-[(4-fluorophenyl)methyl]-12,14-dioxo-6,8, 11,13-tetraazatetracyclo[7.7.0.0$^{2,7}$.0$^{11,15}$]hexadeca-1(9),2(7),3,5-tetraen-13-yl}propionic acid (Enantiomer A);

3-{8-[(4-fluorophenyl)methyl]-12,14-dioxo-6,8,11,13-tetraazatetracyclo[7.7.0.0$^{2,7}$.0$^{11,15}$]hexadeca-1(9),2(7),3,5-tetraen-13-yl}propionic acid (Enantiomer B);

3-(6-(4-fluorobenzyl)-11,11-dimethyl-1,3-dioxo-5,6,11,11a-tetrahydro-1H-imidazo[1',5':1,6]pyrido[3,4-b]indol-2(3H)-yl)propanoic acid;

(S)-3-(1,3-dioxo-6-((2-(trifluoromethyl)thiazol-5-yl)methyl)-11,11a-dihydro-1H-imidazo[1',5':1,6]pyrido[3,4-b]indol-2(3H,5H,6H)-yl)propanoic acid;

(S)-3-(6-(4-methoxybenzyl)-1,3-dioxo-11,11a-dihydro-1H-imidazo[1',5': 1,6]pyrido[3,4-b]indol-2(3H,5H,6H)-yl)propanoic acid;

(S)-3-(6-(2,4-dichlorobenzyl)-1,3-dioxo-11,11a-dihydro-1H-imidazo[1',5': 1,6]pyrido[3,4-b]indol-2(3H,5H,6H)-yl)propanoic acid;

(S)-3-(6-(4-chloro-2-fluorobenzyl)-1,3-dioxo-11,11a-dihydro-1H-imidazo[1',5':1,6]pyrido[3,4-b]indol-2(3H,5H,6H)-yl)propanoic acid;

(S)-3-(6-(2,4-difluorobenzyl)-1,3-dioxo-11,11a-dihydro-1H-imidazo[1',5': 1,6]pyrido[3,4-b]indol-2(3H,5H,6H)-yl)propanoic acid;

(S)-3-(6-((6-fluoropyridin-3-yl)methyl)-1,3-dioxo-11,11a-dihydro-1H-imidazo[1',5':1,6]pyrido[3,4-b]indol-2(3H,5H,6H)-yl)propanoic acid;

3-{8-[(4-fluorophenyl)methyl]-12,14-dioxo-6,8,11,13-tetrazatetracyclo[7.7.0.0$^{2,7}$.0$^{11,15}$]hexadeca-1(9),2(7),3,5-tetraene-13-yl}-2,2-dimethyl propionic acid;

3-{8-[(4-fluorophenyl)methyl]-16,16-dimethyl-12,14-dioxo-6,8,11,13-tetrazatetracyclo[7.7.0.0$^{2,7}$.0$^{11,15}$]hexadeca-1(9),2(7),3,5-tetraene-13-yl}propionic acid;

(S)-3-(6-(4-fluorobenzyl)-1,3-dioxo-11,11a-dihydro-1H-imidazo[1',5':1,6]pyrido[3,4-b]indol-2(3H,5H,6H)-yl)-N-(methylsulfonyl)propanamide;

(S)-3-(6-(4-fluorobenzyl)-1,3-dioxo-11,11a-dihydro-1H-imidazo[1',5':1,6]pyrido[3,4-b]indol-2(3H,5H,6H)-yl)-N-(phenylsulfonyl)propanamide;

2-((2H-tetrazol-5-yl)methyl)-6-(4-fluorobenzyl)-5,6,11,11a-tetrahydro-1H-imidazo[1',5':1,6]pyrido[3,4-b]indole-1,3(2H)-dione; or 3-{8-[(4-fluorophenyl)methyl]-16,16-dimethyl-12,14-dioxo-6,8,11,13-tetrazatetracyclo[7.7.0.0$^{2,7}$.0$^{11,15}$]hexadeca-1(9),2(7),3,5-tetraene-13-yl}-2,2-dimethylpropionic acid;

or a pharmaceutically acceptable salt, or solvate thereof of any one of the preceding compounds.

10. The compound of claim 8, or a pharmaceutically acceptable salt or solvate thereof:
wherein:
$L^1$ is —CH$_2$—; and

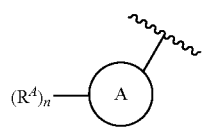

is phenyl; 3-fluorophenyl; 4-fluorophenyl; 3-chlorophenyl; 4-chlorophenyl; 3,5-difluorophenyl; 2,4-difluorophenyl; 3,5-dichlorophenyl; 2,4-dichlorophenyl; 2-methoxypyridin-5-yl; 2-ethoxypyridin-5-yl; 2-chloropyridin-5-yl; 2-trifluoromethylthiazol-5-yl; thien-2-yl; or 5-chlorothien-2-yl.

11. A compound having the following structure, or a pharmaceutically acceptable salt or solvate thereof:

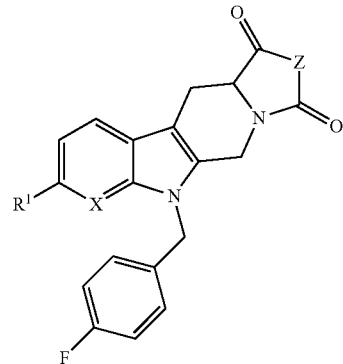

wherein:
$R^1$ is H or Cl;
X is —CH= or —N=;
Z is

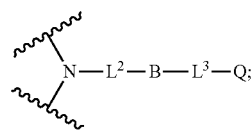

$L^2$ is $C_1$-$C_6$alkylene;
B is absent;
$L^3$ is absent or $C_3$-$C_6$cycloalkylene; and
Q is —CO$_2$H, —CO$_2$(C$_1$-C$_6$alkyl), —OH, or —OP(=O)(OH)$_2$.

12. The compound of claim 11, or a pharmaceutically acceptable salt thereof, wherein:
$L^2$ is —CH$_2$—, —CH$_2$CH$_2$—, —CH$_2$CH$_2$CH$_2$—, or —CH$_2$CH$_2$CH$_2$CH$_2$—.

13. The compound of claim 11, or a pharmaceutically acceptable salt thereof, wherein:
-$L^2$-B-$L^3$-Q is —CH$_2$CO$_2$H, —CH$_2$CH$_2$CO$_2$H, —CH$_2$CH$_2$OH, —CH$_2$CH(CH$_3$)CO$_2$H, —CH$_2$C(CH$_3$)$_2$CO$_2$H, —CH$_2$CH(CH$_2$CH$_3$)CO$_2$H, —CH$_2$C(CH$_2$CH$_3$)$_2$CO$_2$H, —C(CH$_3$)$_2$CH$_2$CO$_2$H, —CH$_2$CH$_2$CH$_2$CO$_2$H, —CH$_2$CH(CH$_3$)CH$_2$CO$_2$H, —CH$_2$C(CH$_3$)$_2$CH$_2$CO$_2$H, —CH$_2$CH$_2$CH(CH$_3$)CO$_2$H, —CH$_2$CH$_2$C(CH$_3$)$_2$CO$_2$H, —CH$_2$C(—CH$_2$CH$_2$—)CO$_2$H, —CH$_2$CH$_2$C(—CH$_2$CH$_2$—)CO$_2$H, or —CH$_2$C(—(CH$_2$)$_3$—)CO$_2$H.

14. The compound of claim 11, or a pharmaceutically acceptable salt thereof, wherein:
-$L^2$-B-$L^3$-Q is —CH$_2$CH$_2$CO$_2$H, or —CH$_2$CH$_2$OH.

15. The compound of claim 11, or a pharmaceutically acceptable salt thereof, wherein the compound has the following structure:

161

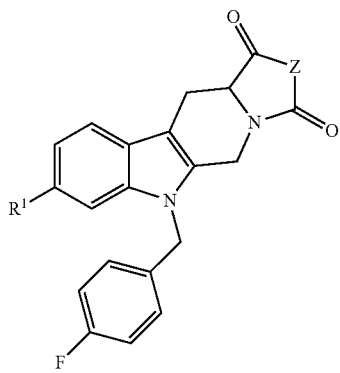

wherein:
R¹ is H or Cl;
Z is

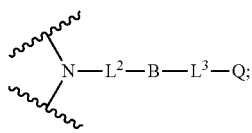

and
-L²-B-L³-Q is —CH₂CO₂H, —CH₂CH₂CO₂H, or —CH₂CH₂OH.

16. The compound of claim 11, or a pharmaceutically acceptable salt thereof, wherein the compound has the following structure:

162

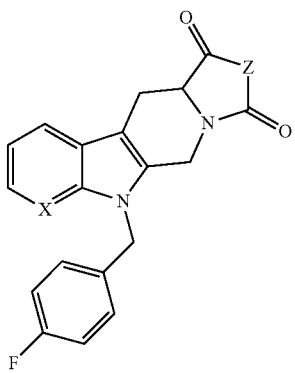

wherein:
Z is

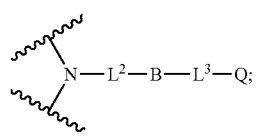

and
-L²-B-L³-Q is —CH₂CO₂H, —CH₂CH₂CO₂H, or —CH₂CH₂OH.

17. A pharmaceutical composition comprising a compound of claim 1, or a pharmaceutically acceptable salt, or solvate thereof, and at least one pharmaceutically acceptable excipient.

* * * * *